US010584129B2

(12) United States Patent
Alonso-de Diego et al.

(10) Patent No.: US 10,584,129 B2
(45) Date of Patent: *Mar. 10, 2020

(54) SUBSTITUTED 6,7-DIHYDROPYRAZOLO[1,5-A]PYRAZINES AS NEGATIVE ALLOSTERIC MODULATORS OF MGLUR2 RECEPTORS

(71) Applicant: Janssen Pharmaceutica NV, Beerse (BE)

(72) Inventors: Sergio-Alvar Alonso-de Diego, Toledo (ES); José Maria Cid-Núñez, Toledo (ES); Óscar Delgado-González, Santa Crus de Tenerife (ES); Annelies Marie Antonius Decorte, Berchem (BE); Michiel Luc Maria Van Gool, Madrid (ES); Gregor James MacDonald, Zoersel (BE); Antonius Adrianus Hendrikus Petrus Megens, Beerse (BE); Andrés Avelino Trabanco-Suárez, Olias del Rey (ES); Aránzazu García-Molina, Toledo (ES); José Ignacio Andrés-Gil, Madrid (ES)

(73) Assignee: Janssen Pharmaceuticals NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/123,009

(22) Filed: Sep. 6, 2018

(65) Prior Publication Data
US 2019/0055257 A1    Feb. 21, 2019

Related U.S. Application Data

(63) Continuation of application No. 14/896,230, filed as application No. PCT/EP2014/061478 on Jun. 3, 2014, now Pat. No. 10,106,542.

(30) Foreign Application Priority Data

Jun. 4, 2013  (EP) .................................... 13170447
Jun. 27, 2013 (EP) .................................... 13173939
Apr. 29, 2014 (EP) .................................... 14166450

(51) Int. Cl.
C07D 487/04     (2006.01)

(52) U.S. Cl.
CPC ................................. C07D 487/04 (2013.01)

(58) Field of Classification Search
CPC .................................................. C07D 487/04
USPC ......................................................... 544/350
See application file for complete search history.

(56) References Cited

U.S. PATENT DOCUMENTS

| 2,976,146 | A | 3/1961 | Salminen et al. |
| 4,051,244 | A | 9/1977 | Mattioda et al. |
| 4,066,651 | A | 1/1978 | Brittain et al. |
| 4,146,716 | A | 3/1979 | Cox et al. |
| 4,196,207 | A | 4/1980 | Webber |
| 4,256,738 | A | 3/1981 | Woitun et al. |
| 4,358,453 | A | 11/1982 | Bristol et al. |
| 4,550,166 | A | 10/1985 | Moran et al. |
| 4,866,074 | A | 9/1989 | Spada et al. |
| 4,898,654 | A | 2/1990 | Toda et al. |
| 4,978,663 | A | 12/1990 | Effland et al. |
| 5,032,602 | A | 7/1991 | Fey et al. |
| 5,130,442 | A | 7/1992 | Meisel et al. |
| 5,175,157 | A | 12/1992 | Psiorz et al. |
| 5,204,198 | A | 4/1993 | Bugner et al. |
| 5,236,917 | A | 8/1993 | Dunlap et al. |
| 5,254,543 | A | 10/1993 | Hanko et al. |
| 5,260,293 | A | 11/1993 | Baker et al. |
| 5,280,026 | A | 1/1994 | Brown et al. |
| 5,332,750 | A | 7/1994 | Mederski et al. |
| 5,356,911 | A | 10/1994 | Muller-Gliemann et al. |
| 5,366,981 | A | 11/1994 | Vecchietti et al. |
| 5,371,074 | A | 12/1994 | Dunlap et al. |
| 5,374,513 | A | 12/1994 | Ohzeki et al. |
| 5,378,720 | A | 1/1995 | Hlasta et al. |
| 5,407,948 | A | 4/1995 | Fey et al. |
| 5,418,243 | A | 5/1995 | Angerbauer et al. |
| 5,424,435 | A | 6/1995 | Hani et al. |
| 5,473,077 | A | 12/1995 | Monn et al. |
| 5,498,774 | A | 3/1996 | Mitsudera et al. |
| 5,500,420 | A | 3/1996 | Maiese |
| 5,512,576 | A | 4/1996 | Desai et al. |

(Continued)

FOREIGN PATENT DOCUMENTS

BE         841390 A       11/1976
CA      1019323 A1       10/1977

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Alfonso R Gennaro, 18th edition Remington's—Pharmaceutical Sciences, 18th edition Remington's—Pharmaceutical Sciences, 1990, Part 8_ Pharmaceutical preparations and their Manufacture_ pp. 1435-1714, Part 8.
Alper, et al., Agonist-Stimulated [35S]GTBgS Binding, Current Protocols in Pharmacology, 1998, pp. 1-10, vol. 2 Issue 6.

(Continued)

Primary Examiner — Douglas M Willis

(57) ABSTRACT

The present invention relates to novel 6,7-dihydropyrazolo [1,5-a]pyrazin-4(5H)-one derivatives as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

25 Claims, 7 Drawing Sheets

(56) References Cited

U.S. PATENT DOCUMENTS

| | | |
|---|---|---|
| 5,532,242 A | 7/1996 | Cliffe |
| 5,596,012 A | 1/1997 | Dunlap et al. |
| 5,602,145 A | 2/1997 | Samanen |
| 5,650,422 A | 7/1997 | Dunlap et al. |
| 5,654,307 A | 8/1997 | Bridges et al. |
| 5,675,013 A | 10/1997 | Hani et al. |
| 5,710,274 A | 1/1998 | Yuan et al. |
| 5,723,463 A | 3/1998 | Hofgen et al. |
| 5,741,798 A | 4/1998 | Lazer et al. |
| 5,801,179 A | 9/1998 | Van Lommen et al. |
| 5,814,645 A | 9/1998 | Kanellakopulos et al. |
| 5,855,654 A | 1/1999 | Willingham et al. |
| 5,859,020 A | 1/1999 | Preuss et al. |
| 5,869,428 A | 2/1999 | Morishima et al. |
| 5,874,432 A | 2/1999 | Dunlap et al. |
| 5,922,773 A | 7/1999 | Lipton et al. |
| 5,948,911 A | 9/1999 | Pamukcu et al. |
| 5,958,931 A | 9/1999 | Adam et al. |
| 6,013,672 A | 1/2000 | Ye et al. |
| 6,022,869 A | 2/2000 | Faull |
| 6,054,588 A | 4/2000 | Adam et al. |
| 6,093,718 A | 7/2000 | Waterson et al. |
| 6,100,268 A | 8/2000 | Van Lommen et al. |
| 6,103,475 A | 8/2000 | Burnett, Jr. et al. |
| 6,107,342 A | 8/2000 | Adam et al. |
| 6,110,920 A | 8/2000 | Rochus et al. |
| 6,121,278 A | 9/2000 | Jackson et al. |
| 6,130,217 A | 10/2000 | Arnold et al. |
| 6,133,271 A | 10/2000 | Pamukcu et al. |
| 6,136,861 A | 10/2000 | Chenard |
| 6,143,783 A | 11/2000 | Monn et al. |
| 6,162,804 A | 12/2000 | Bilodeau et al. |
| 6,169,091 B1 | 1/2001 | Cockerill et al. |
| 6,172,058 B1 | 1/2001 | Tercero et al. |
| 6,204,292 B1 | 3/2001 | Kozikowski et al. |
| 6,262,068 B1 | 7/2001 | Atwal et al. |
| 6,262,074 B1 | 7/2001 | Otten et al. |
| 6,284,759 B1 | 9/2001 | He |
| 6,313,127 B1 | 11/2001 | Waterson et al. |
| 6,316,498 B1 | 11/2001 | Nakazato et al. |
| 6,333,428 B1 | 12/2001 | Nakazato et al. |
| 6,358,975 B1 | 3/2002 | Eliasson et al. |
| 6,361,571 B1 | 3/2002 | Goettel et al. |
| 6,403,588 B1 | 6/2002 | Hayakawa et al. |
| 6,407,094 B1 | 6/2002 | Adam et al. |
| 6,432,958 B1 | 8/2002 | He |
| 6,433,014 B1 | 8/2002 | Acher et al. |
| 6,455,528 B1 | 9/2002 | Adachi et al. |
| 6,465,484 B1 | 10/2002 | Biiodeau et al. |
| 6,472,392 B1 | 10/2002 | Starck et al. |
| 6,479,436 B1 | 11/2002 | Otten et al. |
| 6,498,180 B1 | 12/2002 | Collado Cano et al. |
| 6,509,328 B1 | 1/2003 | Adam et al. |
| 6,569,863 B1 | 5/2003 | Gerritsma et al. |
| 6,586,441 B2 | 7/2003 | Borroni et al. |
| 6,607,563 B2 | 8/2003 | Ohashi et al. |
| 6,664,250 B2 | 12/2003 | Atwal et al. |
| 6,670,307 B2 | 12/2003 | Schnatterer et al. |
| 6,835,726 B2 | 12/2004 | Cushing et al. |
| 6,977,266 B2 | 12/2005 | Tada et al. |
| 7,393,549 B2 | 7/2008 | Ebinuma |
| 7,456,289 B2 | 11/2008 | Hsieh et al. |
| 7,572,807 B2 | 8/2009 | Li et al. |
| 7,579,360 B2 | 8/2009 | Li et al. |
| 7,700,593 B2 | 4/2010 | Zhang et al. |
| 7,879,837 B2 | 2/2011 | Hayashi et al. |
| 7,960,563 B2 | 6/2011 | Johnson et al. |
| 7,977,325 B2 | 7/2011 | Schwede et al. |
| 8,252,937 B2 | 8/2012 | Cid-Nunez et al. |
| 8,299,101 B2 | 10/2012 | Cid-Núñez et al. |
| 8,399,493 B2 | 3/2013 | Bolea et al. |
| 8,937,060 B2 | 1/2015 | Cid-Nunez et al. |
| 9,012,448 B2 | 4/2015 | Cid-Núñez et al. |
| 2001/0011087 A1 | 8/2001 | Wehner et al. |
| 2002/0009713 A1 | 1/2002 | Miller et al. |
| 2002/0022636 A1 | 2/2002 | Li et al. |
| 2002/0028813 A1 | 3/2002 | Jackson et al. |
| 2002/0041880 A1 | 4/2002 | DeFeo-Jones et al. |
| 2002/0137770 A1 | 9/2002 | Nara et al. |
| 2002/0147362 A1 | 10/2002 | Kozikowski |
| 2002/0193367 A1 | 12/2002 | Adam et al. |
| 2002/0198197 A1 | 12/2002 | Adam et al. |
| 2003/0027807 A1 | 2/2003 | Wehner et al. |
| 2003/0055085 A1 | 3/2003 | Wagenen et al. |
| 2003/0109504 A1 | 6/2003 | Brotchie et al. |
| 2003/0130264 A1 | 7/2003 | Jaen |
| 2003/0134902 A1 | 7/2003 | Nakazato et al. |
| 2003/0158155 A1 | 8/2003 | Hori et al. |
| 2003/0162802 A1 | 8/2003 | Guo et al. |
| 2003/0166639 A1 | 9/2003 | Adam et al. |
| 2003/0171380 A1 | 9/2003 | Arvanitis et al. |
| 2003/0199692 A1 | 10/2003 | Biediger et al. |
| 2003/0207882 A1 | 11/2003 | Stocker et al. |
| 2003/0207916 A1 | 11/2003 | Cheng et al. |
| 2004/0006114 A1 | 1/2004 | Coleman et al. |
| 2004/0034040 A1 | 2/2004 | Eggenweiler et al. |
| 2004/0043388 A1 | 3/2004 | Come et al. |
| 2004/0049032 A1 | 3/2004 | Charrier et al. |
| 2004/0053914 A1 | 3/2004 | Gharagozloo et al. |
| 2004/0063955 A1 | 4/2004 | Biediger et al. |
| 2004/0077599 A1 | 4/2004 | Curry |
| 2004/0097562 A1 | 5/2004 | Olesen et al. |
| 2004/0101833 A1 | 5/2004 | Lazdunski et al. |
| 2004/0102521 A1 | 5/2004 | Collado-Cano et al. |
| 2004/0106791 A1 | 6/2004 | Yoakim et al. |
| 2004/0116489 A1 | 6/2004 | Massey et al. |
| 2004/0127936 A1 | 7/2004 | Salahieh et al. |
| 2004/0132723 A1 | 7/2004 | Yoakim et al. |
| 2004/0138204 A1 | 7/2004 | Harrington, Jr. |
| 2004/0138238 A1 | 7/2004 | Dhanoa et al. |
| 2004/0167123 A1 | 8/2004 | Pratt et al. |
| 2004/0176385 A1 | 9/2004 | Nuss et al. |
| 2004/0204448 A1 | 10/2004 | Muller et al. |
| 2004/0220222 A1 | 11/2004 | Galley et al. |
| 2005/0004142 A1 | 1/2005 | Adams et al. |
| 2005/0026935 A1 | 2/2005 | Ford et al. |
| 2005/0054819 A1 | 3/2005 | Catalano et al. |
| 2005/0070538 A1 | 3/2005 | Cheng et al. |
| 2005/0107412 A1 | 5/2005 | Maw et al. |
| 2005/0113283 A1 | 5/2005 | Solow-Cordero et al. |
| 2005/0187227 A1 | 8/2005 | Himmelsbach et al. |
| 2005/0245530 A1 | 11/2005 | Borzilleri et al. |
| 2006/0083676 A1 | 4/2006 | Lesage et al. |
| 2006/0240501 A1 | 10/2006 | Ebinuma |
| 2007/0032469 A1 | 2/2007 | Isaac et al. |
| 2007/0066582 A1 | 3/2007 | Herold et al. |
| 2007/0213323 A1 | 9/2007 | Imogai et al. |
| 2007/0275984 A1 | 11/2007 | Imogai et al. |
| 2008/0221179 A1 | 9/2008 | Gaul et al. |
| 2008/0286265 A1 | 11/2008 | Gaul et al. |
| 2008/0306077 A1 | 12/2008 | Clayton et al. |
| 2009/0031422 A1 | 1/2009 | Aaron et al. |
| 2009/0111855 A1 | 4/2009 | Gaul et al. |
| 2009/0124609 A1 | 5/2009 | Albrecht et al. |
| 2009/0124612 A1 | 5/2009 | Albrecht et al. |
| 2009/0203668 A1 | 8/2009 | Li et al. |
| 2009/0275751 A1 | 11/2009 | Nagato et al. |
| 2009/0318436 A1 | 12/2009 | Albrecht et al. |
| 2010/0063054 A1 | 3/2010 | Bressi et al. |
| 2010/0063092 A1 | 3/2010 | Cid-Núñez et al. |
| 2010/0087487 A1 | 4/2010 | Cid-Núñez et al. |
| 2010/0099715 A1 | 4/2010 | Cid-Núñez et al. |
| 2010/0166655 A1 | 7/2010 | Imogai et al. |
| 2010/0240688 A1 | 9/2010 | Cid-Nunez et al. |
| 2010/0240706 A1 | 9/2010 | Cid-Nunez et al. |
| 2010/0286206 A1 | 11/2010 | Cid-Nunez et al. |
| 2010/0292241 A1 | 11/2010 | Brnardic et al. |
| 2011/0009441 A1 | 1/2011 | Trabanco-Suarez et al. |
| 2011/0245232 A1 | 10/2011 | Braje et al. |
| 2011/0245247 A1 | 10/2011 | Braje et al. |
| 2011/0275624 A1 | 11/2011 | Cid-Nunez et al. |
| 2011/0306642 A1 | 12/2011 | Cid-Nunez |
| 2012/0035167 A1 | 2/2012 | Cid-Nunez et al. |
| 2012/0135977 A1 | 5/2012 | Beshore et al. |

(56) References Cited

U.S. PATENT DOCUMENTS

| | | |
|---|---|---|
| 2012/0184525 A1 | 7/2012 | Cid-Nunez et al. |
| 2012/0184527 A1 | 7/2012 | Cic-Nunez et al. |
| 2012/0184528 A1 | 7/2012 | Cic-Nunez et al. |
| 2012/0309793 A1 | 12/2012 | Duvey et al. |
| 2013/0109052 A1 | 5/2013 | Yan et al. |
| 2013/0150412 A1 | 6/2013 | Cid-Nunez et al. |
| 2013/0196992 A1 | 8/2013 | Cid-Nunez et al. |
| 2013/0197019 A1 | 8/2013 | Cid-Nunez et al. |
| 2013/0310555 A1 | 11/2013 | Chong |

FOREIGN PATENT DOCUMENTS

| | | |
|---|---|---|
| CA | 2035144 A1 | 7/1991 |
| CA | 2390948 A1 | 12/2000 |
| CN | 1842532 A | 10/2006 |
| CN | 102002040 A | 4/2011 |
| DE | 195057522 A1 | 9/1996 |
| EP | 82023 A2 | 6/1983 |
| EP | 0154190 A1 | 9/1985 |
| EP | 0292840 A2 | 11/1988 |
| EP | 308020 A2 | 3/1989 |
| EP | 365486 A2 | 4/1990 |
| EP | 0373423 B1 | 6/1990 |
| EP | 0379806 A2 | 8/1990 |
| EP | 430385 A2 | 6/1991 |
| EP | 0441718 A1 | 8/1991 |
| EP | 447118 A2 | 9/1991 |
| EP | 452002 A2 | 10/1991 |
| EP | 478195 A1 | 4/1992 |
| EP | 0530702 A1 | 3/1993 |
| EP | 0542059 B1 | 5/1993 |
| EP | 547708 A1 | 6/1993 |
| EP | 548934 A1 | 6/1993 |
| EP | 557016 A1 | 8/1993 |
| EP | 0447891 B1 | 4/1994 |
| EP | 482939 A1 | 4/1994 |
| EP | 612746 A1 | 8/1994 |
| EP | 626378 A1 | 11/1994 |
| EP | 0728759 A1 | 8/1996 |
| EP | 0756200 B1 | 1/1997 |
| EP | 799826 A1 | 10/1997 |
| EP | 838458 A1 | 4/1998 |
| EP | 856255 A2 | 8/1998 |
| EP | 0903343 A1 | 3/1999 |
| EP | 955301 A2 | 11/1999 |
| EP | 1203766 A2 | 5/2002 |
| EP | 1277726 A1 | 1/2003 |
| EP | 1459765 A1 | 9/2004 |
| EP | 2005/002585 A1 | 1/2005 |
| EP | 1006112 A1 | 6/2006 |
| EP | 1764099 A2 | 3/2007 |
| EP | 1764367 A1 | 3/2007 |
| EP | 2039687 A1 | 3/2009 |
| EP | 2327704 A1 | 6/2011 |
| EP | 2666775 A1 | 11/2013 |
| GB | 1392849 A | 4/1975 |
| GB | 1502312 A | 3/1978 |
| JP | 50106981 | 8/1975 |
| JP | 53082783 | 7/1978 |
| JP | 57052334 | 11/1982 |
| JP | 6110557 A | 1/1986 |
| JP | 2124871 | 5/1990 |
| JP | H02503317 | 10/1990 |
| JP | 2277044 | 11/1990 |
| JP | 5204071 | 8/1993 |
| JP | 6211797 | 8/1994 |
| JP | 6211798 | 8/1994 |
| JP | 7070018 | 3/1995 |
| JP | 7101861 | 4/1995 |
| JP | 10029979 A | 2/1998 |
| JP | 10045750 | 2/1998 |
| JP | 2000072731 | 3/2000 |
| JP | 2000072751 | 3/2000 |
| JP | 2001089367 | 4/2001 |
| JP | 2002003401 | 1/2002 |
| JP | 105085 A | 4/2002 |
| JP | 2002308882 | 10/2002 |
| JP | 2003/012653 | 1/2003 |
| JP | 2004/525192 A | 8/2004 |
| JP | 2004339080 | 12/2004 |
| JP | 2005/531501 A | 10/2005 |
| JP | 2008509714 | 4/2008 |
| JP | 2008/513414 A | 5/2008 |
| RU | 2143433 C1 | 12/1999 |
| SU | 509578 A1 | 4/1976 |
| SU | 1796625 A1 | 2/1993 |
| WO | 1984_00544 A1 | 2/1984 |
| WO | 1984_00685 A1 | 3/1984 |
| WO | 1991_09848 A1 | 7/1991 |
| WO | 1992_18115 A1 | 10/1992 |
| WO | 1993_01195 A1 | 1/1993 |
| WO | 1993_15056 A1 | 8/1993 |
| WO | 199419315 A1 | 9/1994 |
| WO | 199504733 A1 | 2/1995 |
| WO | 199506032 A1 | 3/1995 |
| WO | 199511233 A1 | 4/1995 |
| WO | 199517397 A1 | 6/1995 |
| WO | 199524393 A1 | 9/1995 |
| WO | 199535293 A1 | 12/1995 |
| WO | 199605828 A1 | 2/1996 |
| WO | 199606167 A1 | 2/1996 |
| WO | 199615108 A1 | 5/1996 |
| WO | 199622021 A1 | 7/1996 |
| WO | 199633974 A1 | 10/1996 |
| WO | 199637481 A1 | 11/1996 |
| WO | 199641639 A1 | 12/1996 |
| WO | 199710229 A1 | 3/1997 |
| WO | 199710238 A1 | 3/1997 |
| WO | 97/21701 A1 | 6/1997 |
| WO | 199746532 A1 | 12/1997 |
| WO | 199748724 A2 | 12/1997 |
| WO | 199806724 A1 | 2/1998 |
| WO | 98/11075 A1 | 3/1998 |
| WO | 199817668 A1 | 4/1998 |
| WO | 199824780 A2 | 6/1998 |
| WO | 1998/032762 A1 | 7/1998 |
| WO | 1998/38168 A1 | 9/1998 |
| WO | 1998/050384 A1 | 11/1998 |
| WO | 1999/006041 A1 | 2/1999 |
| WO | 1999/11622 A1 | 3/1999 |
| WO | 1999/11628 A1 | 3/1999 |
| WO | 1999/11649 A1 | 3/1999 |
| WO | 199912532 A2 | 3/1999 |
| WO | 199916755 A1 | 4/1999 |
| WO | 199918096 A1 | 4/1999 |
| WO | 199921992 A2 | 5/1999 |
| WO | 199931062 A1 | 6/1999 |
| WO | 199931066 A1 | 6/1999 |
| WO | 199932448 A1 | 7/1999 |
| WO | 199933829 A1 | 7/1999 |
| WO | 199936072 A1 | 7/1999 |
| WO | 199952893 | 10/1999 |
| WO | 199953956 A1 | 10/1999 |
| WO | 1999/062906 A2 | 12/1999 |
| WO | 2000/003990 A1 | 1/2000 |
| WO | 2000012089 A1 | 3/2000 |
| WO | 2000021934 A1 | 4/2000 |
| WO | 2000034244 A1 | 6/2000 |
| WO | 2000053605 A1 | 9/2000 |
| WO | 2000061126 A2 | 10/2000 |
| WO | 2000069816 A1 | 11/2000 |
| WO | 2000073283 A1 | 12/2000 |
| WO | 2001010846 A2 | 2/2001 |
| WO | 2001/029025 A2 | 4/2001 |
| WO | 2001/032632 A2 | 5/2001 |
| WO | 2001032644 A2 | 5/2001 |
| WO | 2001046190 A1 | 6/2001 |
| WO | 2001/53288 A1 | 7/2001 |
| WO | 2001055132 A1 | 8/2001 |
| WO | 2001056990 A2 | 8/2001 |
| WO | 2001/068097 A1 | 9/2001 |
| WO | 2001/70713 A1 | 9/2001 |
| WO | 2001/72712 A1 | 10/2001 |
| WO | 2001/83421 A1 | 11/2001 |

(56) References Cited

FOREIGN PATENT DOCUMENTS

| | | |
|---|---|---|
| WO | 2001/83431 A1 | 11/2001 |
| WO | 2001/083481 A1 | 11/2001 |
| WO | 2001085716 A1 | 11/2001 |
| WO | 2001/096308 A1 | 12/2001 |
| WO | 2002/002568 A1 | 1/2002 |
| WO | 2002/010807 A1 | 2/2002 |
| WO | 2002/012236 A1 | 2/2002 |
| WO | 2002/14282 A1 | 2/2002 |
| WO | 2002/22598 A1 | 3/2002 |
| WO | 2002/28837 A1 | 4/2002 |
| WO | 2002/51849 A1 | 7/2002 |
| WO | 2002074025 A2 | 9/2002 |
| WO | 2002079498 A1 | 10/2002 |
| WO | 2002/090333 A1 | 11/2002 |
| WO | 2002/094264 A1 | 11/2002 |
| WO | 2002/096318 A2 | 12/2002 |
| WO | 2002/096363 A2 | 12/2002 |
| WO | 2002/096873 A1 | 12/2002 |
| WO | 2002/102807 A1 | 12/2002 |
| WO | 2002098869 A2 | 12/2002 |
| WO | 2003011293 A2 | 2/2003 |
| WO | 2003/029209 A2 | 4/2003 |
| WO | 2003/035639 A1 | 5/2003 |
| WO | 2003/044021 A2 | 5/2003 |
| WO | 2003042989 A1 | 5/2003 |
| WO | 2003/051481 A2 | 6/2003 |
| WO | 2003047577 A2 | 6/2003 |
| WO | 2003051842 A2 | 6/2003 |
| WO | 03/059884 A1 | 7/2003 |
| WO | 2003/062392 A2 | 7/2003 |
| WO | 2003055878 A1 | 7/2003 |
| WO | 2003059871 A1 | 7/2003 |
| WO | 03/068230 A1 | 8/2003 |
| WO | 2003064428 A1 | 8/2003 |
| WO | 2003065994 A2 | 8/2003 |
| WO | 2003068750 A1 | 8/2003 |
| WO | 2003070712 A1 | 8/2003 |
| WO | 2003076405 A1 | 9/2003 |
| WO | 2003082191 A2 | 10/2003 |
| WO | 2003084610 A1 | 10/2003 |
| WO | 2003092595 A2 | 11/2003 |
| WO | 2003/104217 A2 | 12/2003 |
| WO | 2003099808 A1 | 12/2003 |
| WO | 2003105846 A1 | 12/2003 |
| WO | 2004000846 A1 | 12/2003 |
| WO | 2004004720 A1 | 1/2004 |
| WO | 2004011441 A1 | 2/2004 |
| WO | 2004014859 A2 | 2/2004 |
| WO | 2004014920 A1 | 2/2004 |
| WO | 2004/018386 A2 | 3/2004 |
| WO | 2004/024936 A2 | 3/2004 |
| WO | 2004017950 A2 | 3/2004 |
| WO | 2004019863 A2 | 3/2004 |
| WO | 2004021984 A2 | 3/2004 |
| WO | 2004024150 A2 | 3/2004 |
| WO | 2004/029060 A1 | 4/2004 |
| WO | 2004/031189 A1 | 4/2004 |
| WO | 2004/041818 A1 | 5/2004 |
| WO | 2004043927 A1 | 5/2004 |
| WO | 2004/054979 A1 | 7/2004 |
| WO | 2004/065380 A1 | 8/2004 |
| WO | 2004/067002 A2 | 8/2004 |
| WO | 2004/072025 A2 | 8/2004 |
| WO | 2004/076413 A2 | 9/2004 |
| WO | 2004/078175 A2 | 9/2004 |
| WO | 2004/078176 A1 | 9/2004 |
| WO | 2004/080981 A1 | 9/2004 |
| WO | 2004/092123 A3 | 10/2004 |
| WO | 2004/092135 A2 | 10/2004 |
| WO | 2005/002552 A2 | 1/2005 |
| WO | 2005/007144 A2 | 1/2005 |
| WO | 2005/021552 A1 | 3/2005 |
| WO | 2005/028445 A2 | 3/2005 |
| WO | 2005/040337 A2 | 5/2005 |
| WO | 2005/061507 A1 | 7/2005 |
| WO | 2005/080356 A1 | 9/2005 |
| WO | 2005/097052 A1 | 10/2005 |
| WO | 2005/100365 A1 | 10/2005 |
| WO | 2005/123703 | 12/2005 |
| WO | 2006/012622 A2 | 2/2006 |
| WO | 2006/014918 A2 | 2/2006 |
| WO | 2006/015158 A1 | 2/2006 |
| WO | 2006/015737 A1 | 2/2006 |
| WO | 2006/018727 A2 | 2/2006 |
| WO | 2006/020879 A1 | 2/2006 |
| WO | 2006/029980 A1 | 3/2006 |
| WO | 2006/030031 A1 | 3/2006 |
| WO | 2006/030032 A1 | 3/2006 |
| WO | 2006/030847 A1 | 3/2006 |
| WO | 2006/047237 A2 | 5/2006 |
| WO | 2006/050803 A1 | 5/2006 |
| WO | 2006/057860 A1 | 6/2006 |
| WO | 2006/057869 A1 | 6/2006 |
| WO | 2006/071730 A1 | 7/2006 |
| WO | 2006/074041 A2 | 7/2006 |
| WO | 2006/091496 A2 | 8/2006 |
| WO | 2006/109876 A1 | 10/2006 |
| WO | 2006/137350 A1 | 12/2006 |
| WO | 2007/021308 A1 | 2/2007 |
| WO | 2007/021309 A1 | 2/2007 |
| WO | 2007/027669 A1 | 3/2007 |
| WO | 2007/031558 A1 | 3/2007 |
| WO | 2007/039439 A1 | 4/2007 |
| WO | 2007/059257 A2 | 5/2007 |
| WO | 2007/078523 A2 | 7/2007 |
| WO | 2007/084314 A2 | 7/2007 |
| WO | 2007/095024 A1 | 8/2007 |
| WO | 2007/103760 A2 | 9/2007 |
| WO | 2007/104783 A2 | 9/2007 |
| WO | 2007/113276 A1 | 10/2007 |
| WO | 2007/122258 A1 | 11/2007 |
| WO | 2007/135527 A2 | 11/2007 |
| WO | 2007/135529 A2 | 11/2007 |
| WO | 2008/001115 A2 | 1/2008 |
| WO | 2008/006540 A1 | 1/2008 |
| WO | 2008/008539 A2 | 1/2008 |
| WO | 2008/012622 A2 | 1/2008 |
| WO | 2008/012623 A1 | 1/2008 |
| WO | 2008/032191 A2 | 3/2008 |
| WO | 2008/045393 A2 | 4/2008 |
| WO | 2006/057855 A2 | 5/2008 |
| WO | 2008/051197 A2 | 5/2008 |
| WO | 2008/076225 A2 | 6/2008 |
| WO | 2008/078091 A1 | 7/2008 |
| WO | 2008/078100 A2 | 7/2008 |
| WO | 2008/100715 A1 | 8/2008 |
| WO | 2008/0107125 A1 | 9/2008 |
| WO | 2008/107479 A1 | 9/2008 |
| WO | 2008/107480 A1 | 9/2008 |
| WO | 2008/107481 A1 | 9/2008 |
| WO | 2008/112483 A2 | 9/2008 |
| WO | 2008/124085 A2 | 10/2008 |
| WO | 2008/130853 A1 | 10/2008 |
| WO | 2006/141239 A1 | 11/2008 |
| WO | 2008/145616 A1 | 12/2008 |
| WO | 2008/150232 A1 | 12/2008 |
| WO | 2008/150233 A1 | 12/2008 |
| WO | 2009/004430 A1 | 1/2009 |
| WO | 2009/033702 A1 | 3/2009 |
| WO | 2009/033703 A1 | 3/2009 |
| WO | 2009/033704 A1 | 3/2009 |
| WO | 2009/041567 A1 | 4/2009 |
| WO | 2009/045753 A1 | 4/2009 |
| WO | 2009/062676 A2 | 5/2009 |
| WO | 2009/091374 A2 | 7/2009 |
| WO | 2009/094265 A1 | 7/2009 |
| WO | 2009/095872 A1 | 8/2009 |
| WO | 2009/110901 A1 | 9/2009 |
| WO | 2009/118292 A1 | 10/2009 |
| WO | 2009/124609 A1 | 10/2009 |
| WO | 2009/130232 A1 | 10/2009 |
| WO | 2009/140163 A1 | 11/2009 |
| WO | 2009/140166 A2 | 11/2009 |
| WO | 2009/148403 A1 | 12/2009 |

(56) References Cited

FOREIGN PATENT DOCUMENTS

| | | |
|---|---|---|
| WO | 2009/009062 A1 | 1/2010 |
| WO | 2010/022076 A1 | 2/2010 |
| WO | 2010/022081 A1 | 2/2010 |
| WO | 2010/025890 A1 | 3/2010 |
| WO | 2010/043396 A1 | 4/2010 |
| WO | 2010/060589 A1 | 6/2010 |
| WO | 2010/063054 A1 | 6/2010 |
| WO | 2010/089303 A1 | 8/2010 |
| WO | 2010/114726 A1 | 10/2010 |
| WO | 2010/117926 A1 | 10/2010 |
| WO | 2010/130422 A1 | 11/2010 |
| WO | 2010/130423 A1 | 11/2010 |
| WO | 2010/130424 | 11/2010 |
| WO | 2010/141360 A1 | 12/2010 |
| WO | 2011/022312 A1 | 2/2011 |
| WO | 2011/034741 A1 | 3/2011 |
| WO | 2011/034828 A1 | 3/2011 |
| WO | 2011/034830 A1 | 3/2011 |
| WO | 2011/134832 A1 | 3/2011 |
| WO | 2011/051490 A2 | 5/2011 |
| WO | 2011/109277 A1 | 9/2011 |
| WO | 2011/116356 A2 | 9/2011 |
| WO | 2011/136723 A1 | 11/2011 |
| WO | 2011/137046 A1 | 11/2011 |
| WO | 2011/156245 A2 | 12/2011 |
| WO | 2012/021382 A1 | 2/2012 |
| WO | 2012/035078 A1 | 3/2012 |
| WO | 2012/062750 A1 | 5/2012 |
| WO | 2012/062751 A1 | 5/2012 |
| WO | 2012/062752 A1 | 5/2012 |
| WO | 2012/083224 A1 | 6/2012 |
| WO | 2012/143726 A1 | 10/2012 |
| WO | 2012/151136 A1 | 11/2012 |
| WO | 2012/151139 A1 | 11/2012 |
| WO | 2012/151140 A1 | 11/2012 |
| WO | 2013/012915 A1 | 1/2013 |
| WO | 2013/012918 A1 | 1/2013 |
| WO | 2013/066736 A1 | 5/2013 |
| WO | 2013/154878 A1 | 10/2013 |
| WO | 2013/156869 A1 | 10/2013 |
| WO | 2013/174822 A1 | 11/2013 |
| WO | 2013/192343 A1 | 12/2013 |
| WO | 2013/192347 A1 | 12/2013 |
| WO | 2013/192350 A1 | 12/2013 |
| WO | 2014/064028 A1 | 5/2014 |
| WO | WO2014/195311 A1 | 12/2014 |

OTHER PUBLICATIONS

Bigotti, et al, Synthesis of C[CH(RF)NH]Gly-peptides: The dramatic effect of a single fluorine atom on the diastereocontrol of the key aza-Michael reaction, Journal of Fluorine Chemistry, Jun. 27, 2008, pp. 767-774, 129.

Cid Jose Maria et al, Discovery of 3-Cyclopropylmethyl-7-(4-phenylpiperidin-1-yl)-8-trifluoromethyl[1,2,4]trizaolo [4,3-a]pyridine (JNJ-42153605: A Positive Allosteric Modulator of the Metabotropic Glutamate 2 Receptor, Journal of Medicinal Chemistry, Oct. 16, 2012, pp. 8770-8789, 55.

Dinklo Theo et al., Characterization of 2-[[4-Fluoro-3-(trifluoromethyl)phenyl]amino]-4-(4-pridinyl)-5-thiazolemethanol (JNJ-1930942), a Novel Positive Allosteric Modulator of the 7 Nicotinic Acetycholine Receptor☐S, The Journal of Pharmacology and Experimental Therapeutics, 2011, pp. 560-574, vol. 336 No. 2.

Embrechts S., et al., Longitudinal characterisation of the TauPS2APP mouse model of Alzheimer's disease in a two trial discrimination task of visuo-spatial recognition memory, 45th European Brain and Behaviour Society Meeting Sep. 6-9, 2013 Munich, Sep. 6, 2009, p. 202, not applicable.

Ferraguti, et al, Metabotropic glutamate receptors, Cell & Tissue Research, Jul. 18, 2006, pp. 483-504, vol. 326.

Gilfillian, et al., Synthesis and biological evaluation of novel 2,3-dihydro-1H-1,5-benzodiazepin-2-ones; potential imaging agents of the metabotropic glutamate 2 receptor, Med. Chem. Commun., May 29, 2013, pp. 1118-1123, vol. 4 Issue 7.

Goeldner, et al., Cognitive impairment in major depression and the mGlu2 receptor as a therapeutic target, Neuropharmacology, Aug. 3, 2013, pp. 337-346, vol. 64.

Guy A. Higgins et al., Pharmacological manipulation of mGlu2 receptors influences, Neuropharmacology, 2004, pp. 907-917, vol. 46.

Hickinbottom, English translation of the relevent from reaction of organic complonents, Reactions of organic compounds, 1939, pp. 360-362, Page Number.

Kelmendi, et al, The role of the Glutamatergic system in the pathophysiology and treatment of mood disorders, Primary Psychiatry, 2006, pp. 80-86, vol. 13 Issue 10.

Koike et al., Role of BDNF/TrkB signaling in antidepressant-iike effects of a group II metabotropic glutamate receptor antagonist in animal models of depression, Behavioural Brain Research, 2013, pp. 48-52, vol. 238.

Li Jingjie et al., Palladium-Catalyzed Oxidative Rearrangement of Tertiary Allylic Alcohols to Enones with Oxygen in Aqueour Solvent, Organic Letters, Oct. 3, 2014, pp. 5370-5373, No. 16.

Moscow., Chemicai Encyclopedia, Soviet encyclopedia, 1988, pp. 242-243, vol. 1.

NCT01457677, View of NCT01457877 on Feb. 18, 2014, ClinicalTrials.gov Archive, Feb. 18, 2014, pp. 1-3, not applicable.

Niswender, et al., Metabotropic Glutamate Receptors: Physiology, Pharmacology, and Disease, Annu.Rev. Pharmacol Toxicol., 2010, pp. 395-322, vol. 50.

Schaffhauser et al, Pharmacological Characterization and Identification of Amino Acids Involved in the Positive Modulation of Metabotropic Glutamate Receptor Subtype 2, Molecular Pharmacoiogy, Jun. 13, 2003, pp. 798-810, vol. 64, No. 4.

Shigemoto, et al., Differential Presynaptic Localizaiton of Metabotropic Glutamate Receptor Subtypes in the Rat Hippocampus, The Journal of Neuroscience, Oct. 1, 1997, pp. 7503-7522, vol. 17 Issue 19, Society for Neuroscience.

International Search Report for PCT/EP2014/061478 dated Aug. 5, 2014.

A H V Schapira., Science, medicine, and the future, BMJ, 1999, pp. 311-314, vol. 318.

A. Carlsson., The Neurochemicai Circuitry of Schizophrenia, The Neurochemical Circuitry Pharmacopsycharity, 2006, pp. 10-14, vol. 39 Issue 1, Georg Thieme Verlag KG Stuttgart.

A. Copani, Activation of Metabotropic Glutamate Receptors Protects Cultured Neurons Against Apoptosis induced by b-Amyloid Peptide, Molecular Pharmacology, 1995, pp. 890-897, vol. 47.

A.-M. Linden et al, Comparison of c-Fos induction in the brain by the mGlu2/3 receptor antagonist LY341495 and agonist LY354740: Evidence for widespread endogenous tone at brain mGlu2/3 receptors in vivo, Neuropharmacology, May 5, 2005, pp. 120-134, vol. 49.

A.M.Spiegel., Defects in G protein-Coupled Signal Transduction in Human Disease, Annual Review of Physiology, 1995, pp. 143-170, vol. 58.

A.Shekhar., GABA receptors in the region of the dorsomedial hypothalamus of rats regulate anxiety in the elevated plus-maze test. I. Behavioral measures, Brain Research, Jun. 8, 1993, pp. 9-16, vol. 627, Elsevier Science Publishers B.V.

Abi-Saab, The NMDA Antagonist Model for Schizophrenia: Promise and Pitfalls, Pharmacopsychiatry, 1998, pp. 104-109, vol. 31.

Abshire,et al., Injection of L-Allylglycine Into the Posterior Hypothalamus in Rats Causes Decreases in Local GABA Which Correlate With Increases in Heart Rate, Neuropharmacology, May 12, 1988, pp. 1171-1177, vol. 27 Issue 11.

Adam, et al., Symptomatic Treatment of Huntington Disease, The Journal of the American Society for Experimental NeuroTherapeutics, 2008, pp. 181-197, vol. 5, The American Society for Experimental NeuroTherapeutics, Inc.

Adams, et al., Effect of Clozapine, Haloperidol, or M100907 on Phencyclidine-Activates Glutamate Efflux in the Prefrontal Cortex, Society of Biological Psychiatry, 2001, pp. 750-757, vol. 50, Issue 10.

Addex., Addex Partner Completes ADX71149 Phase I Program, Addex Therapeutics, Aug. 25, 2010, pp. 1-2, Page Number.

(56) References Cited

OTHER PUBLICATIONS

Addex., Addex Partner Doses First Patient in Phase 2 Clinical Study of AD, Addex Therapeutics, Sep. 17, 2012, pp. 1-2, Page Number.
Addex., Addex Partner to Initiate Phase 2 Clinical Trial od ADX71149, Addex Therapeutics, Jun. 5, 2012, pp. 1-2, Page Number.
Addex., Addex Reports Top-line dtav from a successful Phase 2a Clinical Study with ADX71149 in Schizophrenia Patients, Addex Therapeutics, Nov. 5. 2012, pp. 1-3, Page Number.
Addington, et al., A depression rating scale for schizophrenics, Schizophrenia Research, 1990, pp. 247-251, vol. 3. Elsevier Science Publishers B.V.
Ader, et al., Effects of Chlorpromazine on the Acquisition and Extinction of an Avoidance Response in the Rat, Chlorpromazine and Behavior, May 22, 1957, pp. 144-148, vol. 131.
Agaria, et al., Intrapallidal metabotropic glutamate receptor activation in a rat model of Parkinson's disease: Behavioral and histological analyses, Brain Research, Jan. 30, 2008, pp. 189-196, vol. 1203, Elsevier B.V.
Aghajanian, et al., Serotonin model of schizophrenia: emerging role of glutamate mechanisms 1, Brain Research Reviews, 2000, pp. 302-312, vol. 31, Elsevier Science B.V.
Agid, et al., How can drug discovery for psychiatric disorders be improved, Nature Reviews, 2007, pp. 189-201, vol. 6, Nature Publishing Group.
Agnieszka Palucha., Are compounds acting at metabotropic glutamate receptors the answer to treating depression?, Expert Opin. Investig. Drugs, 2006, pp. 1545-1553, vol. 15 Issue 12, lnforma UK Ltd.
Ago, et al., Activation of metabotropic glutamate 2/3 receptors attenuates methamphetamine-induced hyperlocomotion and increase in prefrontal serotonergic neurotransmission, Psychopharmacology, Apr. 13, 2011, pp. 443-452, vol. 217, Springer-Verlag.
Ahnaou et al, Modulation of group II metabotropic glutamate receptor (mGlu2) elicits common changes in rat and mice sieep—wake architecture, European Journal of Pharmacology, Nov. 17, 2008, pp. 62-72, vol. 603.
Ainslie, et al., Practical Drug Evaluation Method, Arch Gen Psychiat, 1965, pp. 368-373, vol. 12.
Al-Omran et al, Studies with Polyfunctionally Substituted Heteroaromatics: New Routes for the Synthesis of Polyfunctionally Substituted Pyridines and 1,2,4-Triazolo[1,5-a]pyridines, Heteroatom Chemistry, 1995, pp. 545-551, vol. 6, No. 6.
Al-Shamma, et al., Nelotanserin, a Novel Selective Human 5-Hydroxytryptamine2A Inverse Agonist for the Treatment of Insomnia, The Journal of Pharmacology and Experimental Therapeutics, 2010, pp. 281-290, vol. 332 Issue 1.
Alagarsamy, et al, Coordinate regulation of metabotropic glutamate receptors, Signalling mechanisms, 2001, pp. 357-362, vol. 11.
Alan Nadin and Timothy Harrison, Synthesis of Tricyclic Pyridones by Radical Cyclization, Tetrahedron Letters, 1999, pp. 4073-4076, vol. 40.
Albasanz, et al., Internalization of metabotropic glutamate receptor in C6 cells through clathrin-coated vesicles, Molecular Brain Research, Jan. 8, 2002, pp. 54-66, vol. 99, Elsevier Science B.V.
Albert Mondon and Karsten Krohn, Synthese des Narciprimins und verwandter Vergindungen, Chemische Berichte, 1972, pp. 3726-2747, vol. 105.
Alberto Chiarugi et al, Novel Isoquinolinond-Derived Inhibitors of Poly(ADP-ribose) Polymerase-1: Pharmacological Characterization and Neuroprotective Effects in an in vitro Model of Cerebral Ischemia, Journal of Pharmacology and Experimental Therapeutics, 2003, pp. 943-949, vol. 305 No. 3.
Alderson, et al., Purification and Characterization of a Soluble Cyclic Nucleotide-Independent Ca2+-Calmodulin-Sensitive Protein Kinase from Rat Brain, J. Neurochem, 1986, pp. 594-603, vol. 46 Issue 2, International Society for Neurochemrstry.
Aleppo, et al., Metabotropic Glutamate Receptors and Neuronal Toxicity, Advances in Experimental Medicine and Biology, 1992, pp. 137-145, vol. 318, Springer-Verlag New York Inc.

Alexander, et al., Metabotropic glutamate receptors as a strategic target for the treatment of epilepsy, Epilepsy Research, Jun. 19, 2006, pp. 1-22, vol. 71, Elsevier B.V.
Alfonso R. Gennaro, Pharmaceutical Sciences, Remington's, 1990, pp. 1435-1712, 18th edition.
Allen, et al., Group II Metabotropic Glutamate Receptor Activation Attenuates Traumatic Neuronal Injury and Improves Neurological Recovery after Traumatic Brain Injury1, The Journal of Pharmacology and Experimental Therapeutics, 1999, pp. 112-120, vol. 290.
Alley, et al., Memantine Lowers Amyloid-b Peptide Levels in Neuronal Cultures and in APP/PS1 Transgenic Mice, Journal of Neuroscience Research, 2010, pp. 143-154, vol. 88, Wiley-Liss, Inc.
Altamura, et al., Designing outcome studies to determine efficacy and safety of antipsychotics for 'real world' treatment of schizophrenia, Journal of Neuropsychopharmacology, Feb. 4, 2010, pp. 971-973, vol. 13.
Altamura, et al., Plasma and Platelet Excitatory Amino Acids in Psychiatric Disorders, Am J Psychiatry, 1993, pp. 1731-1733, vol. 150.
Altamura, et al., Plasma concentrations of excitatory amino acids, serine, glycine, taurine and histidine in major depression, European Neuropsychopharmacology Supplement, Apr. 5, 1995, pp. 71-75, page number.
Amiri, et al., A Role for Leu118 of Loop E in Agonist Binding to the 7 Nicotinic Acetylcholine Receptor, Molecular Pharmacology, Mar. 13, 2008, pp. 1659-1667, vol. 73 Issue 6.
Amitai, et al., Effects of metabotropic glutamate receptor 2/3 agonism and antagonism on schizophrenia-like cognitive deficits induced by phencyclidine in rats, European Journal of Pharmacology, Apr. 2, 2010, pp. 67-80, vol. 639.
Andreescu, et al., Comorbid anxiety and depression: be te noire or quick fix, The British Journal of Psychiatry, 2012, pp. 179-181, vol. 200.
Andreescu, et al., Effect of comorbid anxiety on treatment response and relapse risk in late-life depression, British Journal of Psychiatry, 2007, pp. 344-349, vol. 190.
Andreescu, et al., The Default Mode Network in Late-Life Anxious Depression; Am J Geriatr Psychiatry, 2011, pp. 980-983, vol. 19 Issue 11.
Andres, et al., 2-(Dimethylaminomethyi)-tetrahydroisoxazolopyridobenzazepine Derivatives. Synthesis of a New 5-HT2C Antagonist with Potential Anxiolytic Properties, Bioorganic & Medicinal Chemistry Letters, Sep. 16, 2002, pp. 3573-3577. vol. 12, Elsevier Science Ltd.
Andres, et al., Synthesis, Evaluation; and Radiolabeling of New Potent Positive Allosteric Modulators of the Metabotropic Glutamate Receptor 2 as Potential Tracers for Positron Emission Tomography Imaging, Journal of Medicinal Chemistry, Sep. 20, 2012, pp. 8685-8699, vol. 55.
Angelo Gavezzotti, Are Crystal Structures Predictable?, Accounts of Chemical Research, 1994, pp. 309-314, vol. 27.
Angenstein, et al,, Activation of metabotropic glutamate receptors increases endogenous protein kinase C substrate phosphorylation in adult hippocampal slices, Brain Research, 1997, pp. 46-54, vol. 745.
Angers, et al., Dimerization: An Emerging Concept for G Protein-Coupled Receptor Ontogeny and Function, Annual Review of Pharmacology and Toxicology, 2002, pp. 409-435, vol. 42.
Anna Atlante et al, Glutamate neurotoxicity, oxidative stress and mitochondria, FEBS Letters, 2001, pp. 1-5, vol. 497.
Anthony N. Van Den Pol., Presynaptic Metabotropic Glutamate Receptors in Adult and Developing Neurons: Autoexcitation in the Olfactory Bulb, The Journal of Comparative Neurology, Jan. 18, 1995, pp. 253-271, vol. 359, Wiley-Liss. Inc.
Aparicio-Legarza, et al., Deficits of [3H]d-aspartate binding to glutamate uptake sites in striatal and accumbens tissue in patients with schizophrenia, Neuroscience Letters, Jul. 24, 1997, pp. 13-16, vol. 232, Elsevier Science Ireland Ltd.
Aparicio-Legarza,et al, Increased density of glutamate/N-methyl-D-aspartate receptors in putamen from schizophrenic patients, Neuroscience Letters, Dec. 19, 1997, pp. 143-146, vol. 241.
Aronica, et al., Metabotropic Glutamate Receptors in Cultured Cerebellar Granule Cells:Developmental Profile, Journal of Neurochemistry, 1993, pp. 559-565, vol. 60.

(56) References Cited

OTHER PUBLICATIONS

Aronica, et al., Pharmacological Characterization of Metabotropic Glutamate Receptors in Cultured Cerebellar Granule Cells, Neurochemical Research, 1993, pp. 605-612, vol. 18 Issue 5.

Aronica, et al., Status Epilepticus-Induced Alterations in Metabotropic Glutamate Receptor Expression in Young and Adult Rats, The Journal of Neuroscience, Nov. 1, 1997, pp. 8588-8595, vol. 17 Issue 21.

Aronson, et al., Triiodothyronine Augmentation in the Treatment of Refractory Depression, Arch Gen Psychiatry. 1996, pp. 842-848, vol. 53.

Arriza, et al., Functional Comparisons of Three Glutamate Transporter Subtypes Cloned from Human Motor Cortex, The Journal of Neuroscience, 1994, pp. 5559-5569, vol. 14 , Issue 9.

Arthur Christopoulos, Allosteric Binding Sites on Cell-Structure Receptors: Novel Targets for Drug Discovery, Nature Reviews, 2002, pp. 198-210, vol. 1 March.

Astrazeneca., AZD8529 Single Ascending Dose Study (SAD), ClinicalTrials.gov, Sep. 18, 2008, Placebo, vol. NCT00755378.

Athina Markou,, The Role of Metabotropic Glutamate Receptors in Drug Reward, Motivation and Dependence, Drug News Perspect, 2007, pp. 103-108, vol. 20 Issue 2, Prous Science.

Attwell, et al., Anticonvulsant and glutamate release-inhibiting properties of the highly potent metabotropic glutamate receptor agonist, Brain Research, Jul. 7, 1998, pp. 138-143, vol. 805, Elsevier Science B.V.

Auer, et al., Reduced Glutamate in the Anterior Cingulate Cortex in Depression: An In Vivo Proton Magnetic Resonance Spectroscopy Study, Biol Psychiatry, 2000, pp. 305-313, vol. 47, Society of Biological Psychiatry.

Auerbach, et al., Mutations causing syndromic autism define an axis of synaptic pathophysiology, Nature, Dec. 1, 2011, pp. 63-68, vol. 480, Macmillan Publishers Limited.

Aultman, et al., Distinct Contributions of glutamate and dopamine receptors to temporal aspects of rodent working memory using a clinically relevant task, Psychopharmacology, 2001, pp. 353-364, vol. 153, Springer-Verlag.

Austin, et al., Symptomatic and neuroprotective effects following activation of nigral group III metabotropic glutamate receptors in rodent models of Parkinson's disease, British Journal of Pharmacology, 2010, pp. 1741-1753, vol. 160, The British Pharmacological Society.

Awouters, et al., Effects on general behavior and interactions with central nervous system, Pharmacol&Therapeutics, 1991, pp. 73-89, vol. 19 Issue 5, American Chemical Society.

Ayalew, et al., Convergent functional genomics of schizophrenia: from comprehensive understanding to genetic risk prediction, Molecular Psychiatry, May 15, 2012, pp. 1-19, page number, Macmillan Publishers Limited.

Ayan-Oshodi, et al., Adverse Events in Healthy Subjects Exposed to Single and Multiple Doses of LY2140023 Monohydrate, Journal of Clinical Psychopharmacology, 2012, pp. 408-411, vol. 32 Issue 3, Lippincott Wlliams & Wilkins.

Backstrom, et al., Suppression of alcohol self-administration and cue-induced reinstatement of alcohol seeking by the mGlu2/3 receptor agonist LY379268 and the mGlu8 receptor agonist (S)-3,4-DCPG, European Journal of Pharmacology, Oct. 26, 2005, pp. 110-118, vol. 528.

Badawy, et al., Epilepsy: Ever-Changing States of Cortical Excitability, Neuroscience, 2012, pp. 89-99, vol. 222, Elsevier Ltd.

Baffa, et al., Norepinephrine and Serotonin Transporter Genes: Impact on Treatment Response in Depression, Neuropsychobiology, 2010, pp. 121-131, vol. 62 Issue 2, S.Karger AG.

Bagby, et al., Psychosocial and clinical predictors of response to pharmacotherapy for depression, J Psychiatry Neurosci, Jun. 13, 2002, pp. 250-257, vol. 27 Issue 4, Canadian Medical Association.

Bakker et al., Reduction of hippocampal hyperactivity improves cognition in amnestic mild cognitive impairment, Neuron, 2012, pp. 467-474, vol. 74, Elsevier Inc.

Bakker, et al., Activation of the metabotropic glutamate receptor 2 (mGlu2) by orthosteric and allosteric ligands, Abbott Neuroscience, 2010, Poster, Poster 642.6/E30.

Balazs, et al., Metabotropic Glutamate Receptor Agonists Potentiate Cyclic AMP Formation Induced by Forskolin or j3-Adrenergic Receptor Activation in Cerebral Cortical Astrocytes in Culture, Journal of Neurochemistry, Jan. 6, 1998, pp. 2446-2458, vol. 70 Issue 6, International Society for Neurochemistry.

Balestrieri, et al., Assessing mixed anxiety-depressive disorder. A national primary care survey, Psychiatry Research, 2010, pp. 197-201, vol. 176.

Bandelow, et al., Adjunct Quetiapine XR in Patients With Major Depressive Disorder: A Pooled Analysis of Data From Patients With Anxious Depression, 1 Department of Psychiatry and Psychotherapy, 2011, pp. 605, vol. P02-11.

Bao Ting Zhu, The Competitive and Noncompetitive Antagonism of Receptor-Mediated Drug Actions in the Presence of Spare Receptors, Journal of Pharmacological and Toxicological Methods, 1993, pp. 85-91, vol. 29 Issue 2, Elsevier Science Publishing Co. Inc.

Bar-Peled, et al., Distribution of Glutamate Transporter Subtypes During Human Brain Development, Journal of Neurochemistry, Jul. 29, 1997, pp. 2571-2580, vol. 69 Issue 6, International Society for Neurochemistry.

Barbara J Mason., Acamprosate in the Treatment of Alcohol Dependence, Expert Opin, 2005, pp. 2103-2115, vol. 6 Issue 12.

Barda, et al., SAR study of a subtype selective allosteric potentiator of metabotropic glutamate 2 receptor, N-(4-phenoxyphenyl)-N-(3-pyridinylmethyl)ethanesulfonamide, Bioorganic & Medicinal Chemistry Letters, Apr. 10, 2004, pp. 3099-3102, vol. 14, Elsevier Ltd.

Barker, et al., A temporally distinct role for group I and group 81 metabotropic glutamate receptors in object recognition memory, MGlu receptors and recognition mernoryLearning & Memory, 2006, pp. 178-186, vol. 13 Issue 2, Cold Spring Harbor Laboratort Press ISSN.

Barnes, et al., A review of central 5-HT receptors and their function, Neuropharmacology, Jan. 21, 1999, pp. 1083-1152, vol. 38, Elsevier Science Ltd.

Bartha, et al., Measurement of Glutamate and Glutamine in the Medial Prefrontal Cortex of Never-Treated Schizophrenic Patients and Healthy Controls by Proton Magnetic Resonance Spectroscopy, Arch Gen Psychiatry, 1997, pp. 959-965, vol. 54.

Barton, et al., Comparison of the effect of glutamate receptor modulators in the 6 Hz and maximal electroshock seizure models, Epilepsy Research, Aug. 4, 2003, pp. 17-26, vol. 56.

Basan, et al., Valproate for schizophrenia (Review), Cochrane Database of Systematic Reviews, 2008, pp. 1-38, Issue 2.

Batchelor, et al., Novel Synaptic Potentials in Cerebellar Purkinje Cells: Probable Mediation by Metabotropic Glutamate Receptors, Neuropharmacology, 1993, pp. 11-20, vol. 32 Issue 1, Pergamon Press Ltd.

Battaglia, et al., Selective activation of group-II metabotropic glutamate receptors is protective against excitotoxic neuronal death, European Journal of Pharmacology, Jul. 21, 1998, pp. 271-274, vol. 356, Elsevier Science B.V.

Bauer, et al., Extended-Release Quetiapine as Adjunct to an Antidepressant in Patients With Major Depressive Disorder: Results of a Randomized, Placebo-Controlled, Double-Blind Study, J Clin Psychiatry, 2009, pp. 540-549, vol. 70 Issue 4, Physicians Postgraduate Press, Inc.

Bauzo, et al., Interactions between the mGluR2/3 agonist, LY379268, and cocaine on in vivo neurochemistry and behavior in squirrel monkeys, Pharmacology, Biochemistry and Behavior, Aug. 22, 2009, pp. 204-210, vol. 94, Elsevier Inc.

Bech P., The Bech-Rafaelsen Melancholia Scale (MES) in clinical trials of therapies in depressive disorders: a 20-year review of its use as outcome measure, Acta Psychiatr Scand, 2002, pp. 252-264, vol. 106.

Bech, et al., Quantitative rating of depressive states., Acta Psychiatr Scand, 1975, pp. 161-170, vol. 51 Issue 3.

Beesdo, et al., Incidence and Risk Patterns of Anxiety and Depressive Disorders and Categorization of Generalized Anxiety Disorder, Arch Gen Psychiatry, 2010, pp. 47-57, vol. 67 Issue 1, American Medical Association.

(56) References Cited

OTHER PUBLICATIONS

Behrens, et al., Ketamine-Induced Loss of Phenotype of Fast-Spiking Interneurons Is Mediated by NADPH-Oxidase, Science, Dec. 7, 2007, pp. 1645-1647, vol. 318.
Belenikin, et al., Comparative Analysis of the Ligand-Binding Sites of the Metabotropic Glutamate Receptors mGluR1-mGluR8, Doklady Biochemistry and Biophysics, 2002, pp. 251-256, vol. 386.
Beljouw, et al., The course of untreated anxiety and depression, and determinants of poor one-year outcome: a one-year cohort study, BMC Psychiatry, 2010, pp. 1-10, vol. 10 ssue 86.
Bell, et al., Altered synaptic function in Alzheimer's disease, European Journal of Pharmacology, Jun. 27, 2006, pp. 11-21; vol. 545, Elsevier B.V.
Bellani, et al., Brain anatomy of major depression ||. Focus on amygdala, Epidemiology and Psychiatric Science, Mar. 28, 2011, pp. 33-36, vol. 20 Issue 1.
Bellesi, et al., The mGluR2/3 Agonist LY379268 Blocks the Effects of GLT-1 Upregulation on Prepulse Inhibition of the Startle Reflex in Adult Rats, Neuropsychopharmacology, 2010, pp. 1253-1260, vol. 35, Nature Publishing Group.
Belousov, et al., Non-cholinergic excitation in neurons after a chronic glutamate receptor blockade, NeuroReport, Jan. 19, 2004, pp. 113-117, vol. 15 Issue 1.
Benca, et al., Sleep and Psychiatric Disorders, Arch Gen Psychiatry, 1992, pp. 651-670, vol. 49.
Beneyto, et al., Abnormal Glutamate Receptor Expression in the Medial Temporal Lobe in Schizophrenia and Mood Disorders, Neuropsychopharmacology, Feb. 14, 2007, pp. 1888-1902, vol. 32, Nature Publishing Group.
Benilova, et al., The toxic Aβ oligomer and Alzheimer's disease: an emperor in need of clothes, nature neuroscience, Jan. 29, 2012, pp. 349-357, vol. 15 Issue 3, Nature America, Inc.
Benneyworth et al, A Selective Positive Allosteric Modulator of Metabotropic Glutamate Receptor Subtype 2 Blocks a Hallucinogenic Drug Model of Psychosis, Molecular Pharmacology, 2007, pp. 477-484, vol. 72, No. 2.
Benneyworth, et al., Chronic Phenethylamine Hallucinogen Treatment Alters Behavioral Sensitivity to a Metabotropic Glutamate 2/3 Receptor Agonist, Neuropsychopharmacology, 2008, pp. 2206-2216, vol. 33, Nature Publishing Group.
Benquet, et al., Two Distinct Signaling Pathways Upregulate NMDA Receptor Responses via Two Distinct Metabotropic Glutamate Receptor Subtypes, The Journal of Neuroscience, 2002, pp. 9679-9686, vol. 22 Isuue 22, Society for Neuroscience.
Benson, et al., A Comparison of Observational Studies and Randomized, Controlled Trials, The New England Journal of Medicine, Jun. 22, 2000, pp. 1878-1886, vol. 342 Issue 25, Massachusetts Medical Society.
Bergink, et al., Metabotropic glutamate II receptor agonists in panic disorder: a double blind clinical trial with LY354740, International Clinical Psychopharmacology, May 24, 2005, pp. 291-293, vol. 20, Lippincott Williams & Wilkins.
Berman, et al., The Efficancy and Safety of Aripiprazole as Adjunctive Therapy in Major Depressive Disorder: A Multicenter, Randomized, Double-Blind,Placebo-Controlled Study, J Clin Psychiatry, 2007, pp. 843-853, vol. 68 Issue 6.
Berthele, et al., Distribution and developmental changes in metabotropic glutamate receptor messenger RNA expression in the rat lumbar spinal cord, Developmental Brain Research, 1999, pp. 39-53, vol. 112, Elsevier Science B.V.
Berthele, et al., Expression of metabotropic glutamate receptor subtype mRNA (mGluR1-8) in human cerebellum, NeuroReport, Dec. 16, 1999, pp. 3861-3867, vol. 10 Issue 18, Lippincott Williams & Wilkins.
Bertrand, et al., Common and Selective Molecular Determinants Involved in Metabotopic Glutamate Receptor Agonist Activity, Journal of Medicinal Chemistry, 2002, pp. 3171-3183, vol. 45 Issue 15, American Chemical Society.

Bespalov, et al., Behavioral characterization of the mGlu group II/III receptor antagonist, LY-341495, in animal models of anxiety and depression, European Journal of Pharmacology, 2008, pp. 96-102, vol. 592, Elsevier B.V.
Bespalov, et al., Habituation Deficits Induced by Metabotropic Glutamate Receptors 2/3 Receptor Blockade in Mice: Reversal by Antipsychotic Drugs, The Journal of Pharmacology and Experimental Therapeutics, 2007, pp. 944-950, vol. 320 issue 2.
Bessho, et al., Glutamate and Quisqualate Regulate Expression of Metabotropic Glutamate Receptor mRNA in Cultured Cerebellar Granule Cells, Journal of Neurochemistry, 1993, pp. 253-259, vol. 60 Issue 1, International Society for Neurochemistry.
Bessis, et al., Metabotropic Glutamate Receptors: Exciting Possibilities in Excitatory Transmission, Celltransmissions, 2000, pp. 3-10, vol. 17 Issue 3.
Bijl, et al., Current and residual functional disability associated with psychopathology: ®ndings from the Netherlands Mental Health Survey and Incidence Study (NEMESIS), Psychological Medicine, 2000, pp. 657-668, Issue 30, Cambridge University Press.
Bilkei Gorzo, et al., mCPP-induced anxiety in the light-dark box in rats—a new method for screening anxiolytic activity, Psychopharmacology, 1998, pp. 291-298, vol. 136, Springer-Verlag.
Binder, et al., Association of Polymorphisms in Genes Regulating the Corticotropin-Releasing Factor System With Antidepressant Treatment Response, Arch Gen Psychiatry, 2010, pp. 369-370, vol. 67 Issue 4, American Medical Association.
Black, et al., Compound A, a Novel,Potent and Selective mGluR2 Positive Allosteric Modulator: II. Effects in Models Predictive . . . , Society for Neuroscience, 2010, pp. 12-17, Poster 767.7.
Blaha, et al., Stimulation of the Ventral Subiculum of the Hippocampus Evokes Glutamate Receptor-mediated Changes in Dopamine Efflux in the Rat Nucleus Accumbens, European Journal of Neuroscience, 1997, pp. 902-911, vol. 9, European Neuroscience Association.
Blanco, et al., Changes in the prevalence of non-medical prescription drug use and drug use disorders in the United States: 1991-1992 and 2001-2002, Drug and Alcohol Dependence, Apr. 9, 2007, pp. 252-260, vol. 90, Elsevier Ireland Ltd.
Boatman et al, Alkylations at the Methyl or a-Methylene Group of 6- or 4-Alkyl-3-cyano-2(1)-pyridones through Dianions, Journal of Organic Chemistry, Nov. 1965, pp. 3593-3597, vol. 30, No. 11.
Bockaert, et al., Metabotropic glutamate receptors: an original family of G protein-coupled receptors, Fundarn Clin PlioriiIncol, Jun. 10, 1993, pp. 473-485, vol. 7, Elsevier, Paris.
Bockaert, et al., Molecular tinkering of G protein-coupled receptors: an evolutionary success, The EMBO Journal, Jan. 19, 1999, pp. 1723-1729, vol. 18 Issue 7.
Bodick, et al., Protocols to Demonstrated Slowing of Alzheimer Disease Progression Position Paper from the International Working Group on Harmonization of Dementia Drug Guidelines, Alzheimer Disease and Asciated Disorders, 1997, pp. 50-53, vol. 11 Supplementary 3.
Boldyrev, et al., Homocysteine and its Derivatives as Possible Modulators of Neuronal and Non-Neuronal Cell Glutamate Receptors in Alzheimer's Disease, Journal of Alzheimer's Disease, 2007, pp. 219-228, vol. 11, IOS Press.
Bolton, et al., Exploring the Correlates of Sucide Attempts Among Individulas With Major Depressive Disorder Findings From the National Epidemiologic Survey on Alochol and Related Conditions, J Clin Psychiatry, 2008, pp. 1139-1149, vol. 69 Issue 7.
Bonanno, Chronic Antidepressants Reduce Depolarization-Evoked Glutamate Release and Protein Interactions Favoring Formationof SNARE Complex in Hippocampus, The Journal of Neuroscience, 2005, pp. 3270-3279, vol. 25 Issue 13.
Bond, et al., Neuroprotective Effects of LY379268, a Selective mGlu2/3 Receptor Agonist: Investigations into Possible Mechanism of Action In Vivo, The Journal of Pharmacology and Experimental Therapeutics, Apr. 27, 2000, pp. 800-809, vol. 294 Issue 3.
Bond, et al., Pharmacology of Metabotropic Glutamate Receptor-mediated Enhancement of Responses to Excitatory and Inhibitory Amino Acids on Rat Spinal Neurones In Vivo, Neuropharmacology, Mar. 31, 1995, pp. 1015-1023, vol. 34 Issue 8, Elsevier Science Ltd.

(56) References Cited

OTHER PUBLICATIONS

Bonnefous, et al., Biphenyl-indanones: Allosteric potentiators of the metabotropic glutamate subtype 2 receptor, Bioorganic & Medicinal Chemistry Letters, Jul. 19, 2005, pp. 4354-4358, vol. 15, Elsevier Ltd.
Boris-Moller, et al., Changes in the extracellular levels of glutamate and aspartate during ischemia and hypoglycemia, Experimental Brain Research, Feb. 16, 1998, pp. 277-284, vol. 121, Springer-Verlag.
Bortolotto, et al., Roles of metabotropic glutamate receptors in LTP and LTD in the hippocampus, Current Opinion in Neurobiology, 1999, pp. 299-304, vol. 9, Elsevier Science Ltd.
Boules, et al., Neurotensin Agonists Potential in the Treatment of Schizophrenia, CNS Drugs, 2007, pp. 13-23, vol. 21 Issue 1. Adis Data Information BV.
Bouvrais-Veret, et al., Microtubule-associated STOP protein deletion triggers restricted changes in dopaminergic neurotransmission, Journal of Neurochemistry, 2008, pp. 745-756, vol. 104, International Society for Neurochemistry.
Boyette, et al., Factor structure of the Yale-Brown Obsessive-Compulsive Scale (Y-BOCS) in a large sample of patients with schizophrenia or related disorders and comorbid obsessive-compulsive symptoms, Psychiatry Research, 2011, pp. 409-413, vol. 186, Elsevier Ireland Ltd.
Brabet, et al., Comparative effect of L-CCG-I, DCG-IV and g-carboxy-L-glutamate on all cloned metabotropic glutamate receptor subtypes, Neuropharmacology, Apr. 28, 1998, pp. 1043-1051, vol. 37, Elsevier Science Ltd.
Bradford, Marion M., A Rapid and Sensitive Method for the Quantitation of Microgram Quantities of Protein Utilizing the Principle of Protein-Dye Binding, Analytical Biochemistry, 1976, pp. 248-254, vol. 72.
Bradley et al, Activation of Group II Metabotropic Glutamate Receptors Inhibits Synaptic Excitation of the Substantia Nigra Pars Reticulata, The Journal of Neuroscience, May 1, 2000, pp. 3085-3094, vol. 20, No. 9.
Braff, et al., Human studies of prepulse inhibition of startle: normal subjects, patient groups, and pharmacological studies, Psychopharmacology, Jun. 26, 2001, pp. 234-258, vol. 156, Springer-Verlag.
Braish et al, Construction of the (1a,5a,6a)-6-Amino-3-azabicyclo[3.1.0]hexane Ring System, Synlett, 1996, pp. 1100-1102.
Brauner-Osborne, et al., A New Highly Selective Metabotropic Excitatory Amino Acid Agonist: 2-Amino-4-(3-hydroxy-5-methylisoxazol-4-yl)butyric Acid, Journal of Medicinal Chemistry; Jul. 1, 1996, pp. 3188-3194, vol. 39 Issue 16, American Chemical Society.
Brauner-Osborne, et al., Interaction of CPCCOEt with a chimeric mGlu1b and calcium sensing receptor, NeuroReport, Dec. 16, 1999, pp. 3923-3925, vol. 10 Issue 18, Lippincott Williams & Wilkins.
Brauner-Osborne, et al., Molecular pharmacology of 4-substituted glutamic acid analogues at ionotropic and metabotropic excitatory amino acid receptors, European Journal of Pharmacology, Aug. 12, 1997, pp. R1-R3, vol. 335, Elsevier Science B.V.
Brauner-Osborne, et al., Pharmacology of (S)-homoquisqualic acid and (S)-2-amino-5-phosphonopentanoic acid [(S)-AP5] at cloned metabotropic glutamate receptors, Pharmacology of (S)-homoquisqualic acid and (S)-AP5, 1998, pp. 269-274, vol. 123.
Brauner-Osborne, et al., Structure, Pharmacology and Therapeutic Prospects of Family C G-Protein Coupled Receptors, Current Drug Targets, 2007, pp. 169-184, vol. 8 Issue 1, Bentham Science Publishers Ltd.
Breier, et al., Association of Ketamine-Induced Psychosis With Focal Activation of the Prefrontal Cortex in Healthy Volunteers, Am J Psychiatry, Jan. 15, 1997, pp. 805-811, vol. 154 Issue 6.
Bremner, et al., Development and Preliminary Psychometric Properties of an Instrument for the Measurement of Childhood Trauma: The Early Trauma Inventory, Depression and Anxiety, Jan. 28, 2000, pp. 1-12, vol. 12, Wiley-Liss, Inc.
Bremner, et al., Psychometric Properties of the Early Trauma Inventory—Self Report, J Nerv Ment Dis, 2007, pp. 211-218, vol. 195 Issue 3, Lippincott Wlliams & Wilkins.
Brian Dean., The cortical serotonin2A receptor and the pathology of schizophrenia: a likely accomplice, Journal of Neurochemistry, 2003, pp. 1-13, vol. 85, International Society for Neurochemistry.
Brighty et al, Synthesis of (1a,5a,6a)-6-Amino-3-azabicyclo [3.1.0]hexane, a Novel Achiral Diamine, Synlett, Nov. 1996, pp. 1097-1099.
Brnardic, et al., 3-Aryl-5-phenoxymethy1-1,3-oxazolidin-2-ones as positive allosteric modulators of mGluR2 for the treatment of schizophrenia: Hit-to-lead efforts, Bioorganic & Medicinal Chemistry Letters, Mar. 31, 2010, pp. 3129-3133, vol. 20, Elsevier Ltd.
Broekkamp,et al., Major Tranquillizers Can Be Distinguished From Minor Tranquillizers on the Basis of Effects on Marble Burying and Swim-Induced Grooming in Mice, European Journal of Pharmacology, Apr. 29, 1986, pp. 223-229, vol. 126.
Bruce J, Kinon et al, A Multicenter, Inpatient, Phase 2, Double-BLind, Placebo-Controlled Dose-Ranging Study of LY2140023 Monohydrate in Patients With DSM-IV Schizophrenia, J.of Clinical Psychopharmacology, 2011, pp. 349-355, vol. 31, No. 3.
Bruno, et al., Activation of Class ∥ or ∥∥ Metabotropic Glutamate Receptors Protects Cultured Cortical Neurons Against Excitotoxic Degeneration, European Journal of Neuroscience, 1906, pp. 1906-1913, vol. 7, European Neuroscience Association.
Bruno, et al., Activation of Metabotropic Glutamate Receptors Coupled to Inositol Phospholipid Hydrolysis Amplifies NMDA-induced Neuronal Degeneration in Cultured Cortical Cells, Neuropharmacology, Apr. 20, 1995, pp. 1089-1098, vol. 34 Issue 8, Elsevier Science Ltd.
Bruno, et al., Excitatory Amino Acids and Neurotoxicity, Fuctional Neurology, Jun. 18, 1993, pp. 279-292, vol. 8 Issue 4.
Bruno, et al., Metabotropic glutamate receptors and neurodegeneration, Progress in Brain Research, 1998, pp. 209-221, vol. 116, Elsevier Science BV.
Bruno, et al., Metabotropic Glutamate Receptors and Neuronal Degeneration in Culture, Advances in Neurology, 1996, pp. 47-52, vol. 71.
Bruno, et al., Molecular Dynamics Simulation of the Heterodimeric mGluR2/5HT2A Complex. An Atomistic Resolution Study of a Potential New Target in Psychiatric Conditions, J. Chem, Inf, Feb. 24, 2009, pp. 1602-1616, vol. 49 Issue 6, American Chemical Society.
Bruno, et al., Neuroprotection by Glial Metabotropic Glutamate Receptors Is Mediated by Transforming Growth Factor-B, The Journal of Neuroscience, Dec. 1, 1998, pp. 9594-9600, vol. 18 Issue 23, Society of Neuroscience.
Bruno, et al., The Neuroprotective Activity of Group-∥ Metabotropic Glutamate Receptors Requires New Protein Synthesis and Involves a Glial-Neuronal Signaling, The Journal of Neuroscience, Mar. 15, 1997, pp. 1891-1897, vol. 17 Issue 6, Society for Neuroscience.
Buisson, et al., The Inhibitory mGluR Agonist, s-4-caVrboxy-3-hydroxy-phenylglycine Selectively Attenuates NMDA Neurotoxicity and Oxygen-Glucose Deprivation-induced Neuronal Death, Neuropharmacology, Apr. 26, 1995, pp. 1031-1037, vol. 34 Issue 8, Elsevier Science Ltd.
Bunch, et al., Excitatory amino acid transporters as potential drug targets, Expert Opin. Ther. Targets, 2009, pp. 719-731, vol. 13 Issue 6, Informa UK Ltd.
Bunney, et al., Norepinephrine in Depressive Reactions, Arch Gen Psychiat, 1965, pp. 483-494, vol. 13.
Burford, et al., Strategies for the identification of allosteric modulators of G-protein-coupled receptors, Biochemical Pharmacology, 2011, pp. 1-12, vol. 10778, Elsevier Inc.
Bushell, et al., Pharmacological antagonism of the actions of group II and III mGluR agonists in the lateral perforant path of rat hippocampal slices, British Journal of Pharmacology, 1996, pp. 1457-1462, vol. 117, Stockton Press.
Bustillo, et al., 1H-MRS at 4 Tesla in minimally treated early schizophrenia, Molecular Psychiatry, 2010, pp. 629-636, vol. 15, Nature Publishing Group.

(56) References Cited

OTHER PUBLICATIONS

Butterfield, et al., The Glutamatergic System and Alzheimer's Disease, CNS Drugs, 2003, pp. 641-652, vol. 17 Issue 9, Adis Data Information BV.
Byrnes, et al., Metabotropic Glutamate Receptors as Targets for Multipotential Treatment of Neurological Disorders, Neurotherapeutics, 2009, pp. 94-107, vol. 6 issue 1, The American Society for Experimental NeuroTherapeutics, Inc.
C. Herdeis and C. Hartke, A Facile Entry to the 2-Azabicyclo[2.2.2]octane-6-one Skeleton via [4+2],- Cycloaddition, A Facile Entry to the 2-Azabicyclo[2.2.2]octane-6-one Skeleton via [4+2]-Cycloaddition, Jan. 1988, pp. 76-78, 1.
C.J.Carter., Schizophrenia susceptibility genes converge on interlinked pathways related to glutamatergic transmission and long-term potentiation, oxidative stress and oligodendrocyte viability, Schizophrenia Research, 2006, pp. 1-14, vol. 86, Elsevier B.V.
Cacabelos, et al., The Glutamatergic System and Neurodegeneration in Dementia: Preventive Strategies in Alzheimer's Disease, International Journal of Geriatric Psychiatry, 1999, pp. 3-47, vol. 14, John Wiley & Sons, Ltd.
Cai, et al., Local potentiation of excitatory synapses by serotonin and its alteration in rodent models of depression, Natue Neoroscience, 2013, pp. 464-472, vol. 16 Issue 4, Nature America, Inc.
Calabresi, et al., Antiepileptic drugs in migraine: from clinical aspects to cellular mechanisms, Trends in Pharmacological Sciences, 2007, pp. 188-195, vol. 28 Issue 4.
Campbell,et al., An update on regional brain volume differences associated with mood disorders, Current opinion in Psychiatry, 2006, pp. 25-33, vol. 19, Lippincott Williams & Wikins.
Caraci, et al., Metabotropic glutamate receptors in neurodegeneration/neuroprotection: Still a hot topic?, Neurochemistry International, 2012, pp. 559-565, vol. 61, Elsevier Ltd.
Caraci,et al, Targeting Group II Metabotropic Glutamate (mGlu) Receptors for the Treatment of Psychosis Associated with Alzheimer's Disease . . . , Molecular Pharmacology, 2011, pp. 618-626, vol. 79 Issue 3.
Carlsson, et al., Eurotransmitter Aberrations in Schizophrenia: New Perspectives and Therapeutic Implications, Neurotransmitters in Schizophrenia, 1997, pp. 75-94, vol. 61 Issue 2, Elsevier Science Inc.
Carol A. Tamminga., Schizophrenia and Glutamatergic Transmission, Critical Reviews in Neurobiology, 1998, pp. 21-36, vol. 12 Issue 1-2.
Carrie K. Jones et al, Analgesic effects of the selective group II (mGlu2/3) metabotropic glutamate receptor agonists LY379268 and LY389795 in persistent and inflammatory models after acute and repeated dosing, Neuropharmacology, May 5, 2005, pp. 206-218, vol. 49.
Cartmell et al, Regulation of Neurotransmitter Release by Metabotropic Glutamate Receptors, Journal of Neurochemistry, 2000, pp. 889-907, vol. 75.
Cartmell, et al, The Potent, Selective mGlu2/3 Receptor Agonist LY379268 Increases Extracellular Levels of Dopamine, 3,4-Dihydroxyphenylacetic Acid, Homovanillic Acid, and 5-Hydroxyindole-3-Acetic Acid in the Medial Prefrontal Cortex of the Freely Moving Rat, Journal of Neurochemistry, 2000, pp. 1147-1154, vol. 75 Issue 3, Lippincott Williams & Wilkins; Inc.
Cartmell, et al., Acute increases in monoamine release in the rat prefrontal cortex by the mGlu2/3 agonist LY379268 are similar in profile to risperidone, not locally mediated, and can be elicited in the presence of uptake blockade, Neuropharmacology, 2001, pp. 847-855, vol. 40, Elsevier Science Ltd.
Cartmell, et al., Attenuation of specific PCP-evoked behaviors by the potent mGlu2/3 receptor agonist, LY379268 and comparison with the atypical antipsychotic, clozapine, Psychopharmacology, 2000, pp. 423-429, vol. 148, Springer-Verlag.
Cartmell, et al., Dopamine and 5-HT turnover are increased by the mGlu2/3 receptor agonist LY379268 in rat medial prefrontal cortex, nucleus accumbens and striatum, Brain Research, 2000, pp. 376-384, vol. 887, Elsevier Science B.V.
Cartmell, et al., Effect of metabotropic glutamate receptor activation on receptor-mediated cyclic AMP responses in primary cultures of rat striatal neurones, Brain Research, 1998, pp. 191-199, vol. 791, Elsevier Science B.V.
Cartmell, et al., The Metabotropic Glutamate 2/3 Receptor Agonists LY354740 and LY379268 Selectively Attenuate Phencyclidine versus d-Amphetamine Motor Behaviors in Rats, The Journal of Pharmacology and Experimental Therapeutics, 1999, pp. 161-170, vol. 291 Issue 1.
Cartmell, et al., The mGlu receptor agonist LY379268 selectively blocks 2r3 amphetamine ambulations and rearing, European Journal of Pharmacology, 2000, pp. 221-224, vol. 400, Elsevier Science B.V.
Cartmell, et al., Tolerance to the motor impairment, but not to the reversal of PCP-induced motor activities by oral administration of the mGlu2/3 receptor agonist, LY379268, Naunyn-Schmiedeberg's Arch Pharmacol, 2000, pp. 39-46, vol. 361, Springer-Verlag.
Casado, et al., GPCR homomers and heteromers: A better choice as targets for drug development than GPCR monomers?, Pharmacology & Therapeutics, 2009, pp. 248-257, vol. 124, Elsevier Inc.
Castagne, et al., Preclinical Behavioral Models for Predicting Antipsychotic Activity, Advances in Pharmacology, 2009, pp. 381-418, vol. 57, Elsevier Inc.
Catania, et al., Desensitization of Metabotropic Glutamate Receptors in Neuronal Cultures, Journal of Neurochemistry, 1991, pp. 1329-1335, vol. 56 Issue 4, Raven Press, Ltd.
Catania, et al., Group I Metabotropic Glutamate Receptors: A Role in Neurodevelopmental Disorders?, Mol Neurobiol, 2007, pp. 298-307, vol. 35, Humana Press Inc.
Catania, et al., Homoltigous Desensitizationofmetabolotropic Glutamatereceptors in Neuronal Cultures, Pharmacological Research, 1990, pp. 79-80, vol. 22, The Italian Pharmacological Society.
Catania, et al., Metabotropic Glutamate Receptor Heterogeneity in Rat Brain, Molecular Pharmacology, 1994, pp. 626-636, vol. 45.
Catania, et al., Metabotropic Glutamate Receptors Are Differentially Regulated During Development, Neuroscience, 1994, pp. 481-495, vol. 61 Issue 3, Elsevier Science Ltd.
Cavalli, et al., Multi-target-Directed Ligands to Combat Neurodegenerative Diseases, Journal of Medicinal Chemistry, 2008, pp. 1-26, page number, American Chemical Society.
Cavanni, et al., Pharmacological analysis of carboxyphenylglycines at metabotropic glutamate receptors, European Journal of Pharmacology, 1994, pp. 9-15, vol. 269.
Celanire, et al., Recent advances in the drug discovery of metabotropic glutamate receptor 4 (mGluR4) activators for the treatment of CNS and non-CNS disorders, Expert Opin. Drud Discov, 2012, pp. 261-280, vol. 7, issue 3.
Chaki, et al., mGlu2/3 and mGlu5 receptors: Potential targets for novel antidepressants, Neuropharmacology, 2013, pp. 40-52, vol. 66, Elsevier Ltd.
Chaki, et al., Targeting of Metabotropic Glutamate Receptors for the Treatment of Schizophrenia, Current Pharmaceutical Design, 2011, pp. 94-102, vol. 17 Issue 2, Bentham Science Publishers Ltd.
Chaki,et al., Anxiolytic- and antidepressant-like profile of a new CRF1 receptor antagonist, R278995/CRA0450, European Journal of Pharmacology, 2004, pp. 145-158, vol. 485.
Chakos, et al., Baseline Use of Concomitant Psychotropic Medications to Treat Schizophrenia in the CATIE Trial, Psychiatric Services, 2006, pp. 1094-1101, vol. 57 Issue 8.
Chakrabarty, et al, Glutamatergic Dysfunction in OCD, Neuropsychopharmacology, 2005, pp. 1735-1740, vol. 30, Nature Publishing Group.
Charles H. Large, Do NMDA receptor antagonist models of schizophrenia predict the clinical efficacy of antipsychotic drugs?, Journal of Psychopharmacology, 2007, pp. 283-301, vol. 21 Issue 3, British Association for Psychopharmacology.
Charney, et al ., Life Stress, Genes, and Depression: Multiple Pathways Lead to Increased Risk and New Opportunities for Intervention, Sciences STKE, Mar. 23, 2004, pp. 1-11, vol. 225 issue 5.
Charney, et al, Effects of Yohimbine in Healthy Subjects and Patients With Agoraphobia and Panic Disorder, Arch Gen Psychiartry, 1984, pp. 751-763, vol. 41.

(56) References Cited

OTHER PUBLICATIONS

Charney, et al., Increased Anxiogenic Effects of Caffeine in Panic Disorders, Arch Gen Psychiatry, 1985, pp. 233-243, vol. 42.

Chaudhari, et al., A metabotropic glutamate receptor variant functions as a taste receptor, nature neuroscience, 2000, pp. 113-119, vol. 3 Issue 2, Nature America Inc.

Chavez-Noriega, et al., Metabotropic Glutamate Receptors: Potential Drug Targets for the Treatment of Schizophrenia, Current Drug Targets—CNS & Neurological Disorders, 2002, pp. 261-281, vol. 1 Issue 3, Bentham Science Publishers Ltd.

Chavis, et al., Facilitatory Coupling between a Glutamate Metabotropic Receptor and Dihydropyridine-Sensitive Calcium Channels in Cultured Cerebellar Granule Cells, The Journal of Neuroscience, 1995, pp. 135-143, vol. 15 Issue 1, Society for Neuroscience.

Chavis, et al., Modulation of Calcium Channels by Metabotropic Glutamate Receptors in Cerebellar Granule Cells, Neuropharmacology, 1995, pp. 929-937, vol. 34 Issue 8, Elsevier Science Ltd.

Chen, et al., Second-generation antipsychotics in major depressive disorder ; update and clinical prespective, Current Opinion in Psychiatry, 2011, pp. 10-17, vol. 24, Wolters Kluwer Health | Lippincott Williams & Wilkins.

Chen, et al., The Chemical biology of clinically tolerated NMDA receptor antagonists, Journal of Neurochemistry, 2006, pp. 1611-1626, vol. 97.

Chiechio, et al., Epigenetic Modulation of mGlu2 Receptors by Histone Deacetylase inhibitors in the Treatment of Inflammatory Pain, Molecular Pharmacology, Mar. 2, 2009, pp. 1014-1020, vol. 75 Issue 5.

Chiechio, et al., Transcriptional regulation of type-2 metabotropic glutamate receptors: an epigenetic path to novel treatments for chronic pain, Trends in Pharmacological Sciences, 2010, pp. 153-160, vol. 31 Issue 4, Elsevier Ltd.

Chin, et al., Awake Rat Pharmacological Magnetic Resonance Imaging as a Translational Pharmacodynamic Biomarker: Metabotropic Glutamate 2/3 Agonist Modulation of Ketamine-Induced Blood Oxygenation Level Dependence Signals, The Journal of Pharmacology and Experimental Therapeutics, 2011, pp. 709-715, vol. 336 Issue 3.

Chin, et al., Awake Rat Pharmacological MRI as a Translational Pharmacodynamic Biomarker: mGluR2/3 Agonist Modulation of Ketamine-induced BOLD Signals, Ketamine phMRI in Awake Rat as a Pharmacodynamic Biomarker, Dec. 20, 2010, pp. 1-22, page number, American Society for Pharmacology and Experimental Therapeutics.

Chin,et al., Amyloid Protein Modulates Glutamate-Mediated Neurotransmission in the Rat Basal Forebrain: Involvement of Presynaptic Neuronal Nicotinic Acetylcholine and Metabotropic Glutamate Receptors, The Journal of Neuroscience, 2007, pp. 9262-9269, vol. 27 Issue 35, Society for Neuroscience.

Choi, et al., Methods for Antagonizing Glutamate Neurotoxicity, Cerebrovasc Brain Metab Rev, 1990, pp. 105-147, vol. 2.

Chojnacka-Wojcik, et al., Glutamate receptor ligands as anxiolytics, Current Opinion in Investigational Drugs, 2001, pp. 1112-1119, vol. 2 Issue 8, Pharama Press.

Christie Morrill and Neelakandha S. Mani, Synthesis of 4-Arylpiperidines from, Organic Letters, 2007, pp. 1505-1508, vol. 9, No. 8.

Christopoulos, et al., G Protein-Coupled Receptor Allosterism and Complexing, Pharmacological Reviews, 2002, pp. 323-374, vol. 54 Issue 2.

Cid, et al., Discovery of 1,4-Disubstituted 3-Cyano-2-pyridones: A New Class of Positive Allosteric Modulators of the Metabotropic Glutamate 2 Receptor, Journal of Medicinal Chemistry, Feb. 24, 2012, pp. 2388-2405, vol. 55, American Chemical Society.

Cid, et al., Discovery of 1,5-Disubstituted Pyridones: A New Class of Positive Allosteric Modulators of the Metabotropic Glutamate 2 Receptor, ACS Chemical Neuroscience, Aug. 23, 2010, pp. 788-795, vol. 1, American Chemical Society.

Citrome., Adjunctive Aripiprazole, Olanzapine, or Quetiapine for Major Depressive Disorder: An Analysis of Number Needed to Treat, Number Needed to Harm, and Likelihood to be Helped or Harmed, Neurological and Neurospsychiatric Disorders, 2010, pp. 39-48, vol. 122 Issue 4, Postgraduate Medicine.

Clark, et al., Effects of the mGlu2/3 receptor agonist LY379268 on motor activity in phencyclidine-sensitized rats, Pharmacology, Biochemistry and Behavior, Feb. 21, 2002, pp. 339-346, vol. 73, Elsevier Science Inc.

Clark, et al., synthesis of Thieno[2,3-d]pyrimidines from 4,6-Dichloropyrimidine-5-carbaldehydes, ?, 1993, pp. 1065-1072, vol. 30.

Clark_et_al., Tripartite Model of Anxiety and Depression: Psychometric Evidence and Taxonomic Implications, Journal of Abnormal Psychology, 1991, pp. 316-336, vol. 100 Issue 3.

Claude Agami et al, An Efficient Synthesis of Polysubstituted 3-halo-2(1 H)-Pyridinones, Synthesis, 2002, pp. 79-82, vol. 52 No. 4.

Claude Guérémy et al., 2-Amino-6-chloro-4-(N-methylpiperazino)pyrimidines, Inhibitors of Spiperidol Binding, Journal of Medicinal Chemistry, 1982, pp. 1459-1465, vol. 25, No. 12.

Claudia Flohr et al., Poly(ADP-ribosyl)ation accelerates DNA repair in a pathway dependent on Cockayne syndrome B protein, Nucleic Acids Research, 2003, pp. 5332-5337, vol. 31, No. 18.

Claus Herdeis and Anna Dimmerling, A Three-Step Synthesis of δ-Aminolaevulinic Acid, Arch. Pharm. (Weinheim), 1984, pp. 304-306, vol. 317.

Claus Herdeis and Claudia Hartke, [4+2]Cycloadducts of 5-Benzyloxy-2-Pyridone with Electron Deficient Dienophiles, Regio- and Stereochemistry, Heterocycles, 1989, pp. 287-296, vol. 9, No. 2.

Claus Herdeis and Claudia Hartke-Karger, Stereochemistry and Reactivity of Phenylsulfonyl-substituted 2-Azabicyclo[2.2.2]octane-6-ones, Arch. Pharm. (Weinheim), 1990, pp. 937-942, vol. 323.

Clayton, et al., Follow-Up and Family Study of Anxious Depression, Am J Psycharitry, 1991, pp. 1512-1517, vol. 148.

Cleary, et al., Factor Analysis of the Hamilton Depression Scale, Drugs Exptl, Clin., 1977, pp. 115-120, vol. 1.

Clements, et al., The Time Course of Glutamate in the Synaptic Cleft, Science, Nov. 27, 1992, pp. 1498-1501, vol. 258.

Cleva, et al., Positive Allosteric Modulators of Type 5 Metabotropic Glutamate Receptors(mGluR5) and their Therapeutic Potential for the treatmeent of CNS Disorder, Molecules, 2011, pp. 2097-2106, vol. 16.

Cloninger, et al., The Empirical Structure of Psychiatric Comorbidity and Its Theoretical Significance, The Empirical Structure of Psychiatric Comorbidity, 1990, pp. 439-462, page number.

Cohen, et al., A Global Measure of Perceived Stress, Journal of Health and Social Behavior, 1983, pp. 385-396, vol. 24 Issue 4, American Sociological Association.

Colangelo, et al., Differential effects of acute administration of clozapine or haloperidol on local cerebral glucose utilization in the rat, Brain Research, May 13, 1997, pp. 273-278, vol. 768, Elsevier Science B.V.

Collingridge, et al., Excitatory amino acid receptors and synaptic plasticity, TIPS, 1990, pp. 290-296, vol. 11, Elsevier Science Publishers Ltd.

Collins, et al., Arachidonic acid metabolites and the synaptic potentiation evoked by activation of metabotropic glutamate receptors, European Journal of Pharmacology, 1998, pp. 213-216, vol. 342, Elsevier Science B.V.

Collins, et al., From ligand binding to gene expression: new insights into the regulation of G-protein-coupled receptors, TIBS, 1992, pp. 37-39, vol. 17, Elsevier Science Publishers.

Colpaert, et al., A Critical Study on RO/4/1284 Antagonism in Mice, Arch. int, Pharmacodyn, 1975, pp. 40-90, vol. 215.

Colzi, et al., Monoamine Oxidase-A Inhibitors and Dopamine Metabolism in Rat Caudatus: Evidence That an Increased Cytosolic Level of Dopamine Displaces Reversible Monoamine Oxidase-A Inhibitors in Vivo, The Journal of Pharmacology and Expermental Therapeutics, 1993, pp. 103-111, vol. 265 Issue 1.

Conigrave, et al., Allosteric activation of plasma membrane receptors—physiological implications and structural origins, Progress in Biophysics & Molecular Biology, 2003, pp. 219-240, vol. 81, Elsevier Science Ltd.

(56) References Cited

OTHER PUBLICATIONS

Conn, et al., Activation of metabotropic glutamate receptors as a novel approach for the treatment of schizophrenia, Cell press, Dec. 6, 2008, pp. 25-31, vol. 30 Issue 1, Elsevier Ltd.
Conn, et al., Allosteric modulators of GPCRs: a novel approach for the treatment of CNS disorders, Nature Reviews, 2009, pp. 41-54, vol. 8, Macmillan Publishers Limited.
Conn, et al., Metabotropic Glutamate Receptors in the Basal Ganglia Motor Circuit, Neuroscience, 2005, pp. 787-798, vol. 6, Nature Publishing Group.
Conn, et al., Pharmacology and Functions of Metabotropic Glutamate Receptors, Annu. Rev. Pharmacol. Toxicol, 1997, pp. 205-237, vol. 37, Annual Reviews Inc.
Conn., Physiological Roles and Therapeutic Potential of Metabotropic Glutamate Receptors, Ann.N.Y.Acad.Sci and Author as P.Jeffrey Conn, 2003, pp. 12-21, vol. 1003, New York Academy of Sciences.
Connolly, et al., A Review of the Evidence for Antidepressant Augmentation, Combination and Switching Strategies, Drugs, 2011, pp. 43-64, vol. 71 Issue 1, Adis Data information B.V.
Cook, et al., Behavioral Effects of Some Psychopharmacological Agents, Effects of Psychopharmacological, 1957, pp. 740-752, page number.
Cook, et al., Diethylaminoalkyi Ester Hydrochlorides of N-Alkyl-4-carbostyrilcarboxylic Acid, ?, Jan. 20, 1952, pp. 543-544, vol. 74.
Cook, et al., Effects of drugs on avoidance and escape behavior, ?, 1964, pp. 818-835, vol. 23.
Copeland, et al., Positive allosteric modulation reveals a specific role for mGlu2 receptors in sensory processing in the thalamus, The Journal of Physiology, 2012, pp. 937-951, vol. 590 Issue 4, The Physiological Society.
Corey R. Hopkins., Is There a Path Forward for mGlu2 Positive Allosteric Modulators for the Treatment of Schizophrenia, ACS Chemical Neuroscience, Feb. 20, 2013, pp. 211-213, vol. 4, American Chemical Society.
Corlett, et al., Giutamatergic Model Psychoses: Prediction Error, Learning, and Inference, Neuropsychopharmacology Reviews, 2011, pp. 294-315, vol. 36, Nature Publishing Group.
Corti, et al., The Use of Knock-Out Mice Unravels Distinct Roles for mGlu2 and mGlu3 Metabotropic Glutamate Receptors in Mechanisms of Neurodegeneration/Neuroprotection, The Journal of Neuroscience, Aug. 1, 2007, pp. 8297-8306, vol. 27 Issue 31, Society for Neuroscience.
Coryell, et al., Effects of anxiety on the long-term course of depressive disorders, The British Journal of Psychiatry, 2012, pp. 210-215, vol. 200.
Costantino et al, Modeling of Poly(ADP-ribose)polymerase (PARP)Inhibitors. Docking of Ligands and Quantitative Structure—Activity Relationship Analysis, Journal of Medicinal Chemistry, 2001, pp. 3786-3794, vol. 44.
Cozzi, et al., Type 2 Metabotropic Glutamate (mGlu) Receptors Tonically Inhibit Transmitter Release in Rat Caudate Nucleus: In Wvo Studies with (2S,1' S,2'5,3R)-2-(2'= carboxy-3'-phenylcyclopropyl)glycine, a New Potent and Selective Antagonist, European Journal of Neuroscience, 1997, pp. 1350-1355, vol. 9, European Neuroscience Association.
CPMP., The Clinical Investigation of Medicinal Products in the Treatment of Schizophrenia, Human Medicines Evalutions Unit, Feb. 26, 1998, pp. 1-10, vol. 559 issue 95.
Craddock, et al., The genetics of schizophrenia and bipolar disorder: dissecting psychosis, J Med genet, 2005, pp. 193-204, vol. 42.
Cropley, et al., Molecular Imaging of the Dopaminergic System and its Association with Human Cognitive Function, Biol Psychiatry, 2006, pp. 898-907, vol. 59, Society of Biological Psychiatry.
Cube, et al., 3-(2-Ethoxy-4-{4-[3-hydroxy-2-methyl-4-(3-methylbutanoyl)- phenoxy]butoxy}phenyl)propanoic acid: a brain penetrant allosteric potentiator at the metabotropic glutamate receptor 2 (mGluR2), Bioorganic & Medicinal Chemistry Letters, 2005, pp. 2389-2393, vol. 15, Elsevier Ltd.
Cymbalta, Highlights of Prescribing Information, ?, 2004, pp. 1-28, page number.

D'Onofrio, et al., Neuroprotection mediated by glial group-II metabotropic glutamate receptors requires the activation of the MAP kinase and the phosphatidylinositol-3-kinase pathways, Journal of Neurochemistry, 2001, pp. 435-445, vol. 78, International Society for Neurochemistry.
D. J. Laurie et al., Cloning, Distribution and Functional Expression of the Human mGlu6 Metabotropic Glutamate Receptor, Neuropharmacology, 1997, pp. 145-152, vol. 36, No. 2.
D. Michelson, et al., Clinical studies with mGluR2/3 agonists: LY354740 compared with placebo in patients with generalized anxiety disorder, Abstracts/Neuropharmacology, 2005, pp. 257, vol. 49.
D.F. Klein, Mixed anxiety depression for and against, L 'Encephale, 1993, pp. 493-495, vol. 19.
Dale, et al., Mechanisms of metabotropic glutamate receptor desensitization: role in the patterning of effector enzyme activation, Neurochemistry International, Feb. 28, 2002, pp. 319-326, vol. 41, Elsevier Science Ltd.
Dale, et al., Spatial-Temporal Patterning of Metabotropic Glutamate Receptormediated Inositol 1,4,5-Triphosphate, Calcium, and Protein Kinase C Oscillations, The Journal of Biological Chemistry, Jul. 18, 2001, pp. 35900-35908, vol. 276 Issue 38.
Daniel C. Javitt, Giutamatergic theories of schizophrenia, Isr J Psychiatry Relat Sci., 2010, pp. 4-16, vol. 47 Issue 1.
Daniel L. Comins and Gao Jianhua, N- vs. O-Alkylation in the Mitsunobu Reaction of 2-Pyridone, Tetrahedron Letters, 1994, pp. 2819-2822, vol. 35.
Daniel Oehlrich., Positive Allosteric Modulation of Mglur2 Receptors in the Treatment of CNS Disorders, Neuroscience Med Chem, 2012, pp. 1-31, pp. 31.
Daniel R Weinberger., Schizophrenia drug says goodbye to dopamine, Nature Medicine, 2007, pp. 1018-1019, vol. 13 Issue 9, Nature Publishing Group.
Daniel R. Weinberger, The Biological basis of Schizophrenia: New Directions, J. Clin. Psychiatry, 1997, pp. 22-27, vol. 58 Issue 10.
Danner, et al., Integrating patients' views into health technology assessment: Analytic hierarchy process (AHP) as a method to elicit patient preferences, International Journal of Technology Assessment in Health Care, 2011, pp. 369-375, vol. 27 Issue 4, Cambridge University Press.
Dario Braga et al, Making crystals from crystals: a green route to crystal engineering and polymorphism, Chemical Communications, Jun. 15, 2005, pp. 3635-3645, No. 29.
Dash, et al., Long-Term Homeostasis of Extracellular Glutamate in the Rat Cerebral Cortex across Sleep and Waking States, The Journal of Neuroscience, Jan. 21, 2009, pp. 620-629, vol. 29 Issue 3, Society for Neuroscience.
Datta, et al., Microinjection of glutamate into the pedunculopontine tegmentum induces REM sleep and wakefulness in the rat, American Journal of Physiology Regulatory, Integrative and Comparative Physiology, 2001, pp. 752-759, vol. 280.
David H. Adams et al, A long-term, phase 2, multicenter, randomized, open-label, comparative safety study of pomaglumetad methionil (LY2140023 monohydrate) versus atypical antipsychotic standard of care in patients with schizophrenia, BMC Psychiatry, 2013, pp. 143, 13.
Davidson, et al., Achieving Remission With Venlafaxine and Fluoxetine in Major Depression: Its Relationship to Anxiety Symptoms, Depression and Anxiety, Feb. 26, 2002, pp. 4-13, vol. 16.
Davidson, et al., Differential Effects of Neuroleptic and Other Psychotropic Agents on Acquistion of Avoidance in Rats, Life Sciences, Apr. 19, 1976, pp. 1279-1284, vol. 18 Issue 11.
Davis., Pharmacological and Anatomical Analysis of Fear Conditioning Using the Fear-Potentiated Startle Paradigm, Behavioral Neuroscience, 1986, pp. 814-824, vol. 100 Issue 6, the American Psychological Association, Inc.
Dawson, et al., Novel analysis for improved validity in semi-quantitative 2-deoxyglucose autoradiographic imaging, Journal of Neuroscience Methods, Jul. 29, 2008, pp. 25-35, vol. 175, Elsevier B,V.
De Blasi, et al., Molecular determinants of metabotropic glutamate receptor signaling, TRENDS in Pharmacological Sciences, 2001, pp. 114-120, vol. 22 Issue 3, Elsevier Science Ltd.

(56) References Cited

OTHER PUBLICATIONS

De Montis, et al., Selective adenylate cyclase increase in the limbic area of long-term imipramine-treated rats, European Journal of Pharmacology, Feb. 20, 1990, pp. 169-174, vol. 180, Elsevier Science Publishers B.V.

Dedeurwaerdere,et al, Memantine-induced brain activation as a model for the rapid screening of potential novel antipsychotic compounds: exemplified by activity of an mGlu2/3 receptor agonist, Psychopharmacology, 2011, pp. 505-514, vol. 214.

Del Rio, et al., Differential coupling of G-protein-linked receptors to Ca2+ mobilization through inositol(1,4,5) trisphosphate or ryanodine receptors in cerebellar granule cells in primary culture, European Journal of Neuroscience, 1999, pp. 3015-3022, vol. 11, European Neuroscience Association.

Delille, et al., Heterocomplex formation of 5-HT2A-mGlu2 and its relevance for cellular signaling cascades, Neuropharmacology, Jan. 16, 2012, pp. 1-8, vol. 62, Elsevier Ltd.

Delille, et al., The two faces of the pharmacological interaction of mGlu2 and 5-HT2A e Relevance of receptor heterocomplexes and interaction through functional brain pathways, Neuropharmacology, Feb. 4, 2013, pp. 296-305, vol. 70, Elsevier Ltd.

Del'Guidice, et al., Messing Up with Traffic: Different Effects of Antipsychotic Agents on Glutamate Receptor Complexes in Vivo, Molecular Pharmacology, Feb. 26, 2008, pp. 1339-1342, vol. 73 Issue 5.

Derks, et al., Kraepelin Was Right: A Latent Class Analysis of Symptom Dimensions in Patients and Controls, Schizophrenia Bulletin, 2012, pp. 495-505, vol. 38 Issue 3, Oxford University Press.

Desseilles, et al., Assessing the Adequacy of Past Antidepressant Trails: A Clinician's Guide to the Antidepressant Treatment Response Questionnaire, J Clin Psychiatry, 2011, pp. 1152-1154, vol. 72 Issue 8.

Dhami, et al., G Protein-coupled Receptor Kinase 2 Regulator of G Protein Signaling Homology Domain Binds to Both Metabotropic Glutamate Receptor 1a and Gaq to Attenuate Signaling, The Journal of Biological Chemistry, Feb. 4, 2004, pp. 16614-16620, vol. 279 Issue 16.

Dhami, et al., Regulation of metabotropic glutamate receptor signaling, desensitization and endocytosis, Pharmacology & Therapeutics, 2006, pp. 260-271, vol. 111, Elsevier Inc.

Dhanya, et al., Design and Synthesis of an Orally Active Metabotropic Glutamate Receptor Subtype-2 (mGluR2) Positive Allosteric Modulator (PAM) That Decreases Cocaine Self-Administration in Rats, Journal of Medicinal Chemistry, 2011, pp. 342-353, vol. 54 Issue 1.

Dhonnchadha, et al., Anxiolytic-like effects of 5-HT2 ligands on three mouse models of anxiety, Behavioural Brain Research, 2003, pp. 203-214, vol. 140, Elsevier Science B.V.

Di Liberto, et al., Group II Metabotropic Glutamate Receptor Activation by Agonist LY379268 Treatment Increases the Expression of Brain Derived Neurotrophic Factor in the Mouse Brain, Neuroscience, 2010, pp. 863-873, vol. 165, Elsevier Ltd.

Dingledine, et al., Excitatory amino acid receptors in epilepsy, TIPS, 1990, pp. 334-338, vol. 11.

Dingledine, et al., Peripheral Glutamate Receptors: Molecular Biology and Role in Taste Sensation 1,2, J.Nutr, 2000, pp. 1039S-1042S, vol. 130.

Dino Gnecco et al., Oxidation of chiral non-racemic pyridinium salts to enantiopure 2-pyridine and 3-alkyl-2-pyridones, Tetrahedron:Asymmetry, 1998, pp. 2027-2029, vol. 9.

Doherty, et al., Fuctional Interacations between cannabinoid and metabotropic glutamate receptors in the central nervous system, Current Opinion in Pharmacology, 2003, pp. 46-53, vol. 3.

Doherty, et al., Rapid internalization and surface expression of a fuctional, fluorescently tagged G-protein-coupled glutamate, Biochem J, 1999, pp. 415-422, vol. 341, Biochemical Society.

Domschke,et al., Anxious versus non-anxious depression: difference in treatment outcome, Journal of Psychopharmacology, 2010, pp. 621-622, vol. 24 Issue 4.

Donald Posluns, An Analysis of Chlorpromazine-Induced Suppression of the Avoidance Response, Psychopharmacologia, Mar. 1, 1962, pp. 361-373, vol. 3.

Donck,et al., Low dose subchronic phencyclidine (PCP) pretreatment potentiates acute PCP-induced hyperlocomotion in adult rats: A model of schizophrenia, Neuroscience, 2011, pp. 1-2, Poster name II22.

Doreulee, et al., The Role of the mGLuR Allosteric Modulation in the NMDA-Hypofunction Model of Schixophrenia, Georgian Medical News, 2009, pp. 59-65, vol. 177.

Doumazane, et al., A new approach to analyze cell surface protein complexes reveals specific heterodimeric metabotropic glutamate receptors, The FASEB Journal. Research Communication, 2011, pp. 66-77, vol. 25.

Doumazane, et al., Illuminating the activation mechanisms and allosteric properties of rnetabotropic glutamate receptors, PNAS Early Edition, 2013, pp. 1-10, page number.

Downey, et al., Ecdysone-Based System for Controlled Inducible Expression of Metabotropic Glutamate Receptor Subtypes 2,5, and 8, Journal of Biomolecular Screening, 2005, pp. 641-848, vol. 10 Issue 8.

Doyle, et al., Quantifying the attenuation of the ketamine phMRl response in humans: a validation using antipsychotic and giutamatergic agents., Modulation of the phMRl response to ketamine, Jan. 31, 2013, pp. 1-42, page number.

Dr Basil Wakefield., Fluorinated Pharmaceuticals: Fluorinated Compounds are of Increasing Interest as Pharmaceuticals, and an Extensive Range of Techniques for Making Them is Now Available, Innovations in Pharmaceutical Technology, 2003, pp. 74-78, Page Number.

Dr. Jose Cid., Discovery of a potent and orally bioavailable Positive Allosteric Modulator of mGluR2 for the treatment of CNS disorders, 16th SCI/RSC Medicinal Chemistry Symposium, 2011, pp. 1-26, Page Number.

Dr. Jose Cid., JNJ-42153605: A Novel Positive Allosteric Modulator of mGluR2 for the Treatment of CNS disorders, RICT 2012—48th International Conference on Medicinal Chemistry, 2012, pp. 1-44, Page Number.

Drevets, et al., F unctional anatomical correlates of antidepressant drug treatment assessed using PET measures of regional glucose metabolism, European Neuropsychopharmacology, 2002, pp. 527-544, vol. 12, Elsevier Science B.V.

Drew, et al., Multiple metabotropic glutamate receptor subtypes modulate GABAergic neurotransmission in rat periaqueductal grey neurons in vitro, Neuropharmacology, Jan. 19, 2004, pp. 927-934, vol. 46, Elsevier Ltd.

Duncan R. Groebe, Screening for positive allosteric modulators of biological targets, Drug Discovery Today, 2006, pp. 632-639, vol. 11.

Duncan, et al., Comparison of the Effects of Clozapine, Risperidone, and Olanzapine on Ketamine-Induced Alterations in Regional Brain Metabolisml , The Journal of Pharmacology and Experimental Therapeutics, 2000, pp. 8-14, vol. 293 Issue 1.

Duncan, et al., Differential effects of clozapine and haloperidol on ketamine-induced brain metabolic activation, Brain Research, 1998, pp. 65-75, vol. 812.

Duncan, et al., Metabolic mapping of the rat brain after subanesthetic doses of ketamine: potential relevance to schizophrenia, Brain Research, 1998, pp. 181-190, vol. 787, Elsevier Science B.V.

Duncan, et al., Topographic Patterns of Brain Activity in Response to Swim Stress: Assessment by 2-Deoxyglucose Uptake and Expression of Fos-like Immunoreactivity, The Journal of Neuroscience, 1993, pp. 3932-3943, vol. 13 Issue 9.

Duong et al, A 'Biogenetic Like' Synthesis of Perloline, 6-(3,4-Dimethoxyphenyl)-5-hydroxy-5,6-dihydrobenzo[c][2,7]naphthyridin-4(3H)-one, Australian Journal of Chemistry, 1983, pp. 1431-1440, vol. 36.

Duplantier, et al., 3-Benzyl-1,3-oxazolidin-2-ones as mGluR2positive allosteric modulators: Hit-to lead and lead optimization, Bioorganic & Medicinal Chemistry Letters, Mar. 14, 2009, pp. 2524-2529, vol. 19.

(56) References Cited

OTHER PUBLICATIONS

Durand, et al., Role of metabotropic glutamate receptors in the control of neuroendocrine function, Neuropharmacology, Jun. 12, 2008, pp. 577-583, vol. 55.
During, et al., Extracellular hippocampal glutamate and spontaneous seizure in the conscious human brain, Lancet, 1993, pp. 1607-1610, vol. 341 Issue 8861.
Dutar, et al., Pharmacological characterization of an unusual mGluR-evoked neuronal hyperpolarization mediated by activation of GIRK channels, Neuropharmacology, 1999, pp. 467-475, vol. 38.
D'Alessandro, et al., The identification of structurally novel, selective, orally bioavailable positive modulators of mGluR2, Bioorganic & Medicinal Chemistry Letters, 2010, pp. 759-762, vol. 20, Elsevier Ltd.
D'Antoni, et al., Metabotropic Glutamate Receptors in Glial Cells, Neurochem Res, 2008, pp. 2436-2443, vol. 33.
D'Ascenzo, et al., mGluR5 stimulates gliotransmission in the nucleus accumbens, PNAS; Feb. 6, 2007, pp. 1995-2000, vol. 104 Issue 6.
D'Onofrio, et al., Advances in the identification of g-secretase inhibitors for the treatment of Alzheimer's disease, Expert Opinion on Investigational Drugs, 2012, pp. 19-37, vol. 7 Issue 1.
Eduardo Dunayevich et al, Efficacy and Tolerability of an mGlu2/3 Agonist in the Treatment of Generalized Anxiety Disorder, Neuropsychopharmacology, Jul. 16, 2007, pp. 1603-1610, vol. 33.
Eduardo E. Benarroch, MD., Metabotropic glutamate receptors Synaptic modulators and therapeutic targets for neurologic disease, Neurology, Mar. 18, 2008, pp. 964-968, vol. 70, AAN Enterprises, Inc.
Egan, et al., Neurobiology of schizophrenia, Neurobiology, 1997, pp. 701-707, vol. 7.
Egashira, et al., Impaired social interaction and reduced anxiety-related behavior in vasopressin V1a receptor knockout mice, Behavioural Brain Research, 2007, pp. 01-05, vol. 4938.
Eintrei, et al., Effects of diazepam and ketamine administered individually or in combination on regional rates of gulcose utilization in rat brain, British Journal of Anaesthesia, 1999, pp. 596-602, vol. 82, Issue 4.
Eli Lily and Company, Lilly Stops Phase III Development of Pomaglumetad Methionil for the Treatment of Schizophrenia Based on Efficacy Results; Lily Press Release., Aug. 29, 2012, p. 1, 1 page.
Elia, et al., Genome-wide copy number variation study associates metabotropic glutamate receptor gene networks with attention deficit hyperactivity disorder, Nature Genetics, Dec. 4, 2011, pp. 01-09, page number.
Ellenbroek, et al., Animal Models with construct validity for schizophrenia, Behavioural Pharmacoigy, 1990, pp. 469-490, vol. 1.
Emmitte,et al., Recent Advances in the Design and Development of Novel Negative Allosteric Modulators of Mglu5, Chem, Neurosci., 2011, pp. 411-432, vol. 2.
Ende, et al., Parkinson's disease mice and human umbilical cord blood, J. Med, 2002, pp. 173-180, vol. 33.
Engin, et al., The effects of intra-cerebral drug infusions on animals' unconditioned fear reactions: A systematic review, Progress in Neuro-Psychopharmacology & Biological Psychiatry, Apr. 8, 2008, pp. 1399-1419, vol. 32.
Enomoto, et al, Phencyclidine and Genetic Animal Models of Schizophrenia Developed in Relation to the Glutamate Hypothesis, Methods Find Exp Clin Pharmacol, Jun. 7, 2007, pp. 291-301, vol. 29, Issue 4.
Eric Hostetler., PET Tracer Discovery for Subtype-Specific Mglur Allosteric Modulators: Challenges and Insights Presentation Slides 7th International Meeting on Metabotropic Glutamate Receptors, Merck, Discovery for Subtype, 2011, pp. 01-08, Page Number.
Eric J. Nestler., Common Molecular and Cellular Substrates of Addiction and Memory, Neurobiol of Learning and Memory, 2002, pp. 637-647, vol. 76.
Ershov et al, Chemical Abstracts, Chemical Abstracts, 1985, pp. 678 (abstract 178221f), vol. 103.

Ester J. Filinger, Effect of a Reserpine-like Agent on the Release and Metabolism of [3H]NA in Cell Bodies and Terminals, General Pharamacology, 1994, pp. 1039-1043, vol. 25 Issue 5.
Etkin, et al, Common Abnormalities and Disorder-Specific Compensation During Implicit Regulation of Emotional Processing in Generalized Anxiety and Major Depressive Disorders, Am J Psychiatry, 2011, pp. 968-978, vol. 168.
Etkin, et al., Neurobiology of Anxiety: From Neural Circuits to Novel Solutions, Depression and Anxiety, 2012, pp. 355-358, vol. 29.
Evan P. Lebois., Neither typical nor atypical: LY404039 provides proof of concept that selective targeting of mGluR2/3 receptors is a valid mechanism for obtaining antipsychotic efficacy, Current Topics in Medicinal Chemistry, 2008, pp. 1480-1481, vol. 8, Issue 16.
Ezquerra, et al., Efficient Reagents for the Synthesis of 5-, 7-, and 5,7-Substituted Indoles Starting from Aromatic Amines: Scope and Limitations, J. Org. Chem, May 29, 1996, pp. 5804-5812, vol. 61.
F. Matrisciano et al., Metabotropic glutamate receptors and neuroadaptation to antidepressants: imipramine-induced down-regulation of b-adrenergic receptors in mice treated with metabotropic glutamate 2/3 receptor ligands, Journal of Neurochemistry, 2005, pp. 1345-1352, vol. 93.
F. Matrisciano et al., Synergism between fluoxetine and the mGlu2/3 receptor agonist, LY379268, in an in vitro model for antidepressant drug-induced neurogenesis, Neuropharmacology, 2008, pp. 428-437, vol. 54.
F. Moroni, Poiy(ADP-ribose) polymerase inhibitors attenuate necrotic but not apoptotic neuronal death in experimental models of cerebral ischemia, Cell Death and Differentiation, 2001, pp. 921-932, vol. 8.
Fagni, et al., Identification and functional roles of metabotropic glutamate receptor-interacting proteins, Seminars in Cell & Developmental Biology, 2004, pp. 289-296, vol. 15.
Farabaugh, et al, Anxious Depression and early changes in the HAMD-17 anxiety-somatization factor items and antidepressant treatment outcome, Int Clin Psychopharmacol, Jul. 1, 2011, pp. 214-217, vol. 25, Issue 4.
Faries, et al., The Double-Blind Variable Placebo Lead-in Period: Results From Two Antidepressant Clinical Trials, Journal of Clinical Psychopharmacology, 2001, pp. 561-568, vol. 21.
Fava, et al., Anxiety Disorder in major Depression, Comprehensive Psychiatry, 2000, pp. 97-102, vol. 41 Issue 2.
Fava, et al., Clinical correlates and symptom patterns of anxious depression among patients with major depressive disorder in STAR*D, Psychological Medicine, 2004, pp. 1299-1308, vol. 34.
Fava, et al., Difference in Treatment Outcome in Outpatients With Anxious Versus Nonanxious Depression: A STAR*D Report, Am J Psychiatry, 2008, pp. 342-351, vol. 165.
Fava, et al., Evidence for the Role of Metabotropic Glutamate (mGlu)2 Not mGlu3 Receptors in the Preclinical Antipsychotic Pharmacology of the mGlu2/3 Receptor Agonist, The Journal of Pharmacology and Experimental Therapeutics, Apr. 17, 2008, pp. 209-217, vol. 326.
Fava, et al., Major Depressive Subtypes and Treatment Response, Biol Psychiatry, 1997, pp. 568-576, vol. 42.
Fava, et al., Reliability and Validity of the Massachusetts General Hospital Cognitive and Physical Functioning Questionnaire, Psychother Psychosom, Feb. 13, 2009, pp. 91-97, vol. 78, S. Karger AG, Basel.
Fava, et al., The Efficacy and Tolerability of Duloxetine in the Treatment of Anxious Versus Non-Anxious Depression: A Post-Hoc Analysis of an Open-Label Outpatient Study, Annals of clinical psychiatry, 2007, pp. 187-195, vol. 19, Issue 3.
Fava, et al., The Problem of the Placebo Response in Clinical Trails for Psychiatric Disorders: Culprits, Possible Remedies and a Novel Study Design Approach, Psychotherapy and Psychosomatics, 2003, pp. 115-127, vol. 72.
Fava, et al., What Clinical and Symptom Features and Comorbid Disorders Characterize Outpatients With Anxious Major Depressive Disorder: A Replication and Extension, The Canadian Journal of Psychiatry, 2006, pp. 823-835, vol. 51.
Fawcett, et al, Anxiety Syndromes and Their Relationship to Depressive Illness, J Clin Psychiarty, 1983, pp. 8-11, vol. 44.

(56) References Cited

OTHER PUBLICATIONS

Fawcett, et al., The Detection and Consequences of Anxiety in Clinical Depression, J Clin Psychiatry, 1997, pp. 35-40, vol. 58.
FDA Center for Drug Evaluation and Research, 2003, NDA 21-487, Pharmacology Reviews, 2003, pp. ix.
Feeley Kearney, et al, mGluRs: a target for pharmacotherapy in Parkinson disease, Experimental Neurology, Jul. 17, 2003, pp. 30-36, vol. 184, Elsevier Inc.
Feenstra, et al., Local Activation of Metabotropic Glutamate Receptors Inhibits the Handling-Induced Increased Release of Dopamine in the Nucleus Accumbens but Not that of Dopamine or Noradrenaline in the Prefrontal Cortex: Comparison with Inhibition of Ionotropic Receptors, Journal of Neurochemistry, 1988, pp. 1104-1113, vol. 70, Lippincott—Raven.
Feinber et al, The selective group mGlu2/3 receptor agonist LY379268 suppresses REM sleep and fast EEG in the rat, Pharmacology, Biochemistry and Behavior, 2002, pp. 467-474, vol. 73.
Feinberg, et al., The Metabotropic Glutamate (mGLU)2/3 Receptor Antagonist LY341495 [2S-2-Amino-2(1S,2S-2-carboxycyclopropyl-1-yl)-3-(xanth-9-yl)propanoic Acid] Stimulates Waking and Fast Electroencephalogram Power and Blocks the Effects, The Journal of Pharmacology and Experimental Therapeutics, 2005, pp. 826-833, vol. 312.
Fell, et al, N-(4-((2-(trifluoromethyl)-3-hydroxy-4-(isobutyryl)phenoxy)methyl) benzyl)-1-methyl-1H-imidazole-4-carboxamide (THIIC), a Novel Metabotropic Glutamate 2 Potentiator with Potential Anxiolytic/ Antidepressant Properties, The Journal of Pharmacology and Experimental Therapeutics, 2011, pp. 165-177, vol. 336 Issue 1.
Fell, et al., Activation of metabotropic glutamate (mGlu)2 receptors suppresses histamine release in limbic brain regions following acute ketamine challenge, Neuropharmacology, 2010, pp. 632-639, vol. 58.
Fell, et al., Group II metabotropic glutamate receptor agonists and positive allosteric modulators as novel treatments for schizophrenia, Neuropharmacology, 2012, pp. 1473-1483, vol. 62.
Fell, et al., In Vitro and In Vivo Evidence for a Lack of Interaction with Dopamine D2 Receptors by the Metabotropic Glutamate 2/3 Receptor Agonists, The Journal of Pharmacology and Experimental Therapeutics, Sep. 14, 2009, pp. 1126-1136, vol. 331 Issue 3.
Fendt, et al., Metabotropic glutamate receptors are involved in amygdaloid plasticity, European Journal of Neuroscience, Mar. 5, 2002, pp. 1535-1541, vol. 15.
Fenton, et al., The Role of a Prescription in Anxiety Medication Use, Abuse, and Dependence, Am J Psychiatry, 2010, pp. 1247-1253, vol. 167.
Ferraguti, et al., Activation of the extracellular signal-regulated kinase 2 by metabotropic glutamate receptors, European Journal of Neuroscience, 1999, pp. 2073-2082, vol. 11.
Ferraguti, et al., Metabotropic Glutamate 1 Receptor: Current Concepts and Perspectives, Pharmacological Reviews, 2008, pp. 536-581, vol. 30 Issue 4.
Ferris, et al., Interactions between LY354740, a Group II metabotropic agonist and the GABAA-benzodiazepine receptor complex in the rat elevated plus-maze, Journal of Psychopharmacology, 2001, pp. 76-82, vol. 15, Issue 2.
Feyissa, et al, Elevated level of metabotropic glutamate receptor 2/3 in the prefrontal cortex in major depression, Progress in Neuro-Psychopharmacology & Biological Psychiatry, 2010, pp. 279-283, vol. 34.
Fiorella, et al., The role of the 5-HT2A and 5.HT2c receptors in the stimulus effects of hallucinogenic drugs I: Antagonist correlation analysis, Psychopharmacology, 1995, pp. 347-356, vol. 121, Springer-Verlag.
Fisher, et al, Antinociceptive effects following intrathecal pretreatment with selective metabotropic glutamate receptor compounds in a rat model of neuropathic pain, Pharmacology, Biochemistry and Behavior, Feb. 18, 2002, pp. 411-418, vol. 73.
Fisher, et al., Intrathecal administration of the mGluR compound, (S)-4CPG, attenuates hyperalgesia and allodynia associated with sciatic nerve constriction injury in rats, Pain, 1998, pp. 59-66, vol. 77.
Fisher, et al., The contribution of metabotropicglutamatereceptors(mGluRs)to formalin-inducednociception, Pain, 1996, pp. 255-263, vol. 68.
Flint, et al., Anxious Depression in Elderly Patients, The American Journal of Geriatric Psychiatry, 1997, pp. 107-115, vol. 5.
Flor, et al., Molecular Cloning, Functional Expression and Pharmacological Characterization of the Human Metabotropic Glutamate Receptor Type 2, European Journal of Neuroscience, 1995, pp. 622-629, vol. 7.
Fonnum, et al., Role of Glutamate and Glutamate Receptors in Memory Function and Alzheimer's Disease, Glutamate and Memory, 1995, pp. 475-486, vol. 757.
Francesco, et al., Activation of Group-II Metabotropic Glutamate Receptors Promotes DNA Demethylation in the Mouse Brain, Molecular Pharmacology, Apr. 19, 2011, pp. 1-52, Page Number.
Franco, et al., Novel pharmacological targets based on receptor heteromers, Brain Researh Reviews, Jun. 20, 2008, pp. 475-482, vol. 58.
Franco, et al., The Two-State Dimer Receptor Model: A General Model for Receptor Dimers, Molecular Pharmacology, 2006, pp. 1905-1912, vol. 69 Issue 6.
Frank, et al., Depression and health-related quality of life for low-income African-American women in the U.S., Quality of Life Research, Apr. 19, 2005, pp. 2293-2301, vol. 14.
Faruli, et al., Among the twenty classical L-amino acids, only glutamate directly activates metabotropic glutamate receptors, Neuropharmacology, 2006, pp. 245-253, vol. 50.
Frederick J. Ehlert., Analysis of Allosterism in Functional Assays, The Journal of Pharmacology and Experimental Therapeutics, Jul. 20, 2005, pp. 740-754, vol. 315.
Freedman, et al., Desensitization of G Protein-Coupled Receptors, Recent Progress in Hormone Reserch, 1996, pp. 319-353, vol. 51.
Freedman, et al., Schizopherenia, The New England Journal of Medicine, 2003, pp. 1738-1749, vol. 349.
French, et al., Subfield-specific immediate early gene expression associated with hippocampal long-term potentiation in vivo, European Journal of Neuroscience, 2001, pp. 968-976, vol. 13.
Fribourg, et al., Decoding the Signaling of a GPCR Heteromeric Complex Reveals a Unifying Mechanism of Action of Antipsychotic Drugs, Cell, Nov. 23, 2011, pp. 1011-1023, vol. 147.
Fricker, et al., Effects of N-acetylaspartylglutarnate (NAAG) at group II mGluRs and NMDAR, Neuropharrnacology, 2009, pp. 1060-1067, vol. 56.
Fujii, et al., A chemical LTP induced by co-activation of metabotropic and N-methyl-D-aspartate glutamate receptors in hippocampal CA1 neurons, Brain Research, 2004, pp. 20-28, vol. 999.
Fujimoto, et al., Motor and cognitive function evaluation following experimental traumatic brain injury, Neuroscience and Biobehavioral Reviews, 2004, pp. 365-378, vol. 28.
Furukawa, et al., Antidepressants plus benzodiazepines for major depression, Cochrane Database of Systematic Reviews, 2009, pp. 1-29, Issue 3.
Fuxe, et al., Integrated signaling in heterodimers and receptor mosaics of different types of GPCRs of the forebrain: relevance for schizophrenia, J Neural Transm, Jan. 21, 2009, pp. 923-939, vol. 116.
G. Bernhard Landwehrmeyer et al., Riluzole in Huntington's Disease: A 3-Year, Randomized Controlled Study, Ann. Neurol., 2007, pp. 262-272, vol. 62.
Gabor Imre., The Preclinical Properties of a Novel Group II Metabotropic Glutamate Receptor Agonist LY379268, Journal compilation, 2007, pp. 444-464, vol. 13 Issue 4.
Galici et al, A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, The Journal of Pharmacology and Experimental Therapeutics, 2005, pp. 1181-1187, vol. 315.
Galici et al, Biphenyl-indanone A, a Positive Allosteric Modulator of the Metabotropic Glutamate Receptor Subtype 2, Has Antipsychotic-

(56) References Cited

OTHER PUBLICATIONS and Anxiolytic-Like Effects in Mice, The Journal of Pharmacology and Experimental Therapeutics, 2006, pp. 173-185, vol. 318, No. 1.
Galimberti, et al., Long-Term Rearrangements of Hippocampal Mossy Fiber Terminal Connectivity in the Adult Regulated by Experience, Neuron, Jun. 1, 2006, pp. 749-763, vol. 50.
Gama, et al., Heterodimerization of Calcium Sensing Receptors with Metabotropic Glutamate Receptors in Neurons, The Journal of Biological Chemistry, Aug. 6, 2001, pp. 39053-39059, vol. 276.
Garbaccio, et al, Discovery of Oxazolobenzimidazoles as Positive Allosteric Modulators for the mGluR2 Receptor, ACS Medicinal Chemistry Letters, Jul. 12, 2010, pp. 406-410, vol. 1.
Garrido Sanabria, et al, Impaired expression and function of group II metabotropic glutamate receptors in pilocarpine-treated chronically epileptic rats, Brain Research, 2008, pp. 165-176, vol. 1240.
Garriock, et al, Genetic Studies of Drug Response and Side Effects in the STAR*D Study, Part 1, Society Clinical Psychopharmacology, 2009, pp. 1186-1187, vol. 70, Issue 8.
Gasparini, et al., Allosteric Modulators for mGlu Receptors, Neuropharmacology, 2007, pp. 187-194, vol. 5.
George K. Aghajanian, Modeling "psychosis" in vitro by inducing disordered neuronal network activity in cortical brain slices, Psychopharmacology, Feb. 25, 2009, pp. 575-585, vol. 206.
George Krieger, The Plasma Level of Cortisol as a Predictor of Suicide, ?, 1974, pp. 237-240, ?.
Gerald W. Vogel., Evidence for REM Sleep Deprivation As the Mechanism of Action of Antidepressant Drugs, Prog. Neuro-Psychopharmncol fr Biol. Psychiot, 1983, pp. 343-349, vol. 7, Pergamon Press.
Geraldine C. B. Harriman et al., Synthesis of 4-Substituted 4-Arylpiperidines, Tetrahedron Letters, 2000, pp. 8853-8856, vol. 41.
Gerard J. Marek, Metabotropic giutarnate2/3 (mGlu2/3) receptors, schizophrenia and cognition, European Journal of Pharmacology, Apr. 2, 2010, pp. 81-90, vol. 639, Elsevier B.V. All rights reserved.
Gerber, et al., Metabotropic glutamate receptors: intracellular signaling pathways, Pharmacology, 2007, pp. 56-61, vol. 7.
Gewirtz,et al., Behavioral Evidence for Interactions between a Hallucinogenic Drug and Group II Metabotropic Glutamate Receptors, Neuropsychopharmacology, Apr. 25, 2000, pp. 569-576, vol. 23 Issue 5, Elsevier Science Inc.
Ghose, et al., Differential Expression of Metabotropic Glutamate Receptors 2 and 3 in Schizophrenia: A Mechanism for Antipsychotic Drug Action?, Am J Psychiatry, 2009, pp. 812-820, vol. 166 Issue 7.
Gill, et al., Immunochemical localization of the metabotropic glutamate receptors in the rat heart, Brain Research Bulletin, 1999, pp. 143-146, vol. 48 Issue 2.
Gilling, et al., Potency, voltage-dependency, agonist concentration-dependency, blocking kinetics and partial untrapping of the uncompetitive N-methyl-D-aspartate (NMDA) channel blocker memantine at human NMDA (GluN1/GluN2A) receptors, Neuropharmacology, Jan. 13, 2009, pp. 866-875, vol. 56.
Gilmour, et al., Diverse and often opposite behavioural effects of NMDA receptor antagonists in rats: implications for "NMDA antagonist modelling" of schizophrenia, Psychopharmacology, May 7, 2009, pp. 203-216, vol. 205.
Girardi, et al., Differential Expression of Cerebellar Metabotropic Glutamate Receptors mGLUR2/3 and mGLUR4a after the Administration of a Convulsant Drug and the Adenosine Analogue Cyclopentyladenosine, Neurochem Res, Mar. 31, 2007, pp. 1120-1128, vol. 32.
Gjoni, et al., Receptor activation involving positive allosteric modulation, unlike full agonism, does not result in GABAB receptor desensitization, Neuropharmacology, 2008, pp. 1293-1299, vol. 55.
Gleason, et al., Blockade of phencyclidine-induced hyperlocomotion by olanzapine, clozapine and s, Psychopharmacology, 1997, pp. 79-84, vol. 129.

Gleeson, et al., Generation of a Set of Simple, Interpretable ADMET Rules of Thumb, Journal of Medicinal Chemistry, 2008, pp. 817-834, vol. 51.
Glick, et al., A Double-Blind Randomized Trial of Mood Stabilizer Augmentation Using Lamotrigine and Valproate for Patients With Schizophrenia Who Are Stabilized and Partially Responsive, Journal of Clinical Psychopharmacology, 2009, pp. 267-271, vol. 29 Issue 3.
Glick, et al., Concomitant Medications May Not Improve Outcome of Antipsychotic Monotherapy for Stabilized Patients With nonacute Schizophrenia, J Clin Pyschiatry, 2006, pp. 1261-1265, vol. 67.
Glin, et al., The Intermediate Stage of Sleep in Mice, Physiology & Behavior, 1991, pp. 951-953, vol. 50.
Goff, et al., Lamotrigine as Add-On Therapy in Schizophrenia: Results of 2 Placebo-Controlled Trials, Journal of Clinical Psychopharmacology, 2007, pp. 582-589, vol. 27 issue 6.
Goldberg, et al., Novel Non-Benzodiazepine Anxiolytics, Neuropharmacology, 1983, pp. 1499-1504, vol. 22.
Gonzalez Maeso, et al., Psychedelics and schizophrenia, Trends in Neurosciences, Mar. 5, 2009, pp. 225-232, vol. 32 Issue 4, Elsevier Ltd.
Gonzalez-Maeso, et al, Identification of a serotonin/glutamate receptor complex implicated in psychosis, Nature, Mar. 6, 2008, pp. 93-97, vol. 452, Nature PublishingGroup.
Goodman, et al., The Yale-Brown Obsessive Compulsive Scale, Arch Gen Psychiatry, 1989, pp. 1006-1011, vol. 46.
Goodman_et_al., The Pharmacological Basis of Therapeutics, Chapter 21—Pharmacotherapy of the Epilepsies, 2011, pp. 1-27, 12th edition.
Goodwin, et al., Advantages and disadvantages of combination treatment with antipsychotics, European Neuropsychopharmacology, 2009, pp. 520-532, vol. 19.
Gorcs, et al., Immunohistochemical visualization of a metabotropic glutamate receptor, Neuro Report, 1993, pp. 283-286, vol. 4.
Gorman, et al., A Hypothesized Role for Dendritic Remodeling in the Etiology of mood and Anxiety Disorder, The Journal of Neuropsychiatry and Clinical, 2010, pp. 256-264, vol. 22.
Gorman, et al., Anxiogenic Effects of Co2 and Hyperventilation in patients With panic Disorder, Am J Psychiatry, 1994, pp. 547-553, vol. 151.
Goudet, et al., Asymmetric Functioning of Dimeric Metabotropic Glutamate Receptors Disclosed by Positive Allosteric Modulators, The Journal of Biological Chemistry, 2005, pp. 24380-24385, vol. 280.
Goudet, et al.. Metabotropic receptors for glutamate and GABA in pain, Brain Research Reviews, 2009, pp. 43-56, vol. 60.
Gouzoulis Mayfrank, et al, Inhibition of Return in the Human 5HT2A Agonist and NMDA Antagonist Model of Psychosis, Neuropsychopharmacology, Aug. 24, 2006, pp. 431-441, vol. 31.
Gouzoulis Mayfrank, et al., Psychological Effects of (S)-Ketamine and N,N Dimethyltryptamine (DMT):A Double-Biind,Cross-Over Study in Healthy Volunteers, Pharmacopsychiatry, 2005, pp. 301-311, vol. 38.
Govek et al, Benzazoles as allosteric potentiators of metabotropic glutamate receptor 2 (mGluR2): Efficacy in an animal model for schizophrenia, Bioorganic & Medicinal Chemistry Letters, 2005, pp. 4068-4072, vol. 15.
Gozzi, et al, Differential Effects of Antipsychotic and Glutamatergic Agents on the phMRI Response to Phencyclidine, Neuropsychopharmacology, 2008, pp. 1690-1703, vol. 33.
Gregor J. MacDonald, Positive Allosteric Modulation of mGluR2 Receptors in the treatment of CNS Disorders, Neuroscience Medicinal Chemistry, 2010, pp. 1-29, vol. 3.
Gregor J. MacDonald, The Design of Allosteric Modulators for the treatment of CNS disorders, Neuroscience Medicinal Chemistry, Feb. 21, 2012, pp. 1-36, vol. 11.
Gregor J. MacDonald, The Design of Mglur Modulators for the Treatment of CNS Disorders, Stockholm, 2013, pp. 1-1, vol. 19.
Gregory, et al, Allosteric modulation of metabotropic glutamate receptors: Structural insights and therapeutic potential, Neuropharmacology, 2011, pp. 66-81, vol. 60.
Gregory, et al, Overview of Receptor Allosterism, Current Protocols in Pharmacology, 2010, pp. 1.21.1-1.21.34, vol. 51.

(56) References Cited

OTHER PUBLICATIONS

Gregory, et al, Prefrontal GFroup II Metabotropic Glutamate Receptor Activation Decreases Performance on a Working Memory Task, Ann. N.Y.Acad.Sci, 2003, pp. 405-409, vol. 1003.

Grillon,et al, Anxiolytic effects of a novel group II metabotropic glutamate receptor agonist (LY354740) in the fear-potentiated startle paradigm in humans, Psychopharmacology, Apr. 23, 2003, pp. 446-454, vol. 168.

Grueter, et al, Group II and III Metabotropic Glutamate Receptors Suppress Excitatory Synaptic Transmission in the Dorsolateral Bed Nucleus of the Stria Terminalis, Neuropsychopharmacology, 2005, pp. 1302-1311, vol. 30, Nature Publishing Group.

Grzegorz Czapski et al., Effect of poly (ADP-ribose) polymerase inhibitors on oxidative stress evoked hydroxyl radical level and macromolecules oxidation in cell free system of rat brain cortex, Neuroscience Letters, 2004, pp. 45-48, vol. 356.

Gu, et al, Expression of Functional Metabotropic Glutamate Receptors in Primary Cultured Rat Osteoblasts: Cross-Talk With N-Methyl-d-Aspartate Receptors, The Journal of Biological Chemistry, Aug. 18, 2000, pp. 34252-34259, vol. 275.

Gu,et al, Distribution of metabotropic glutamate 2 and 3 receptors in the rat forebrain: Implication in emotional responses and central disinhibition, Brain Research, 2008, pp. 47-62, vol. 1197.

Guerineau, et al, Activation of a nonselective Cationic Conductance by Metabotropic Glutamatergic and Muscarinic Agonists in CA3 Pyramidal neurons of the Rat Hippocampus, The Journal of Neuroscience, 1995, pp. 4395-4407, vol. 15, issue 6, Society of Neuroscience.

Guerineau, et al, G-Protein-mediated desensitization of metabotropic glutamatergic and muscarinic reponses in CA3 cells in rat hippocampus, Journal of Physiology, 1997, pp. 487-496, vol. 500.

Guimaraes. et al, Ritanserin facilitates anxiety in a simulated public-speaking paradigm, Journal of Psychopharmacology, 1997, pp. 225-231, vol. 11, Issue 3.

Gupta, et al, Metabotropic Glutamate Receptor Protein Expression in the Prefrontal Cortex and Striatum in Schizophrenia, SYNAPSE, 2005, pp. 123-131, vol. 57.

Gurevich, et al, Alterations in the Cortical Serotonergic System in Schizophrenia: A Postmortem Study, Biol Psychiatry, 1997, pp. 529-545, vol. 42.

H. Erlenmeyer and J. P. Jung, Über einige Derivate des 2-Aminothiazols, Heveltica Chimica Acta, 1949, pp. 35-38, vol. XXXII.

H. Förstl and A. Kurz, Clinical features of Alzheimer's disease, Eur. Arch. Psychiatry Clin. Neurosci., 1999, pp. 288-290, vol. 249.

H. M. Eisa et al., Synthesis of some novel tetrazole derivatives as potential antimicrobial agents, Pakinstan Journal of Scientific and Industrial Research, 1990, pp. 417-420, vol. 33.

Haak, et al., metabotropic Glutamate Receptor Activation Modulates Kainate and Serotonin Calcium Response in Astrocytes, Journal of Neuroscience, Mar. 1, 1997, pp. 1825-1837, vol. 17 Issue 5, Society for Neuroscience.

Hackler, et al., Selective Potentiation of the Metabotropic Glutamate Receptor Subtype 2 Blocks Phencyclidine-Induced Hyperlocomotion and Brain Activation, Neuroscience, Mar. 27, 2010, pp. 209-218, vol. 168, Elsevier Ltd. All rights reserved.

Hamilton., Standardised Assessment and Recording of Depressive Symptoms, Psychiat.Neurol.Neurochir., 1969, pp. 201-205, vol. 72, Elsevier Publishing Company.

Hampson, et al., Characterization of Two Alternatively Spliced Forms of a Metabotropic Glutamate Receptor in the Central Nervous System of the Rat, Neuroscience, 1994, pp. 325-336, vol. 60 Issue 2, Elsevier Science Ltd.

Handan Gunduz-Bruce, The acute effects of NMDA antagonism: From the rodent to the human brain, Brain Researh Reviews, 2009, pp. 279-286, vol. 60.

Handley,et al., Effects of alpha-adrenoceptor agonists and antagonists in a maze-exploration model of "fear"- motivated behaviour, Archives of Pharmacology, 1984, pp. 1-5, vol. 327.

Hanna, et al., Differentiating the roles of mGlu2 and mGlu3 receptors using LY541850, an mGlu2 agonist/mGlu3 antagonist, Neuropharmacology, Feb. 29, 2012, pp. 1-8, page number, Elsevier Ltd.

Hansen, et al., Glutamate joins the ranks of immunomodulators, Nature Medicine, 2010, pp. 856-858, vol. 16 Issue 8.

Happe, et al., Agonist-stimulated [35 S]GTPgS autoradiography: optimization for high sensitivity, European Journal of Pharmacology, May 8, 2001, pp. 1-13, vol. 422, Published by Elsevier Science B.V.

Harald, et al., Meta-review of depressive subtyping models, Journal of Affective Disorders, 2012, pp. 126-140, vol. 139, Elsevier B.V. All rights reserved.

Haro, et al., The Clinical Global Impression—Schizophrenia scale: a simple instrument to measure the diversity of symptoms present in schizophrenia, Acta Psychiatrica Scandinavica, 2003, pp. 16-23, vol. 107 Issue 416, Blackwell Munksgaard.

Harrison, et al, The group II metabotropic glutamate receptor 3 (mGluR3, mGlu3, GRM3): expression, function and involvement in schizophrenia, Journal of Psychopharmacology, 2008, pp. 308-322, vol. 22 Issue 3, British Association for Psychopharmacology.

Hartveit, et al, Expression of the mRNA of Seven Metabotropic Glutamate Receptors (mGluR1 to 7) in the Rat Retina. An In Situ Hybridization Study on Tissue Sections and isolated Cells, European Journal of Neuroscience, Feb. 1, 1995, pp. 1472-1483, vol. 7, European Neuroscience Association.

Hascup, et al., An allosteric modulator of metabotropic glutamate receptor (mGluR2),(+)-TFMPIP, inhibits restraint stress-induced phasic glutamate release in rat prefrontal cortex, Journal of Neurochemistry, 2012, pp. 619-627, vol. 122.

Hashimoto, et al., Increased Levels of Glutamate in Brains from Patients with Mood Disorders. Biol Psychiatry, 2007, pp. 1310-1316, vol. 62, Society of Biological Psychiatry.

Hasin, et al., Epidemiology of major Depressive Disorder, Arch Gen Psychiatry, 2005, pp. 1097-1106, vol. 62.

Hasler, et al., Reduced Prefrontal Glutamate/Glutamine and y-Aminobutyric Acid Levels in Major Depression Determined Using Proton Magnetic Resonance Spectroscopy, Arch Gen Psychiatry, 2007, pp. 193-200, vol. 64.

Hassan Imogai et al., cis-Disubstituted Cyclopropanes via Asymmetric Catalytic Cyclopropenation: Synthesis of Cyclopropyl-dehydroamino Acids and of Dictyopterene C', Helvetica Chimica Acta, 1998, pp. 1754-1764, vol. 81.

Hawgood, et al., Anxiety disorders and suicidal behaviour: an update, Current Opinion in Psychiatry, 2008, pp. 51-64, vol. 21, Wolters Kluwer Health | Lippincott Williams & Wlkins.

Helton et al, Anxiolytic and Side-Effect Profile of LY354740: A Potent, Highly Selective, Orally Active Agonist for Group II Metabotropic Glutamate Receptors, The Journal of Pharmacology and Experimental Therapeutics, 1998, pp. 651-660, vol. 284.

Helton, et al., LY354740: a Metabotropic Glutamate Receptor Agonist which Arneliorates Symptoms of Nicotine Withdrawal in Rats, Neurophammcology,, Sep. 11, 1997, pp. 1511-1516, vol. 36, Published by Elsevier Science Ltd, All rights reserved.

Hemstapat, et al, A Novel Family of Potent Negative Allosteric Modulators of Group II Metabotropic Glutamate Receptors, The Journal of Pharmacology and Experimental Therapeutics, Apr. 5, 2007, pp. 254-264, vol. 322 Issue 1, Pharmacology and Experimental Therapeutics.

Henry, et al., The mGluR5 antagonist MPEP, but not the mGluR2/3 agonist LY314582, augments PCP effects on prepulse inhibition and locomotor activity, Neuropharmacology, Sep. 11, 2002, pp. 1199-1209, vol. 43, Elsevier Science Ltd.

Hermans, et al,' Structural, signalling and regulatory properties of the group I metabotropic glutamate receptors : prototypic family C G-protein-coupled receptors, Biochem.J., 2001, pp. 465-484, vol. 359, Biochemical Society.

Herrero, et al., Functional Switch from Facilitation to Inhibition in the Control of Glutamate Release by Metabotropic Glutamate Receptors, The Journal of Biological Chemistry, 1998, pp. 1951-1958, vol. 273 Issue 4, Biochemistry and Molecular Biology, Inc.

(56) References Cited

OTHER PUBLICATIONS

Herrero, et al., Positive feedback of glutamate exocytosis by metabotropic presynaptic receptor stimulation, Nature, Nov. 12, 1992, pp. 163-166, vol. 360.

Herrero, et al., Rapid Desensitization of the Metabotropic Glutamate Receptor that Facilitates Glutamate Release in Rat Cere brocort ical Nerve Terminals, European Journal of Neuroscience, 1994, pp. 115-120, vol. 6, European Neuroscience Association.

Herrmann, et al., Human EEG gamma oscillations in neuropsychiatric disorders, Clinical Neurophysiology, Oct. 25, 2005, pp. 2719-2733, vol. 116.

Hetzenauer, et al., Individual contribution of metabotropic glutamate receptor (mGlu) 2 and 3 to c-Fos expression pattern evoked by mGlu2/3 antagonism, Psychopharmacology, Sep. 24, 2008, pp. 1-13, vol. 201, The Author, bution of meta.

Higashida, et al, Subtype-specific coupling with ADP-ribosyl cyclase of metabotropic glutamate receptors in retina, cervical superior ganglion and NG108-15 cells, Journal of Neurochemistry, 2003, pp. 1148-1158, vol. 85, International Society for Neurochemistry.

Hijzen, et al., Predictive validity of the potentiated startle response as a behavioral model for anxiolyUc drugs, Psychopharmacology, 1995, pp. 150-154, vol. 118, Springer-Verlag.

Hirao, et al., Preparation of Optically Active 8,8'-Disubstituted 1,1'-Biisoguinole, Heterocycles, 1996, pp. 415-422, vol. 42. No. 1.

Hlavackova, et al., Evidence for a single heptahelical domain being turned on upon activation of a dimeric GPCR, The EMBO Journal, Jan. 20, 2005, pp. 499-509, vol. 24 issue 3, European Molecular Biology Organization.

Hoang, et al., Expression of metabotropic glutamate receptors in nodose ganglia and the nucleus of the solitary tract, Am J Physiol Heart Circ Physiol, 2001, pp. H457-H462, vol. 281, American Physiological Society.

Hoeben, et al., Prediction of Serotonin 2A Receptor (5-HT2AR) Occupancy in Man From Nonclinical Pharmacology Data, Exposure vs. 5-HT2AR Occupancy Modeling Used to Help Design a Positron Emission Tomography (PET) Study in Healthy Male Subjects., Annual Meeting of the Population Approach Group in Europe, 2013, pp. 1-2, Page number.

Hoffman, et al, Human and Economic Burden of Generalized Anxiety Disorder, Depression and Anxiety, 2008, pp. 72-90, vol. 25, Wiley-Liss, Inc.

Hofmeijer-Sevink, et al., Clinical relevance of comorbidity in anxiety disorders: A report from the Netherlands Study of Depression and Anxiety (NESDA), Journal of Affective Disorders, Jan. 10, 2012, pp. 106-112, vol. 137, Elsevier B.V.

Hohnadel, et al, Effect of repeated nicotine exposure on high-affinity nicotinic acetylcholine receptor density in spontaneously hypertensive rats, Neuroscience Letters, Mar. 4, 2005, pp. 158-163, vol. 382, Elsevier Ireland Ltd.

Holcomb, et al, Effects of Noncompetitive NMDA Receptor Blockade on Anterior Cingulate Cerebral Blood Flow in Volunteers with Schizophrenia, Neuropsychopharmacology, Jul. 20, 2005, pp. 2275-2282, vol. 30, Nature Publishing Group.

Holden, Excited by Glutamate, Science, Jun. 20, 2003, pp. 1866-1868, vol. 300.

Holloway, et al., Prenatal Stress induces Schizophrenia-Like Alterations of Serotonin 2A and Metabotropic Glutamate 2 Receptors in the Adult offspring: Role of Maternal immune System, The Journal of Neuroscience, Jan. 16, 2013, pp. 1088-1098, vol. 33 issue 3.

Holscher, et al., Metabotropic glutamate receptor activation and blockade: their role in long-term potentiation, learning and neurotoxicity, Neuroscience and Biobehavioral Reviews, 1999, pp. 399-410, vol. 23, Elsevier Science Ltd.

Homayoun, et al., Activation of Metabotropic Glutamate 2/3 Receptors Reverses the Effects of NMDS Receptor Hypofunction on Prefrontal Cortex unit Activity in Awake Rats, Journal of Neurophysiology, 2005, pp. 1989-2001, vol. 93 Issue 4, American Physiological Society.

Homayoun, et al., Group 5 metabotropic glutamate receptors: Role in modulating cortical activity and relevance to cognition, European Journal of Pharmacology, Apr. 2, 2010, pp. 33-39, vol. 639, Elsevier B.V.

Homayoun, et al., Orbitofrontal cortex neurons as a common target for classic and glutamatergic antipsychotic drugs, PNAS, Nov. 18, 2008, pp. 18041-18046, vol. 105 issue 46, The National Academy of Sciences.

Honer, et al., Clozapine Alone versus Clozapine and risperidone with Refractory Schizopherenia, The New England Journal of Medicine, Feb. 2, 2006, pp. 472-482, vol. 354 Issue 5, massachusetts Medical society.

Hook, et al., Neuroproteases in peptide Nerotransmission and Neurodegenerative Diseases Applications to Drug Discovery Research, Biodrugs, 2006, pp. 105-119, vol. 20.

Horiguchi, et al., Interaction of mGlu2/3 agonism with clozapine and lurasidone to restore novel object recognition in subchronic phencyclidine-treated rats, Psychopharmacology, Mar. 25, 2011, pp. 13-24, vol. 217, Springer-Verlag.

Horiguchi, et al., nteractions among the atypical antipsychotic drug (ADP), lurasidone, 5-HT1A and metabotropic glutamate receptor 2/3 (mGluR2/3) . . . , Department of Psychiatry and Pharmacology, 2010, p. 1, 1 page.

Horst Böhme and Karl-Heinrich Weisel, β-Substituierte Enamine, X: Darstellung und Umsetzungen von 3-Arylamino-2-halogencrotononitrilen, Chemische Berichte, 1976, pp, 2908-2913, vol. 109.

Houamed, et al., Cloning, Expression, and Gene Structure of a G Protein-Coupled Glutamate Receptor from Rat Brain, Science, Mar. 29, 1991, pp. 1318-1321, vol. 252.

Hsia, et al., Evidence Against a Role for Metabotropic Glutamate Receptors in Mossy Fiber LTP: the Use of Mutant Mice and Pharmacological Antagonists, Neuropharmacology,, Jul. 12, 1995, pp. 1567-1572, vol. 34 Issue 11, Elsevier Science Ltd.

Hu, et al., Altered profile of gene expression in rat hearts induced by chronic nicotine consumption, Biochemical and Biophysical Research Communications, Aug. 29, 2002, pp. 729-736, vol. 297, Elsevier Science.

Hu, et al., Emotion Enhances Learning via Norepinephrine Regulation of AMPA-Receptor Trafficking, Cell, Oct. 5, 2007, pp. 160-173, vol. 131, Elsevier Inc.

Hu, et al., Glutamate receptors in preclinical research on Alzheimer's disease: Update on recent advances, Pharmacology, Biochemistry and Behavior, 2012, pp. 855-862, vol. 100, Elsevier Inc.

Hu, et al., Identification of Glutamate Receptors and Transporters in Mouse and Human Sperm, Journal of Andrology, 2004, pp. 140-146, vol. 25 Issue 1, American Society of Andrology.

Hu, et al., Pyrimidine methyl anilines: selective potentiators for the metabotropic glutamate 2 receptor, Bioorganic & Medicinal Chemistry Letters, Aug. 24, 2004, pp. 5071-5074, vol. 14, Elsevier Ltd.

Hu, et al., The Regulation of Dopamine Transmission by Metabotropic Glutamate Receptors1, The Journal of Pharmacology and Experimental Therapeutics, 1999, pp. 412-416, vol. 289, Pharmacology and Experimental Therapeutics.

Huang, et al, Interdomain movements in metabotropic glutamate receptor activation, PNAS, Sep. 13, 2011, pp. 15480-15485, vol. 108 Issue 37.

Huang, et al., (MMM36) Potentiation of the Novel Atypical Antipsychotic Drug Lurasidone-induced DopamineEfflux in rat medial Prefrontal Cortex . . . , Department of Psychiartry and pharmacology, 2010, p. 1, 1 page.

Huang, et al., Alzheimer Mechanisms and Therapeutic Strategies, Cell, Mar. 16, 2012, pp. 1204-1222, vol. 148, Elsevier Inc.

Huang, et al., Inhibition of Microtubule Formation by Metabotropic Glutamate Receptors, Journal of Neurochemistry, 2000, pp. 104-113, vol. 74, International Society for Neurochemistry.

Huang, et al, Prevalence, Correlates, and Comorbidity of nonmedical Precription Drug Use and drug Use Disorder in the United States: Results of the national Epidemiology Survey on Alocohal and related Conditions, J Clin Psychiatry, 2006, pp. 1062-1073, vol. 67 Issue 7.

(56) References Cited

OTHER PUBLICATIONS

Hucho, et al., Epac Mediates a cAMP-to-PKC Signaling in inflammatory Pain: An Isolectin B4(+) Neuron-Specific Mechanism, The Journal of Neuroscience, Jun. 29, 2005, pp. 6119-6126, vol. 25 Issue 26, Society for Neuroscience.
Hucho, et al., Estrogen controls PKCε-dependent mechanical hyperalgesia through direct action on nociceptive neurons, European Journal of Neuroscience, 2006, pp. 527-534, vol. 24.
Huey, et al., Development of Subtle Psychotic Symptoms with Memantine: A Case Report, J Clin Psychiatry, 2005, pp. 658-659, vol. 66 Issue 5.
Hughes et al, Progress in the Mitsunobu reaction. A review, Organic Preparations and Procedures International, 1996, pp. 127-164, vol. 28, No. 2.
Hughes, The Mitsunobu Reaction, Organic Reactions, 1992, pp. 335-656, vol. 42.
Huntington Study Group, Dosage effects of riluzole in Huntington's disease: A multicenter placebo-controlled study, Neurology, 2003, pp. 1551-1556, vol. 61.
Hyoung-Gon Lee et al., The role of metabotropic glutamate receptors in Alzheimer's disease, Acta Neurobiol. Exp., 2004, pp. 89-98, vol. 64.
I. Ralph C. Bick, Photo-oxidative cleavage: an alternative method for degrading bisbenzylisoquinoline alkaloids, Journal of Natural Products, 1986, pp. 373-385, vol. 49 No. 3 May-Jun.
Iacovelli, et al., Regulation of Group II Metabotropic Glutamate Receptors by G Protein-Coupled Receptor Kinases: mGlu2 Receptors Are Resistant to Homologous Desensitization, Molecular Pharmacology, Jan. 22, 2009, pp. 991-1003, vol. 75 Issue 4, Pharmacology and Experimental Therapeutics.
Imre, et al, Subchronic administration of LY354740 does not modify ketamine-evoked behavior and neuronal activity in rats, European Journal of Pharmacology, Jun. 27, 2006, pp. 77-81, vol. 544, Elsevier B.V.
Imre, et al., Dose-response characteristics of ketamine effect on locomotion, cognitive function and central neuronal activity, Brain Research Bulletin, Feb. 10, 2006, pp. 338-345, vol. 69, Elsevier Inc.
Imre, et al., Effects of the mGluR2/3 agonist LY379268 on ketamine-evoked behaviours and neurochemical changes in the dentate gyrus of the rat, Pharmacology, Biochemistry and Behavior, Jul. 18, 2006, pp. 392-399, vol. 84, Elsevier Inc.
Insel_et_al., Research Domain Criteria (Rdoc): Toward a New Classification Framework for Research on Mental Disorders, Am. J. Psychiatry, Jul. 2010, pp. 748-751, vol. 167 No. 7.
Inta, et al., Mice with genetically altered glutamate receptors as models of schizophrenia: A comprehensive review, Neuroscience and Biobehavioral Reviews, Jul. 24, 2009, pp. 285-294, vol. 34, Elsevier Ltd.
Ionescu, et al., Defining anxious depression: a review of the literature, CNS Spectrums, Jan. 31, 2013, pp. 1-9, page number, Cambridge University Press.
Iovieno, et al., Does the Presence of an open-lable Antidepressant Treatment Period Influence study outcome in Clinical Trails Examining Augmentation / Combination Strategies in Treatment Partial Responder/Nonresponders with major Depressive Disorder?, J Clin Psychiatry, 2012, pp. e1-e8, page number.
Irifune, et al., Riluzole; a Glutamate Release inhibitor, Induces Loss of Righting Reflex, Antinociception, and Immobility in Response to Noxious Stimulation in Mice, Anesth Analg, 2007, pp. 1415-1421, vol. 104 Issue 6, International Anesthesia Research Society.
Irving J. Borowitz, Organophosphorus chemistry. III. The reactions of triphenylphosphine with secondary a-bromo ketones and with 2-bromodimedone, Journal of Organic Chemistry, 1966, pp. 4031-4037, vol. 31 No. 12.
Irving W Wainer., A Chromatographic method characterizes allosteric interactions between drugs and their targets, Nature Biotechnology, 2004, pp. 1376-1377, vol. 22 Issue 11.
J. Craig Nelson., Anxiety Does Not Predict Response to Duloxetine in Major Depression: Results of a Pooled Analysis of Individual Patient Data From 11 Placebo-Controlled Trials, Depression and Anxiety, 2010, pp. 12-18, vol. 27, Wiley-Liss, Inc.
J. Konieczny et al, LY354740, a group II metabotropic glutamate receptor agonist with potential antiparkinsonian properties in rats, Naunyn-Schmiedebergs Arch.Pharmacology, Jul. 21, 1998, pp. 500-502, vol. 358.
J.-Y. Lan et al., Activation of Metabotropic Glutamate Receptor-1 Accelerates NMDA Receptor Trafficking, Abstracts/Neuropharmacology, 2002, pp. 294, vol. 43.
J.C.Watkins., L-Glutamate as a central Neurotransmitter: Looking Back, Biochemical Society Transactions, Apr. 11, 2000, pp. 297-310, vol. 28 Issue 4, Biochemical Society.
J.Craig Nelson., Anxious Depression and Response to Treatment, Am J Psychiatry, 2008, pp. 297-299, vol. 165 Issue 3.
Jablensky, et al., Polymorphisms associated with normal memory variation also affect memory impairment in schizophrenia, Genes, Brain and Behavior, 2011, pp. 410-417, vol. 10.
Jack M. Gorman Comorbid Depression and Anxiety Spectrum Disorders, Depression and Anxiety, 1997, pp. 160-168, vol. 4.
Jain et al, A One-Step Preparation of Functionalized 3-Cyano-2-Pyridones, Tetrahedron Letters, 1995, pp. 3307-3310, vol. 36, No. 19.
James E. Barrett, mGluR2-Positive Allosteric Modulators: Therapeutic Potential for Treating Cocaine Abuse?, Neuropsychopharmacology, Jun. 7, 2010, pp. 2007-2008, vol. 35.
James M. Stone., Imaging the Glutamate System in Humans: Relevance to Drug Discovery for Schizophrenia, Current Pharmaceutical Design, 2009, pp. 2594-2602, vol. 15 issue 22, Bentham Science Publishers Ltd.
James N.C. Kew., Positive and negative allosteric modulation of metabotropic glutamate receptors: emerging therapeutic potential, Pharmacology & Therapeutics, 2004, pp. 233-244, vol. 104, Elsevier Inc. Ail rights reserved.
Jan Fawcett., Treating Impulsivity and Anxiety in the Sucidal Patient, Annals New york Academy of sciences, 2001, pp. 94-105, page number.
Jane, et al,, Potent Antagonists at the L-AP4- and (I&3??)-ACPDsensitive Presynaptic Metabotropic Glutamate Receptors in the Neonatal Rat Spinal Cord, Neuropharmacology 1996, pp. 1029-1035, vol. 35 Issue 8, Elsevier Science Ltd.
Janssen Research & Development, LLC, A Study of JNJ-40411813 as Supplementary Treatment to an Antidepressant in Adults With Depression and Anxiety Symptoms, ClinicalTrials.gov, Apr. 20, 2012, Placebo, vol. NCT01582815.
Janssen Research & Development, LLC, Investigation of the Safety, Tolerability and Potential Therapeutic Effects of JNJ-40411813 in Patients With Schizophrenia, ClinicalTrials.gov, Mar. 24, 2011, Placebo, vol. NCT01323205.
Janssens, et al., Glutamate receptor subunit expression in primary neuronal and secondary glial cultures, Journal of Neurochemistry, 2001, pp. 1457-1474, vol. 77, International Society for Neurochemistry.
Javitt, et al., Recent Advances in the Phencyclidine Model of Schizophrenia, Am j Psychiatry, 1991, pp. 1301-1308, vol. 148 Issue 10.
Jayne Cartmell et al, Characterization of [3H]-(2S,2'R,3'R)-2-(2',3'-dicarboxycyclopropyl)glycine ([3H]-DCG IV) binding to metabotropic rnGlu2 receptor-transfected cell membranes, British Journal of Pharmacology, 1998, pp. 497-504, vol. 123.
Jean-Pierre Marquet et al., No. 736—Furannes et pyrroles disubstitués en 2,3. VIII.—Nouvelle method de synthése des furo [2,3-d]pyrimidines substitueés en position 4 et de certains thiéno[2,3-d]pyrimidines, Bulletin de la Societe Chimique de France, 1969, pp. 4344-4348, No. 12.
Jeffrey L. Cummings et al., Behavioral effects of memantine in Alzheimer disease patients receiving donepezil treatment, Neurology, 2006, pp. 57-63, vol. 67.
Jenkins, et al., Disturbances in social interaction occur along with pathophysiological deficits following sub-chronic phencyclidine administration in the rat, Behavioural Brain Research, 2008, pp. 230-235, vol. 194, Elsevier B.V. All rights reserved.
Jensen_et_al., Allosteric Modulation of the Calcium-Sensing Receptor, Current Neuropharmacology, 2007, pp. 180-186, vol. 5 No. 3.

(56) References Cited

OTHER PUBLICATIONS

Jermy M. Henley., Characterization of the allosteric modulatory protein associated with non-NMDA receptors, Biochemical Society Transactions, 1993, pp. 1-5, vol. 21.

Jhee_et_al., B-amyloid therapies in Alzheimer's disease, Expert Opinion on Investigational Drugs, 2001, pp. 593-605, vol. 10 No. 4.

Jie Zhang et al., Neuroprotective effects of poly(ADP-ribose) polymerase inhibition on focal cerebral ischemia, Portland Press Proceedings, 1998, pp. 125, vol. 15 (Biology of Nitric Oxide, Part 6).

Jin, et al., The mGluR2 Positive Allosteric Modulator BINA Decreases Cocaine Self-Administration and Cue-induced Cocaine-Seeking and Counteracts Cocaine-Induced Enhancement of Brain Reward Function in Rats, Neuropsychopharmacology, 2010, pp. 2021-2036, vol. 35, Nature Publishing Group.

Jingami, et al., Structure of the metabotropic glutamate receptor, Current Opinion in Neurobiology, 2003, pp. 271-278, vol. 13, Elsevier Science Ltd.

Joffe, et al., Anxious and Nonanxious Depression, Am j Psychiatry, 1993, pp. 1257-1258, vol. 150 Issue 8.

Joffe, et al., Lifetime History of Depression and Anxiety Disorders as a Predictor of Quality of Life in Midlife Women in the Absence of Current Illness Episodes, Arch Gen Psychiatry, 2012, pp. 484-492, vol. 69 Issue 5, American Medical Association.

Johansen, et al., Excitatory Amino Acid Receptor Ligands: Resolution, Absolute Stereochemistry, and Enantiopharmacology of 2-Amino-3-(4-butyl-3-hydroxyisoxazol-5-yl)propionic Acid, Journal of Medicinal Chemistry, 1998, pp. 930-939, vol. 41 Issue 6, American Chemical Society.

John Dunlop., Glutamate-based therapeutic approaches: targeting the glutamate transport system, Current Opinion in Pharmacology, 2006, pp. 103-107, vol. 6, Elsevier Ltd.

John M. Hettema., The Nosologic Relationship Between Generalized Anxiety Disorder and Major Depression; Depression and Anxiety, 2008, pp. 300-316, vol. 25, Wiley-Liss, Inc.

John, et al., Rapid changes in glutamate levels in the posterior hypothalamus across sleep-wake states in freely behaving rats, Am J Physiol Regul Integr Comp Physiol, 2008, pp. R2041-R2049, vol. 295.

Johnson & Johnson Pharmaceutical Research & Development, L.L.C., A Dose-Ranging Study of JNJ-40411813 in Healthy Male Volunteers, ClinicalTrials.gov, May 19, 2011, JNJ-40411813, vol. NCT01358006.

Johnson & Johnson Pharmaceutical Research & Development, L.L.C., A Study of [11C] JNJ-42491293, a Possible PET Ligand for the mGlu2 Receptor, in Healthy Adult Volunteers, ClinicalTrials.gov, May 12, 2011, [11C] JNJ-42491293 [11C] JNJ-42491293 + JNJ-40411813, vol. NCT01359852.

Johnson & Johnson Pharmaceutical Research & Development, L.L.C., Ketamine Challenge Study With JNJ-40411813, ClinicalTrials.gov, Apr. 8, 2010, normal saline, ketamine, Placebo, vol. NCT01101659.

Johnson et al, Allosteric modulators of metabotropic glutamate receptors: lessons learnt from mGlu1, mGlu2 and mGlu5 potentiators and antagonists, Biochemical Society Transactions, 2004, pp. 881-887, vol. 32.

Johnson et al, Discovery of Allosteric Potentiators for the Metabotropic Glutamate 2 Receptor: Synthesis and Subtype Selectivity of N-(4-(2-Methoxyphenoxy)phenyl)-N-(2,2,2-trifluoroethylsulfonyl)pyrid-3-ylmethylamine, Journal of Medicinal Chemistry, 2003, pp. 3189-3192, vol. 46.

Johnson et al, Selective, Non-Amino Acid Allosteric mGlu2 Receptor Potentiators Inhibit Dural Plasma Protein Extravasation; A Potential Role in the Treatment of Migraine, Neuropharmacology, 2002, pp. 291, vol. 43.

Johnson, et al., Activation of group II metabotropic glutamate receptors induces long-term depression of excitatory synaptic transmission in the substantia nigra pars reticulata, Neuroscience Letters, 2011, pp. 102-106, vol. 504, Elsevier Ireland Ltd.

Johnson, et al., Disruption of GABAergic tone in the dorsomedial hypothalamus attenuates responses in a subset of serotonergic neurons in the dorsal raphe nucleus following lactate-induced panic, Journal of Psychopharmacology, 2008; pp. 642-652, vol. 22 Issue 6.

Johnson, et al., Group II metabotropic glutamate receptor type 2 allosteric potentiators prevent sodium lactate-induced panic-like response in panic-vulnerable rats, Journal of Psychopharmacology, 2013, pp. 152-161, vol. 27 Issue 2.

Johnson, et al., Species Variations in Transmembrane Region V of the 5-Hydroxytryptamine Type 2A Receptor Alter the Structure—Activity Relationship of Certain Ergolines and Tryptamines, Molecular Pharmacology,, 1994, pp. 277-286, vol. 45.

Johson et al, Metabotropic glutamate 2 receptor potentiators: receptor modulation, frequency-dependent synaptic activity, and efficacy in preclinical anxiety and psychosis model(s), Psychopharmacology, 2005, pp. 271-283, vol. 179.

Jones, et al., A Rotarod Suitable for Quantitative Measurements of Motor In. coordination in Naive Mice, Naunyn Schmiedebergs Archives Experimental Pathology Pharmacology, 1968, pp. 211, vol. 259 Issue 2.

Jones, et al., Characterization of a Novel Positive Allosteric Modulator of the Metabotropic Glutamate Receptor 4 (mGlu4) with Oral Efficacy in an Antiparkinsonian Animal Model, Journal of Medicinal Chemistry, 2011, pp. 7639-7647, vol. 54.

Jones, et al., The mGluR2/3 agonist LY379268 reverses post-weaning social isolation-induced recognition memory deficits in the rat, Psychopharmacology, 2011, pp. 269-283, vol. 214.

Jong Gun Lee et al., Benzylic Bromination of Alkylbenzenes with Sodium Bromate-Bromotrimethylsilane, Bull. Korean Chem. Soc., 1995, pp. 371-374, vol. 16, No. 4.

Jorn Arnt, Differential effects of classical and newer antipsychotics on the hypermotility induced by two dose levels of D-amphetamine, European journal of Pharmacology, 1995, pp. 55-62, vol. 283.

Jorn Arnt., Pharmacological Specificity of Conditioned Avoidance Response Inhibition in Rats: Inhibition by Neuroleptics and Correlation to Dopamine Receptor Blockade, Acta Pharmacol et toxicol, Apr. 20, 1982, pp. 321-329, vol. 51.

Joseph T. Coyle, The GABA-giutamate connection in schizophrenia: which is the proximate cause?, Biochemical Pharmacology, 2004, pp. 1507-1514, vol. 68, Elsevier Inc.

Julio-Pieper, et al., Exciting Times beyond the Brain: Metabotropic Glutamate Receptors in Peripheral and Non-Neural Tissues, Pharmacological Reviews, 2011, pp. 35-58, vol. 63 Issue 1.

Justine Kent., Safety, Tolerability and Potential Therapeutic Efficacy of a Novel Glutamate Modulator As Adjunctive Treatment in Patients With Schizophrenia, APA Meeting, 2013, pp. 1, Poster.

Kagaya, et al., Heterologous supersensitization between serotonin2 and alpha2-adrenergic receptor-mediated intracellular calcium mobilization in human platelets, Journal of Neural Transmission, 1992, pp. 25-36, vol. 88, Springer-Verlag.

Kahn, et al., Group 2 metabotropic glutamate receptors induced long term depression in mouse striatal slices, Neuroscience Letters, Oct. 15, 2001, pp. 178-182, vol. 316, Elsevier Science Ireland Ltd.

Kalivas, et al., Repeated Cocaine Administration Alters Extracellular Glutamate in the Ventral Tegmental Area, Journal of Neurochemistry, 1998, pp. 1497-1502, vol. 70 Issue 4, International Society for Neurochemistry.

Kambe et al, A Convenient Method for the Preparation of 2-Pyridone Derivates, Synthesis, Dec. 1977, pp. 841-842, No. 12.

Kapur, et al., From dopamine to salience to psychosis—linking biology, pharmacology and phenomenology of psychosis, Schizophrenia Research, Mar. 8, 2005, pp. 59-68, vol. 79, Elsevier B.V.

Kari A. Johnson et al, Glutamate Receptors as Therapeutic Targets for Parkinson's Disease, CNS & Neurological Disorders—Drug Targets, 2009, pp. 475-491, vol. 8.

Karl Gewald et al., Heterocyclen aus CH-aciden Nitrilen, VIII. 2-Amino-thiophene aus methylenaktiven Nitrile Carbonylverbindungen und Schwefel, Chemische Berichte, 1966, pp. 94-100, vol. 99.

Karl Gewald, Heterocyclen aus CH-aciden Nitrile, VII. 2-Amino-thiophene aus a-Oxo-mercaptanen und methylenaktiven Nitrile, Chemische Berichte, 1965, pp. 3571-3577, vol. 98.

Karlsson, et al., Loss of Glial Glutamate and Aspartate Transporter (Excitatory Amino Acid Transporter 1) Causes Locomotor Hyperactivity and Exaggerated Responses to Psychotomimetics: Rescue

(56) References Cited

OTHER PUBLICATIONS by Haloperidol and Metabotropic Glutamate 2/3 Agonist, Biol Psychiatry, 2008, pp. 810-814, vol. 64, Society of Biological Psychiatry.
Kato., Molecular genetics of bipolar disorder and depression, Psychiatry and Clinical Neurosciences, 2007, pp. 3-19, vol. 61.
Katon, et al., Major Depression: The Importance of Clinical Characteristics and Treatment Response to Prognosis, Depression and Anxiety, 2010, pp. 19-26, vol. 27, Wiley-Liss, Inc.
Kaupmann, et al., Expression Cloning of GABA receptors uncovers similarity to metabotropic glutamate receptors, Nature, Mar. 20, 1997; pp. 239-246, vol. 386.
Kawabata, et al., Diversity of Calcium Signaling by Metabotropic Glutamate Receptors, The Journal of Biological Chemistry, 1998, pp. 17381-17385, vol. 273 issue 28.
Kearney, et al., Intrasubthalamic Nucleus Metabotropic Glutamate Receptor Activation: A Behavioral, FOS Immunohistochemical and [14C]2-Deoxyglucose Autoradiographic Study, Neuroscience, 2000, pp. 409-416, vol. 95 Issue 2, Elsevier Science Ltd.
Kearney, et al., Metabotropic Glutamate Agonist-Induced Rotation: APharmacological, FOS Immunohistochemical and [14c]-2-Deoxyglucose Autoradiographic Study, The Journal of Neuroscience, Jun. 1, 1997, pp. 4415-4425, vol. 17 Issue 11.
Kehne, et al., Anxiolytic effects of buspirone and gepirone in the fear-potentiated startle paradigm, Psychopharmacology, 1988, pp. 8-13, vol. 94, Springer-Verlag.
Keller, et al., Anxiety Symptom Relief in Depression Treatment Outcomes, J Clin Psychiatry, 1995, pp. 22-29, vol. 56 Issue 6.
Kellner et al, Effects of a metabotropic giutamate2/3 receptor agonist (LY544344/LY354740) on panic anxiety induced by cholecystokinin tetrapeptide in healthy humans: preliminary results, Psychopharmacology, 2005, pp. 310-315, vol. 179.
Kenakin, et al., Seven Transmembrane Receptors as Shapeshifting Proteins: The Impact of Allosteric Modulation and Functional Selectivity on New Drug Discovery, Pharmacological Reviews, 2010, pp. 265-304, vol. 62 Issue 2, Pharmacology and Experimental Therapeutics.
Kenakin, et al., Signalling bias in new drug discovery: detection, quantification and therapeutic impact, Nature Reviews | Drug Discovery, 2013, pp. 205-216, vol. 12.
Kenakin., Collateral efficacy in drug discovery: taking advantage of the good (allosteric) nature of 7TM receptors, Trends in Pharmacological Sciences, 2007, pp. 407-415, vol. 28 Issue 8.
Kendler, et al., Major Depression and Generalized and Disorder, Arch Gen psychiatry, 1992, pp. 716-722, vol. 49.
Kenji Hashimoto., Emerging role of glutamate in the pathophysiology of major depressive disorder, Brain Researchre Views, May 28, 2009, pp. 105-123, vol. 61, Elsevier B.V. All rights reserved.
Kenneth S. Kendler., The Nosologic Validity of Paranoia (Simple Delusional Disorder), Arch Gen Psychiatry, 1980, pp. 699-706, vol. 37.
Kennett, et al., Evidence That 5-HT2c receptor antagonists are anxiolytic in the rat Geiier-Seifter model of anxiety, Psychopharmacology, 1994, pp. 90-96, vol. 114.
Kenny, et al., Group II Metabotropic and -Amino-3-hydroxy-5-methyl-4 isoxazole Propionate (AMPA)/Kainate Glutamate Receptors Regulate the Deficit in Brain Reward Function Associated with Nicotine Withdrawal in Rats, The Journal of Pharmacology and Experimental Therapeutics, 2003, pp. 1068-1076, vol. 306 Issue 3.
Kenny, et al., The ups and downs of addiction: role of metabotropic glutamate receptors, Trends in Pharmacological Sciences, 2004, pp. 265-272, vol. 25 Issue 5, Elsevier Ltd.
Kessler, et al ., The Epidemiology of Co-Occurring Addictive and Mental Disorders: Implications for Prevention and Service Utilization, American Journal of Orthopsychiatry, 1996, pp. 17-31, vol. 66 Issue 1.
Kessler, et al., Comorbid Major Depression and Generalized Anxiety Disorders in the National Comorbidity Survey follow-up, Psychol Med., 2008, pp. 365-374, vol. 38 Issue 3.
Kessler, et al., Epidemiology of Anxiety Disorders, Behavioral Neurobilogy of Anxiety and its Treatment., 2010, pp. 21-35, vol. 2.
Kessler, et al., Impairment in Pure and Comorbid Generalized Anxiety Disorder and Major Depression at 12 Months in Two National Surveys, American Journal of Psychiatry, 1999, pp. 1915-1923, vol. 156 issue 12.
Kessler, et al., Lifetime and 12-Month Prevalence of DSM-III-R Psychiatric Disorders in the United States, Arch Gen Psych.iatry., 1994, pp. 8-19, vol. 51.
Kessler, et al., Rethinking the duration requirement for generalized anxiety disorder: evidence from the National Comorbidity Survey Replication, Psychological Medicine, 2005, pp. 1073-1082, vol. 35.
Kessler, et al., The Epidemilogy of Major Depressive Disorder Results Form the National Comorbidity Survey Replication (NCS-R), JAMA, Jun. 18, 2003, pp. 3095-3105, vol. 289 Issue 23.
Kew, et al., Activity-dependent presynaptic autoinhibition by group II metabotropic glutamate receptors at the perforant path inputs to the dentate gyrus and CA1, Neuropharmacology, 2001, pp. 20-27, vol. 40, Elsevier Science Ltd.
Kew, et al., Differential regulation of synaptic transmission by mGlu2 and mGlu3 at the perforant path inputs to the dentate gyrus and CA1 revealed in mGlu2-/-mice, Neuropharmacology, 2002, pp. 215-221, vol. 43, Elsevier Science Ltd. All rights reserved.
Kew, et al., Ionotropic and metabotropic glutamate receptor structure and pharmacology, Psychopharmacology, Feb. 25, 2005, pp. 4-29, vol. 179, Springer-Verlag.
Khimia., Khimiia Geterotsiklicheskikh Soedinenii, KHIM Geterotikl Soedin, 1985, pp. 646-4-649, vol. 5.
Khimia., Khimiia Geterotsiklicheskikh Soedinenii, KHIM Geterotikl Soedin, 1986, pp. 1118-1123, vol. 8.
Kilama et al, A New Synthetic Approach to the C-D Ring Portion of Streptonigrin Analogues, Journal of Heterocyclic Chemistry, Jul.-Aug. 1990, pp. 1437-1440, vol. 27.
Kilbride, et al., Presynaptic Group II mGluR Inhibition of Short-Term Depression in the Medial Perforant Path of the Dentate Gyrus In Vitro, Journal of Neurophysiology, Mar. 13, 2001, pp. 2509-2515, vol. 85.
Kilbride, et al., Presynaptic inhibitory action of the group II metabotropic glutamate receptor agonists, LY354740 and DCG-IV, European Journal of Pharmacology, 1998, pp. 149-157, vol. 356, Elsevier Science B.V.
Kilts., The Changing Roles and Targets for Animal Models of Schizophrenia, Biol Psychiatry, 2001, pp. 845-855, vol. 50.
Kim, et al., Activation of Metabotropic Glutamate Receptors in the Rat Nucleus Accumbens Increases Locomotor Activity in a Dopamine-Dependent Manner1, The Journal of Pharmacology and Experimental Therapeutics, 1997, pp. 962-968, vol. 283 issue 2, Pharmacology and Experimental Therapeutics.
Kim, et al., Group II Metabotropic Glutamate Receptor Stimulation Triggers Production and Release of Alzheimer's Amyloid 42 from Isolated Intact Nerve Terminals, The Journal of Neuroscience, Mar. 17, 2010, pp. 3870-3875, vol. 30 Issue 11.
Kim, et al., Metabotropic Glutamate Receptors in the Rat Nucleus Accumbens Contribute to Amphetamine-Induced Locomotionl, The Journal of Pharmacology and Experimental Therapeutics, 1998, pp. 317-322, vol. 284 Issue 1, Pharmacology and Experimental Therapeutics.
Kim, et al., Metabotropic Glutamate Receptors: Phosphorylation and Receptor Signaling, Journal of Neuroscience Research, 2008, pp. 1-10, vol. 86, Wiley-Liss, Inc.
Kim, et al., Neurofilament-M Interacts with the D1 Dopamine Receptor to Regulate Cell Surface Expression and Desensitization, The Journal of Neuroscience, Jul. 15, 2002, pp. 5920-5930, vol. 22 Issue 14, Society for Neuroscience.
Kim, et al., Predictors of 12-week remission in a nationwide cohort of people with depressive disorders: the CRESCEND study, Hum. Psychopharmacol Clin Exp, Feb. 23, 2011, pp. 41-50, vol. 26, John Wiley & Sons, Ltd.
Kingston, et al., LY341495 is a nanomolar potent and selective antagonist of group II metabotropic glutamate receptors, Neuropharmacology, 1998, pp. 1-12, vol. 37, Elsevier Science Ltd.

(56) References Cited

OTHER PUBLICATIONS

Kingston, et al., Neuroprotection by metabotropic glutamate receptor agonists: LY354740, LY379268 and LY389795, European Journal of Pharmacology, 1999, pp. 155-165, vol. 377, Elsevier Science B.V.
Kingston, et al., Neuroprotective Actions of Novel and Potent Ligands of Group I and Group II Metabotropic Glutamate Receptors, Annals New York Academy of Sciences, 1999, pp. 438-449, vol. 890.
Kiselyov, A one-pot synthesis of polysubstituted imidazo[1,2-a]pyridines, Tetrahedron Letters, 2006, pp. 2941-2944, vol. 47.
Kitano et al, Synthesis and antifouling activity of 3-isocyanotheonellin and its analogues, Journal of The Chemical Society-perkin Transactions I, 2002, pp. 2251-2255.
Klein, et al., Glutamatergic Activation of Hippocampal Phospholipase D: Postnatal Fading and Receptor Desensitization, Journal of Neurochemistry, 1998, pp. 1679-1685, vol. 70 issue 4, International Society for Neurochemistry.
Knesevich, et al., Validity of the Hamilton Rating Scale for Depression, Brit. J. Psychiat., 1977, pp. 49-52, vol. 131.
Kniazeff, et al., Closed state of both binding domains of homodimeric mGlu receptors is required for full activity, Nature Structural & Molcular Bollogy, 2004, pp. 706-713, vol. 11 Issue 8.
Knight, et al., Pharmacological characterisation of the agonist radioligand binding site of 5-HT2A, 5-HT2B and 5-HT2C receptors, Naunyn-Schrniedeberg's Arch Pharmacol, 2004, pp. 114-123, vol. 370, Springer-Verlag.
Knoflach, et al., A Potent Orally Active Non-Competitive Group II Metabotropic Glutamate Receptor Antagonist With Cognitive Enhancing Properties, Taormina Sicily-Italy, 2005, pp. 1-1, Poster.
Kodama, et al., Enhanced glutamate release during REM sleep in the rostromedial medulla as measured by in vivo microdialysis, Brain Research, 1998, pp. 178-161, vol. 780, Elsevier Science B.V. All rights reserved.
Koh, et al., Deficits in social behavior and sensorimotor gating in mice lacking phospholipase Cb1, Genes, Brain and Behavior, 2008, pp. 120-128, vol. 7, Blackwell Publishing Ltd.
Koh, et al., Non-NMDA Receptor-Mediated Neurotoxicity in Cortical Culture, The Journal of Neuroscience, 1990, pp. 693-705, vol. 10 Issue 2.
Koh, et al., Treatment Strategies Targeting Excess Hippocampal Activity Benefit Aged Rats with Cognitive Impairment, Neuropsychopharmacology, 2010, pp. 1016-1025, vol. 35.
Komossa, et al., Second-generation antipsychotics for major depressive disorder and dysthymia, Cochrane Database of Systematic Reviews, 2012, pp. 1-214, Issue 12, JohnWiley & Sons, Ltd.
Konarski, et al., Volumetric neuroimaging investigations in mood disorders: bipolar disorder versus major depressive disorder, Bipolar Disorders, 2008, pp. 1-37, vol. 10.
Konstantakopoulos, et al., Lamotrigine-associated exacerbation of positive symptoms in paranoid schizophrenia, Schizophrenia Research, 2008, pp. 325-326, vol. 98.
Koolschijn, et al., Brain Volume Abnormalities in Major Depressive Disorder: A Meta-Analysis of Magnetic Resonance Imaging Studies, Human Brain Mapping, 2009, pp. 3719-3735, vol. 30.
Koroshetz, et al., Emerging treatments for stroke in humans, Trends in Pharamocol. Sci., 1996, pp. 227-233, vol. 17.
Kostrzewa, et al., Supersensitized D1 Receptors Mediate Enhanced Oral Activity After Neonatal 6-OHDA, Pharmacology Biochemistry & Behavior, 1991, pp. 677-682, vol. 39, Pergamon Press plc.
Kotlinska, et al., The role of group I mGlu receptors in the expression of ethanol-induced conditioned place preference and ethanol withdrawal seizures in rats, European Journal of Pharmacology, 2011, pp. 154-161, vol. 670, Elsevier B.V.
Koulen, et al., Group II and Group 111 Metabotropic Glutamate Receptors in the Rat Retina: Distributions and Developmental Expression Patterns, European Journal of Neuroscience, 1996, pp. 2177-2187, vol. 8.
Kowal, et al., A [35S]GTPgS binding assessment of metabotropic glutamate receptor standards in Chinese hamster ovary cell lines expressing the human metabotropic receptor subtypes 2 and 4, Neuropharmacology, 1998, pp 179-187, vol. 37.
Kowal, et al., Functional calcium coupling with the human metabotropic glutamate receptor subtypes 2 and 4 by stable co-expression with a calcium pathway facilitating G-protein chimera in Chinese hamster ovary cells, Biochemical Pharmacology, 2003, pp. 785-790, vol. 66.
Krishnan, et al., The molecular neurobiology of depression, Nature, Oct. 16, 2008, pp. 894-902, vol. 455.
Krivoy, et al., The possible involvement of metabotropic glutamate receptors in schizophrenia, European Neuropsychopharmacology, 2008, pp. 395-405, vol. 18, Elsevier B.V, and ECNP, All rights reserved.
Krohnke, et al., "Methylketon-Addukte Der Chinolinium-Und Isochinolinium-Reihe", "Methylketon-Addukte Der Chinolinium-Und Isochinolinium-Reihe", Jun. 12, 1956, pp. 211-228, Page Number.
Krystal, et al., Comparative and interactive Human Psychopharmacologic Effects of Ketamine and Amphetamine, Arch Gen Psychiatry, Mar. 18, 2005, pp. 985-995, vol. 62.
Krystal, et al., Neuroplasticity as a target for the pharmacotherapy of anxiety disorders, mood disorders, and schizophrenia, Drug Discovery Today, 2009, pp. 690-697, vol. 14.
Krystal, et al., NMDA receptor antagonist effects, cortical giutamatergic function, and schizophrenia: toward a paradigm shift in medication development, Psychopharmacology, Sep. 2, 2003, pp. 215-233, vol. 169.
Krystal, et al., Potential Psychiatric Applications of Metabotropic Glutamate Receptor Agonists and Antagonists, CNS Drugs, 2010, pp. 669-693, vol. 24 Issue 8, Adis Data Information BV. All rights reserved.
Krystal, et al., Preliminary evidence of attenuation of the disruptive effects of the NMDA glutamate receptor antagonist, ketamine, on working memory by pretreatment with the group II metabotropic glutamate receptor agonist, LY354740, in healthy human subjects, Psychopharmacology, 2005, pp. 303-309, vol. 179.
Krystal, et al., Subanesthetic Effects of the Noncompetitive NMDA Antagonist, Ketamine, in Humans, Arch Gen Psychiatry, 1994, pp. 199-214, vol. 51.
Krystal,et al., N-methyl-D-aspartate glutamate receptors and alcoholism: reward, dependence, treatment, and vulnerability, Pharmacology & Therapeutics, 2003, pp. 79-94, vol. 99.
Kubo, et al., Structural Basis for a Ca21-Sensing Function of the Metabotropic Glutamate Receptors, Science, Mar. 13, 1998, pp. 1722-1725, vol. 279.
Kubokawa, et al., Cloning and characterization of a bifunctional metabotropic receptor activated by both extracellular calcium and glutamate, FEBS Letters, 1996, pp. 71-76, vol. 392.
Kucukibrahimoglu, et al., The change in plasma GABA, glutamine and glutamate levels in fluoxetine- or S-citalopram-treated female patients with major depression, Eur J Clin Pharmacol, 2009, pp. 571-577, vol. 65.
Kufahl, et al, Enhanced Sensitivity to Attenuation of Conditioned Reinstatement by the mGluR2/3 Agonist LY379268 and Increased Functional Activity of mGluR2/3 in Rats with a History of Ethanol Dependence, Neuropsychopharmacology, 2011, pp. 1-12, ?, American College of Neuropsychopharmacology.
Kugaya, et al., Beyond Monoamines: Glutamatergic Function in Mood Disorders, CNS Spectrums, 2005, pp. 808-818, vol. 10 Issue 10.
Kullmann, et al., Extrasynaptic glutamate spillover in the hippocampus: evidence and implications, TINS, 1998, pp. 8-14, vol. 21 Issue 1.
Kunio Yui et al., Studies of Amphetamine or Methamphetamine Psychosis in Japan. Relation of Methamphetamine Psychosis to Schizophrenia, Annals of the New York Academy of Sciences, 2000, pp. 1-12, vol. 914.
Kunishima, et al., Structural basis of glutamate recognition by a dimeric metabotropic glutamate receptor, Nature, Oct. 26, 2000, pp. 971-977, vol. 407.
Kurita, et al., HDAC2 regulates atypical antipsychotic responses through the modulation of mGlu2 promoter activity, Nature Neuroscience, 2012, pp. 1245-1254, vol. 15 Issue 9.

(56) References Cited

OTHER PUBLICATIONS

Kurumaji, et al., Effects of MK-801 Upon Local Cerebral Glucose Utilisation in Conscious Rats and in Rats Anaesthetised with Halothane, Journal of Cerebral Blood Flow and Metabolism, 1989, pp. 786-794, vol. 9 Issue 6.
Kłodzinska, et al., Roles of group II metabotropic glutamate receptors in modulation of seizure activity, Naunyn-Schmiedeberg's Arch Pharmacol, 2000, pp. 283-288, vol. 361.
Kłodzinska,et al., Group II mGlu receptor agonists inhibit behavioural and electrophysiological effects of DOI in mice, Pharmacology, Biochemistry and Behavior, Feb. 8, 2002, pp. 327-332, vol. 73, Elsevier Science.
Kłodzińska, et al., Selective Group II Glutamate Metabotropic Receptor Agonist LY354740 Attenuates Pentetrazole- and Picrotoxin-Induced Seizures, Polish Journal of Pharmacology, 1999, pp. 543-545, vol. 51.
L Fuentes et al, Synthesis of Heterocyclic Compounds, Synthesis of Heterocyclic Compounds, 1984, 768-770, 1.
L. H. Klemm et al., Chemistry of Thienopyridines. VIII. Substitution Products Derived from Thieno[2,3-b]pyridine 7-Oxide (1), Journal of Heterocyclic Chemistry, 1970, pp. 81-89, vol. 7, No. 1.
L. Yakovidis et al., Copper(II) Complexes of Thieno[2,3-d]pyrimidine Derivatives, Inorganica Chimica Acta, 1988, pp. 165-167, vol. 151.
Lahti, et al, Ketamine activites psychosis and alters limbic blood flow in schizopherenia, Neuro Report, 1995, pp. 869-872, vol. 6 Issue 6, Rapid Communications of Oxford Ltd.
Lam, et al, Effects of the selective metabotropic glutamate agonist LY354740 in a rat model of permanent ischaemia, Neuroscience Letters, 1998, pp. 121-123, vol. 254.
Lambeng,et al., Selective Mglur2 Negative Allosteric Modulators Reverse the Scopolamine-Induced Memory Deficit in the Novel Object Recognition Test, Society for Neuroscience 40th Annual Meeting, Nov. 2010, pp. 1, ?.
Lambert, et al, Current Issues in Schizophrenia: Overview of Patient Acceptability, Functioning Capacity and Quality of Life, CNS Drugs, 2004, pp. 5-17, vol. 18 Issue 2.
Lamers, et al., Comorbidity Patterns of Anxiety and Depressive Disorder in a Large Cohort Study: the Netherland Study of Depression and Anxiety (NESDA), J Clin Psychiatry, 2011, pp. 341-348, vol. 72, issue 3.
Lamotrigine, Highlights of Prescribing Information, Highlights of Prescribing Information, 2012, pp. 1-64, ?.
Landen, et al., A randomized, Double-Blind, Placebo-Controiied Trial of Buspirone in Combination With an SSRI in patients With Treatment-Refractory Depression, J Clin Psychiatry, 1998, pp. 664-668, vol. 59 Issue 12.
Landin, et al, The Impact of Restrictive Entry Criterion During the Placebo Lead-In Period, Biometrics, 2000, pp. 271-278, vol. 56.
Landmark., Antiepileptic drugs in non-epilepsy disorders: relations between mechanisms of action and clinical efficacy, CNS Drugs 2006, vol. 22(1), 2006, pp. 27-47, vol. 1.
Lane, et al., Bridging the gap: bitopic ligands of G-protein-coupled receptors, Trends in Pharmacological Sciences, 2013, pp. 59-66, vol. 34 Issue 1.
Lang, et al, Molecular Mechanisms of Depression: Perspectives on New Treatment Strategies, Cellular Physiology and Biochemistry, May 31, 2013, pp. 761-777, vol. 31, S. Karger AG, Basel.
Lang, et al, Molecular Mechanisms of Schizophrenia, Cellular Physiology and Biochemistry, Sep. 11, 2007, pp. 687-702, vol. 20, S, Karger AG, Basel.
Langmead, et al., Ligand properties and behaviours in an allosteric age, Trends in Pharmacological Sciences, 2012, pp. 621-622, vol. 33 Issue 12.
Langmead,, Screening for Positive Allosteric Modulator: Assessment of Modulator Concentration-Response Curves as a Screening Paradigm, Journal of Biomolecular Screening, 2007, pp. 668-676, vol. 12, Issue 5.
Large,et al., The potential role of lamotrigine in schizophrenia, Psychopharmacology, 2005, pp. 415-436, vol. 181.
Larock et al,—, Comprehensive Organic Transformations, 1989, pp. 595-596.
Larsson,, Neurochemical and behavioral studies on ethanol and nicotine interactions, Neuroscience and Biobehavioral Reviews, 2004, pp. 713-720, vol. 27, Elsevier Ltd.
Laruelle, et al, Glutamate, Dopamine and Schizophrenia from Pathaphysiology to Treatment, Annals New York Academy Science, 2003, pp. 138-158, vol. 1003.
Laruelle, et al., Relationships between Radiotracer Properties and Image Quality in Molecular Imaging of the Brain with Positron Emission Tomography, Molecular Imaging and Biology, 2003, pp. 363-375, vol. 5 Issue 6, Elsevier Inc.
Larzabal, et al, Distribution of the group II metabotropic glutamate receptors (mGluR2/3) in the enteric nervous system of the rat, Neuroscience Letters, 1999, pp. 91-94, vol. 276, Elsevier Science Ireland Ltd.
Laughren, et al, The scientific and ethical basis for placebo-controlled trials in depression and schizophrenia: an FDA perspective, Eur Psychiatry, 2001, pp. 418-423, vol. 16, Éditions scientifiques et médicales Elsevier SA.
Laughren, et al., Food and Drug Administration perpective on Negative Symptoms in Schizophrenia as a Target Claim, Schizophrenia Bulletin, 2006, pp. 220-222, vol. 32 Issue 2.
Lavreysen, et al, JNJ16259685, a highly potent, selective and systemically active mGlu1 receptor antagonist, Neuropharmacology, 2004, pp. 961-972, vol. 47.
Lavreysen, et al, Pharmacological Characterization of JNJ-40068782, a New Potent, Selective, and Systemically Active Positive Allosteric Modulator of the mGlu2 Receptor and Its Radioligand [3H]JNJ-40068782s, The Journal of Pharmacology and Experimental Therapeutics, 2013, pp. 514-527, vol. 346.
Lavreysen, et al., [3H]R214127: A Novel High-Affinity Radioligand for the mGlu1 Receptor Reveals a Common Binding Site Shared by Multiple Aliosteric Antagonists, Molecular Pharmacology, 2003, pp. 1062-1093, vol. 63 Issue 5.
Lavreysen, et al., The Development of Mg1u2 Pams: Identification of JNJ-40068782 as a Novel Tool Compound, Allosteric Modulator Drug Discovery Congress, Nov 2010, pp. 34, poster.
Lavreysen, et al., Therapeutic Potential of Group III Metabotropic Glutamate Receptors, Current Medicinal Chemistry, 2008, pp. 671-664, vol. 15 Issue 7, Bentham Science Publishers Ltd.
Lavreysen, et al., "JNJ-40068782: A Novel Potent, Selective and Systemically Active Positive Allosteric Modulator of the Mglu2 Receptor", Society for Neuroscience Annual Meeting, 2010, pp. 1-1, Abstract.
Lavreysen,et al., A Study on the Molecular Interaction Between Mglu2 Receptor Agonists and Positive Allosteric Modulators, Society for Neuroscience Annual Meeting, 2009, pp. 1, Poster.
Lavreysen,et al., A study on the molecular interaction between mGlu2 receptor agonists and positive allosteric modulators., International Meeting on Metabotropic Glutamate Receptors, 2008, pp. 1, Abstract.
Lawrence C. Kuo, Allosteric cofactor-mediated enzyme cooperativity: A theoretical treatment, Proc. Nati. Acad. Sci. USA, 1983, pp. 5243-5247, vol. 80.
Leach, et al., Allosteric GPCR modulators: taking advantage of permissive receptor pharmacology, Trends in Pharmacological Sciences, 2007, pp. 382-389, vol. 28, Issue 8.
Leach, et al., Quantification of Allosteric Interactions at G Protein-Coupled Receptors Using Radioligand Binding Assays, Current Protocols in Pharmacology, 2011, pp. 1.22.1-1.22.41, vol. 52, John Wiley & Sons, Inc.
Lecci, et al., Pharmacological validation of a novel animal model of anticipatory anxiety in mice, Psychopharmacology, Jan. 2, 1990, pp. 255-261; vol. 101.
Lee, et al., Amyloid precursor protein processing is stimulated by metabotropic glutamate receptors, Proc. Natl. Acad. Sci., 1995, pp. 8083-8087, vol. 92.
Lee, et al., Characterization of the inward current induced by metabotropic glutamate receptor stimulation in rat ventromedial hypothalamic neurones, Journal of Physiology, 1997, pp. 649-663, vol. 504, Issue 3.

(56) References Cited

OTHER PUBLICATIONS

Lee, et al., G lutamatergic afferent projections to the dorsal raphe nucleus of the rat, Brain Research, 2003, pp. 57-71, vol. 963.

Lee, et al., The effect of mGluR2 activation on signal transduction pathways and neuronal cell survival, Brain Research, 2009, pp. 244-250; vol. 1249.

Lee, et al., The mGlu2/3 receptor agonist LY354740 suppresses immobilization stress-induced increase in rat prefrontal cortical BDNF mRNA expression, Neuroscience Letters, 2006, pp. 328-332, vol. 398.

Lee,et al., Low Doses of Cannabinoids Enhance the Antinociceptive Effects of Intracisternally Administered Mglurs Groups II and III Agonists in Forrnalin-induced Tmj Nociception in Rats, Pain, 2008, pp. 367-375, vol. 139, Issue 2.

Leeson, et al., The influence of drug-like concepts on decision-making in medicinal chemistry, Nature Reviews, 2007, pp. 881-890, vol. 6.

Leever, et al., Identification of a Site in GluR1 and GluR2 That Is Important for Modulation of Deactivation and Desensitization, Molecular Pharmacology, 2003, pp. 5-10, vol. 64 Issue 1.

Lennon, et al., Metabotropic glutamate receptor mGlu2 is resistant to homologous agonist-induced desensitization but undergoes protein kinase C-mediated heterologous desensitization, European Journal of Pharmacology, 2010, pp. 29-37, vol. 649.

Lenox, et al., Mechanism of Action of Antidepressants and Mood Stabilizers, Neuropsychopharmacology, 2002, pp. 1139-1163, vol. 79.

Leo, et al., The application of nuclear magnetic resonance-based metabonomics to the dominant-submissive rat behavioral model, Analytical Biochemistry, 2005, pp. 174-178, vol. 339.

Lerner, et al., The Work Limitations Questionnaire, Medical Care, 2001, pp. 72-85, vol. 39, Issue 1, Lippincott Williams & Wilkins, Inc.

Leucht, et al., Second-generation versus fi rst-generation antipsychotic drugs for schizophrenia: a meta-analysis, Lancet, 2009, pp. 31-41, vol. 373.

Levine et al, The mGLU2/3 Receptor Agonist, LY354740, Reduces Panic Anxiety Induced by a CO2 Challenge in Patients Diagnosed with Panic Disorder, Neuropharmacology, 2002, pp. 273-318, vol. 43.

Levitz, et al., Optical control of metabotropic glutamate receptors, Nature Neuroscienence, Mar. 3, 2013, pp. 507-518, vol. 16, Issue 4.

Lewis, et al., Congnitive Dysfunction in Schizophrenia, Arch Neurol, 2006, pp. 1372-1376, vol. 63.

Lewis., The molecular choreography of a store-operated calcium channel, Nature, 2007, pp. 284-287, vol. 446, Nature Publishing-Group.

Leysen, et al., [3H]Ketanserin (R 41 468), a Selective 3H-Ligand for Serotonin2 Receptor Binding Sites, Molecular Pharmacology, 1982, pp. 301-314, vol. 21.

Leysen, et al., Receptor interactions of new antipsychotics: relation to pharmacodynamic and clinical effects, International journal of psychiatrynin Clinical practice, 1998, pp. S3-S17, vol. 2.

Lglesias, et al., Metabotropic glutamate receptor/phospholipase C system in female rat heart, Brain Research, Jan. 9, 2007, pp. 1-11, vol. 1153, Elsevier B.V.

Li, et al., Design and synthesis of 4-arylpiperidinyl amide and N-arylpiperdin-3-yl-cyclopropane carboxamide derivatives as novel melatonin receptor ligands, Bioorganic & Medicinal Chemistry Letters, 2011, pp. 1236-1242, vol. 21, Elsevier Ltd. All rights reserved.

Li, et al., Evaluation of the motor initiation hypothesis of APD-induced conditioned avoidance decreases, Pharmacology, Biochemistry and Behavior, 2004, pp. 811-819, vol. 78.

Lieberman, et al., A Randomized, Placebo-Controlled Study of Memantine as Adjunctive Treatment in Patients with Schizophrenia, Neuropsychopharmacology, 2009, pp. 1322-1329, vol. 34, Nature Publishing Group.

Lieberman, et al., Antipsychotic Drugs: Comparison in Animal Models of Efficacy, Neurotransmitter Regulation, and Neuroprotection, Pharmacological Reviews, 2008, pp. 358-403, vol. 60 Issue 3.

Lieberman, et al., Effectiveness of Antipsychotic Drugs in Patients with Chronic Schizopherenia, The New England Journal of Medicine, Sep. 22, 2005, pp. 1209-1223, vol. 353 issue 12.

Lieberman, et al., Serotonergic Basis of Antipsychotic Drug Effects in Schizophrenia, Biol Psychiatry, 1998, pp. 1099-1117, vol. 44, Society of Biological Psychiatry.

Liebowitz, et al., Biological Accompaniments of Lactate-Induced Panic, Psychopharmacology, 1984, pp. 43-44, vol. 20 Issue 1.

Liebowitz, et al., Lactate Provocation of Panic Attacks, Arch Gen Psychiatry, 1964, pp. 764-770, vol. 41.

Liechti, et al., Metabotropic glutamate 2/3 receptor activation induced reward deficits but did not aggravate brain reward deficits associated with spontaneous nicotine withdrawal in rats, biochemical pharmacology, 2007, pp. 1299-1307, vol. 74, Elsevier Inc. All rights reserved.

Liechti, et al., Metabotropic Glutamate 2/3 Receptors in the Ventral Tegmental Area and the Nucleus Accumbens Shell Are Involved in Behaviors Relating to Nicotine Dependence, The Journal of Neuroscience, 2007, pp. 9077-9085, vol. 27 Issue 34, Society for Neuroscience.

Liechti, et al., Role of the Glutamatergic System in Nicotine Dependence, CNS Drugs, 2008, pp. 705-724, vol. 22 Issue 9, Adis Data Information BV. All rights reserved.

Liechti,et al., Interactive effects of the mGlu5 receptor antagonist MPEP and the mGlu2/3 receptor antagonist LY341495 on nicotine self-administration and reward deficits associated with nicotine withdrawal in rats, European Journal of Pharmacology, 2007, pp. 164-174, vol. 554, Elsevier B.V. All rights reserved.

Lin, et al., A Meta-Analytic Review of Double-Blind, placebo-Controlled trails of Antidepressant Efficacy of Omega-3 Fatty Acids, J Clin Psychiatry, 2007, pp. 1056-1061, vol. 68 Issue 7.

Lindemann, et al, CTEP: A Novel, Potent, Long-Acting, and Orally Bioavailabie Metabotropic Glutamate Receptor 5 inhibitor, The Journal of Pharmacology and Experimental Therapeutics, Aug. 15, 2011, pp. 474-486, vol. 339 Issue 2, Pharmacology and Experimental Therapeutics.

Linden, et al, Anxiolytic Activity of the MGLU2/3 Receptor Agonist LY354740 on the Elevated Plus Maze is Associated with the Suppression of Stress-Induced c-Fos in the Hippocampus and Increases in c-Fos Induction in Several Other Stress-Sensitive Brain Regions, Neuropsychopharmacology, 2004, pp. 502-513, vol. 29, Nature Publishing Group All rights reserved.

Linden, et al., Anxiolytic-iike activity of the mGLU2/3 receptor agonist LY354740 in the elevated plus maze test is disrupted in rnetabotropic glutamate receptor 2 and 3 knock-out mice, Psychopharmacology, Dec. 24, 2004, pp. 284-291, vol. 179.

Linden, et al., Effects of mGiu2 or mGlu3 receptor deletions on mGlu2/3 receptor agonist (LY354740)-induced brain c-Fos expression: Specific roles for mGlu2 in the amygdala and subcortical nuclei, and mGlu3 in the hippocampus, Neuropharmacology, Mar. 10, 2006, pp. 213-228, vol. 51, Elsevier Ltd. All rights reserved.

Linden, et al., Use of MGLUR2 and MGLUR3 knockout mice to explore in vivo receptor specificity of the MGLUR2/3 selective antagonist LY341495, Neuropharmacology, May 15, 2009, pp. 172-182, vol. 57, Elsevier Ltd. All rights reserved.

Lindsley, et al., Progress Towards validating the NMDA Receptor Hypofunction Hypothesis of Schizophrenia, Current Topic in Medicinal Chemistry, 2006, pp. 771-785, vol. 6, Bentham Science Publisher Ltd.

Linn, et al., Activation of Metabotropic Glutamate Receptors Modulates the Voltage-Gated Sustained Calcium Current in a Teleost Horizontal Cell, Journal of neurophysiology, 1999, pp. 425-434, vol. 81 Issue 2.

Lipton,et al., Excitatory Amino Acids as a Final Common Pathway for Neurologic Disorders, The New England Journal of Medicine, 1994, pp. 613-622, vol. 330, No. 9.

Lisa Giovannelli et al., Comet Assay as a Novel Approach for Studying DNA Damage in Focal Cerebral Ischemia: Differential Effects of NMDA Receptor Antagonists and Poly(ADP-Ribose)

(56) References Cited

OTHER PUBLICATIONS

Polymerase Inhibitors, Journal of Cerebral Blood Flow and Metabolism, 2002, pp. 697-704, vol. 22.
Lissin, et al., An immunocytochemical Assay for Activity-Dependent Redistribution of Glutamate Receptors from the Postsynaptic Plasma Membrane, Redistribution of Glutamate, 1999, pp. 550-553, vol. 868.
Liu, et al., A unified theory of Two-Stage Adaptive Designs, Journal of the American Statistical Association, 2002, pp. 1034-1041, vol. 97 Issue 460.
Liu, et al., Doubly Randomized Delayed-Start Design for Enrichment Studies with Responders or Nonresponders, Journal of Biopharmaceutical Statistics, May 31, 2012, pp. 737-757, vol. 22 Issue 4, Taylor & Francis Group, LLC.
Liu, et al., Pharmacogenetic analysis of the mGlu2/3 agonist LY2140023 monohydrate in the treatment of schizophrenia, The Pharmacogenomics Journal, Dec. 21, 2010, pp. 01-09, ?, Macmillan Publishers Limited. All rights reserved.
Liu, et al., Ischemic Insults Direct Glutamate Receptor Subunit 2-Lacking AMPA Receptors to Synaptic Sites, The Journal of Neuroscience, May 17, 2006, pp. 5309-5319, vol. 26 Issue 20.
Lopez Rodriguez, et al., Changes in Extracellular Glutamate Levels in Rat Orbitofrontal Cortex During Sleep and Wakefulness, Archives of Medical Research, 2007, pp. 52-55, vol. 38, IMSS. Published by Elsevier Inc.
Lorenzetti, et al., Structural brain abnormalities in major depressive disorder: A selective review of recent MRI studies, Journal of Affective Disorders, Feb. 23, 2009, pp. 1-17, vol. 117, Published by Elsevier B.V.
Lorrain, et al., Group II mGlu Receptor Activation Suppresses Norepinephrine Release in the Ventral Hippocampus and Locomotor Responses to Acute Ketamine Challenge, Neuropsychopharmacology, Jun. 25, 2003, pp. 1622-1632, vol. 28, Nature Publishing Group All rights reserved.
Lou, et al., Allosteric modulation of the presynaptic Ca21 sensor for vesicle fusion, Nature, May 26, 2005, pp. 497-501, vol. 435, Nature Publishing Group.
Lourenco, et al., Differential distribution of metabotropic glutamate receptor subtype mRNAs in the thalamus of the rat, Brain Research, 2000, pp. 93-105, vol. 854, Elsevier Science B.V. All rights reserved.
Lowe, et al., Effects of a novel mGlu2/3 receptor agonist prodrug, LY2140023 monohydrate, on central monoamine turnover as determined in human and rat cerebrospinal fluid, Psychopharmacology, Aug. 17, 2011, pp. 1-12, Page Number, Springer-Verlag.
Lowry, et al., Serotonergic Systems, Anxiety, and Affective Disorder, Ann. N.Y. Acad. Sci, 2008, pp. 86-94, vol. 1148, New York Academy of Sciences.
Lujan, et al., Glutamate and GABA Receptor Signalling in the Developing Brain, Neuroscience, 2005, pp. 567-580, vol. 130, Elsevier Ltd.
Luscher, et al., Group 1 mGluR-Dependent Synaptic Long-Term Depression: Mechanisms and Implications for Circuitry and Disease, Neuron, Feb. 25, 2010, pp. 445-459, vol. 65.
Lyon, et al., Altered Hippocampal Expression of Glutamate Receptors and Transporters in GRM2 and GRM3 Knockout Mice, Synapse, Apr. 8, 2008, pp. 842-850, vol. 62, Wiley-Liss, Inc.
Lyon, et al., Fractionation of Spatial Memory in GRM2/3 (mGlu2/mGlu3) Double Knockout Mice Reveals a Role for Group II Metabotropic Glutamate Receptors at the Interface Between Arousal and Cognition, Neuropsychopharmacology, Aug. 10, 2011, pp. 1-13, ?, American College of Neuropsychopharmacology.
M-L. G. Wadenberg., Conditioned Avoidance Response in the Development of New Antipsychotics, Current Pharmaceutical Design, 2010, pp. 358-370, vol. 16 Issue 3, Bentham Science Publishers Ltd.
M. Arundine and M. Tymianski, Molecular mechanisms of glutamate-dependent neurodegeneration in ischemia and traumatic brain injury, Cellular and Molecular Life Sciences, 2004, pp. 657-668, vol. 61.
M. Foster Olive., Cognitive effects of Group I metabotropic glutamate receptor ligands in the context of drug addiction, European Journal of Pharmacology, 2010, pp. 47-58, vol. 639, Elsevier B.V.
M. Foster Olive., Metabotropic Glutamate Receptor Ligands as Potential Therapeutics for Addiction, Current Drug Abuse Reviews, 2009, pp. 83-98, Volujme 2 Issue 1, Bentham Science Publishers Ltd.
MacChiarulo, et al., The Role of Electrostatic Interaction in the Molecular Recognition of Selective Agonists to Metabotropic Glutamate Receptors, Proteins, 2003, pp. 609-619, vol. 50, Wiley-Liss, Inc.
Macek, et al., Differential involvement of group II and Group III mGluRs as Autoreceptors at Lateral and medial Perforant Path Synapses, Journal of Neurophysiology, 1996, pp. 3798-3806, vol. 76 Issue 6, The American Pliysioiogical Society.
Macek, et al., Protein Kinase C and A3 Adenosine Receptor Activation Inhibit Presynaptic metabotropic Glutamate Receptor (mGluR) Function and Uncouple mGluR Function and Uncouple mGluRs from GTP-Binding Proteins, The Journal of Neuroscience, Aug. 15, 1998, pp. 6138-6146, vol. 18 Issue 16, Society of Neuroscience.
MacKrill,, Protein-protein interactions in intracellular ca2+-Release Channel function, Biochem.J., 1999, pp. 345-361, vol. 337, Biochemical Society.
Maeda, et al., Different roles of group I and group II metabotropic glutamate receptors on phencyclidine-induced dopamine release in the rat prefrontal cortex, Neuroscience Letters, 2003, pp. 171-174, vol. 336, Elsevier Science Ireland Ltd. All rights reserved.
Maeng, et al., Cellular Mechanisms Underlying the Antidepressant Effects of Ketamine: Role of -Amino-3-Hydroxy-5-Methylisoxazole-4-Propionic Acid Receptors, Biol Psychiatry, May 23, 2007, pp. 349-352, vol. 63.
Maeso, et al., Hallucinogens Recruit Specific Cortical 5-HT2A Receptor-Mediated Signaling Pathways to Affect Behavior, Neuron, Feb. 1, 2007, pp. 439-452, vol. 53.
Maeso, et al., Transcriptome Fingerprints Distinguish Hallucinogenic and Nonhallucinogenic 5-Hydroxytryptamine 2A Receptor Agonist Effects in Mouse Somatasensory Cortex, The Journal of Neuroscience, Oct. 2, 2003, pp. 8836-8843, vol. 23, Issue 26.
Maione, et al., Characterisation of mGluRs which modulate nociception in the PAG of the mouse, Neuropharmacology, Jun. 17, 1998, pp. 1475-1483, vol. 37, Elsevier Science Ltd. All rights reserved.
Makoff, et al., Molecular characterization and localization of human metabotropic glutamate receptor type 3 1, Molecular Brain Research, Jan. 16, 1996, pp. 55-63, vol. 40, Elsevier Science B.V. All rights reserved.
Malames, et al., N-Substituted Spirosuccinimide, Spiropyridazine, Spiroazetidine, and Acetic Acid Aldose Reductase Inhibitiors Derived From Isoquinoline-1,3-Dinoes. 2., J Med Chem., Jan. 11, 1994, pp. 2059-2070, vol. 37 Issue 13.
Malatynska, et al., Assessing activity onset time and efficacy for clinically effective antidepressant and antimanic drugs in animal models based on dominant-submissive relationships, Neuroscience and Biobehavioral Reviews, 2007, pp. 904-919, vol. 31, Elsevier Ltd.
Malatynska, et al., Dominant-submissive behavior as models of mania and depression, Neuroscience and Biobehavioral Reviews, 2005, pp. 715-737, vol. 29.
Malatynska, et al., Levels of mRNA Coding for α-, β-, and γ-Synuclein in the Brains of Newborn, Juvenile, and Adult Rats, Journal of Molecular Neuroscience, Feb. 12, 2006, pp. 269-277, vol. 29, Humana Press Inc.
Malatynska, et al., Reduction of dominant or submissive behaviors as models for antimanic or antidepressant drug testing: Technical considerations, Journal of Neuroscience Methods, May 29, 2007, pp. 175-182, vol. 165, Elsevier B.V.
Malatynska, et al., Submissive behavior in mice as a test for antidepressant drug activity, Pharmacology, Biochemistry and Behavior, Sep. 26, 2005, pp. 306-313, vol. 82, Elsevier Inc. All rights reserved.
Malenka, et al., LTP and LTD: An Embarrassment of Riches, Neuron, Sep. 30, 2004, pp. 5-21, vol. 44 Issue 1, Cell Press.
Malherbe, et al., Identification of Essential Residues Involved in the Glutamate Binding Pocket of the Group II Metabotropic Glutamate Receptor, Molecular Pharmacology, Aug. 6, 2001, pp. 944-954, vol. 60 Issue 5, Pharmacology and Experimental Therapeutics.

(56) References Cited

OTHER PUBLICATIONS

Malherbe, et al., Opposite effects of Zn on the in vitro binding of [3H]LY354740 to recombinant and native metabotropic glutamate 2 and 3 receptors, Journal of Neurochemistry, 2005, pp. 150-160, vol. 94, International Society for Neurochemistry.

Malhi, et al., Recognizing the Anxious Face of Depression, The Journal of Nervous and Mental Disease, 2002, pp. 366-373, vol. 190 Issue 6, Lippincott Williams & Wilkins.

Malhotra, et al., NMDA Receptor Function and Human Cognition: The Effects of Ketamine in Healthy Volunteers, Neuro Psychopharmacology, 1996, pp. 301-307, vol. 14 Issue 5, Elsevier Science Inc.

Mansbach, et al., Blockade of potentiated startle responding in rats by 5-hydroxytryptamine IA receptor ligands, European Journal of Pharmacology, 1988, pp. 375-383, vol. 156, Elsevier Science Publishers B.V.

Marcotte, et al., Animal Models of Schizophrenia: A Critical Review, Psychiatry Neuroscience, Mar. 19, 2001, pp. 395-410, vol. 26 Issue 5.

Marcus, et al., The Efficacy and Safety of Aripiprazole as Adjunctive Therapy in Major Depressive Disorder, Journal of Clinical Psychopharmacology, 2008, pp. 156-165, vol. 28 Issue 2, Lippincott Williams & Wilkins.

Marek, et al., 5-Hydroxytryptamine2A (5-HT2A) receptor regulation in rat prefrontal cortex: Interaction of a phenethylamine hallucinogen and the metabotropic glutamate2/3 receptor agonist LY354740, Neuroscience Letters, May 2, 2006, pp. 256-260, vol. 403, Elsevier Ireland Ltd. All rights reserved.

Marek, et al., Glutamatergic (N-Methyl-D-aspartate Receptor) Hypofrontality in Schizophrenia: Too Little Juice or a Miswired Brain?, Molecular Pharmacology, 2010, pp. 317-326, vol. 77 Issue 3, Pharmacology and Experimental Therapeutics.

Marek, et al., Physiological Antagonism between 5-Hydroxytryptamine2A and Group II Metabotropic Glutamate Receptors in Prefrontal CortexI , The Journal of Pharmacology and Experimental Therapeutics, 2000, pp. 76-87, vol. 292 issue 1.

Marek, et al., The Electrophysiology of Prefrontal Serotonin Systems: Therapeutic Implications for Mood and Psychosis, Biol Psychiatry, Jan. 22, 1998, pp. 1118-1127, vol. 44, Society of Biological Psychiatry.

Marek,, Metabotropic glutamate 2/3 receptors as drug targets, Current Opinion in Pharmacology, 2004, pp. 18-22, vol. 4, Elsevier Ltd. All rights reserved.

Mark A. Geyer., Are cross-species measures of sensorimotor gating useful for the discovery of procognitive cotreatments for schizophrenia?, Dialogues in Clinical Neuroscience, 2006, pp. 9-16, vol. 8.

Mark E Fraley, Positive allosteric modulators of the metabotropic glutamate receptor 2 for the treatment of schizophrenia, Expert Opinion Ther. Patents, Sep. 1, 2009, pp. 1259-1276 (XP008121279), vol. 19, No. 9.

Martella, et al, Enhanced sensitivity to group II mGlu receptor activation at corticostriatal synapses in mice lacking the familial parkinsonism-linked genes PINK1 or Parkin, Experimental Neurology, 2009, pp. 388-396, vol. 215, Elsevier Inc. All rights reserved.

Martin, et al., Cellular Localization of a Metabotropic Glutamate Receptor in Rat Brain, Neuron, 1992, pp. 259-270, vol. 9, Cell Press.

Martin, et al., Cross-talk between L-adrenergic and metabotropic glutamate receptors in rat C6 glioma cells, Biochimica et Biophysica Acta, Mar. 5, 1998, pp. 186-192, vol. 1393, Elsevier Science B.V. All rights reserved.

Masashi Hamaguchi et al., Effects of hetero atom substituents in the decomposition of pyrazolines: abnormal behavior of methoxy group compared with arylthio or arylseleno group, Heterocycles, 1986, pp. 2111-2115, vol. 24.

Masu, et al., Sequence and expression of a metabotropic glutamate receptor, Nature, Feb. 28, 1991, pp. 760-764, vol. 349.

Matrisciano, et al., Defective group-II metaboropic glutamate receptors in the hippocampus of spontaneously depressed rats, Neuropharmacology, May 18, 2008, pp. 525-531, vol. 55, Elsevier Ltd. All rights reserved.

Matrisciano, et al., Group-Ii metabotropic glutamate receptor ligands as adjunctive drugs in the treatment of depression: a new strategy to shorten the latency of antidepressant medication?, Molecular Psychiatry, 2007, pp. 704-706, vol. 12, Nature Publishing Group.

Matrisciano, et al., Imipramine treatment up-regulates the expression and function of mGlu2/3 metabotropic glutamate receptors in the rat hippocampus, Neuropharmacology, Apr. 11, 2002, pp. 1008-1015, vol. 42, Elsevier Science Ltd.

Matthew J. Fisher et al., Non-Peptide RGD Surrogates Which Mimic a Gly-Asp B-Turn: Potent Antagonists of Platelet Glycoprotein IIb-IIIa, Journal of Medicinal Chemistry, 1997, pp. 2085-2101, vol. 40.

Maurel, et al., Cell-surface protein-protein interaction analysis with timeresolved FRET and snap-tag technologies: application to GPCR oligomerization, Nat Methods, 2008, pp. 561-567, vol. 5 Issue 6.

Max Hamilton, The Assessment of Anxiety States by Rating, Annual general meeting of the British psychological Society, 1959, pp. 50-55, page number.

Max Hamilton., A Rating Scale for Depression, J. Neurol. Neurosurg. Psychiat, 1960, pp. 56-62, vol. 23.

Max Hamilton., Diagnosis and Rating of Anxiety, The World's knowledge, 1969, pp. 76-79, page number.

Maxwell, et al., Ketamine Produces Lasting Disruptions in Encoding of Sensory Stimuli, The Journal of Pharmacology and Experimental Therapeutics, 2006, pp. 315-324, vol. 316 Issue 1, Pharmacology and Experimental Therapeutics.

May, et al, Allosteric Modulation of G Protein-Coupled Receptors, Annu. Rev. Pharrnacol. Toxicol, 2007, pp. 14.1-14.51, vol. 47, Annual Reviews All rights reserved.

May, et al., Regional Serotonin Receptor Studies: Chronic Methysergide Treatment Induces a Selective and Dose-Dependent Decrease in Serotonin-2 Receptors in Mouse Cerebral Cortex, Life Sciences, Feb, 24, 1986, pp. 1741-1747, vol. 38, Pergamon Press Ltd.

Mayers, et al., Antidepressants and their effect on sleep, human psychopharmacology, Oct, 17, 2005, pp. 533-559, vol. 20, John Wiley & Sons, Ltd.

Mayo Clinic Staff, Mental Illness, ?, 2012, pp. 1-13, Page Number.

McClintock, et al., Assessing anxious features in depressed outpatients, International Journal of Methods in Psychiatric Research, Nov. 4, 2011, pp. e69-e82, vol. 20 Issue 4, John Wiley & Sons, Ltd.

McDermott, et al., Design and analysis of two-period studies of potentially disease-modifying treatments, Controlled Clinical Trials, May 28, 2002, pp. 635-649, vol. 23, Elsevier Science Inc. All rights reserved.

McElvain, et al., Piperidine Derivatives. XXX. 1,4-Dialky1-4-arylpiperidines, Journal of the American Society, Aug. 5, 1958, pp. 3915-3923, vol. 80 Issue 15.

McEvoy, et al., Effectiveness of Clozapine versus olanzapine, Quetiapine , and Risperidone in Patients With Chronic Schizophrenia Who Did Not Respond to Prior Atypical Antipsychotic Treatment, Am J Psychiatry, 2006, pp. 600-610, vol. 163.

McIntyre, et al, Quetiapine Adjunct to Selective Serotonin Reuptake Inhibitors or Venlafaxine in Patients With Major Depression, Comorbid Anxiety, and Residual Depressive Symptoms: A Randomized, Placebo-Controlled Pilot Study, Depression and Anxiety, 2007, pp. 487-494, vol. 24, Wiley-Liss, Inc.

Meador Woodruff, et al., Glutamate receptor expression in schizophrenic brain 1, Brain Research Reviews, 2000, pp. 288-294, vol. 31, Elsevier Science B.V. All rights reserved.

Melancon, et al., Allosteric Modulation of 7 Transmembrane Spanning Receptors: Theory, Practice and Opportunities for CNS Drug Discovery1 , J Med Chem, Feb. 23, 2012, pp. 1445-1464, vol. 55 Issue 4.

Melartin, et al., Current Comorbidity of Psychiatric Disorders Among DSM-IV Major Depressive Disorder Patients in Psychiatric Care in the vantaa Depression Study, J Clin Psychiatry, 2002, pp. 126-134, vol. 63 Issue 2.

(56) References Cited

OTHER PUBLICATIONS

Meldrum, et al., Excitatory Amino Acid Neurotoxicity and Neurodegenerative Disease, Trends in Pharmacological Sciences, 1990, pp. 379-387, vol. 11 Issue 9.

Meldrum, et al., Glutamate receptors and transporters in genetic and acquired models of epilepsy, Epilepsy Research, 1999, pp. 189-204, vol. 36.

Meltzer, et al., Illuminating the molecular basis for some antipsychotic drug-induced metabolic burden, PNAS, Feb. 27, 2007, pp. 3019-3020, vol. 104 Issue 9.

Meltzer, et al., Serotonin receptors : their key role in drugs to treat schizophrenia, Progress in Neuro-Psychopharmacology & Biological Psychiatry, Sep. 9, 2003, pp. 1159-1172, vol. 27 Issue 7.

Merikangas, et al., Longitudinal Trajectories of Depression and Anxiety in a Prospective Community Study, Arch Gen Psychiatry, Oct. 2003, pp. 993-1000, vol. 60.

Mezler, et al., LY-2140023,a prodrug of the group II metabotropic glutamate receptor agonist LY-404039 for the potential treatment of schizophrenia, Curretn Opinion in Investigational Drugs, 2010, pp. 833-845, vol. 11 Issue 7.

Michael A. Gray et al., Functionalisation of 2-Methoxy-6-Methylpyridine, Synthetic Communications, 1994, pp. 1367-1379, vol. 24, No. 10.

Michael Davis and Michael J. Hudson, 2,1-Benzisothiazoles. XII. [1]. The Use of N-Substituted-2,1-Benzisothiazolium Salts as Synthetic Equivalents of o-Aminobenz-aldehydes. A Simple Synthesis of Some 2-Quinoiones, Journal of Heterocyclic Chemistry, 1983, pp. 1707-1708, vol. 20.

Michael Davis, Diazepam and Flurazepam Effects on Conditioned Fear as Measured With the Potentiated Startle Paradigm, Psychopharmacology, 1979, pp. 1-7, vol. 62, Springer-Verlag.

Michael E. Thase., Depression and sleep: pathophysiology and treatment, Dialogues in Clinical Neuroscience, 2006, pp. 217-226, vol. 8 issue 2, LLS SAS.

Michael E.Thase., Augmentation Strategies for Depression: History and Concepts, CNS Spectr, 2007, pp. 3-5, vol. 12:12 Issue 22, MBL Commuincations.

Michael J. Marino and P. Jeffrey Conn, Glutamate-based therapeutic approaches: allosteric modulators of metabotropic glutamate receptors, Current Opinion in Pharmacology, 2006, pp. 98-102, vol. 6.

Michael J. Panzer, M.D., Are SSRIs Really More Effective for Anxious Depression?, Annals of Clinical Psychiatry, 2005, pp. 23-29, vol. 17 Issue 1, Taylor and Francis Inc.

Michael, et al., Metabolic Changes Within the Left Dorsolateral Prefrontal Cortex Occurring with Electroconvulsive Therapy in Patients with Treatment Resistant Unipolar Depression, Psychol Med, 2003, pp. 1277-184, vol. 33 Issue 7.

Michael, et al., Neurotrophic Effects of Eletroconvuisive Therapy: A Proton Magnetic Resonance Study of the Left Amygdalar Region in Patients with Treatment-Resistant Depression, Neuropsychopharmacology, 2003, pp. 720-725, vol. 28 Issue 4.

Miller, et al., Mechanisms of Action of Antipsychotic Drugs of Different Classes, Refractoriness to Therapeutic Effects of Classical Neuroleptics, and Individual Variation in Sensitivity to Their Actions: Part I, Current Neuropharmacology, 2009, pp. 302-314, vol. 7.

Miller, et al., Roles of Metabotropic Glutamate Receptors in Brain Plasticity and Pathology Current Neuropharmacology, Annals of the New York Academy of Sciences, 1995, pp. 460-474, vol. 757.

Mills, et al., Epidemiology and Reporting of Randomized Trials Employing Re-Randomization of Patient Groups: A Systematic Survey, Contemporary Clinical Trials, 2007, pp. 268-275, vol. 28.

Mitchell, et al., An Update on the Role of Glutamate in the Pathophysiology of Depression, Acta Psychiatrica Scandinavica, 2010, pp. 192-210, vol. 122 Issue 3.

Mitri, et al., Divergent Evolution in Metabotropic Glutamate Receptors. A New Receptor Activated by an Endogenous Ligand Different from Glutamate in Insects, Journal of Biological Chemistry, 2004, pp. 9313-9320, vol. 279 Issue 10.

Mittal, et al., Impact of Comorbid Anxiety Disorders on Health-Related Quality of Live Among Patients with Major Depressive Disorder, Psychiatric Services, 2006, pp. 1731-1737, vol. 57 issue 12.

Miuller, et al., The Immunological Basis of Glutamatergic Disturbance in Schizophrenia: Towards an Integrated View, J Neural Transm, 2007, pp. 269-280, vol. 72.

Miyamoto, et al., Effects of Ketamine, Mk-801, and Amphetamine on Regional Brain 2-Deoxyglucose Uptake in Freely Moving Mice, Neuropsychopharmacology, 2000, pp. 400-412, vol. 22.

Miyamoto, et al., Treatments for Schizophrenia: A Critical Review of Pharmacology and Mechanisms of Action of Antipsychotic Drugs, Mol, Psychiatry, 2005, pp. 79-104, vol. 10.

Modafferi, et al., Morphine Withdrawal Increases Metabotropic Glutamate 2/3 Receptors Expression in Nucleus Accumbens, Neurochemistry, 2008, pp. 911-914, vol. 19 Issue 9.

Moffitt, et al., Depression and Generalized Anxiety Disorder, Arch. Gen. Psychiatry, 2007, pp. 651-660, vol. 64.

Moghaddam, et al., Activation of Giutamatergic Neurotransmission by Ketamine: A Novel Step in the Pathway from NMDA Receptor Blockade to Dopaminergic and Cognitive Disruptions Associated with the Prefrontal Cortex, J Neurosci, 1997, pp. 2921-2927, vol. 17 issue 8.

Moghaddam, et al., From Revolution to Evolution: the Glutamate Hypothesis of Schizophrenia and Its Implication for Treatment, Neuropsychopharmacology, 2012, pp. 4-15, vol. 37 issue 8.

Moghaddam, et al., Reversal of Phencyclidine Effects by a Group II Metabotropic Glutamate Receptor Agonist in Rats, Stem cell, Aug. 28, 1998, pp. 1349-1352, vol. 281.

Moghaddam, et al., Targeting Metabotropic Glutamate Receptors for Treatment of the Cognitive Symptoms of Schizophrenia, Psychopharmacology, 2004, pp. 39-44, vol. 174 issue 1.

Mohammed Mohammed Yousif et al., Studies on Tertiary Amine Oxides, LXXV. Reactions of Aromatic N-oxides with Meldrum's Acid in the Presence of Acetic Anhydride, Chem. Pharm. Bull., 1982, pp. 1680-1691, vol. 30, No. 5.

Moldrich et al, Glutamate metabotropic receptors as targets for drug therapy in epilepsy, European Journal of Pharmacology, 2003, p. 3-16, vol. 476.

Moldrich, et al., Anti-Epileptic Activity of Group II Metabotropic Glutamate Receptor Agonists (--)-2-Oxa-4-Aminobicyclo[3.1.0]Hexane-4,6-Dicarboxylate (Ly379268) and (--)-2-Thia-4-Aminobicyclo[3.1.0]Hexane-4,6-Dicarboxylate (Ly389795), Neuropharmacology, 2001, pp. 08-18, vol. 14.

Moldrich, et al., Astrocyte Mglu(2/3)-Mediated Camp Potentiation is Calcium Sensitive: Studies in Murine Neuronal and Astrocyte Cultures, Neuropharmacology, 2002, pp. 189-203, vol. 43 Issue 2.

Moldrich, et al., Emerging Signalling and Protein Interactions Mediated via Metabotropic Glutamate Receptors Moidrich _et_al., Curr. Drug Targets. CNS Neurol, Disord, 2003, pp. 109-122, vol. 02 Issue 2.

Molina; et al.; Polymorphic Variation at the Serotonin 1-A Receptor Gene is Associated with Comorbid Depression and Generalized Anxiety, Curr. Drug Targets. CNS Neurol. Disord, 2011, pp. 195-201, vol. 21.

Molinaro, et al., Activation of Mglu2/3 Metabotropic Glutamate Receptors Negatively Regulates the Stimulation of Inositol Phospholipid Hydrolysis Mediated by 5-Hydroxytryptamine2a Serotonin Receptors in the Frontal Cortex of Living Mice,, Mol. Pharmacol., 2009, pp. 379-387, vol. 76 Issue 2.

Mongin et al, Advanced in the directed metailation of azines and diazines (pyridines, pyrimidines, pyrazines, pyridazines, quinolines, benzodiazines and carbolines). Part 1, Tetrahedron, 2001, pp. 4059-4090, vol. 57.

Monn et al., Synthesis, Pharmacological Characterization, and Molecular Modeling of Heterobicyclic Amino Acids, Journal of Medicinal Chemistry, 1999, pp. 1027-1040, vol. 42 issue 6.

Monn, et al., Design, Synthesis, and Pharmacological Characterization of (+)-2-Aminobicyclo[3.1.0]Hexane-2,6-Dicarboxylic Acid, J Med Chem, 1997, pp. 528-537, vol. 40.

Monn, et al., Synthesis and Metabotropic Glutamate Receptor Activity of S-Oxidized Variants of (-)-4-Amino-2-Thiabicyclo-[3.1.0]Hexane-4,6-Dicarboxylate: Identification of Potent, Selective,

(56) References Cited

OTHER PUBLICATIONS and Orally Bioavailable Agonists for Mglu2/3 Receptors, J. Med. Chem, 2007, pp. 233-240, vol. 50.
Monti, et al., Conventional and Power Spectrum Analysis of the Effects of Zolpidem on Sleep Eeg in Patients with Chronic Primary Insomnia, Sleep, 2000, pp. 1075-1084, vol. 23.
Moore et al, Cycloadditions of Cyanoketenes to Cinnamylideneamines and Benzylideneamines. Synthetic Scope, Stereochemistry, and Mechanism, Journal of Organic Chemistry, 1985, pp. 4231-4238, vol. 50.
Mora, et al.; Role of 5-Ht2a and 5-Ht2c Receptor Subtypes in the Two Types of Fear Generated by the Elevated T-Maze, Pharmacology Biochemistry and Behavior, 1997, pp. 1051-1057, vol. 58.
Moreno, et al., Group II Metabotropic Glutamate Receptors and Schizophrenia, Cell Mol. Life Sci, 2009, pp. 3777-3785, vol. 66 Issue 23.
Moreno, et al., Maternal Influenza Viral Infection Causes Schizophrenia-Like Alterations of 5-Ht2a and Mglu2 Receptors in the Adult Offspring; Journal of Neuroscience, 2011, pp. 1663-1872, vol. 31 Issue 5.
Moreno, et al., Metabotropic Glutamate Mglu2 Receptor is Necessary for the Pharmacological and Behavioral Effects Induced by Hallucinogenic 5-Ht2a Receptor Agonists, Neurosci, 2011, pp. 76-79, vol. 493.
Moreno, et al., Pindolol Augmentation of Treatment-Resistant Depressed Patientss, J Clin Psychiatry, 1997, pp. 437-439, vol. 58.
Morgan, et al., Is Persistent Ketamine Use a Valid Model of the Cognitive and Oculomotor Deficits in Schizophrenia, Biol. Psychiatry, 2009, pp. 1099-1102, vol. 65 issue 12.
Morikawa, et al., Two Intracellular Pathways Mediate Metabotropic Glutamate Receptor-Induced Ca2+ Mobilization in Dopamine Neurons, Journal of Neuroscience, 2003, pp. 149-157, vol. 23 issue 01.
Morishima, et al., Enhanced Cocaine Responsiveness and Impaired Motor Coordination in Metabotropic Glutamate Receptor Subtype 2 Knockout Mice , Proc. Natl. Acad. Sci, 2005, pp. 4170-4175, vol. 102 issue 11.
Morishita, et al., Clonazepam as a Therapeutic Adjunct to Improve the Management of Depression: A Brief Review, Hum Psychopharmacol Clin Exp, 2009, pp. 191-198, vol. 24.
Morpurgo, et al., Drug-Induced Modifications of Discriminated Avoidance Behavior in Rats, Psychopharmacol, 1965, pp. 91-99, vol. 08.
Morrison, et al., Schizophrenia: More Evidence for Less Glutamate, Expert Rev Neurother, 2007, pp. 29-31, vol. 07 Issue 01.
Moussawi, et al., Group II Metabotropic Glutamate Receptors (Mglu2/3) in Drug Addicti, European Journal of Pharmacology, 2010, pp. 115-122, vol. 639.
Mudge, et al., Genomic Convergence Analysis of Schizophrenia: Mrna Sequencing Reveals Altered Synaptic Vesicular Transport in Post-Mortem Cerebellum, Plos One, 2008, pp. 01-24, vol. 3 Issue 11.
Mukhin, et al., Mgiur Modulation of Post-Traumatic Neuronal Death: Role of NMDA Receptors, Neuroreport, 2008, pp. 2561-2566, vol. 08 Issue 11.
Muly, et al., Group II Metabotropic Glutamate Receptors in Anxiety Circuitry: Correspondence of Physiological Response and Subcellular Distribution, J Comp Neurol, 2007, pp. 682-700, vol. 505 Issue 06.
Muntasir, et al., Inverse Agonist Activity of Sarpogrelate, A Selective 5-Ht2a-Receptor Antagonist, at the Constitutively Active Human 5-Ht2a Receptor, Journal of Pharmacological Sciences, 2006, pp. 189-195, vol. 102 Issue 02.
Murck, et al., State Markers of Depression in Sleep Eeg: Dependency on Drug and Gender in Patients Treated with Tianepine or Paroxetine, Journal of Pharmacological Sciences, 2003, pp. 348-358, vol. 28 Issue 02.
Mutel et al, Characterization of (2S, 2'R, 3'R)-2-(2',3'[3H]-Dicarboxycyclopropyl)glycine Binding in Rat Brain, Journal of Neurochemistry, 1998, pp. 2558-2564, vol. 71, No. 6.
Mutel, Therapeutic potential of non-competitive, subtype-selective metaboltropic glutamate receptor ligands, Expert Opinion on Therapeutic Patents, 2002, pp. 1845-1852, vol. 12, No. 12.
Muto, et al., Structures of the Extracellular Regions of the Group II/III Metabotropic Glutamate Receptors, Proc. Natl. Acad. Sci. USA, 2007, pp. 3759-3764, vol. 104 Issue 10.
N. Hovelsø et al., Therapeutic Potential of Metabotropic Glutamate Receptor Modulators, Current Neuropharmacology, 2012, pp. 12-48, vol. 10.
N. Seneca., Recent Advances in Positron Emission Tomography Imaging of Brain, Drugs of the Future, 2011, pp. 601-613, vol. 36 Issue 8.
N/A, Allosteric regulation, Wikipedia, 2010, pp. 1-4, PAge Number.
Nabeshima, et al., Animal Model of Schizophrenia Dysfunction of NMDA Receptor-Signaling in Mice following Withdrawal from Repeated Administration of Phencyclidine, Ann. N.Y. Acad. Sci, 2006, pp. 160-168, vol. 1086.
Naimoli, et al., Compound A, A Novel Potent and Selective mGluR2 Positive Allosteric Modulator: Efects in Clinically Relevant Translational Cognition Models That Could Be Used as Biomarkers, society for neuroscience, 2010, pp. 12-17, Poster 767-1.
Nakamura et al, An Efficient Synthesis of Platelet-Activating Factor (PAF) via 1-0-Alkyl-2-0-(3-isoxazoly1)-SN-Glycero-3-phosphocholine, a new paf agonist utilization of the 3-isoxazolyloxy group as a protected hydroxyl, Tetrahedron Letters, 1990, pp. 699-702, vol. 31, No. 5.
Nakanishi et al, Glutamate receptors: brain function and signal transduction, Brain Research Reviews, 1998, pp. 230-235, vol. 26.
Nakano et al, 1-Alkyl-3-phenylpyridinium 1-Alkyl-2(1H)-pyridone 3-Phenyl 5-Phenyl, Annual Report of Tohoku College of Pharmacy, 1998, pp. 145-148, Annual Report of Tohoku College of Pharmacyol. 45.
Nasca, et al., L-acetylcarnitine causes rapid antidepressant effects through the epigenetic induction of mG1u2 receptors, PNAS, 2013, pp. 4804-4809, vol. 110 issue 12.
Neale, et al., The neurotransmitter N-acetylaspartylglutamate in models of pain, ALS, diabetic neuropathy, CNS injury and schizophrenia, Trends Pharmacological Sciences, 2005, pp. 477-484, vol. 26 Issue 9.
Neki, et al., Metabotropic Glutamate Receptors mGluR2 and mGluR5 Are Expressed in Two Non-Overlapping Populations of GolgI Cells in the Rat Cerebellum, Neuroscience, 1996, pp. 815-826, vol. 75 Issue 3, Elsevier Science Ltd.
Neki, et al., Pre- and postsynaptic localization of a metabotropic glutamate receptor, mGluR2, in the rat brain: an immunohistochemical study with a monoclonal antibody, Neuroscience Letters, 1996, pp. 197-200, vol. 202, Elsevier Science Ireland Ltd.
Nell et al, Preparation of 4-amino-3,5-dicyano-2-thiopyridines as cardiovascular agents, CA149:32326, 2008, pp. 1-1, Page Number.
Nelson, et al., Anxiety does not predict response to antidepressant treatment in late life depression: results of a meta-analysis, Int J Geriatr Psychiatry, Mar. 30, 2009, pp. 539-544, vol. 24, John Wiley & Sons, Ltd.
Nelson, et al, Species Differences in the Pharmacology of the 5-Hydroxytryptamine2 Receptor: Structurally Specific Differentiation by Ergolines and Tryptamines, The Journal of Pharamacology and Experimental Therapeutics, Feb. 8, 1993, pp. 1272-1279, vol. 265 Issue 3.
Neugebauer, et al., Groups II and III Metabotropic Glutamate Receptors Differentially Modulate Brief and Prolonged Nociception in Primate STT Cells, J Neurophysiol, Sep. 11, 2000, pp. 2998-3009, vol. 84, The American Physiological Society.
Neugebauer, et al., Peripheral metabotropic glutamate receptors as drug targets for pain relief, Expert Opin, Ther. Tragets, 2002, pp. 349-361, vol. 6 Issue 3, Ashely Publications LTD.
Neugebauer, et al., Requirement of Metabotropic Glutamate Receptors for the Generation of Inflammation-evoked Hyperexcitability in Rat Spinal Cord Neurons; European Journal of Neuroscience, Mar. 7, 1994, pp. 1179-1186, vol. 6, European Neuroscience Association.
Ngomba, et al., Metabotropic glutamate receptors in the thalamocortical network: Strategic targets for the treatment of absence epilepsy, Epilepsia, May 13, 2011, pp. 1211-1222, vol. 52 Issue 7, International League Against Epilepsy.

(56) References Cited

OTHER PUBLICATIONS

Ngomba, et al., The preferential mGiu2/3 receptor antagonist, LY341495, reduces the frequency of spikeewave discharges in the WAG/Rij rat model of absence epilepsy, Neuropharmacology, 2005, pp. 89-103, vol. 49, Elsevier Ltd.

Nguyen, et al., An in vivo biosensor for neurotransmitter release and in situ receptor activity, Nature Neuroscience, 2010, pp. 127-132, vol. 13 Issue 1.

Nicholls, et al., mGluR2 acts through inhibitory G subunits to regulate transmission and long-term plasticity at hippocampal mossy fiber-CA3 synapses, PNAS, Apr. 18, 2006, pp. 6380-6385, vol. 103 Issue 16, The National Academy of Sciences.

Nicholls, et al., The release and uptake of excitatory amino acids, Tips, 1990, pp. 462-468, vol. 11, Elsevier Science Publishers LTD.

Nicolas, et al., A combined marble burying-locomotor activity test in mice: A practical screening test with sensitivity to different classes of anxiolytics and antidepressants, European Journal of Pharmacology, Jul. 25, 2006, pp. 106-115, vol. 547, Elsevier B.V.

Nicoletti, et al., Lesions of putative giutamatergic pathways potentiate the increase of inositol phospholipid hydrolysis elicited by excitatory amino acids, Brain Research, May 26, 1987, pp. 103-112, vol. 436, Elsevier Science Publishers B.V.

Nicoletti, et al., Metabotropic glutamate receptors: From the workbench to the bedside, Neuropharmacology, 2011, pp. 1017-1041, vol. 60, Elsevier Ltd.

Nicoletti, et al., Metabotropic glutamate receptors: new targets for the control of tumor growth?, Trends in Pharmacological Sciences, Apr. 11, 2007, pp. 206-213, vol. 28 Issue 5.

Nicoletti, et al., Pertussis Toxin Inhibits Signal Transduction at a Specific Metabolotropic Glutamate Receptor in Primary Cultures of Cerebellar Granule Cells, Neuropharmocology, 1988, pp. 551-556, vol. 27 Issue 6.

Nielson et al., Phosphoramides XIV. Phosphorus pentozide and amine hydrochlorides as reagents in the synthesis of thieno{2,3-d pyrimidin-4(3H)-ones, Chemica Scripta, Nov. 3, 1980, pp. 135-138, vol. 18.

Niemegeers, et al., Direct measurement of the pH in the stomach of the conscious rat, using a special electrode, Experientia, 1979, pp. 1538-1539, vol. 35.

Niemegeers, et al., nteraction of Drugs with Apomorphine, Tryptamine and Norepinephrine. A New in VIVO Approach : the ATN—Test in rats, Arch. int, Pharmacodyn, 1977, pp. 238-253, vol. 227.

Niemegeers, et al., Protection of Rats from Compound 48/80-induced Lethality. A simple Test for Inhibitors of mast Cell-Mediated Shock, Arch. int. Pharmacodyn, 1978, pp. 164-176, vol. 234.

Nierenberg, et al., Lithium Augmentation of Nortriptyline for Subjects Resistant to Multiple Antidepressants, Journal of Clinical Psychopharmacology, 2003, pp. 92-95, vol. 23 Issue 1, Lippincott Williams & Wilkins.

Nijholt, et al., Neuronal AKAP150 coordinates PKA and Epac-mediated PKB/Akt phosphorylation, Cellular Signalling, May 16, 2008, pp. 1715-1724, vol. 20, Elsevier Inc.

Nikiforuk, et al., Effects of a Positive Allosteric Modulator of Group II Metabotropic Glutamate Receptors, LY487379, on Cognitive Flexibility and Impulsive-Like Responding in Rats, The Journal of Pharmacology and Experimental Therapeutics, Aug. 18, 2010, pp. 665-673, vol. 335 Issue 3.

Ninomiya et al, Photocyclisation of Enamides. Part 14. Substituent Effects in the Photocyclisation of N-a,B-Unsaturated Acylanilides, Photocyclisation of Enamides. Part 14. Substituent Effects in the Photocyclisation of N-a,B-Unsaturated Acylanilides, 1980, pp. 197-202, n/a.

Nishi et al, Pharmacological characterization of metabotropic glutamate receptor-mediated high-affinity GTPase activity in rat cerebral cortical membranes, British Journal of Pharmacology, May 10, 2000, pp. 1664-1670, vol. 130 No. 7.

Nofzinger, et al., Changes in forebrain function from waking to REM sleep in depression: preliminary analyses of w18FxFDG PET studies, Psychiatry Research: Neuroimaging Section, Jun. 21, 1999, pp. 59-78, vol. 91, Elsevier Science Ireland Ltd.

Noguchi et al, Quantum Chemical Study on Conformational Properties of Bipyridine Cardiotonics, Chem. Pharm. Bull., Aug. 1993, pp. 1331-1336, vol. 41 No. 8.

Norbert Müller., Inflammation and the Glutamate System in Schizophrenia: Implications for Therapeutic Targets and Drug Development, Expert Opin. Ther. Targets, 2008, pp. 1497-1507, vol. 12 Issue 12.

Nordquist, et al., Metabotropic glutamate receptor modulation, translational methods, and biomarkers: relationships with anxiety, Psychopharmacology, Mar. 6, 2008, pp. 389-402, vol. 199, Springer-Verlag.

Norman et al, Structure-Activity Relationships of a Series of Pyrrolo[3,2-d]pyrimidine Derivatives and Related Compounds as Neuropeptide Y5 receptor Antagonists, J. Med. Chem., 2000, pp. 4288-4312, vol. 43 No. 22.

Novellis, et al., Type I and II metabotropic glutamate receptors modulate periaqueductal grey glycine release: interaction between mGlu2/3 and A1 adenosine receptors, Neuropharmacology, Aug. 13, 2002, pp. 1061-1069, vol. 43, Elsevier Science Ltd.

O'Connor, et al., Metabotropic glutamate receptor 7: At the interface of cognition and emotion, European Journal of Pharmacology, 2010, pp. 123-131, vol. 639, Elsevier B.V.

O'Neill, et al., Recent Developments in Metabotropic Glutamate Receptors as Novel Drug Targets, Drugs of the Future, 2010, pp. 307-324, vol. 35 Issue 4.

O'Suilleabhain et al, A Randomized Trial of Amantadine in Huntington Disease, Arch Neurol, 2003, pp. 996-998, vol. 60.

Odagaki, et al., Functional Coupling between Metabotropic Glutamate Receptors and G-proteins in Rat Cerebral Cortex Assessed by Guanosine-5'-O-(3-[35S]thio)triphosphate ([35S]GTPγS) Binding Assay, Basic & Clinical Pharmacology & Toxicology, Mar. 14, 2011, pp. 1-44, page number.

Odagaki, et al., Group II metabotropic glutamate receptor-mediated activation of G-proteins in rat hippocampal and striatal membranes, Neuroscience Letters, 2013, pp. 1-23, page number.

Ohishi, et al., Distribution of a metabotropic glutamate receptor, mGluR2, in the central nervous system of the rat and mouse: an immunohistochemical study with a monoclonal antibody, Neuroscience Research, 1998, pp. 65-82, vol. 30.

Ohishi, et al., Distribution of the Messenger RNA for a Metabotropic Glutamate Receptor, mGluR2, in the Central Nervous System of the Rat, Neuroscience, 1993, pp. 1009-1018, vol. 53 Issue 4.

Ojima, et al., Hydroformylation of Fluoro Olefins, RfCH=CH2, Catalyzed by Group VIII Transition-Metal Catalysts. Crucial Factors for Extremly High Regioselectivity, Journal of American Chemical Society, 1987, pp. 7714-7720, vol. 109.

Olbrich, et al., Frontolimbic glutamate alterations in first episode schizophrenia: Evidence from a magnetic resonance spectroscopy study, The World Journal of Biological Psychiatry, 2008, pp. 59-63, vol. 9 Issue 1, Taylor & Francis.

Oldenziel, et al., In vivo monitoring of extracellular glutamate in the brain with a microsensor, Brain Research, Sep. 7, 2006, pp. 34-42, vol. 1116, Elsevier B.V.

Olivier; et al, Stress-induced hyperthermia and anxiety: pharmacological validation, European Journal of Pharmacology, 2003, pp. 117-132, vol. 463, Elsevier Science B.V.

Olney, et al., NMDA receptor hypofunction model of schizophrenia, Journal of Psychiatric Research, Jul. 16, 1999, pp. 523-533, vol. 33, Elsevier Science Ltd.

Olszewski, et al., NAAG peptidase inhibition reduces locomotor activity and some stereotypes in the PCP model of schizophrenia via group II mGluR, Journal of Neurochemistry, 2004, pp. 876-885, vol. 89, International Society for Neurochemistry.

Olszewski, et al., Phencyclidine and Dizocilpine Induced Behaviors Reduced by N-acetylaspartylglutamate Peptidase Inhibition via Metabotropic Glutamate Receptors, Biol Psychiatry, 2008, pp. 86-91, vol. 63, Society of Biological Psychiatry.

Ong,et al., Localisation of Glutamate Receptors in the Substantia Nigra Pars Compacta of the Monkey, Journal Fur Hirnforschung, 1997, pp. 291-298, vol. 38 Issue 3.

(56) References Cited

OTHER PUBLICATIONS

Oquendo, et al., A Computer Algorithm for Calculating the Adequacy of Antidepressant Treatment in Unipolar and Bipolar Depression, J Clin Psychiatry, 2003, pp. 825-833, vol. 64 Issue 7.

Orlando, et al., The Role of Group I and Group II Metabotropic Glutamate Receptors in Modulation of Striatal NMDA and Quinolinic Acid Toxicity, Experimental Neurology, 2001, pp. 196-204, vol. 167.

Orlowski, et al., D- and L-Stereoisomers of Allylglycine: Convulsive Action and Inhibition of Brain L-Glutamate Decarboxylase, Journnl of Neurochemistry, 1977, pp. 349-353, vol. 28.

Orrenius, et al., Calcium Ions and Oxidative Cell Injury, Annals of Neurology, 1992, pp. S33-S42, vol. 32 Supplementary 42.

Osikowicz, et al., Glutamate Receptor Ligands Attenuate Allodynia and Hyperalgesia and Potentiate Morphine Effects in a Mouse Model of Neuropathic Pain, Pain, 2008, pp. 117-126, vol. 139.

Ossowska, et al., The Role of Glutamate Receptors in Antipsychotic Drug Action, Amino. Acids, 2000, pp. 87-94, vol. 19 Issue 1.

Ossowska, et al., The Striatum as a Target for Anti-Rigor Effects of an Antagonist of Mglur1, but Not an Agonist of Group II Metabotropic Glutamate Receptors, Brain Research, 2002, pp. 88-94, vol. 950.

Othmer, et al., Brain Functions and Psychiatric Disorders, a Clinical View, Sep. 1998, pp. 517-566, vol. 21 Issue 3.

Ottersen, et al., Organization of Glutamate Receptors at the Synapse, European Journal of Neuroscience, 1997, pp. 2219-2224, vol. 9 Issue 11.

Overstreet, et al., A 5-Ht1 a Agonist and a 5-Ht2c Antagonist Reduce Social Interaction Deficit Induced by Multiple Ethanol Withdrawals in Rats, Psychopharmacology, 2003; pp. 344-352, vol. 167.

Ozawa, et al., Glutamate Receptors in the Mammalian Central Nervous System, Progress in Neurobiology, 1998, pp. 581-618, vol. 54 Issue 5.

O'Brien, et al., Molecular mechanisms of glutamate receptor clustering at excitatory synapses, Current Opinion in Neurobiology, 1998, pp. 364-369, vol. 8, Current Biology Ltd.

O'Neill, et al., Effects of Ischaemic Conditions on Uptake of Glutamate, Aspartate, and Noradrenaline by Cell Lines Derived from the Human Nervous System, Journal of Neurochemistry, 1994, pp. 603-611, vol. 63 Issue 2.

P. Bech, Dose-response Relationship of Pregabalin in Patients with Generalized Anxiety Disorder. A Pooled Analysis of Four Placebo-controlled Trials, Pharmacopsychiatry, 2007, pp. 163-168, vol. 40.

P.J.Roberts., Pharmacological Tools for the Investigation of Metabotropic Glutamate Receptors (mGluRs): Phenylglycine Derivatives and Other Selective Antagonists-an Update, Neuropharmacology, May 24, 1995, pp. 813-819, vol. 34 Issue 8, Elsevier Science Ltd.

Page, et al., Metabotropic Glutamate Receptors Inhibit Mechanosensitivity in Vagal Sensory Neurons, Gastroenterology, 2005, pp. 402-410, vol. 128.

Pajer, et al., Discovery of blood transcriptomic markers for depression in animal models and pilot validation in subjects with early-onset major depression, Translational Psychiatry, Apr. 17, 2012, pp. 1-10, vol. 2, Macmillan Publishers Limited.

\* cited by examiner

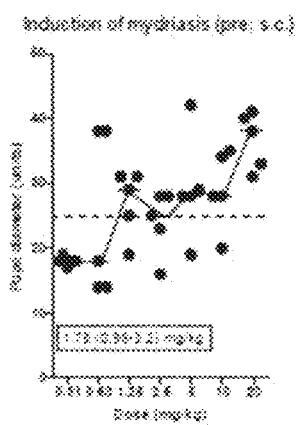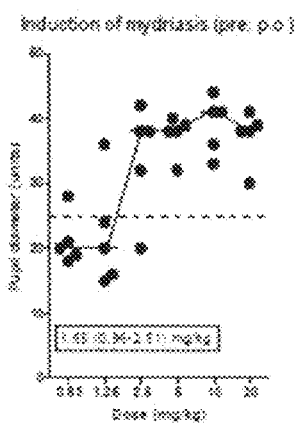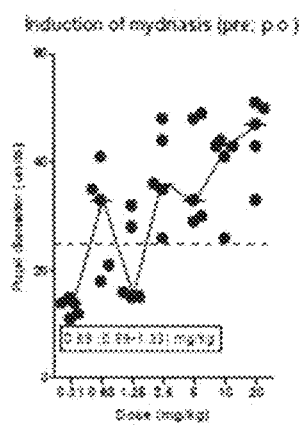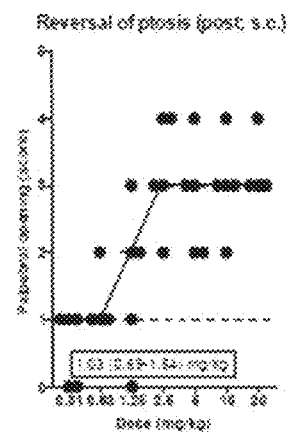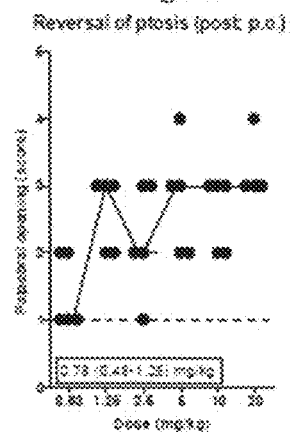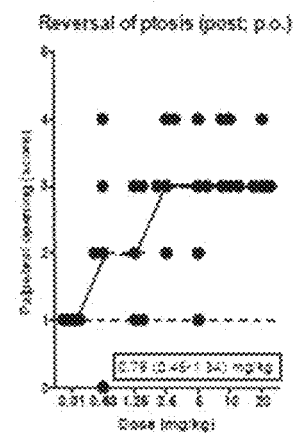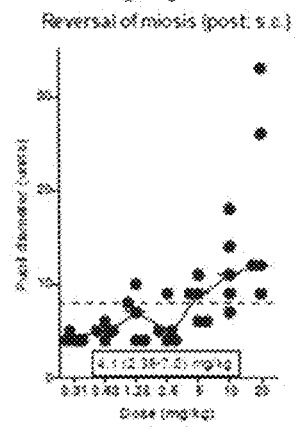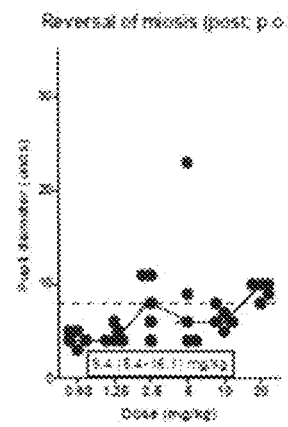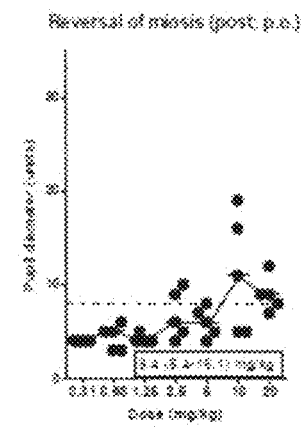

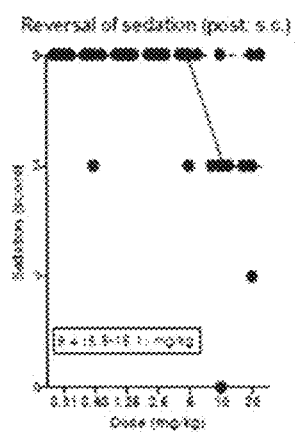 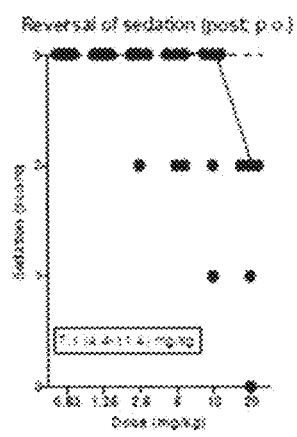 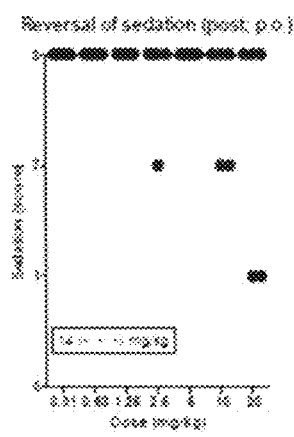

SUBSTITUTED 6,7-DIHYDROPYRAZOLO[1,5-A]PYRAZINES AS NEGATIVE ALLOSTERIC MODULATORS OF MGLUR2 RECEPTORS

This application is a continuation application of U.S. application Ser. No. 14/896,230 filed Dec. 4, 2015 which is the national stage of PCT Application No. PCT/EP2014/061478 filed Jun. 3, 2014, which claims priority from European Patent Application No. 13170447.0, filed Jun. 4, 2013, European Patent Application No. 13173939.3, filed Jun. 27, 2013 and European Patent Application No. 14166450.8 filed Apr. 29, 2014, the entire disclosures of which are hereby incorporated in their entirety.

FIELD OF THE INVENTION

The present invention relates to novel 6,7-dihydropyrazolo[1,5-a]pyrazin-4(5H)-one derivatives of Formula (I)

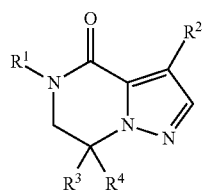

(I)

as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013). Clinical trials are, for example, underway with mGluR2/3 antagonist RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014). WO 2013066736 (Merck Sharp & Dohme Corp.) describes quinoline carboxamide and quinoline carbonitrile compounds as mGluR2 NAMs. WO2013174822 (Domain therapeutics) describes 4H-pyrazolo[1,5-a]quinazolin-5-ones and 4H-pyrrolo[1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD).

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

DESCRIPTION OF THE INVENTION

The present invention is directed to 6,7-dihydropyrazolo[1,5-a]pyrazin-4(5H)-one derivatives of Formula (I)

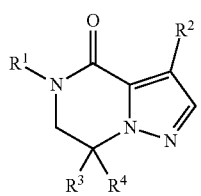

(I)

and stereoisomeric forms thereof,
wherein
$R^1$ is phenyl or 2-pyridinyl, each optionally substituted with one or more substituents each independently selected from the group of halo, $C_{1-4}$alkyl, mono- or poly-halo $C_{1-4}$alkyl, —O—$C_{1-4}$alkyl, —$C_{1-4}$alkyl-O—$C_{1-4}$alkyl, mono- or poly-halo$C_{1-4}$alkyloxy, —$C_{1-4}$alkyl-OH, $C_{1-4}$alkylthio, mono- or poly-halo$C_{1-4}$alkylthio, cyano, $C_{3-7}$cycloalkyl optionally substituted with trifluoromethyl, and —$SF_5$; or is

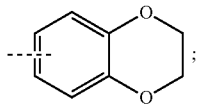

$R^2$ is selected from

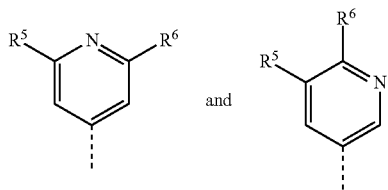

wherein $R^5$ and $R^6$ are each independently selected from the group of hydrogen, halo, cyano, $C_{1-4}$alkyl, —$C_{1-4}$alkyl-OH, $C_{3-7}$cycloalkyl, mono- or poly-halo$C_{1-4}$alkyl, —$C_{1-4}$alkyl-O—$C_{1-4}$alkyl, —O—$C_{1-4}$alkyl, mono- or poly-halo$C_{1-4}$alkyloxy, 1-acetylazetidin-3-yl, and NR'R";

wherein R' is selected from hydrogen and $C_{1-4}$alkyl;

R" is selected from hydrogen and $C_{1-4}$alkyl; or

R' and R" together with the Nitrogen atom to which they are attached form a heterocyclic group selected from the group of 1-azetidinyl, 1-pyrrolidinyl, 1-piperidinyl, 1-piperazinyl, and 4-morpholinyl; wherein each of the heterocyclic groups may be optionally substituted with a substituent selected from halo, hydroxyl, $C_{1-4}$alkyl, mono- or poly-halo$C_{1-4}$alkyl, and —(CO)$C_{1-4}$alkyl;

$R^3$ is selected from hydrogen and $C_{1-4}$alkyl;

$R^4$ is selected from the group of hydrogen, $C_{1-4}$alkyl, mono- or poly-halo$C_{1-4}$alkyl, —$C_{1-4}$alkyl-O—$C_{1-4}$alkyl, and —$C_{1-4}$alkyl-OH;

and the N-oxides, and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament, and to a compound of Formula (I) for use in the treatment or in the prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to the use of a compound of Formula (I) in combination with an additional pharmaceutical agent for use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a method of treating or preventing a central nervous system disorder selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder comprising administering to a subject in need thereof, a therapeutically effective amount of a compound of Formula (I) or a therapeutically effective amount of a pharmaceutical composition according to the invention.

The invention also relates to a product comprising a compound of Formula (I) and an additional pharmaceutical agent, as a combined preparation for simultaneous, separate or sequential use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

DESCRIPTION OF THE FIGURES

In FIG. 1, ▬ corresponds to scopolamine+ JNJ 42153605; - - - corresponds to scopolamine alone; and — — — corresponds to no challenge.

FIGS. 3a-3l show the interaction of Co. No. 1 with reserpine in rats. Shown are the effects on pupil diameter before reserpine challenge (FIGS. 3a-3c) and the reversal of the reserpine-induced ptosis (FIGS. 3d-3f), miosis (FIGS. 3g-3i) and sedation (FIGS. 3j-3l) measured 1 h after s.c. (FIGS. 3a, 3d, 3g, 3j), 1 h after p.o. (FIGS. 3b, 3e, 3h, 3k) and 4 h after p.o. (FIGS. 3c, 3f, 3i, 3l) administration of Co. No. 1.

FIG. 5a: fEPSP amplitude (% of baseline) is shown after the application of LY-354740 (1 μM), followed by the application of Co. No. 1 (10 μM), and then by the application of the mGlu2 antagonist LY-341495, and finally by a washout. At the end of experiments, the AMPA antagonist CNQX (6-cyano-7-nitroquinoxaline-2,3-dione, 50 µM) and kynurenic acid (1 mM) were added as controls to block glutamate-mediated fEPSP.

FIG. 5b: The same experiments as shown in FIG. 5a, but presenting the PPR results. The error bars represent the SEM of 17 independent slices from 4 SD rats. (ACSF=artificial cerebrospinal fluid; fEPSP=field excitatory postsynaptic potential; PPR=paired-pulse ratio; SEM=standard error of the mean).

Monitoring of the post-synaptic response for 80 min shows induction of LTP after weak theta stimulation (at 30 min).

Figure 6A:
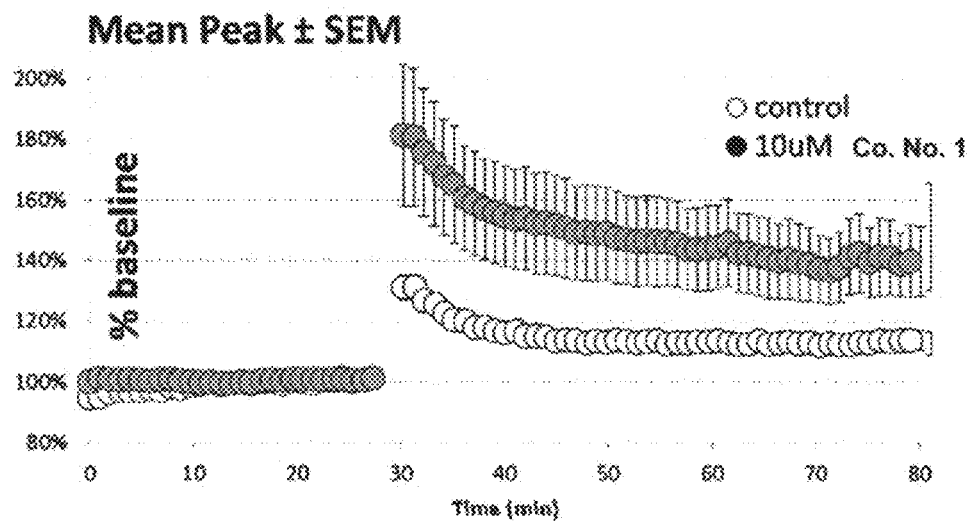
FIGS. 6a-6b show how Co. No. 1 facilitates long-term potentiation in the dentate gyrus of rat hippocampal brain slices.

FIG. 6a: fEPSP in response to the weak theta stimulus under control conditions (vehicle: open circles) and following the application of 10 µM Co. No. 1 (solid circles).

Figure 6B:
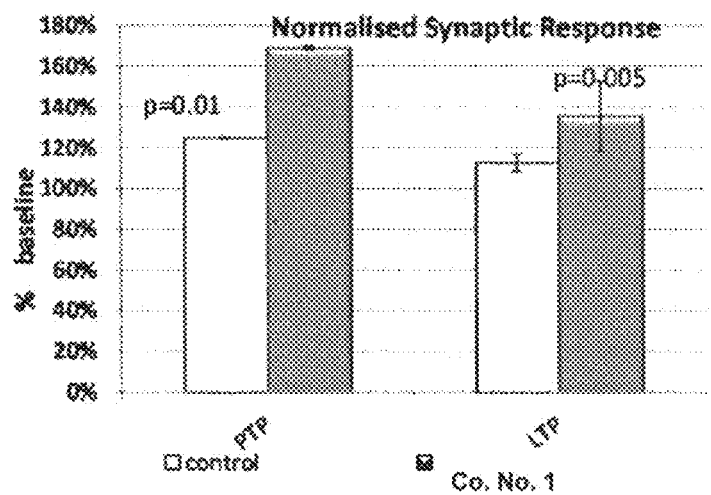

FIG. 6b: PTP and LTP under control conditions and after application of 10 µM Co. No. 1. The error bars represent the SEM of 22 independent slices from 4 SD rats. LTP=long-term potentiation; NAM=negative allosteric modulator; PTP=post-theta potentiation; SEM=standard error of the mean.

DETAILED DESCRIPTION OF THE INVENTION

The present invention relates in particular to compounds of Formula (I) as defined hereinabove, and stereoisomeric forms thereof, wherein $R^1$ is phenyl or 2-pyridinyl, each optionally substituted with one or more substituents each independently selected from the group of halo, $C_{1-4}$alkyl, mono- or poly-halo $C_{1-4}$alkyl, —O—$C_{1-4}$alkyl, —$C_{1-4}$alkyl-O—$C_{1-4}$alkyl, mono- or poly-halo$C_{1-4}$alkyloxy, —$C_{1-4}$alkyl-OH, mono- or poly-halo$C_{1-4}$alkylthio, cyano, and —$SF_5$; or is

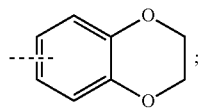;

$R^2$ is selected from

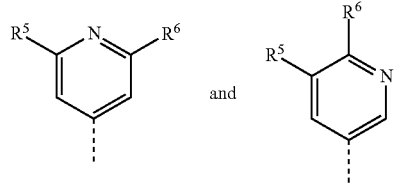

wherein $R^5$ and $R^6$ are each independently selected from the group of hydrogen, halo, cyano, $C_{1-4}$alkyl, —$C_{1-4}$alkyl-OH, $C_{3-7}$cycloalkyl, mono- or poly-halo$C_{1-4}$alkyl, —$C_{1-4}$alkyl-O—$C_{1-4}$alkyl, —O—$C_{1-4}$alkyl, mono- or poly-halo$C_{1-4}$alkyloxy, and NR'R"; wherein R' is selected from hydrogen and $C_{1-4}$alkyl;

R" is selected from hydrogen and $C_{1-4}$alkyl; or

R' and R" together with the Nitrogen atom to which they are attached form a heterocyclic group selected from the group of 1-azetidinyl, 1-pyrrolidinyl, and 1-piperidinyl; wherein each of the heterocyclic groups may be optionally substituted with a halo substituent;

$R^3$ is selected from hydrogen and $C_{1-4}$alkyl;

$R^4$ is selected from the group of hydrogen, $C_{1-4}$alkyl, mono- or poly-halo$C_{1-4}$alkyl, —$C_{1-4}$alkyl-O—$C_{1-4}$alkyl, and —$C_{1-4}$alkyl-OH;

and the N-oxides, and the pharmaceutically acceptable salts and the solvates thereof.

In an additional embodiment, the present invention relates to compounds of Formula (I) as defined hereinabove, and stereoisomeric forms thereof, wherein $R^1$ is phenyl optionally substituted with one, two or three substituents each independently selected from the group of halo, $C_{1-4}$alkyl, mono- or poly-halo$C_{1-4}$alkyl, —O—$C_{1-4}$alkyl, —$C_{1-4}$alkyl-O—$C_{1-4}$alkyl, mono- or poly-halo$C_{1-4}$alkyloxy, mono- or poly-halo$C_{1-4}$alkylthio, cyano, and —$SF_5$;

or 2-pyridinyl optionally substituted with one or two substituents each independently selected from the group of halo, $C_{1-4}$alkyl, mono- or poly-halo$C_{1-4}$alkyl, and —O—$C_{1-4}$alkyl;

$R^2$ is

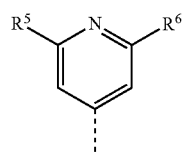

wherein $R^5$ and $R^6$ are each independently selected from the group of hydrogen, halo, cyano, $C_{1-4}$alkyl, $C_{3-7}$cycloalkyl, mono- or poly-halo$C_{1-4}$alkyl, —O—$C_{1-4}$alkyl, mono- or poly-halo$C_{1-4}$alkyloxy, and NR'R";

wherein R' is selected from hydrogen and $C_{1-4}$alkyl;

R" is selected from hydrogen and $C_{1-4}$alkyl; or

R' and R" together with the Nitrogen atom to which they are attached form a heterocyclic group selected from the group of 1-azetidinyl, 1-pyrrolidinyl, and 1-piperidinyl; wherein each of the heterocyclic groups may be optionally substituted with a halo substituent;

$R^3$ is selected from hydrogen and $C_{1-4}$alkyl;

$R^4$ is selected from the group of $C_{1-4}$alkyl, mono- or poly-halo$C_{1-4}$alkyl, and —$C_{1-4}$alkyl-O—$C_{1-4}$alkyl; in particular >$CR^3R^4$ is selected from the group of >$CH(CH_3)$, >$CH(CH_2CH_3)$, >$CH(CH_2F)$, and >$CH(CH_2OCH_3)$;

and the N-oxides, and the pharmaceutically acceptable salts and the solvates thereof.

In an additional embodiment, the present invention relates to compounds of Formula (I) as defined hereinabove, and stereoisomeric forms thereof, wherein $R^1$ is phenyl optionally substituted with one, two or three substituents each independently selected from the group of halo, $C_{1-4}$alkyl, poly-halo$C_{1-4}$alkyl, —O—$C_{1-4}$alkyl, —$C_{1-4}$alkyl-O—$C_{1-4}$alkyl, poly-halo$C_{1-4}$alkyloxy, poly-halo$C_{1-4}$alkylthio, cyano, and —$SF_5$;

or 2-pyridinyl optionally substituted with one or two substituents each independently selected from the group of halo, $C_{1-4}$alkyl, mono- or poly-halo$C_{1-4}$alkyl, and —O—$C_{1-4}$alkyl;

$R^2$ is

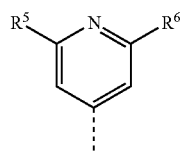

wherein $R^5$ and $R^6$ are each independently selected from the group of hydrogen, cyano, $C_{1-4}$alkyl, poly-halo$C_{1-4}$alkyl, —O—$C_{1-4}$alkyl, and NR'R";

wherein R' is selected from hydrogen and $C_{1-4}$alkyl;

R" is $C_{1-4}$alkyl; or

R' and R" together with the Nitrogen atom to which they are attached form a 1-azetidinyl;

$R^3$ is selected from hydrogen and $C_{1-4}$alkyl;

$R^4$ is selected from the group of $C_{1-4}$alkyl, mono- or poly-halo$C_{1-4}$alkyl, and —$C_{1-4}$alkyl-O—$C_{1-4}$alkyl; in particular >$CR^3R^4$ is selected from the group of >CH(CH$_3$), >CH(CH$_2$CH$_3$), >CH(CH$_2$F), and >CH(CH$_2$OCH$_3$);

and the N-oxides, and the pharmaceutically acceptable salts and the solvates thereof.

In an additional embodiment, the present invention relates to compounds of Formula (I) as defined hereinabove, and stereoisomeric forms thereof, wherein $R^1$ is selected from (a) a substituted phenyl selected from the group of

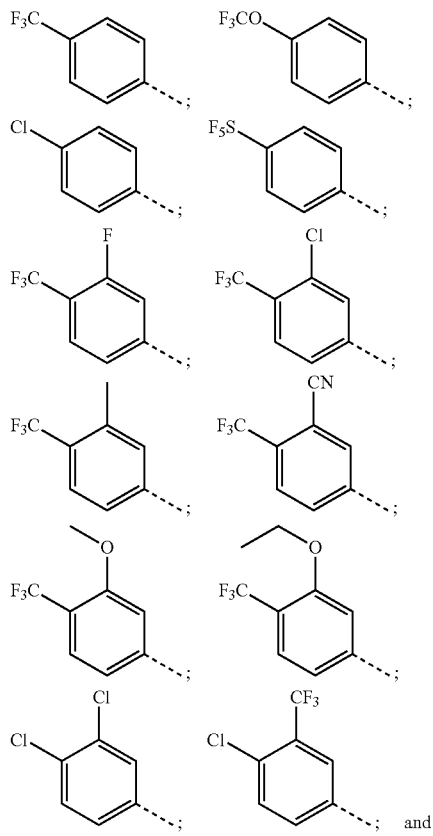

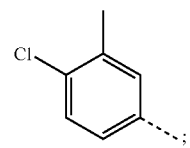

or (b) a substituted 2-pyridinyl selected from the group of

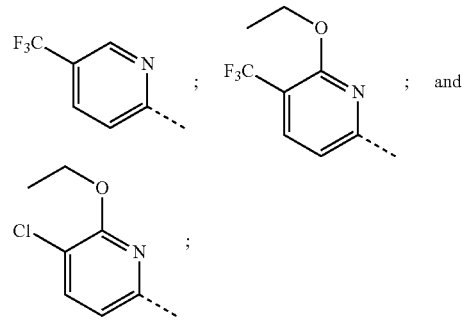

$R^2$ is selected from the group of

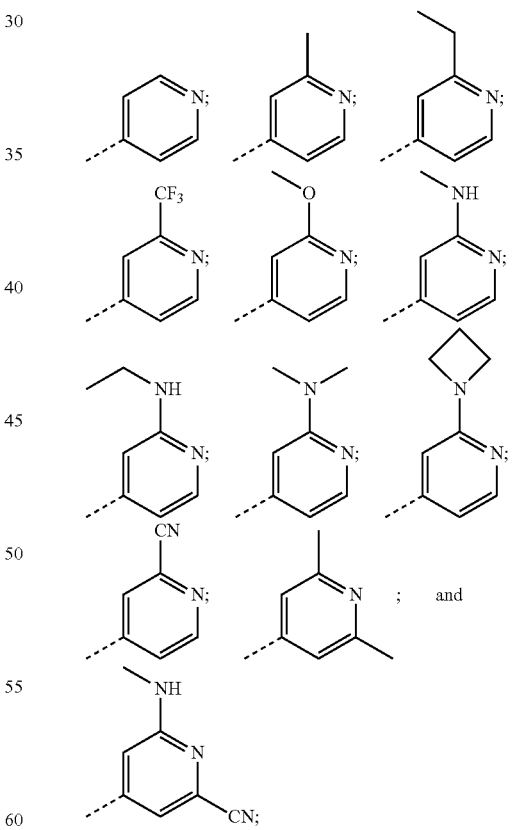

$R^3$ is selected from hydrogen and $C_{1-4}$alkyl;

$R^4$ is selected from the group of $C_{1-4}$alkyl, mono- or poly-halo$C_{1-4}$alkyl, and —$C_{1-4}$alkyl-O—$C_{1-4}$alkyl; in particular >$CR^3R^4$ is selected from the group of >CH(CH$_3$), >CH(CH$_2$CH$_3$), >CH(CH$_2$F), and >CH(CH$_2$OCH$_3$);

and the N-oxides, and the pharmaceutically acceptable salts and the solvates thereof.

In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one;

(7S)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

(7S)-5-(4-Chlorophenyl)-7-methyl-3-(2-methylpyridin-4-yl)-6,7-dihydropyrazolo[1,5-a]pyrazin-4(5H)-one;

(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one;

(7S)-7-Methyl-3-pyridin-4-yl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(3,4-Dichlorophenyl)-7-methyl-3-(2-methylpyridin-4-yl)-6,7-dihydropyrazolo[1,5-a]pyrazin-4(5H)-one;

(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[4-(pentafluoro-$\lambda^6$-sulfanyl)phenyl]-6,7-dihydropyrazolo[1,5-a]pyrazin-4(5H)-one;

(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one;

(7S)-3-(2,6-Dimethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-7-methyl-3-(2-methylpyridin-4-yl)-6,7-dihydropyrazolo[1,5-a]pyrazin-4(5H)-one;

(7S)-5-[3-Fluoro-4-(trifluoromethyl)phenyl]-7-methyl-3-(2-methylpyridin-4-yl)-6,7-dihydropyrazolo[1,5-a]pyrazin-4(5H)-one;

(7S)-5-[4-Chloro-3-(trifluoromethyl)phenyl]-7-methyl-3-(2-methylpyridin-4-yl)-6,7-dihydropyrazolo[1,5-a]pyrazin-4(5H)-one;

5-[(7S)-7-Methyl-3-(2-methylpyridin-4-yl)-4-oxo-6,7-dihydropyrazolo[1,5-a]pyrazin-5(4H)-yl]-2-(trifluoromethyl)benzonitrile;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-3-(2-Ethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-3-(2,6-dimethylpyridin-4-yl)-7-methyl-6,7-dihydropyrazolo[1,5-a]pyrazin-4(5H)-one;

(7S)-5-(3,4-Dichlorophenyl)-3-(2,6-dimethylpyridin-4-yl)-7-methyl-6,7-dihydropyrazolo[1,5-a]pyrazin-4(5H)-one;

(7S)-3-[2-(Ethylamino)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[4-(trifluoromethoxy)phenyl]-6,7-dihydropyrazolo[1,5-a]pyrazin-4(5H)-one;

(7S)-3-[2-(Dimethylamino)pyridin-4-yl]-7-methyl-5-[4-(trifluoromethyl)phenyl]-6,7-dihydropyrazolo[1,5-a]pyrazin-4(5H)-one;

(7S)-5-(5-Chloro-6-ethoxypyridin-2-yl)-7-methyl-3-(2-methylpyridin-4-yl)-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-(3,4-Dichlorophenyl)-3-(2-methoxypyridin-4-yl)-7-methyl-6,7-dihydropyrazolo[1,5-a]pyrazin-4(5H)-one;

(7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one;

4-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-5-[3-Chloro-4-(trifluoromethyl)phenyl]-3-(2-methoxypyridin-4-yl)-7-methyl-6,7-dihydropyrazolo[1,5-a]pyrazin-4(5H)-one;

(7S)-5-[3-Chloro-4-(trifluoromethyl)phenyl]-7-methyl-3-[2-(methylamino)pyridin-4-yl]-6,7-dihydropyrazolo[1,5-a]pyrazin-4(5H)-one;

(7S)-3-(2-Azetidin-1-ylpyridin-4-yl)-7-methyl-5-[4-(trifluoromethyl)phenyl]-6,7-dihydropyrazolo[1,5-a]pyrazin-4(5H)-one;

(7S)-7-Methyl-5-[4-(trifluoromethyl)phenyl]-3-[2-(trifluoromethyl)pyridin-4-yl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}-6-(methylamino)pyridine-2-carbonitrile;

(7S)-3-(2-Methoxypyridin-4-yl)-5-[3-methoxy-4-(trifluoromethyl)phenyl]-7-methyl-6,7-dihydropyrazolo[1,5-a]pyrazin-4(5H)-one;

(7S)-5-[3-Fluoro-4-(trifluoromethyl)phenyl]-7-methyl-3-[2-(methylamino)pyridin-4-yl]-6,7-dihydropyrazolo[1,5-a]pyrazin-4(5H)-one; and (7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

and the N-oxides, and the pharmaceutically acceptable salts and the solvates thereof.

In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one, or a hydrochloride salt, or a sulfate salt, or a methanesulfonate salt, or a maleate salt thereof;

(7S)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

(7S)-5-(4-Chlorophenyl)-7-methyl-3-(2-methylpyridin-4-yl)-6,7-dihydropyrazolo[1,5-a]pyrazin-4(5H)-one or a hydrochloride salt thereof;

(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one or a hydrochloride salt thereof;

(7S)-7-Methyl-3-pyridin-4-yl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(3,4-Dichlorophenyl)-7-methyl-3-(2-methylpyridin-4-yl)-6,7-dihydropyrazolo[1,5-a]pyrazin-4(5H)-one or a hydrochloride salt thereof;

(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[4-(pentafluoro-λ⁶-sulfanyl)phenyl]-6,7-dihydropyrazolo[1,5-a]pyrazin-4(5H)-one;

(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one or a hydrochloride salt thereof;

(7S)-3-(2,6-Dimethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-7-methyl-3-(2-methylpyridin-4-yl)-6,7-dihydropyrazolo[1,5-a]pyrazin-4(5H)-one;

(7S)-5-[3-Fluoro-4-(trifluoromethyl)phenyl]-7-methyl-3-(2-methylpyridin-4-yl)-6,7-dihydropyrazolo[1,5-a]pyrazin-4(5H)-one;

(7S)-5-[4-Chloro-3-(trifluoromethyl)phenyl]-7-methyl-3-(2-methylpyridin-4-yl)-6,7-dihydropyrazolo[1,5-a]pyrazin-4(5H)-one;

5-[(7S)-7-Methyl-3-(2-methylpyridin-4-yl)-4-oxo-6,7-dihydropyrazolin-4-[1,5-a]pyrazin-5(4H)-yl]-2-(trifluoromethyl)benzonitrile;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-3-(2-Ethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-3-(2,6-dimethylpyridin-4-yl)-7-methyl-6,7-dihydropyrazolo[1,5-a]pyrazin-4(5H)-one;

(7S)-5-(3,4-Dichlorophenyl)-3-(2,6-dimethylpyridin-4-yl)-7-methyl-6,7-dihydropyrazolo[1,5-a]pyrazin-4(5H)-one;

(7S)-3-[2-(Ethylamino)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[4-(trifluoromethoxy)phenyl]-6,7-dihydropyrazolo[1,5-a]pyrazin-4(5H)-one;

(7S)-3-[2-(Dimethylamino)pyridin-4-yl]-7-methyl-5-[4-(trifluoromethyl)phenyl]-6,7-dihydropyrazolo[1,5-a]pyrazin-4(5H)-one;

(7S)-5-(5-Chloro-6-ethoxypyridin-2-yl)-7-methyl-3-(2-methylpyridin-4-yl)-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-(3,4-Dichlorophenyl)-3-(2-methoxypyridin-4-yl)-7-methyl-6,7-dihydropyrazolo[1,5-a]pyrazin-4(5H)-one;

(7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one or a hydrochloride salt thereof;

4-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-5-[3-Chloro-4-(trifluoromethyl)phenyl]-3-(2-methoxypyridin-4-yl)-7-methyl-6,7-dihydropyrazolo[1,5-a]pyrazin-4(5H)-one;

(7S)-5-[3-Chloro-4-(trifluoromethyl)phenyl]-7-methyl-3-[2-(methylamino)pyridin-4-yl]-6,7-dihydropyrazolo[1,5-a]pyrazin-4(5H)-one;

(7S)-3-(2-Azetidin-1-ylpyridin-4-yl)-7-methyl-5-[4-(trifluoromethyl)phenyl]-6,7-dihydropyrazolo[1,5-a]pyrazin-4(5H)-one;

(7S)-7-Methyl-5-[4-(trifluoromethyl)phenyl]-3-[2-(trifluoromethyl)pyridin-4-yl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}-6-(methylamino)pyridine-2-carbonitrile;

(7S)-3-(2-Methoxypyridin-4-yl)-5-[3-methoxy-4-(trifluoromethyl)phenyl]-7-methyl-6,7-dihydropyrazolo[1,5-a]pyrazin-4(5H)-one;

(7S)-5-[3-Fluoro-4-(trifluoromethyl)phenyl]-7-methyl-3-[2-(methylamino)pyridin-4-yl]-6,7-dihydropyrazolo[1,5-a]pyrazin-4(5H)-one; and (7S)-7-Methyl-3-(2-methylpyridin-4-yl)-5-[5-(trifluoromethyl)pyridin-2-yl]-6,7-dihydropyrazolo[1,5-a]pyrazin-4(5H)-one.

In an additional embodiment, the present invention relates to compounds of Formula (I) as defined hereinabove, and stereoisomeric forms thereof, wherein R¹ is phenyl, optionally substituted with one, two or three substituents each independently selected from the group of halo, $C_{1-4}$alkyl, poly-halo$C_{1-4}$alkyl, —O—$C_{1-4}$alkyl, —$C_{1-4}$alkyl-OH and cyano; or 2-pyridinyl, substituted with one or two substituents each independently selected from the group of halo, poly-halo $C_{1-4}$alkyl, and —O—$C_{1-4}$alkyl;

R² is

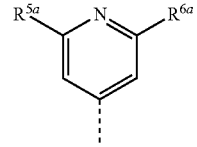

wherein $R^{5a}$ is selected from hydrogen and $C_{1-4}$alkyl, and $R^{6a}$ is selected from the group of hydrogen, $C_{1-4}$alkyl, —$C_{1-4}$alkyl-O—$C_{1-4}$alkyl, —O$C_{1-4}$alkyl, and —$C_{1-4}$alkyl-OH; or

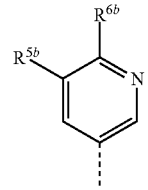

wherein one of $R^{5b}$ and $R^{6b}$ is hydrogen, and the other $R^{5b}$ or $R^{6b}$ is $C_{1-4}$alkyl;

R³ is selected from hydrogen and $C_{1-4}$alkyl;

R⁴ is selected from the group of hydrogen, $C_{1-4}$alkyl, mono- or poly-halo$C_{1-4}$alkyl, and —$C_{1-4}$alkyl-O—$C_{1-4}$alkyl; in particular >CR³R⁴ is selected from the group of >CH₂, >CH(CH₃), >CH(CH₂CH₃), >CH(CH₂F), >CH(CH₂OCH₃) and >C(CH₃)₂; and the N-oxides, and the pharmaceutically acceptable salts and the solvates thereof.

In an additional embodiment, the present invention relates to compounds of Formula (I) as defined hereinabove, and stereoisomeric forms thereof, wherein R¹ is phenyl, optionally substituted with one, two or three substituents each independently selected from the group of fluoro, chloro, methyl, $CF_3$, —O—$CH_3$, —O—$CH_2CH_3$, cyano, —CH($CH_3$)(OH); or 2-pyridinyl, substituted with one or two substituents each independently selected from the group of fluoro, chloro, $CF_3$, and —O—$CH_2CH_3$;

$R^2$ is

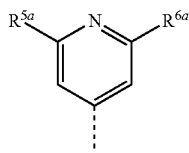

wherein $R^{5a}$ is selected from hydrogen and methyl, and $R^{6a}$ is selected from the group of hydrogen, methyl, —CH$_2$—O—CH$_3$, —O—CH$_3$, and —CH$_2$—OH; or

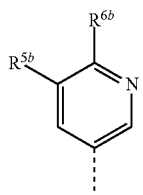

wherein one of $R^{5b}$ and $R^{6b}$ is hydrogen, and the other $R^{5b}$ or $R^{6b}$ is methyl;

$R^3$ is selected from hydrogen and $C_{1-4}$alkyl;

$R^4$ is selected from the group of hydrogen, $C_{1-4}$alkyl, mono- or poly-halo$C_{1-4}$alkyl, and —$C_{1-4}$alkyl-O—$C_{1-4}$alkyl; in particular >CR$^3$R$^4$ is selected from the group of >CH$_2$, >CH(CH$_3$), >CH(CH$_2$CH$_3$), >CH(CH$_2$F), >CH(CH$_2$OCH$_3$) and >C(CH$_3$)$_2$;

and the N-oxides, and the pharmaceutically acceptable salts and the solvates thereof.

In an additional embodiment, the present invention relates to compounds of Formula (I) as defined hereinabove, and stereoisomeric forms thereof, wherein $R^1$ is (a) a phenyl substituent selected from the group of

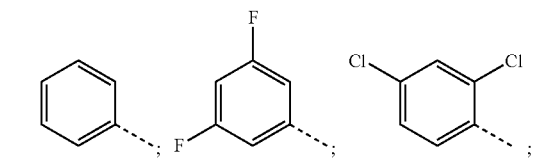

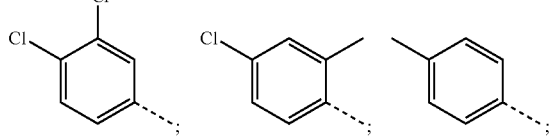

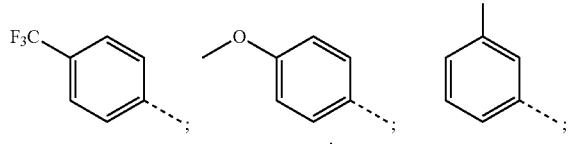

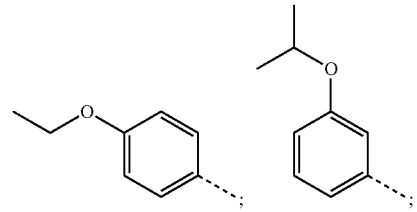

or (b) a 2-pyridin yl substituent selected from the group of

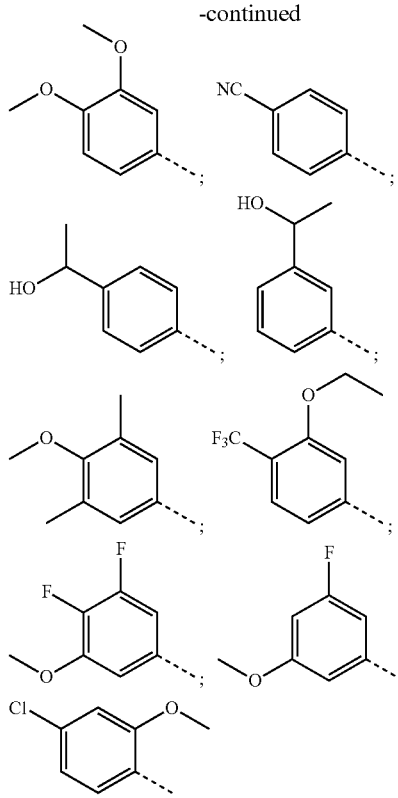

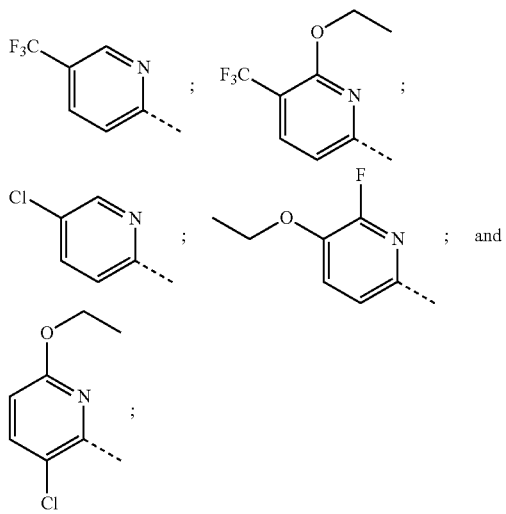

$R^2$ is

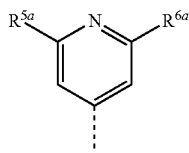

wherein R[5a] is selected from hydrogen and methyl, and R[6a] is selected from the group of hydrogen, methyl, —CH$_2$—O—CH$_3$, —OCH$_3$, —O—CH$_3$, and —CH$_2$—OH; or

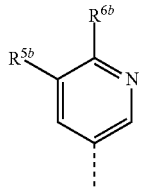

wherein one of R[5b] and R[6b] is hydrogen, and the other R[5b] or R[6b] is methyl;

R$^3$ is selected from hydrogen and C$_{1-4}$alkyl;

R$^4$ is selected from the group of hydrogen, C$_{1-4}$alkyl, mono- or poly-haloC$_{1-4}$alkyl, and —C$_{1-4}$alkyl-O—C$_{1-4}$alkyl; in particular >CR$^3$R$^4$ is selected from the group of >CH$_2$, >CH(CH$_3$), >CH(CH$_2$CH$_3$), >CH(CH$_2$F), >CH(CH$_2$OCH$_3$) and >C(CH$_3$)$_2$;

and the N-oxides, and the pharmaceutically acceptable salts and the solvates thereof.

In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one;

(7S)-7-Methyl-3-pyridin-4-yl-5-[4-(trifluoromethyl)phenyl]-6,7-dihydropyrazolo[1,5-a]pyrazin-4(5H)-one;

(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(5-methylpyridin-3-yl)-5-[4-(trifluoromethyl)phenyl]-6,7-dihydropyrazolo[1,5-a]pyrazin-4(5H)-one;

(7R)-7-Methyl-3-(2-methylpyridin-4-yl)-5-[4-(trifluoromethyl)phenyl]-6,7-dihydropyrazolo[1,5-a]pyrazin-4(5H)-one;

(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

5-[3-Ethoxy-4-(trifluoromethyl)phenyl]-3-(2-methylpyridin-4-yl)-6,7-dihydropyrazolo[1,5-a]pyrazin-4(5H)-one;

(7S)-5-(4-Methoxy-3,5-dimethylphenyl)-7-methyl-3-(2-methylpyridin-4-yl)-6,7-dihydropyrazolo[1,5-a]pyrazin-4(5H)-one;

(7S)-7-Methyl-3-(6-methylpyridin-3-yl)-5-[4-(trifluoromethyl)phenyl]-6,7-dihydropyrazolo[1,5-a]pyrazin-4(5H)-one;

(7S)-5-(4-Methoxyphenyl)-7-methyl-3-(2-methylpyridin-4-yl)-6,7-dihydropyrazolo[1,5-a]pyrazin-4(5H)-one;

3-(2-Methylpyridin-4-yl)-5-[4-(trifluoromethyl)phenyl]-6,7-dihydropyrazolo[1,5-a]pyrazin-4(5H)-one;

(7S)-5-(3,4-Dimethoxyphenyl)-7-methyl-3-(2-methylpyridin-4-yl)-6,7-dihydropyrazolo[1,5-a]pyrazin-4(5H)-one;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-7-Methyl-5-(4-methylphenyl)-3-(2-methylpyridin-4-yl)-6,7-dihydropyrazolo[1,5-a]pyrazin-4(5H)-one;

(7S)-7-Methyl-5-[3-(1-methylethoxy)phenyl]-3-(2-methylpyridin-4-yl)-6,7-dihydropyrazolo[1,5-a]pyrazin-4(5H)-one;

4-[(7S)-7-Methyl-3-(2-methylpyridin-4-yl)-4-oxo-6,7-dihydropyrazolo[1,5-a]pyrazin-5(4H)-yl]benzonitrile;

(7S)-5-(4-Ethoxyphenyl)-7-methyl-3-(2-methylpyridin-4-yl)-6,7-dihydropyrazolo[1,5-a]pyrazin-4(5H)-one;

(7S)-5-(3,5-Difluorophenyl)-7-methyl-3-(2-methylpyridin-4-yl)-6,7-dihydropyrazolo[1,5-a]pyrazin-4(5H)-one;

(7S)-5-(3-Ethoxyphenyl)-7-methyl-3-(2-methylpyridin-4-yl)-6,7-dihydropyrazolo[1,5-a]pyrazin-4(5H)-one;

(7S)-5-(3,4-Difluoro-5-methoxyphenyl)-7-methyl-3-(2-methylpyridin-4-yl)-6,7-dihydropyrazolo[1,5-a]pyrazin-4(5H)-one;

(7S)-5-(3-Fluoro-5-methoxyphenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-phenyl-6,7-dihydropyrazolyl[1,5-a]pyrazin-4(5H)-one;

(7S)-5-[4-(1-Hydroxyethyl)phenyl]-7-methyl-3-(2-methylpyridin-4-yl)-6,7-dihydropyrazolo[1,5-a]pyrazin-4(5H)-one;

(7R)-5-(3,4-Dichlorophenyl)-7-(fluoromethyl)-3-(2-methylpyridin-4-yl)-6,7-dihydropyrazolo[1,5-a]pyrazin-4(5H)-one;

(7R)-5-(3,4-Dichlorophenyl)-7-(methoxymethyl)-3-(2-methylpyridin-4-yl)-6,7-dihydropyrazolo[1,5-a]pyrazin-4(5H)-one; and (7S)-5-(3,4-Dichlorophenyl)-3-[2-(hydroxymethyl)pyridin-4-yl]-7-methyl-6,7-dihydropyrazolo[1,5-a]pyrazin-4(5H)-one;

(7R)-7-Ethyl-3-(2-methylpyridin-4-yl)-5-[4-(trifluoromethyl)phenyl]-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-[3-(1-Hydroxyethyl)phenyl]-7-methyl-3-(2-methylpyridin-4-yl)-6,7-dihydropyrazolo[1,5-a]pyrazin-4(5H)-one;

(7S)-5-(4-Chloro-2-methoxyphenyl)-7-methyl-3-(2-methylpyridin-4-yl)-6,7-dihydropyrazolo[1,5-a]pyrazin-4(5H)-one;

(7S)-5-(2,4-Dichlorophenyl)-7-methyl-3-(2-methylpyridin-4-yl)-6,7-dihydropyrazolo[1,5-a]pyrazin-4(5H)-one;

7,7-Dimethyl-3-(2-methylpyridin-4-yl)-5-[4-(trifluoromethyl)phenyl]-6,7-dihydropyrazolo[1,5-a]pyrazin-4(5H)-one;

(7S)-5-(4-Chloro-2-methylphenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(5-Chloropyridin-2-yl)-7-methyl-3-(2-methylpyridin-4-yl)-6,7-dihydropyrazolo[1,5-a]pyrazin-4(5H)-one;

(7S)-7-Methyl-3-pyridin-4-yl-5-[5-(trifluoromethyl)pyridin-2-yl]-6,7-dihydropyrazolo[1,5-a]pyrazin-4(5H)-one;

(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;

(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;

(7S)-5-(3-Chloro-6-ethoxypyridin-2-yl)-7-methyl-3-(2-methylpyridin-4-yl)-6,7-dihydropyrazolo[1,5-a]pyrazin-4(5H)-one; and (7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

and the N-oxides, and the pharmaceutically acceptable salts and the solvates thereof.

In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one, or a hydrochloride salt, or a sulfate salt, or a methanesulfonate salt, or a maleate salt thereof;

(7S)-7-Methyl-3-pyridin-4-yl-5-[4-(trifluoromethyl)phenyl]-6,7-dihydropyrazolo[1,5-a]pyrazin-4(5H)-one;

(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one or a hydrochloride salt thereof;

(7S)-7-Methyl-3-(5-methylpyridin-3-yl)-5-[4-(trifluoromethyl)phenyl]-6,7-dihydropyrazolo[1,5-a]pyrazin-4(5H)-one;

(7R)-7-Methyl-3-(2-methylpyridin-4-yl)-5-[4-(trifluoromethyl)phenyl]-6,7-dihydropyrazolo[1,5-a]pyrazin-4(5H)-one;

(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

5-[3-Ethoxy-4-(trifluoromethyl)phenyl]-3-(2-methylpyridin-4-yl)-6,7-dihydropyrazolo[1,5-a]pyrazin-4(5H)-one;

(7S)-5-(4-Methoxy-3,5-dimethylphenyl)-7-methyl-3-(2-methylpyridin-4-yl)-6,7-dihydropyrazolo[1,5-a]pyrazin-4(5H)-one;

(7S)-7-Methyl-3-(6-methylpyridin-3-yl)-5-[4-(trifluoromethyl)phenyl]-6,7-dihydropyrazolo[1,5-a]pyrazin-4(5H)-one;

(7S)-5-(4-Methoxyphenyl)-7-methyl-3-(2-methylpyridin-4-yl)-6,7-dihydropyrazolo[1,5-a]pyrazin-4(5H)-one;

3-(2-Methylpyridin-4-yl)-5-[4-(trifluoromethyl)phenyl]-6,7-dihydropyrazolo[1,5-a]pyrazin-4(5H)-one;

(7S)-5-(3,4-Dimethoxyphenyl)-7-methyl-3-(2-methylpyridin-4-yl)-6,7-dihydropyrazolo[1,5-a]pyrazin-4(5H)-one;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-7-Methyl-5-(4-methylphenyl)-3-(2-methylpyridin-4-yl)-6,7-dihydropyrazolo[1,5-a]pyrazin-4(5H)-one;

(7S)-7-Methyl-5-[3-(1-methylethoxy)phenyl]-3-(2-methylpyridin-4-yl)-6,7-dihydropyrazolo[1,5-a]pyrazin-4(5H)-one or a hydrochloride salt thereof;

4-[(7S)-7-Methyl-3-(2-methylpyridin-4-yl)-4-oxo-6,7-dihydropyrazolo[1,5-a]pyrazin-5(4H)-yl]benzonitrile;

(7S)-5-(4-Ethoxyphenyl)-7-methyl-3-(2-methylpyridin-4-yl)-6,7-dihydropyrazolo[1,5-a]pyrazin-4(5H)-one or a hydrochloride salt thereof;

(7S)-5-(3,5-Difluorophenyl)-7-methyl-3-(2-methylpyridin-4-yl)-6,7-dihydropyrazolo[1,5-a]pyrazin-4(5H)-one;

(7S)-5-(3-Ethoxyphenyl)-7-methyl-3-(2-methylpyridin-4-yl)-6,7-dihydropyrazolo[1,5-a]pyrazin-4(5H)-one;

(7S)-5-(3,4-Difluoro-5-methoxyphenyl)-7-methyl-3-(2-methylpyridin-4-yl)-6,7-dihydropyrazolo[1,5-a]pyrazin-4(5H)-one;

(7S)-5-(3-Fluoro-5-methoxyphenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-phenyl-6,7-dihydropyrazolyl-[1,5-a]pyrazin-4(5H)-one;

(7S)-5-[4-(1-Hydroxyethyl)phenyl]-7-methyl-3-(2-methylpyridin-4-yl)-6,7-dihydropyrazolo[1,5-a]pyrazin-4(5H)-one;

(7R)-5-(3,4-Dichlorophenyl)-7-(fluoromethyl)-3-(2-methylpyridin-4-yl)-6,7-dihydropyrazolo[1,5-a]pyrazin-4(5H)-one;

(7R)-5-(3,4-Dichlorophenyl)-7-(methoxymethyl)-3-(2-methylpyridin-4-yl)-6,7-dihydropyrazolo[1,5-a]pyrazin-4(5H)-one; and (7S)-5-(3,4-Dichlorophenyl)-3-[2-(hydroxymethyl)pyridin-4-yl]-7-methyl-6,7-dihydropyrazolo[1,5-a]pyrazin-4(5H)-one;

(7R)-7-Ethyl-3-(2-methylpyridin-4-yl)-5-[4-(trifluoromethyl)phenyl]-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-[3-(1-Hydroxyethyl)phenyl]-7-methyl-3-(2-methylpyridin-4-yl)-6,7-dihydropyrazolo[1,5-a]pyrazin-4(5H)-one;

(7S)-5-(4-Chloro-2-methoxyphenyl)-7-methyl-3-(2-methylpyridin-4-yl)-6,7-dihydropyrazolo[1,5-a]pyrazin-4(5H)-one;

(7S)-5-(2,4-Dichlorophenyl)-7-methyl-3-(2-methylpyridin-4-yl)-6,7-dihydropyrazolo[1,5-a]pyrazin-4(5H)-one;

7,7-Dimethyl-3-(2-methylpyridin-4-yl)-5-[4-(trifluoromethyl)phenyl]-6,7-dihydropyrazolo[1,5-a]pyrazin-4(5H)-one;

(7S)-5-(4-Chloro-2-methylphenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(5-Chloropyridin-2-yl)-7-methyl-3-(2-methylpyridin-4-yl)-6,7-dihydropyrazolo[1,5-a]pyrazin-4(5H)-one;

(7S)-7-Methyl-3-pyridin-4-yl-5-[5-(trifluoromethyl)pyridin-2-yl]-6,7-dihydropyrazolo[1,5-a]pyrazin-4(5H)-one;

(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;

(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;

(7S)-5-(3-Chloro-6-ethoxypyridin-2-yl)-7-methyl-3-(2-methylpyridin-4-yl)-6,7-dihydropyrazolo[1,5-a]pyrazin-4(5H)-one; and (7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

and the pharmaceutically acceptable salts and the solvates thereof.

In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one, or a hydrochloride salt, or a sulfate salt, or a methanesulfonate salt, or a maleate salt thereof;

(7S)-7-Methyl-3-pyridin-4-yl-5-[4-(trifluoromethyl)phenyl]-6,7-dihydropyrazolo[1,5-a]pyrazin-4(5H)-one;

(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one or a hydrochloride salt thereof;

(7R)-7-Methyl-3-(2-methylpyridin-4-yl)-5-[4-(trifluoromethyl)phenyl]-6,7-dihydropyrazolo[1,5-a]pyrazin-4(5H)-one;

(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

5-[3-Ethoxy-4-(trifluoromethyl)phenyl]-3-(2-methylpyridin-4-yl)-6,7-dihydropyrazolo[1,5-a]pyrazin-4(5H)-one;

(7S)-5-(4-Methoxy-3,5-dimethylphenyl)-7-methyl-3-(2-methylpyridin-4-yl)-6,7-dihydropyrazolo[1,5-a]pyrazin-4(5H)-one;

(7S)-7-Methyl-3-(6-methylpyridin-3-yl)-5-[4-(trifluoromethyl)phenyl]-6,7-dihydropyrazolo[1,5-a]pyrazin-4(5H)-one;

(7S)-5-(4-Methoxyphenyl)-7-methyl-3-(2-methylpyridin-4-yl)-6,7-dihydropyrazolo[1,5-a]pyrazin-4(5H)-one;

3-(2-Methylpyridin-4-yl)-5-[4-(trifluoromethyl)phenyl]-6,7-dihydropyrazolo[1,5-a]pyrazin-4(5H)-one;

(7S)-5-(3,4-Dimethoxyphenyl)-7-methyl-3-(2-methylpyridin-4-yl)-6,7-dihydropyrazolo[1,5-a]pyrazin-4(5H)-one;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-7-Methyl-5-[3-(1-methylethoxy)phenyl]-3-(2-methylpyridin-4-yl)-6,7-dihydropyrazolo[1,5-a]pyrazin-4(5H)-one or a hydrochloride salt thereof;

4-[(7S)-7-Methyl-3-(2-methylpyridin-4-yl)-4-oxo-6,7-dihydropyrazolo[1,5-a]pyrazin-5(4H)-yl]benzonitrile;

(7S)-5-(4-Ethoxyphenyl)-7-methyl-3-(2-methylpyridin-4-yl)-6,7-dihydropyrazolo[1,5-a]pyrazin-4(5H)-one or a hydrochloride salt thereof;

(7S)-5-(3,5-Difluorophenyl)-7-methyl-3-(2-methylpyridin-4-yl)-6,7-dihydropyrazolo[1,5-a]pyrazin-4(5H)-one;

(7S)-5-(3-Ethoxyphenyl)-7-methyl-3-(2-methylpyridin-4-yl)-6,7-dihydropyrazolo[1,5-a]pyrazin-4(5H)-one;

(7S)-5-(3,4-Difluoro-5-methoxyphenyl)-7-methyl-3-(2-methylpyridin-4-yl)-6,7-dihydropyrazolo[1,5-a]pyrazin-4(5H)-one;

(7S)-5-(3-Fluoro-5-methoxyphenyl)-7-methyl-3-(2-methylpyridin-4-yl)-6,7-dihydropyrazolo[1,5-a]pyrazin-4(5H)-one;

(7S)-5-[4-(1-Hydroxyethyl)phenyl]-7-methyl-3-(2-methylpyridin-4-yl)-6,7-dihydropyrazolo[1,5-a]pyrazin-4(5H)-one;

(7R)-5-(3,4-Dichlorophenyl)-7-(methoxymethyl)-3-(2-methylpyridin-4-yl)-6,7-dihydropyrazolo[1,5-a]pyrazin-4(5H)-one; and (7S)-5-(3,4-Dichlorophenyl)-3-[2-(hydroxymethyl)pyridin-4-yl]-7-methyl-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-[3-(1-Hydroxyethyl)phenyl]-7-methyl-3-(2-methylpyridin-4-yl)-6,7-dihydropyrazolo[1,5-a]pyrazin-4(5H)-one;

(7S)-5-(4-Chloro-2-methoxyphenyl)-7-methyl-3-(2-methylpyridin-4-yl)-6,7-dihydropyrazolo[1,5-a]pyrazin-4(5H)-one;

(7S)-5-(2,4-Dichlorophenyl)-7-methyl-3-(2-methylpyridin-4-yl)-6,7-dihydropyrazolo[1,5-a]pyrazin-4(5H)-one;

7,7-Dimethyl-3-(2-methylpyridin-4-yl)-5-[4-(trifluoromethyl)phenyl]-6,7-dihydropyrazolo[1,5-a]pyrazin-4(5H)-one;

(7S)-5-(4-Chloro-2-methylphenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(5-Chloropyridin-2-yl)-7-methyl-3-(2-methylpyridin-4-yl)-6,7-dihydropyrazolo[1,5-a]pyrazin-4(5H)-one;

(7S)-7-Methyl-3-pyridin-4-yl-5-[5-(trifluoromethyl)pyridin-2-yl]-6,7-dihydropyrazolo[1,5-a]pyrazin-4(5H)-one;

(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;

(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;

(7S)-5-(3-Chloro-6-ethoxypyridin-2-yl)-7-methyl-3-(2-methylpyridin-4-yl)-6,7-dihydropyrazolo[1,5-a]pyrazin-4(5H)-one; and (7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one.

In an additional embodiment, the present invention relates to compounds of Formula (I) as defined hereinabove, and stereoisomeric forms thereof, wherein $R^1$ is phenyl, optionally substituted with one or more substituents each independently selected from the group of halo, $C_{1-4}$alkyl, mono- or poly-halo$C_{1-4}$alkyl, —O—$C_{1-4}$alkyl, mono- or poly-halo$C_{1-4}$alkyloxy, cyano and —SF$_5$; or is

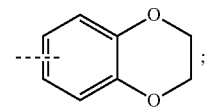

$R^2$ is selected from

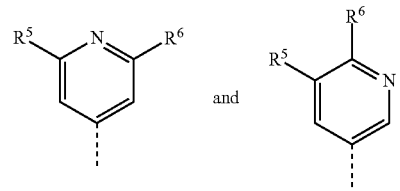

wherein $R^5$ and $R^6$ are each independently selected from the group of hydrogen, $C_{1-4}$alkyl, mono- or poly-halo $C_{1-4}$alkyl, —$C_{1-4}$alkyl-O—$C_{1-4}$alkyl, —O—$C_{1-4}$alkyl, and NR'R'';

wherein R' is selected from hydrogen and $C_{1-4}$alkyl;

R'' is selected from hydrogen and $C_{1-4}$alkyl;

$R^3$ is selected from hydrogen and $C_{1-4}$alkyl;

$R^4$ is selected from the group of hydrogen, $C_{1-4}$alkyl, mono- or poly-halo$C_{1-4}$alkyl, —$C_{1-4}$alkyl-O—$C_{1-4}$alkyl, and —$C_{1-4}$alkyl-OH;

and the pharmaceutically acceptable salts and the solvates thereof.

In an additional embodiment, the present invention relates to compounds of Formula (I) as defined hereinabove, and stereoisomeric forms thereof, wherein $R^1$ is phenyl, optionally substituted with one or more substituents each independently selected from the group of halo, $C_{1-4}$alkyl, mono- or poly-halo$C_{1-4}$alkyl, —O—$C_{1-4}$alkyl, mono- or poly-halo$C_{1-4}$alkoxy, cyano and —SF$_5$; or is

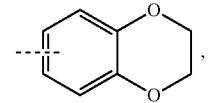

in particular

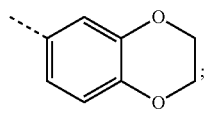

$R^2$ is selected from

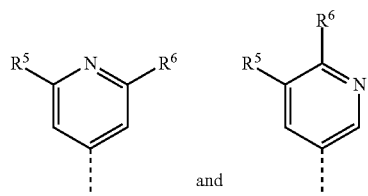

wherein $R^5$ and $R^6$ are each independently selected from the group of hydrogen, $C_{1-4}$alkyl, —$C_{1-4}$alkyl-O—$C_{1-4}$alkyl, —O—$C_{1-4}$alkyl, and NR'R"; wherein R' is hydrogen;

R" is hydrogen;

$R^3$ is selected from hydrogen and $C_{1-4}$alkyl;

$R^4$ is selected from the group of hydrogen and $C_{1-4}$alkyl;

and the pharmaceutically acceptable salts and the solvates thereof.

In an additional embodiment, the present invention relates to compounds of Formula (I) as defined hereinabove, and stereoisomeric forms thereof, wherein $R^1$ is phenyl, optionally substituted with one or more substituents each independently selected from the group of halo, $C_{1-4}$alkyl, poly-halo$C_{1-4}$alkyl and —SF$_5$;

$R^2$ is selected from

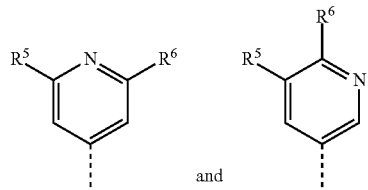

wherein $R^5$ and $R^6$ are each independently selected from the group of hydrogen, $C_{1-4}$alkyl and —O—$C_{1-4}$alkyl;

$R^3$ is selected from hydrogen and $C_{1-4}$alkyl;

$R^4$ is hydrogen;

and the pharmaceutically acceptable salts and the solvates thereof.

In an additional embodiment, the present invention relates to compounds of Formula (I) as defined hereinabove, and stereoisomeric forms thereof, wherein $R^1$ is phenyl, optionally substituted with one or more substituents each independently selected from the group of halo, $C_{1-4}$alkyl, poly-halo$C_{1-4}$alkyl and —SF$_5$;

$R^2$ is selected from

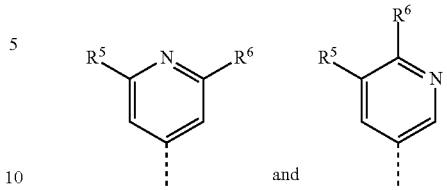

wherein $R^5$ and $R^6$ are each independently selected from the group of hydrogen, $C_{1-4}$alkyl and —O—$C_{1-4}$alkyl;

$R^3$ is hydrogen;

$R^4$ is selected from hydrogen and $C_{1-4}$alkyl;

and the pharmaceutically acceptable salts and the solvates thereof.

In an additional embodiment, the present invention relates to compounds of Formula (I) as defined hereinabove, and stereoisomeric forms thereof, wherein $R^1$ is phenyl, substituted with one, two or three substituents each independently selected from the group of halo, and poly-halo$C_{1-4}$alkyl;

$R^2$ is

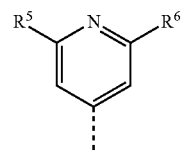

wherein $R^5$ and $R^6$ are each independently selected from the group of hydrogen, $C_{1-4}$alkyl, —O—$C_{1-4}$alkyl, and NR'R";

wherein R' is hydrogen;

R" is $C_{1-4}$alkyl;

$R^3$ is hydrogen;

$R^4$ is hydrogen or $C_{1-4}$alkyl; in particular $R^4$ is $C_{1-4}$alkyl;

and the pharmaceutically acceptable salts and the solvates thereof.

In an additional embodiment, $R^1$ is selected from the group of

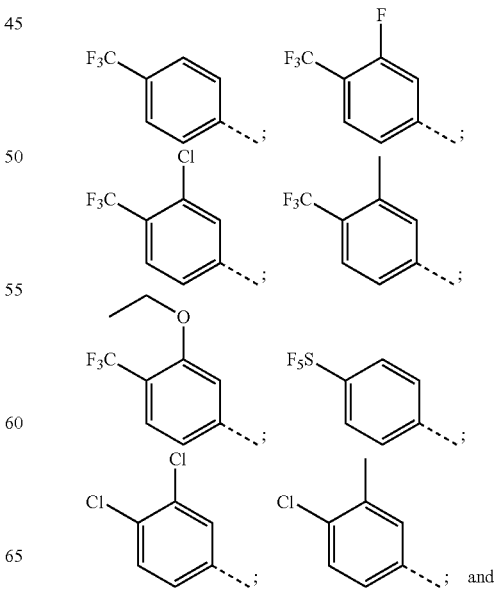

-continued

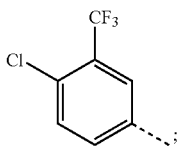

and the rest of variables are as defined in Formula (I) herein.

In an additional embodiment, $R^1$ is selected from the group of

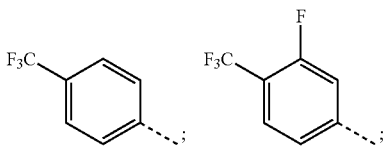

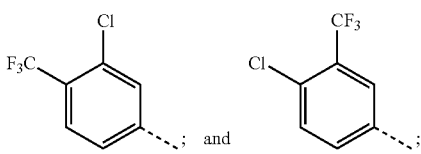

and the rest of variables are as defined in Formula (I) herein;

and the pharmaceutically acceptable salts and the solvates thereof.

In a further embodiment, the present invention relates to compounds of Formula (I) as defined herein wherein $R^3$ is hydrogen and $R^4$ is a substituent different from hydrogen having a configuration as depicted in the Formula (I') below, wherein the 6,7-dihydropyrazolo[1,5-a]pyrazin-4(5H)-one core, $R^1$ and $R^2$ are in the plane of the drawing and $R^4$ is projected above the plane of the drawing (bond shown with a bold wedge), and the rest of variables are as defined in Formula (I) herein

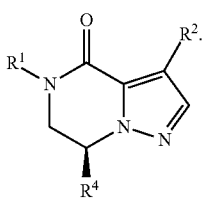
(I')

In a yet further embodiment, the present invention relates to compounds of Formula (I) as defined herein wherein $R^4$ is hydrogen and $R^3$ is a substituent different from hydrogen, for example a $C_{1-4}$alkyl substituent having a configuration as depicted in the Formula (I") below, wherein the 6,7-dihydropyrazolo[1,5-a]pyrazin-4(5H)-one core, $R^1$ and $R^2$ are in the plane of the drawing and $R^3$ is projected above the plane of the drawing (bond shown with a bold wedge), and the rest of variables are as defined in Formula (I) herein

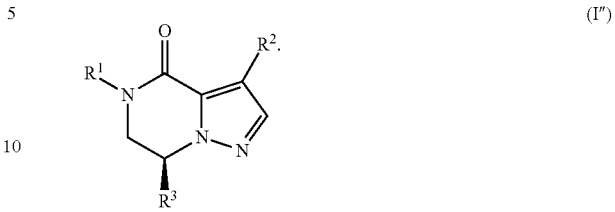
(I")

In an additional embodiment, the present invention relates to compounds of Formula (I') as defined hereinabove, and stereoisomeric forms thereof, wherein $R^1$ is phenyl, substituted with one or two substituents each independently selected from the group of halo, and polyhalo$C_{1-4}$alkyl;

$R^2$ is

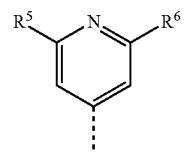

wherein $R^5$ and $R^6$ are each independently selected from the group of hydrogen, $C_{1-4}$alkyl, —O—$C_{1-4}$alkyl, and NR'R";

wherein R' is hydrogen;

R" is $C_{1-4}$alkyl;

$R^4$ is hydrogen or $C_{1-4}$alkyl; in particular $R^4$ is $C_{1-4}$alkyl, more in particular methyl; and the pharmaceutically acceptable salts and the solvates thereof.

In an additional embodiment, the present invention relates to compounds of Formula (I') as defined hereinabove, and stereoisomeric forms thereof, wherein $R^1$ is phenyl, substituted with one or two substituents each independently selected from the group of halo, and polyhalo$C_{1-4}$alkyl;

$R^2$ is

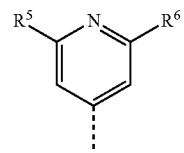

wherein one of $R^5$ and $R^6$ is hydrogen or methyl, in particular hydrogen; and the other one of $R^5$ or $R^6$ is selected from the group of $C_{1-4}$alkyl, —O—$C_{1-4}$alkyl, and NR'R";

wherein R' is hydrogen;

R" is $C_{1-4}$alkyl;

$R^4$ is hydrogen or $C_{1-4}$alkyl; in particular $R^4$ is $C_{1-4}$alkyl, more in particular methyl; and the pharmaceutically acceptable salts and the solvates thereof.

Specific compounds according to the invention include:
(7S)-7-Methyl-3-(2-methylpyridin-4-yl)-5-[4-(trifluoromethyl)phenyl]-6,7-dihydropyrazolo[1,5-a]pyrazin-4(5H)-one;
(7S)-7-Methyl-3-pyridin-4-yl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[4-(pentafluoro-λ⁶-sulfanyl)phenyl]-6,7-dihydropyrazolo[1,5-a]pyrazin-4(5H)-one;

(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one;

(7S)-5-(3,4-Dichlorophenyl)-7-methyl-3-(2-methylpyridin-4-yl)-6,7-dihydropyrazolo[1,5-a]pyrazin-4(5H)-one;

(7S)-5-(4-Chloro-3-methylphenyl)-7-methyl-3-(2-methylpyridin-4-yl)-6,7-dihydropyrazolo[1,5-a]pyrazin-4(5H)-one;

(7S)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

(7S)-5-[4-Chloro-3-(trifluoromethyl)phenyl]-7-methyl-3-(2-methylpyridin-4-yl)-6,7-dihydropyrazolo[1,5-a]pyrazin-4(5H)-one;

(7S)-5-[3-Fluoro-4-(trifluoromethyl)phenyl]-7-methyl-3-(2-methylpyridin-4-yl)-6,7-dihydropyrazolo[1,5-a]pyrazin-4(5H)-one;

7-Methyl-3-(2-methylpyridin-4-yl)-5-[4-(trifluoromethyl)phenyl]-6,7-dihydropyrazolo[1,5-a]pyrazin-4(5H)-one;

(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one;

5-[(7S)-7-Methyl-3-(2-methylpyridin-4-yl)-4-oxo-6,7-dihydropyrazolo[1,5-a]pyrazin-5(4H)-yl]-2-(trifluoromethyl)benzonitrile;

(7S)-3-(2,6-Dimethylpyridin-4-yl)-7-methyl-5-[4-(trifluoromethyl)phenyl]-6,7-dihydropyrazolo[1,5-a]pyrazin-4(5H)-one;

(7S)-5-(4-Chlorophenyl)-7-methyl-3-(2-methylpyridin-4-yl)-6,7-dihydropyrazolo[1,5-a]pyrazin-4(5H)-one;

(7S)-5-(3-Chlorophenyl)-7-methyl-3-(2-methylpyridin-4-yl)-6,7-dihydropyrazolo[1,5-a]pyrazin-4(5H)-one;

(7S)-5-(3-Chloro-4-ethoxyphenyl)-7-methyl-3-(2-methylpyridin-4-yl)-6,7-dihydropyrazolo[1,5-a]pyrazin-4(5H)-one;

(7S)-5-(4-Chloro-3-ethoxyphenyl)-7-methyl-3-(2-methylpyridin-4-yl)-6,7-dihydropyrazolo[1,5-a]pyrazin-4 (5H)-one;

(7S)-5-(4-Chloro-3-methoxyphenyl)-7-methyl-3-(2-methylpyridin-4-yl)-6,7-dihydropyrazolo[1,5-a]pyrazin-4(5H)-one;

(7S)-5-(3-Chloro-4-methoxyphenyl)-7-methyl-3-(2-methylpyridin-4-yl)-6,7-dihydropyrazolo[1,5-a]pyrazin-4 (5H)-one;

(7S)-5-(4-Fluoro-3-methylphenyl)-7-methyl-3-(2-methylpyridin-4-yl)-6,7-dihydropyrazolo[1,5-a]pyrazin-4(5H)-one;

(7S)-3-[2-(Methoxymethyl)pyridin-4-yl]-7-methyl-5-[4-(trifluoromethyl)phenyl]-6,7-dihydropyrazolo[1,5-a]pyrazin-4 (5H)-one;

(7S)-7-Methyl-3-(2-methylpyridin-4-yl)-5-[3-(trifluoromethyl)phenyl]-6,7-dihydropyrazolo[1,5-a]pyrazin-4(5H)-one;

(7S)-7-Methyl-3-(5-methylpyridin-3-yl)-5-[4-(trifluoromethyl)phenyl]-6,7-dihydropyrazolo[1,5-a]pyrazin-4 (5H)-one;

(7S)-5-(3,4-Difluorophenyl)-7-methyl-3-(2-methylpyridin-4-yl)-6,7-dihydropyrazolo[1,5-a]pyrazin-4(5H)-one;

(7R)-7-Methyl-3-(2-methylpyridin-4-yl)-5-[4-(trifluoromethyl)phenyl]-6,7-dihydropyrazolo[1,5-a]pyrazin-4 (5H)-one;

(7S)-5-[4-(Difluoromethoxy)phenyl]-7-methyl-3-(2-methylpyridin-4-yl)-6,7-dihydropyrazolo[1,5-a]pyrazin-4(5H)-one;

(7S)-5-(4-Fluorophenyl)-7-methyl-3-(2-methylpyridin-4-yl)-6,7-dihydropyrazolo[1,5-a]pyrazin-4(5H)-one;

(7S)-3-(5,6-Dimethylpyridin-3-yl)-7-methyl-5-[4-(trifluoromethyl)phenyl]-6,7-dihydropyrazolo[1,5-a]pyrazin-4(5H)-one;

(7S)-5-(4-Chloro-2-fluorophenyl)-7-methyl-3-(2-methylpyridin-4-yl)-6,7-dihydropyrazolo[1,5-a]pyrazin-4(5H)-one;

(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

(7S)-7-Methyl-3-pyridin-3-yl-5-[4-(trifluoromethyl)phenyl]-6,7-dihydropyrazolo[1,5-a]pyrazin-4(5H)-one;

5-[3-Ethoxy-4-(trifluoromethyl)phenyl]-3-(2-methylpyridin-4-yl)-6,7-dihydropyrazolo[1,5-a]pyrazin-4(5H)-one;

(7S)-5-(4-Methoxy-3,5-dimethylphenyl)-7-methyl-3-(2-methylpyridin-4-yl)-6,7-dihydropyrazolo[1,5-a]pyrazin-4(5H)-one;

(7S)-5-(3-Fluoro-4-methoxyphenyl)-7-methyl-3-(2-methylpyridin-4-yl)-6,7-dihydropyrazolo[1,5-a]pyrazin-4(5H)-one;

(7S)-7-Methyl-3-(6-methylpyridin-3-yl)-5-[4-(trifluoromethyl)phenyl]-6,7-dihydropyrazolo[1,5-a]pyrazin-4(5H)-one;

(7S)-3-(6-Aminopyridin-3-yl)-7-methyl-5-[4-(trifluoromethyl)phenyl]-6,7-dihydropyrazolo[1,5-a]pyrazin-4(5H)-one;

(7S)-5-(4-Methoxyphenyl)-7-methyl-3-(2-methylpyridin-4-yl)-6,7-dihydropyrazolo[1,5-a]pyrazin-4(5H)-one;

5-[3-Fluoro-4-(trifluoromethyl)phenyl]-3-(2-methylpyridin-4-yl)-6,7-dihydropyrazolo[1,5-a]pyrazin-4(5H)-one;

3-(2-Methylpyridin-4-yl)-5-[4-(trifluoromethyl)phenyl]-6,7-dihydropyrazolo[1,5-a]pyrazin-4(5H)-one;

(7S)-5-(3,4-Dimethoxyphenyl)-7-methyl-3-(2-methylpyridin-4-yl)-6,7-dihydropyrazolo[1,5-a]pyrazin-4(5H)-one;

(7S)-5-(2,3-Dihydro-1,4-benzodioxin-6-yl)-7-methyl-3-(2-methylpyridin-4-yl)-6,7-dihydropyrazolo[1,5-a]pyrazin-4(5H)-one;

(7S)-5-[3-chloro-4-(trifluoromethyl)phenyl]-3-(2,6-dimethyl-4-pyridyl)-7-methyl-6,7-dihydropyrazolo[1,5-a]pyrazin-4-one;

(7S)-3-[2-(ethylamino)-4-pyridyl]-7-methyl-5-[4-(trifluoromethyl)phenyl]-6,7-dihydropyrazolo[1,5-a]pyrazin-4-one;

(7S)-3-(2-methoxy-4-pyridyl)-7-methyl-5-[4-(trifluoromethyl)phenyl]-6,7-dihydropyrazolo[1,5-a]pyrazin-4-one;

(7S)-3-(2-ethyl-4-pyridyl)-7-methyl-5-[4-(trifluoromethyl)phenyl]-6,7-dihydropyrazolo[1,5-a]pyrazin-4-one;

(7S)-5-(3,4-dichlorophenyl)-3-(2,6-dimethyl-4-pyridyl)-7-methyl-6,7-dihydropyrazolo[1,5-a]pyrazin-4-one;

(7S)-5-[3-(2-Fluoroethoxy)-4-(trifluoromethyl)phenyl]-7-methyl-3-(2-methylpyridin-4-yl)-6,7-dihydropyrazolo[1,5-a]pyrazin-4(5H)-one;

(7S)-3-(2,6-dimethyl-4-pyridyl)-5-[3-ethoxy-4-(trifluoromethyl)phenyl]-7-methyl-6,7-dihydropyrazolo[1,5-a]pyrazin-4-one;

(7S)-5-[3-chloro-4-(trifluoromethyl)phenyl]-7-methyl-3-(4-pyridyl)-6,7-dihydropyrazolo[1,5-a]pyrazin-4-one;

(7S)-3-(2,6-dimethyl-4-pyridyl)-5-[3-methoxy-4-(trifluoromethyl)phenyl]-7-methyl-6,7-dihydropyrazolo[1,5-a]pyrazin-4-one;

7-(fluoromethyl)-3-(2-methyl-4-pyridyl)-5-[4-(trifluoromethyl)phenyl]-6,7-dihydropyrazolo[1,5-a]pyrazin-4-one;

(7S)-3-(2,6-dimethyl-4-pyridyl)-7-methyl-5-[4-(pentafluoro-λ⁶-sulfanyl)phenyl]-6,7-dihydropyrazolo[1,5-a]pyrazin-4-one;

(7S)-5-[4-chloro-3-(trifluoromethyl)phenyl]-3-(2,6-dimethyl-4-pyridyl)-7-methyl-6,7-dihydropyrazolo[1,5-a]pyrazin-4-one;

(7S)-5-[3-ethoxy-4-(trifluoromethyl)phenyl]-7-methyl-3-(4-pyridyl)-6,7-dihydropyrazolo[1,5-a]pyrazin-4-one;

(7S)-7-methyl-5-[4-(pentafluoro-λ⁶-sulfanyl)phenyl]-3-(4-pyridyl)-6,7-dihydropyrazolo[1,5-a]pyrazin-4-one;

(7S)-5-(3,4-dichlorophenyl)-7-methyl-3-(4-pyridyl)-6,7-dihydropyrazolo[1,5-a]pyrazin-4-one;

(7S)-7-methyl-3-(2-methyl-4-pyridyl)-5-[3-(trifluoromethoxy)phenyl]-6,7-dihydropyrazolo[1,5-a]pyrazin-4-one;

5-[(7S)-3-(2,6-dimethyl-4-pyridyl)-7-methyl-4-oxo-6,7-dihydropyrazolo[1,5-a]pyrazin-5-yl]-2-(trifluoromethyl)benzonitrile;

(7S)-5-[3-fluoro-4-(trifluoromethyl)phenyl]-7-methyl-3-(4-pyridyl)-6,7-dihydropyrazolo[1,5-a]pyrazin-4-one;

(7S)-3-(2,6-dimethyl-4-pyridyl)-5-[3-fluoro-4-(trifluoromethyl)phenyl]-7-methyl-6,7-dihydropyrazolo[1,5-a]pyrazin-4-one;

(7S)-5-(4-Chloro-3-fluorophenyl)-7-methyl-3-(2-methylpyridin-4-yl)-6,7-dihydropyrazolo[1,5-a]pyrazin-4(5H)-one;

(7S)-5-(3-chloro-5-fluoro-phenyl)-7-methyl-3-(2-methyl-4-pyridyl)-6,7-dihydropyrazolo[1,5-a]pyrazin-4-one;

(7S)-5-[3-methoxy-4-(trifluoromethyl)phenyl]-7-methyl-3-(4-pyridyl)-6,7-dihydropyrazolo[1,5-a]pyrazin-4-one;

(7S)-5-(4-isopropylphenyl)-7-methyl-3-(2-methyl-4-pyridyl)-6,7-dihydropyrazolo[1,5-a]pyrazin-4-one;

(7S)-7-methyl-3-(2-methyl-4-pyridyl)-5-(4-propylphenyl)-6,7-dihydropyrazolo[1,5-a]pyrazin-4-one;

(7S)-5-[4-Fluoro-3-(trifluoromethyl)phenyl]-7-methyl-3-(2-methylpyridin-4-yl)-6,7-dihydropyrazolo[1,5-a]pyrazin-4(5H)-one;

(7S)-5-[4-chloro-3-(trifluoromethyl)phenyl]-7-methyl-3-(4-pyridyl)-6,7-dihydropyrazolo[1,5-a]pyrazin-4-one;

(7S)-5-[3-(difluoromethoxy)-5-fluoro-phenyl]-7-methyl-3-(2-methyl-4-pyridyl)-6,7-dihydropyrazolo[1,5-a]pyrazin-4-one;

7-ethyl-3-(2-methyl-4-pyridyl)-5-[4-(trifluoromethyl)phenyl]-6,7-dihydropyrazolo[1,5-a]pyrazin-4-one;

(7S)-3-(2-Aminopyridin-4-yl)-7-methyl-5-[4-(trifluoromethyl)phenyl]-6,7-dihydropyrazolo[1,5-a]pyrazin-4(5H)-one;

(7S)-5-(4-chlorophenyl)-3-(2,6-dimethyl-4-pyridyl)-7-methyl-6,7-dihydropyrazolo[1,5-a]pyrazin-4-one;

(7S)-5-(4-chlorophenyl)-7-methyl-3-(4-pyridyl)-6,7-dihydropyrazolo[1,5-a]pyrazin-4-one;

5-[3-Ethoxy-4-(trifluoromethyl)phenyl]-7-(hydroxymethyl)-3-(2-methylpyridin-4-yl)-6,7-dihydropyrazolo[1,5-a]pyrazin-4(5H)-one;

2-Fluoro-4-[(7S)-7-methyl-3-(2-methylpyridin-4-yl)-4-oxo-6,7-dihydropyrazolo[1,5-a]pyrazin-5(4H)-yl]benzonitrile;

(7S)-5-(3-Fluoro-4-methylphenyl)-7-methyl-3-(2-methylpyridin-4-yl)-6,7-dihydropyrazolo[1,5-a]pyrazin-4(5H)-one;

(7S)-5-[4-(2-fluoroethoxy)-3-(trifluoromethyl)phenyl]-7-methyl-3-(2-methyl-4-pyridyl)-6,7-dihydropyrazolo[1,5-a]pyrazin-4-one;

(7S)-7-Methyl-5-(4-methylphenyl)-3-(2-methylpyridin-4-yl)-6,7-dihydropyrazolo[1,5-a]pyrazin-4(5H)-one;

(7S)-7-Methyl-5-[3-(1-methylethoxy)phenyl]-3-(2-methylpyridin-4-yl)-6,7-dihydropyrazolo[1,5-a]pyrazin-4(5H)-one;

4-[(7S)-7-Methyl-3-(2-methylpyridin-4-yl)-4-oxo-6,7-dihydropyrazolo[1,5-a]pyrazin-5(4H)-yl]benzonitrile;

(7S)-5-(4-Ethoxyphenyl)-7-methyl-3-(2-methylpyridin-4-yl)-6,7-dihydropyrazolo[1,5-a]pyrazin-4(5H)-one;

(7S)-5-(3,5-Difluorophenyl)-7-methyl-3-(2-methylpyridin-4-yl)-6,7-dihydropyrazolo[1,5-a]pyrazin-4(5H)-one;

(7S)-5-(3-Ethoxyphenyl)-7-methyl-3-(2-methylpyridin-4-yl)-6,7-dihydropyrazolo[1,5-a]pyrazin-4(5H)-one;

(7S)-5-(3,4-difluoro-5-methoxy-phenyl)-7-methyl-3-(2-methyl-4-pyridyl)-6,7-dihydropyrazolo[1,5-a]pyrazin-4-one;

(7S)-5-(3-fluoro-5-methoxy-phenyl)-7-methyl-3-(2-methyl-4-pyridyl)-6,7-dihydropyrazolo[1,5-a]pyrazin-4-one;

(7S)-7-Methyl-3-(2-methylpyridin-4-yl)-5-phenyl-6,7-dihydropyrazolo[1,5-a]pyrazin-4(5H)-one;

7-(Hydroxymethyl)-3-(2-methyl-4-pyridyl)-5-[4-(trifluoromethyl)phenyl]-6,7-dihydropyrazolo[1,5-a]pyrazin-4-one;

5-[(7S)-3-(2-Methoxypyridin-4-yl)-7-methyl-4-oxo-6,7-dihydropyrazolo[1,5-a]pyrazin-5(4H)-yl]-2-(trifluoromethyl)benzonitrile;

(7S)-5-(4-Chlorophenyl)-3-(2-methoxypyridin-4-yl)-7-methyl-6,7-dihydropyrazolo[1,5-a]pyrazin-4(5H)-one;

5-(3,4-Dichlorophenyl)-3-[2-(dimethylamino)pyridin-4-yl]-7-(fluoromethyl)-6,7-dihydropyrazolo[1,5-a]pyrazin-4(5H)-one (7R or 7S);

5-(3,4-Dichlorophenyl)-3-[2-(dimethylamino)pyridin-4-yl]-7-(fluoromethyl)-6,7-dihydropyrazolo[1,5-a]pyrazin-4(5H)-one (7S or 7R);

(7S)-5-[3-Chloro-4-(trifluoromethyl)phenyl]-3-[2-(3-fluoroazetidin-1-yl)pyridin-4-yl]-7-methyl-6,7-dihydropyrazolo[1,5-a]pyrazin-4(5H)-one;

5-(3,4-Dichlorophenyl)-7-(fluoromethyl)-3-[2-(methylamino)pyridin-4-yl]-6,7-dihydropyrazolo[1,5-a]pyrazin-4(5H)-one;

(7S)-3-[2-(3-Fluoroazetidin-1-yl)pyridin-4-yl]-7-methyl-5-[4-(trifluoromethyl)phenyl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}-6-(methylamino)pyridine-2-carbonitrile;

(7S)-3-(2-Azetidin-1-ylpyridin-4-yl)-5-[3-chloro-4-(trifluoromethyl)phenyl]-7-methyl-6,7-dihydropyrazolo[1,5-a]pyrazin-4(5H)-one;

(7S)-3-(2-Azetidin-1-ylpyridin-4-yl)-5-(3,4-dichlorophenyl)-7-methyl-6,7-dihydropyrazolo[1,5-a]pyrazin-4(5H)-one;

(7S)-5-[3-(Fluoromethyl)-4-(trifluoromethyl)phenyl]-7-methyl-3-(2-methylpyridin-4-yl)-6,7-dihydropyrazolo[1,5-a]pyrazin-4(5H)-one;

(7S)-7-Methyl-5-[4-(trifluoromethyl)phenyl]-3-[2-(trifluoromethyl)pyridin-4-yl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}pyridine-2-carbonitrile;

(7S)-3-[2-(3-Hydroxyazetidin-1-yl)pyridin-4-yl]-7-methyl-5-[4-(trifluoromethyl)phenyl]-6,7-dihydropyrazolo[1,5-a]pyrazin-4(5H)-one;

(7S)-3-(2-Azetidin-1-ylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-7-methyl-3-[2-(methylamino)pyridin-4-yl]-6,7-dihydropyrazolo[1,5-a]pyrazin-4(5H)-one;

(7S)-5-[3-Chloro-4-(trifluoromethyl)phenyl]-3-(2-methoxypyridin-4-yl)-7-methyl-6,7-dihydropyrazolo[1,5-a]pyrazin-4(5H)-one;

(7S)-7-Methyl-3-(2-pyrrolidin-1-ylpyridin-4-yl)-5-[4-(trifluoromethyl)phenyl]-6,7-dihydropyrazolo[1,5-a]pyrazin-4(5H)-one;

(7S)-3-[2-(4-Acetylpiperazin-1-yl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-piperidin-1-ylpyridin-4-yl)-5-[4-(trifluoromethyl)phenyl]-6,7-dihydropyrazolo[1,5-a]pyrazin-4(5H)-one;

(7S)-7-Methyl-3-(2-morpholin-4-ylpyridin-4-yl)-5-[4-(trifluoromethyl)phenyl]-6,7-dihydropyrazolo[1,5-a]pyrazin-4(5H)-one;

4-[(7S)-5-(3,4-Dichlorophenyl)-7-methyl-4-oxo-4,5,6,7-tetrahydropyrazolo[1,5-a]pyrazin-3-yl]pyridine-2-carbonitrile;

(7S)-5-(3,4-Dichlorophenyl)-7-methyl-3-[2-(methylamino)pyridin-4-yl]-6,7-dihydropyrazolo[1,5-a]pyrazin-4(5H)-one;

(7S)-5-(3,4-Dichlorophenyl)-3-[2-(1-hydroxyethyl)pyridin-4-yl]-7-methyl-6,7-dihydropyrazolo[1,5-a]pyrazin-4(5H)-one;

(7S)-3-[2-(Fluoromethyl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[4-(2,2,2-trifluoro-1-methylethyl)phenyl]-6,7-dihydropyrazolo[1,5-a]pyrazin-4(5H)-one;

(7S)-5-(3,4-Dichlorophenyl)-3-[2-(difluoromethyl)pyridin-4-yl]-7-methyl-6,7-dihydropyrazolo[1,5-a]pyrazin-4(5H)-one;

5-(3,4-Dichlorophenyl)-7-(fluoromethyl)-3-(2-methylpyridin-4-yl)-6,7-dihydropyrazolo[1,5-a]pyrazin-4(5H)-one (7S or 7R);

5-(3,4-Dichlorophenyl)-7-(fluoromethyl)-3-(2-methylpyridin-4-yl)-6,7-dihydropyrazolo[1,5-a]pyrazin-4(5H)-one (7R or 7S);

(7S)-5-(3,4-Dichlorophenyl)-3-[2-(fluoromethyl)pyridin-4-yl]-7-methyl-6,7-dihydropyrazolo[1,5-a]pyrazin-4(5H)-one;

5-(3,4-Dichlorophenyl)-7-(methoxymethyl)-3-(2-methylpyridin-4-yl)-6,7-dihydropyrazolo[1,5-a]pyrazin-4(5H)-one (7S or 7R);

5-(3,4-Dichlorophenyl)-7-(methoxymethyl)-3-(2-methylpyridin-4-yl)-6,7-dihydropyrazolo[1,5-a]pyrazin-4(5H)-one (7R or 7S);

7-(Methoxymethyl)-3-(2-methylpyridin-4-yl)-5-[4-(trifluoromethyl)phenyl]-6,7-dihydropyrazolo[1,5-a]pyrazin-4(5H)-one (7R or 7S);

7-(Methoxymethyl)-3-(2-methylpyridin-4-yl)-5-[4-(trifluoromethyl)phenyl]-6,7-dihydropyrazolo[1,5-a]pyrazin-4(5H)-one (7S or 7R);

(7S)-3-(2-Cyclopropylpyridin-4-yl)-5-(3,4-dichlorophenyl)-7-methyl-6,7-dihydropyrazolo[1,5-a]pyrazin-4(5H)-one;

(7S)-3-(2-Ethoxypyridin-4-yl)-7-methyl-5-[4-(trifluoromethyl)phenyl]-6,7-dihydropyrazolo[1,5-a]pyrazin-4(5H)-one;

(7S)-5-(3,4-Dichlorophenyl)-7-methyl-3-[2-(1-methylethyl)pyridin-4-yl]-6,7-dihydropyrazolo[1,5-a]pyrazin-4(5H)-one;

(7S)-5-(3,4-Dichlorophenyl)-3-[2-(hydroxymethyl)pyridin-4-yl]-7-methyl-6,7-dihydropyrazolo[1,5-a]pyrazin-4(5H)-one;

(7S)-7-Methyl-3-[2-(1-methylethyl)pyridin-4-yl]-5-[4-(trifluoromethyl)phenyl]-6,7-dihydropyrazolo[1,5-a]pyrazin-4(5H)-one;

4-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-3-[2-(1-Hydroxyethyl)pyridin-4-yl]-7-methyl-5-[4-(trifluoromethyl)phenyl]-6,7-dihydropyrazolo[1,5-a]pyrazin-4(5H)-one;

(7R)-7-Ethyl-3-(2-methylpyridin-4-yl)-5-[4-(trifluoromethyl)phenyl]-6,7-dihydropyrazolo[1,5-a]pyrazin-4(5H)-one;

(7S)-7-Ethyl-3-(2-methylpyridin-4-yl)-5-[4-(trifluoromethyl)phenyl]-6,7-dihydropyrazolo[1,5-a]pyrazin-4(5H)-one;

(7S)-3-[2-(Difluoromethyl)pyridin-4-yl]-7-methyl-5-[4-(trifluoromethyl)phenyl]-6,7-dihydropyrazolo[1,5-a]pyrazin-4(5H)-one;

(7S)-5-[3,5-Difluoro-4-(trifluoromethyl)phenyl]-7-methyl-3-(2-methylpyridin-4-yl)-6,7-dihydropyrazolo[1,5-a]pyrazin-4(5H)-one;

(7S)-5-(3,4-Dichlorophenyl)-3-(2-ethoxypyridin-4-yl)-7-methyl-6,7-dihydropyrazolo[1,5-a]pyrazin-4(5H)-one;

(7S)-5-(3,4-Dichlorophenyl)-3-(2-ethylpyridin-4-yl)-7-methyl-6,7-dihydropyrazolo[1,5-a]pyrazin-4(5H)-one;

(7S)-3-[2-(Hydroxymethyl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-{4-[1-(trifluoromethyl)cyclopropyl]phenyl}-6,7-dihydropyrazolo[1,5-a]pyrazin-4(5H)-one;

(7S)-5-(3,4-Dichlorophenyl)-7-methyl-3-[2-(1-methylethoxy)pyridin-4-yl]-6,7-dihydropyrazolo[1,5-a]pyrazin-4(5H)-one;

(7S)-7-Methyl-3-[2-(1-methylethoxy)pyridin-4-yl]-5-[4-(trifluoromethyl)phenyl]-6,7-dihydropyrazolo[1,5-a]pyrazin-4(5H)-one;

(7S)-5-(4-Bromophenyl)-7-methyl-3-(2-methylpyridin-4-yl)-6,7-dihydropyrazolo[1,5-a]pyrazin-4(5H)-one;

(7S)-7-Methyl-3-(2-methyl-1-oxidopyridin-4-yl)-5-[4-(trifluoromethyl)phenyl]-6,7-dihydropyrazolo[1,5-a]pyrazin-4(5H)-one;

(7S)-5-(4-tert-Butylphenyl)-7-methyl-3-(2-methylpyridin-4-yl)-6,7-dihydropyrazolo[1,5-a]pyrazin-4(5H)-one;

(7S)-5-(3,4-Dichlorophenyl)-3-(2-methoxypyridin-4-yl)-7-methyl-6,7-dihydropyrazolo[1,5-a]pyrazin-4(5H)-one;

5-(3,4-Dichlorophenyl)-7-(methoxymethyl)-3-(2-methylpyridin-4-yl)-6,7-dihydropyrazolo[1,5-a]pyrazin-4(5H)-one;

7-(Methoxymethyl)-3-(2-methylpyridin-4-yl)-5-[4-(trifluoromethyl)phenyl]-6,7-dihydropyrazolo[1,5-a]pyrazin-4(5H)-one;

(7S)-3-(2-Methoxy-6-methylpyridin-4-yl)-7-methyl-5-[4-(trifluoromethyl)phenyl]-6,7-dihydropyrazolo[1,5-a]pyrazin-4(5H)-one;

(7S)-5-(3,4-Dichlorophenyl)-3-(2-methoxy-6-methylpyridin-4-yl)-7-methyl-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-[3-(1-Hydroxyethyl)phenyl]-7-methyl-3-(2-methylpyridin-4-yl)-6,7-dihydropyrazolo[1,5-a]pyrazin-4(5H)-one;

(7S)-5-[4-(1-Hydroxyethyl)phenyl]-7-methyl-3-(2-methylpyridin-4-yl)-6,7-dihydropyrazolo[1,5-a]pyrazin-4(5H)-one;

(7S)-3-(6-Methoxypyridin-3-yl)-7-methyl-5-[4-(trifluoromethyl)phenyl]-6,7-dihydropyrazolo[1,5-a]pyrazin-4(5H)-one;

5-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-7-Methyl-3-(2-methylpyridin-4-yl)-5-[4-(trifluoromethoxy)phenyl]-6,7-dihydropyrazolo[1,5-a]pyrazin-4(5H)-one;

(7S)-7-Methyl-5-[3-methyl-4-(trifluoromethyl)phenyl]-3-pyridin-4-yl-6,7-dihydropyrazolo[1,5-a]pyrazin-4(5H)-one;

(7S)-7-Methyl-5-[3-(1-methylethoxy)-4-(trifluoromethyl)phenyl]-3-(2-methylpyridin-4-yl)-6,7-dihydropyrazolo[1,5-a]pyrazin-4(5H)-one;

5-[(7S)-7-Methyl-4-oxo-3-pyridin-4-yl-6,7-dihydropyrazolo[1,5-a]pyrazin-5(4H)-yl]-2-(trifluoromethyl)benzonitrile;

(7S)-5-(4-Cyclopropylphenyl)-7-methyl-3-(2-methylpyridin-4-yl)-6,7-dihydropyrazolo[1,5-a]pyrazin-4(5H)-one;

(7S)-3-(2,6-Dimethylpyridin-4-yl)-7-methyl-5-[3-methyl-4-(trifluoromethyl)phenyl]-6,7-dihydropyrazolo[1,5-a]pyrazin-4(5H)-one;

(7S)-5-[3-(Methoxymethyl)-4-(trifluoromethyl)phenyl]-7-methyl-3-(2-methylpyridin-4-yl)-6,7-dihydropyrazolo[1,5-a]pyrazin-4(5H)-one;

(7S)-5-(3,5-Dichlorophenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[4-(2,2,2-trifluoroethoxy)phenyl]-6,7-dihydropyrazolo[1,5-a]pyrazin-4(5H)-one;

(7S)-5-(4-Chloro-2-methoxyphenyl)-7-methyl-3-(2-methylpyridin-4-yl)-6,7-dihydropyrazolo[1,5-a]pyrazin-4(5H)-one;

(7S)-5-[4-(Difluoromethyl)phenyl]-7-methyl-3-(2-methylpyridin-4-yl)-6,7-dihydropyrazolo[1,5-a]pyrazin-4(5H)-one;

(7S)-5-[4-Chloro-3-(difluoromethoxy)phenyl]-7-methyl-3-(2-methylpyridin-4-yl)-6,7-dihydropyrazolo[1,5-a]pyrazin-4(5H)-one;

(7S)-5-(3,4-Dichlorophenyl)-3-(2-fluoropyridin-4-yl)-7-methyl-6,7-dihydropyrazolo[1,5-a]pyrazin-4(5H)-one;

(7S)-7-Methyl-3-(2-methylpyridin-4-yl)-5-[4-(2,2,2-trifluoro-1-methylethoxy)phenyl]-6,7-dihydropyrazolo[1,5-a]pyrazin-4(5H)-one;

(7S)-3-[2-(Dimethylamino)pyridin-4-yl]-7-methyl-5-[4-(trifluoromethyl)phenyl]-6,7-dihydropyrazolo[1,5-a]pyrazin-4(5H)-one;

(7S)-5-(2,4-Dichlorophenyl)-7-methyl-3-(2-methylpyridin-4-yl)-6,7-dihydropyrazolo[1,5-a]pyrazin-4(5H)-one;

(7S)-5-[3-Chloro-4-(difluoromethoxy)phenyl]-7-methyl-3-(2-methylpyridin-4-yl)-6,7-dihydropyrazolo[1,5-a]pyrazin-4(5H)-one;

(7S)-5-[4-Chloro-3-(trifluoromethoxy)phenyl]-7-methyl-3-(2-methylpyridin-4-yl)-6,7-dihydropyrazolo[1,5-a]pyrazin-4(5H)-one;

(7S)-5-(3,4-Dichlorophenyl)-7-methyl-3-(2-methyl-1-oxidopyridin-4-yl)-6,7-dihydropyrazolo[1,5-a]pyrazin-4(5H)-one;

7,7-Dimethyl-3-(2-methylpyridin-4-yl)-5-[4-(trifluoromethyl)phenyl]-6,7-dihydropyrazolo[1,5-a]pyrazin-4(5H)-one;

(7S)-5-(4-Chloro-2-methylphenyl)-7-methyl-3-(2-methylpyridin-4-yl)-6,7-dihydropyrazolo[1,5-a]pyrazin-4(5H)-one;

(7S)-3-(2-Cyclopropylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(difluoromethyl)phenyl]-7-methyl-3-(2-methylpyridin-4-yl)-6,7-dihydropyrazolo[1,5-a]pyrazin-4(5H)-one;

(7S)-7-Methyl-3-(2-piperazin-1-ylpyridin-4-yl)-5-[4-(trifluoromethyl)phenyl]-6,7-dihydropyrazolo[1,5-a]pyrazin-4(5H)-one;

(7S)-7-Methyl-3-(6-piperazin-1-ylpyridin-3-yl)-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-3-[2-(2-fluoroethoxy)pyridin-4-yl]-7-methyl-6,7-dihydropyrazolo[1,5-a]pyrazin-4(5H)-one;

(7S)-5-(4-Chlorophenyl)-7-methyl-3-[2-(methylamino)pyridin-4-yl]-6,7-dihydropyrazolo[1,5-a]pyrazin-4(5H)-one;

5-[(7S)-7-Methyl-3-[2-(methylamino)pyridin-4-yl]-4-oxo-6,7-dihydropyrazolo[1,5-a]pyrazin-5(4H)-yl]-2-(trifluoromethyl)benzonitrile;

(7S)-3-(2-Methoxypyridin-4-yl)-5-[3-methoxy-4-(trifluoromethyl)phenyl]-7-methyl-6,7-dihydropyrazolo[1,5-a]pyrazin-4(5H)-one;

7-(Difluoromethyl)-3-(2-methylpyridin-4-yl)-5-[4-(trifluoromethyl)phenyl]-6,7-dihydropyrazolo[1,5-a]pyrazin-4(5H)-one;

(7S)-5-[3-Fluoro-4-(trifluoromethyl)phenyl]-7-methyl-3-[2-(methylamino)pyridin-4-yl]-6,7-dihydropyrazolo[1,5-a]pyrazin-4(5H)-one;

(7S)-5-[3-Methoxy-4-(trifluoromethyl)phenyl]-7-methyl-3-[2-(methylamino)pyridin-4-yl]-6,7-dihydropyrazolo[1,5-a]pyrazin-4(5H)-one;

5-(3,4-Dichlorophenyl)-7-(fluoromethyl)-3-[2-(methylamino)pyridin-4-yl]-6,7-dihydropyrazolo[1,5-a]pyrazin-4(5H)-one (7R or 7S);

5-(3,4-Dichlorophenyl)-7-(fluoromethyl)-3-[2-(methylamino)pyridin-4-yl]-6,7-dihydropyrazolo[1,5-a]pyrazin-4(5H)-one (7S or 7R);

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(5-Chloropyridin-2-yl)-7-methyl-3-(2-methylpyridin-4-yl)-6,7-dihydropyrazolo[1,5-a]pyrazin-4(5H)-one;

(7S)-5-[6-Chloro-5-(trifluoromethyl)pyridin-2-yl]-7-methyl-3-(2-methylpyridin-4-yl)-6,7-dihydropyrazolo[1,5-a]pyrazin-4(5H)-one;

(7S)-5-[4-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-7-Methyl-3-pyridin-4-yl-5-[5-(trifluoromethyl)pyridin-2-yl]-6,7-dihydropyrazolo[1,5-a]pyrazin-4(5H)-one;

(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[6-methyl-5-(trifluoromethyl)pyridin-2-yl]-6,7-dihydropyrazolo[1,5-a]pyrazin-4(5H)-one;

(7S)-7-Methyl-3-(2-methylpyridin-4-yl)-5-[4-methyl-5-(trifluoromethyl)pyridin-2-yl]-6,7-dihydropyrazolo[1,5-a]pyrazin-4(5H)-one;

(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;

(7S)-5-(3-Chloro-6-ethoxypyridin-2-yl)-7-methyl-3-(2-methylpyridin-4-yl)-6,7-dihydropyrazolo[1,5-a]pyrazin-4(5H)-one;
(7S)-5-(5-Chloro-6-methylpyridin-2-yl)-7-methyl-3-(2-methylpyridin-4-yl)-6,7-dihydropyrazolo[1,5-a]pyrazin-4(5H)-one;
(7S)-3-(2-Fluoropyridin-4-yl)-7-methyl-5-[5-(trifluoromethyl)pyridin-2-yl]-6,7-dihydropyrazolo[1,5-a]pyrazin-4(5H)-one;
(7S)-5-(4-Chloro-5-methylpyridin-2-yl)-7-methyl-3-(2-methylpyridin-4-yl)-6,7-dihydropyrazolo[1,5-a]pyrazin-4(5H)-one;
(7S)-5-[6-Ethoxy-3-(trifluoromethyl)pyridin-2-yl]-7-methyl-3-(2-methylpyridin-4-yl)-6,7-dihydropyrazolo[1,5-a]pyrazin-4(5H)-one;
(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;
(7S)-5-(5-Chloro-6-ethoxypyridin-2-yl)-7-methyl-3-(2-methylpyridin-4-yl)-6,7-dihydropyrazolo[1,5-a]pyrazin-4(5H)-one;
(7S)-5-(5,6-Dichloropyridin-2-yl)-7-methyl-3-(2-methylpyridin-4-yl)-6,7-dihydropyrazolo[1,5-a]pyrazin-4(5H)-one;
(7S)-5-(4,5-Dichloropyridin-2-yl)-7-methyl-3-(2-methylpyridin-4-yl)-6,7-dihydropyrazolo[1,5-a]pyrazin-4(5H)-one;
(7S)-5-[4-Chloro-5-(trifluoromethyl)pyridin-2-yl]-7-methyl-3-(2-methylpyridin-4-yl)-6,7-dihydropyrazolo[1,5-a]pyrazin-4(5H)-one;
(7S)-3-(2,6-Dimethylpyridin-4-yl)-5-[6-ethoxy-5-(trifluoromethyl)pyridin-2-yl]-7-methyl-6,7-dihydropyrazolo[1,5-a]pyrazin-4(5H)-one;
(7S)-5-(5-Chloro-6-methoxypyridin-2-yl)-7-methyl-3-(2-methylpyridin-4-yl)-6,7-dihydropyrazolo[1,5-a]pyrazin-4(5H)-one;
(7S)-5-[6-Methoxy-5-(trifluoromethyl)pyridin-2-yl]-7-methyl-3-(2-methylpyridin-4-yl)-6,7-dihydropyrazolo[1,5-a]pyrazin-4(5H)-one;
(7S)-5-[6-Ethoxy-5-(trifluoromethyl)pyridin-2-yl]-7-methyl-3-pyridin-4-yl-6,7-dihydropyrazolo[1,5-a]pyrazin-4(5H)-one;
(7S)-3-(2-Azetidin-1-ylpyridin-4-yl)-5-[6-methoxy-5-(trifluoromethyl)pyridin-2-yl]-7-methyl-6,7-dihydropyrazolo[1,5-a]pyrazin-4(5H)-one;
(7S)-7-Methyl-3-[2-(methylamino)pyridin-4-yl]-5-[5-(trifluoromethyl)pyridin-2-yl]-6,7-dihydropyrazolo[1,5-a]pyrazin-4(5H)-one;
3-(2-Methylpyridin-4-yl)-5-[5-(trifluoromethyl)pyridin-2-yl]-6,7-dihydropyrazolo[1,5-a]pyrazin-4(5H)-one;
(7S)-5-[4-Iodo-5-(trifluoromethyl)pyridin-2-yl]-7-methyl-3-(2-methylpyridin-4-yl)-6,7-dihydropyrazolo[1,5-a]pyrazin-4(5H)-one;
(7S)-5-(4-Chloro-5-iodopyridin-2-yl)-7-methyl-3-(2-methylpyridin-4-yl)-6,7-dihydropyrazolo[1,5-a]pyrazin-4(5H)-one;
(7S)-7-Methyl-3-[2-(methylamino)-1-oxidopyridin-4-yl]-5-[4-(trifluoromethyl)phenyl]-6,7-dihydropyrazolo[1,5-a]pyrazin-4(5H)-one;
(7S)-3-(2-Chloropyridin-4-yl)-7-methyl-5-[4-(trifluoromethyl)phenyl]-6,7-dihydropyrazolo[1,5-a]pyrazin-4(5H)-one;
7-(1-Hydroxyethyl)-3-(2-methylpyridin-4-yl)-5-[4-(trifluoromethyl)phenyl]-6,7-dihydropyrazolo[1,5-a]pyrazin-4(5H)-one (1R or 1S);

7-(1-Hydroxyethyl)-3-(2-methylpyridin-4-yl)-5-[4-(trifluoromethyl)phenyl]-6,7-dihydropyrazolo[1,5-a]pyrazin-4(5H)-one (1S or 1R);
(7S)-3-(2-Chloropyridin-4-yl)-5-(3,4-dichlorophenyl)-7-methyl-6,7-dihydropyrazolo[1,5-a]pyrazin-4(5H)-one;
5-(3,4-Dichlorophenyl)-7-(hydroxymethyl)-3-(2-methylpyridin-4-yl)-6,7-dihydropyrazolo[1,5-a]pyrazin-4(5H)-one;
(7S)-5-(4,5-Dichloro-2-iodophenyl)-7-methyl-3-(2-methylpyridin-4-yl)-6,7-dihydropyrazolo[1,5-a]pyrazin-4(5H)-one;
(7S)-5-(3,4-Dichloro-2-iodophenyl)-7-methyl-3-(2-methylpyridin-4-yl)-6,7-dihydropyrazolo[1,5-a]pyrazin-4(5H)-one;
5-(3,4-Dichlorophenyl)-7-(fluoromethyl)-3-(2-methylpyridin-4-yl)-6,7-dihydropyrazolo[1,5-a]pyrazin-4(5H)-one;
(7S)-3-(2-Bromopyridin-4-yl)-7-methyl-5-[4-(trifluoromethyl)phenyl]-6,7-dihydropyrazolo[1,5-a]pyrazin-4(5H)-one;
5-(3,4-Dichlorophenyl)-3-(2-fluoropyridin-4-yl)-7-(hydroxymethyl)-6,7-dihydropyrazolo[1,5-a]pyrazin-4(5H)-one;
(7S)-3-(2-Iodopyridin-4-yl)-7-methyl-5-[4-(trifluoromethyl)phenyl]-6,7-dihydropyrazolo[1,5-a]pyrazin-4(5H)-one;
5-(3,4-Dichlorophenyl)-3-(2-fluoropyridin-4-yl)-7-(hydroxymethyl)-6,7-dihydropyrazolo[1,5-a]pyrazin-4(5H)-one (7S or 7R);
5-(3,4-Dichlorophenyl)-3-(2-fluoropyridin-4-yl)-7-(hydroxymethyl)-6,7-dihydropyrazolo[1,5-a]pyrazin-4(5H)-one (7R or 7S);
(7S)-5-[3-Chloro-4-(trifluoromethyl)phenyl]-3-(2-fluoropyridin-4-yl)-7-methyl-6,7-dihydropyrazolo[1,5-a]pyrazin-4(5H)-one;
(7S)-5-[3-Bromo-4-(trifluoromethyl)phenyl]-7-methyl-3-(2-methylpyridin-4-yl)-6,7-dihydropyrazolo[1,5-a]pyrazin-4(5H)-one;
(7S)-5-(4-Iodophenyl)-7-methyl-3-(2-methylpyridin-4-yl)-6,7-dihydropyrazolo[1,5-a]pyrazin-4(5H)-one;
5-(3,4-Dichlorophenyl)-3-[2-(dimethylamino)pyridin-4-yl]-7-(hydroxymethyl)-6,7-dihydropyrazolo[1,5-a]pyrazin-4(5H)-one (7S or 7R);
5-(3,4-Dichlorophenyl)-3-[2-(dimethylamino)pyridin-4-yl]-7-(hydroxymethyl)-6,7-dihydropyrazolo[1,5-a]pyrazin-4(5H)-one (7R or 7S);
5-(3,4-Dichlorophenyl)-7-(hydroxymethyl)-3-[2-(methylamino)pyridin-4-yl]-6,7-dihydropyrazolo[1,5-a]pyrazin-4(5H)-one;
(7S)-3-(2-Chloro-6-methoxypyridin-4-yl)-7-methyl-5-[4-(trifluoromethyl)phenyl]-6,7-dihydropyrazolo[1,5-a]pyrazin-4(5H)-one;
(7S)-3-[6-(1-Acetylazetidin-3-yl)pyridin-3-yl]-7-methyl-5-[4-(trifluoromethyl)phenyl]-6,7-dihydropyrazolo[1,5-a]pyrazin-4(5H)-one
(7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one;
(7S)-5-[6-Methoxy-5-(trifluoromethyl)pyridin-2-yl]-7-methyl-3-[2-(methylamino)pyridin-4-yl]-6,7-dihydropyrazolo[1,5-a]pyrazin-4(5H)-one;
3-(2-Methylpyridin-4-yl)-7-(trifluoromethyl)-5-[4-(trifluoromethyl)phenyl]-6,7-dihydropyrazolo[1,5-a]pyrazin-4(5H)-one;
(7S)-5-[3-(hydroxymethyl)-4-(trifluoromethyl)phenyl]-7-methyl-3-(2-methyl-4-pyridyl)-6,7-dihydropyrazolo[1,5-a]pyrazin-4-one;

(7S)-3-(2-methoxy-4-pyridyl)-5-[6-methoxy-5-(trifluoromethyl)-2-pyridyl]-7-methyl-6,7-dihydropyrazolo[1,5-a]pyrazin-4-one;
(7S)-7-methyl-3-[2-methyl-6-(methylamino)-4-pyridyl]-5-[4-(trifluoromethyl)phenyl]-6,7-dihydropyrazolo[1,5-a]pyrazin-4-one;
(7S)-3-[2-methoxy-6-(methylamino)-4-pyridyl]-7-methyl-5-[4-(trifluoromethyl)phenyl]-6,7-dihydropyrazolo[1,5-a]pyrazin-4-one;
(7S)-3-[2-fluoro-6-(methylamino)-4-pyridyl]-7-methyl-5-[4-(trifluoromethyl)phenyl]-6,7-dihydropyrazolo[1,5-a]pyrazin-4-one;
5-(2,4-dichlorophenyl)-3-(2-methyl-4-pyridyl)-6,7-dihydropyrazolo[1,5-a]pyrazin-4-one;
(7S)-3-[2-(dimethylamino)-4-pyridyl]-5-[3-(hydroxymethyl)-4-(trifluoromethyl)phenyl]-7-methyl-6,7-dihydropyrazolo[1,5-a]pyrazin-4-one;
(7S)-3-[2-(dimethylamino)-4-pyridyl]-5-[3-(fluoromethyl)-4-(trifluoromethyl)phenyl]-7-methyl-6,7-dihydropyrazolo[1,5-a]pyrazin-4-one;
(7S)-3-(2-fluoro-4-pyridyl)-7-methyl-5-[4-(trifluoromethyl)phenyl]-6,7-dihydropyrazolo[1,5-a]pyrazin-4-one;
(7S)-5-(3,4-dichlorophenyl)-3-[2-(dimethylamino)-4-pyridyl]-7-methyl-6,7-dihydropyrazolo[1,5-a]pyrazin-4-one;
(7S)-3-[2-(dimethylamino)-4-pyridyl]-5-[3-(2-fluoroethoxy)-4-(trifluoromethyl)phenyl]-7-methyl-6,7-dihydropyrazolo[1,5-a]pyrazin-4-one;
(7S)-3-[2-(dimethylamino)-4-pyridyl]-5-[6-methoxy-5-(trifluoromethyl)-2-pyridyl]-7-methyl-6,7-dihydropyrazolo[1,5-a]pyrazin-4-one;
(7S)-7-methyl-3-[2-(methylamino)-4-pyridyl]-5-[3-methyl-4-(trifluoromethyl)phenyl]-6,7-dihydropyrazolo[1,5-a]pyrazin-4-one;
(7S)-5-[3-chloro-4-(trifluoromethyl)phenyl]-7-methyl-3-(2-methyl-1-oxido-pyridin-1-ium-4-yl)-6,7-dihydropyrazolo[1,5-a]pyrazin-4-one;
(7S)-3-[2-[ethyl(methyl)amino]-4-pyridyl]-7-methyl-5-[4-(trifluoromethyl)phenyl]-6,7-dihydropyrazolo[1,5-a]pyrazin-4-one;
(7S)-5-[3-chloro-4-(trifluoromethyl)phenyl]-3-[2-[ethyl(methyl)amino]-4-pyridyl]-7-methyl-6,7-dihydropyrazolo[1,5-a]pyrazin-4-one;
(7S)-5-[3-chloro-4-(trifluoromethyl)phenyl]-3-[2-(ethylamino)-4-pyridyl]-7-methyl-6,7-dihydropyrazolo[1,5-a]pyrazin-4-one;
(7S)-3-[2-(ethylamino)-4-pyridyl]-7-methyl-5-[3-methyl-4-(trifluoromethyl)phenyl]-6,7-dihydropyrazolo[1,5-a]pyrazin-4-one;
(7S)-5-(3,4-dichlorophenyl)-3-[2-(ethylamino)-4-pyridyl]-7-methyl-6,7-dihydropyrazolo[1,5-a]pyrazin-4-one;
(7S)-7-methyl-5-[3-methyl-4-(trifluoromethyl)phenyl]-3-[2-(propylamino)-4-pyridyl]-6,7-dihydropyrazolo[1,5-a]pyrazin-4-one;
(7S)-7-methyl-3-[2-(propylamino)-4-pyridyl]-5-[4-(trifluoromethyl)phenyl]-6,7-dihydropyrazolo[1,5-a]pyrazin-4-one;
(7S)-3-[2-(azetidin-1-yl)-4-pyridyl]-7-methyl-5-[3-methyl-4-(trifluoromethyl)phenyl]-6,7-dihydropyrazolo[1,5-a]pyrazin-4-one;
(7S)-3-[2-(isopropylamino)-4-pyridyl]-7-methyl-5-[3-methyl-4-(trifluoromethyl)phenyl]-6,7-dihydropyrazolo[1,5-a]pyrazin-4-one;
(7S)-3-[2-(isopropylamino)-4-pyridyl]-7-methyl-5-[4-(trifluoromethyl)phenyl]-6,7-dihydropyrazolo[1,5-a]pyrazin-4-one;
(7S)-5-[3-chloro-4-(trifluoromethyl)phenyl]-3-[2-(fluoromethyl)-4-pyridyl]-7-methyl-6,7-dihydropyrazolo[1,5-a]pyrazin-4-one;
(7S)-5-[3-chloro-4-(trifluoromethyl)phenyl]-7-methyl-3-[2-(propylamino)-4-pyridyl]-6,7-dihydropyrazolo[1,5-a]pyrazin-4-one;
(7S)-5-(3,4-dichlorophenyl)-7-methyl-3-[2-(propylamino)-4-pyridyl]-6,7-dihydropyrazolo[1,5-a]pyrazin-4-one;
(7S)-5-[3-chloro-4-(trifluoromethyl)phenyl]-3-[2-(isopropylamino)-4-pyridyl]-7-methyl-6,7-dihydropyrazolo[1,5-a]pyrazin-4-one;
(7S)-5-(3,4-dichlorophenyl)-3-[2-(isopropylamino)-4-pyridyl]-7-methyl-6,7-dihydropyrazolo[1,5-a]pyrazin-4-one;

and the pharmaceutically acceptable salts and solvates of such compounds.

In another embodiment, specific compounds according to the invention include:

(7S)-7-Methyl-3-(2-methylpyridin-4-yl)-5-[4-(trifluoromethyl)phenyl]-6,7-dihydropyrazolo[1,5-a]pyrazin-4(5H)-one hydrochloride salt;
(7S)-7-Methyl-3-(2-methylpyridin-4-yl)-5-[4-(trifluoromethyl)phenyl]-6,7-dihydropyrazolo[1,5-a]pyrazin-4(5H)-one sulfate salt;
(7S)-7-Methyl-3-(2-methylpyridin-4-yl)-5-[4-(trifluoromethyl)phenyl]-6,7-dihydropyrazolo[1,5-a]pyrazin-4(5H)-one methane sulfonate salt;
(7S)-7-Methyl-3-(2-methylpyridin-4-yl)-5-[4-(trifluoromethyl)phenyl]-6,7-dihydropyrazolo[1,5-a]pyrazin-4(5H)-one maleate salt;
(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one hydrochloride salt;
(7S)-5-(3,4-Dichlorophenyl)-7-methyl-3-(2-methylpyridin-4-yl)-6,7-dihydropyrazolo[1,5-a]pyrazin-4(5H)-one hydrochloride salt;
(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one hydrochloride salt;
(7S)-5-(4-Chlorophenyl)-7-methyl-3-(2-methylpyridin-4-yl)-6,7-dihydropyrazolo[1,5-a]pyrazin-4(5H)-one hydrochloride salt;
(7S)-5-(3-Chloro-4-ethoxyphenyl)-7-methyl-3-(2-methylpyridin-4-yl)-6,7-dihydropyrazolo[1,5-a]pyrazin-4(5H)-one hydrochloride salt;
(7S)-5-(3-Chloro-4-methoxyphenyl)-7-methyl-3-(2-methylpyridin-4-yl)-6,7-dihydropyrazolo[1,5-a]pyrazin-4(5H)-one hydrochloride salt;
(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one hydrochloride salt;
(7S)-5-(3,4-Difluorophenyl)-7-methyl-3-(2-methylpyridin-4-yl)-6,7-dihydropyrazolo[1,5-a]pyrazin-4(5H)-one hydrochloride salt;
(7S)-5-(4-Fluorophenyl)-7-methyl-3-(2-methylpyridin-4-yl)-6,7-dihydropyrazolo[1,5-a]pyrazin-4(5H)-one hydrochloride salt;
(7S)-5-(3-Fluoro-4-methoxyphenyl)-7-methyl-3-(2-methylpyridin-4-yl)-6,7-dihydropyrazolo[1,5-a]pyrazin-4(5H)-one hydrochloride salt;
(7S)-5-(4-Methoxyphenyl)-7-methyl-3-(2-methylpyridin-4-yl)-6,7-dihydropyrazolo[1,5-a]pyrazin-4(5H)-one hydrochloride salt;
(7S)-7-methyl-3-(2-methyl-4-pyridyl)-5-[3-(trifluoromethoxy)phenyl]-6,7-dihydropyrazolo[1,5-a]pyrazin-4-one hydrochloride salt;

(7S)-5-(3-chloro-5-fluoro-phenyl)-7-methyl-3-(2-methyl-4-pyridyl)-6,7-dihydropyrazolo[1,5-a]pyrazin-4-one hydrochloride salt;

(7S)-5-(4-isopropylphenyl)-7-methyl-3-(2-methyl-4-pyridyl)-6,7-dihydropyrazolo[1,5-a]pyrazin-4-one hydrochloride salt;

(7S)-7-methyl-3-(2-methyl-4-pyridyl)-5-(4-propylphenyl)-6,7-dihydropyrazolo[1,5-a]pyrazin-4-one hydrochloride salt;

(7S)-5-[3-(difluoromethoxy)-5-fluoro-phenyl]-7-methyl-3-(2-methyl-4-pyridyl)-6,7-dihydropyrazolo[1,5-a]pyrazin-4-one hydrochloride salt;

(7S)-7-Methyl-5-[3-(1-methylethoxy)phenyl]-3-(2-methyl-pyridin-4-yl)-6,7-dihydropyrazolo[1,5-a]pyrazin-4(5H)-one hydrochloride salt;

(7S)-5-(4-Ethoxyphenyl)-7-methyl-3-(2-methylpyridin-4-yl)-6,7-dihydropyrazolo[1,5-a]pyrazin-4(5H)-one hydrochloride salt;

(7S)-7-Methyl-3-(2-piperidin-1-ylpyridin-4-yl)-5-[4-(trifluoromethyl)phenyl]-6,7-dihydropyrazolo[1,5-a]pyrazin-4(5H)-one hydrochloride salt;

(7S)-3-(2-Cyclopropylpyridin-4-yl)-5-(3,4-dichlorophenyl)-7-methyl-6,7-dihydropyrazolo[1,5-a]pyrazin-4(5H)-one hydrochloride salt;

(7S)-5-(3,4-Dichlorophenyl)-3-(2-ethoxypyridin-4-yl)-7-methyl-6,7-dihydropyrazolo[1,5-a]pyrazin-4(5H)-one hydrochloride salt;

(7S)-5-(3,4-Dichlorophenyl)-7-methyl-3-[2-(1-methylethoxy)pyridin-4-yl]-6,7-dihydropyrazolo[1,5-a]pyrazin-4(5H)-one hydrochloride salt;

(7S)-7-Methyl-3-[2-(1-methylethoxy)pyridin-4-yl]-5-[4-(trifluoromethyl)phenyl]-6,7-dihydropyrazolo[1,5-a]pyrazin-4(5H)-one hydrochloride salt;

(7S)-3-(2-Cyclopropylpyridin-4-yl)-7-methyl-5-[4-(trifluoromethyl)phenyl]-6,7-dihydropyrazolo[1,5-a]pyrazin-4(5H)-one hydrochloride salt;

(7S)-7-Methyl-3-(2-piperazin-1-ylpyridin-4-yl)-5-[4-(trifluoromethyl)phenyl]-6,7-dihydropyrazolo[1,5-a]pyrazin-4(5H)-one hydrochloride salt, and (7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one hydrochloride salt.

The names of the compounds of the present invention were generated according to the nomenclature rules agreed upon by the Chemical Abstracts Service (C.A.S.) using Advanced Chemical Development, Inc., software (ACD/Name product version 10.01.0.14105, October 2006). In case of tautomeric forms, the name of the depicted tautomeric form of the structure was generated. However it should be clear that the other non-depicted tautomeric form is also included within the scope of the present invention.

Definitions

The notation "$C_{1-4}$alkyl" as used herein alone or as part of another group, defines a saturated, straight or branched, hydrocarbon radical having, unless otherwise stated, from 1 to 4 carbon atoms, such as methyl, ethyl, 1-propyl, 1-methylethyl, butyl, 1-methyl-propyl, 2-methyl-1-propyl, 1,1-dimethylethyl and the like. The notation "—$C_{1-4}$alkyl-OH" as used herein alone or as part of another group, refers to $C_{1-4}$alkyl as defined before, substituted with one OH group at any available carbon atom.

The notation "halogen" or "halo" as used herein alone or as part of another group, refers to fluoro, chloro, bromo or iodo, with fluoro or chloro being preferred.

The notation "mono- and polyhalo$C_{1-4}$alkyl" as used herein alone or as part of another group, refers to $C_{1-4}$alkyl as defined before, substituted with 1, 2, 3 or where possible with more halo atoms as defined before.

The notation "$C_{3-7}$cycloalkyl" as used herein refers to a saturated, cyclic hydrocarbon radical having from 3 to 7 carbon atoms, such as cyclopropyl, cyclobutyl, cyclopentyl, cyclohexyl and cycloheptyl. A particular $C_{3-7}$cycloalkyl group is cyclopropyl.

The N-oxide forms of the compounds according to Formula (I) are meant to comprise those compounds of Formula (I) wherein one or several nitrogen atoms are oxidized to the so called N-oxide, particularly those N-oxides wherein a nitrogen atom in a pyridinyl radical is oxidized. N-oxides can be formed following procedures known to the skilled person. The N-oxidation reaction may generally be carried out by reacting the starting material of Formula (I) with an appropriate organic or inorganic peroxide. Appropriate inorganic peroxides comprise, for example, hydrogen peroxide, alkali metal or alkaline metal peroxides, e.g. sodium peroxide, potassium peroxide/appropriate organic peroxides may comprise peroxy acids such as, for example, benzenecarboperoxoic acid or halo substituted benzenecarboperoxoic acid, e.g. 3-chloroperoxybenzoic acid (or 3-chloroperbenzoic acid), peroxoalkanoic acids, e.g. peroxoacetic acid, alkylhydroperoxides, e.g. tert-butyl hydroperoxide. Suitable solvents, e.g are for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

In a particular embodiment, the invention relates to a compound of Formula (I) wherein
$R^2$ is

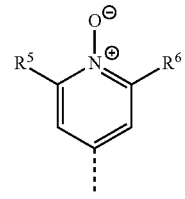

and the rest of variables are as defined herein.

Whenever the term "substituted" is used in the present invention, it is meant, unless otherwise is indicated or is clear from the context, to indicate that one or more hydrogens, preferably from 1 to 3 hydrogens, more preferably from 1 to 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds of Formula (I) and their pharmaceutically acceptable addition salts and solvates thereof may contain one or more centres of chirality and exist as stereoisomeric forms.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S.

Resolved stereoisomers whose absolute configuration is not known can be designated by (+) or (−) depending on the direction in which they rotate plane polarized light.

For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above formula are intended to be included within the scope of the present invention.

It follows that a single compound may exist in both stereisomeric and tautomeric forms.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form, for example $^2$H. Radiolabelled compounds of Formula (I) may comprise a radioactive isotope selected from the group of $^3$H, $^{11}$C, $^{14}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Preparation

The compounds according to the invention can generally be prepared by a succession of steps, each of which is known to the skilled person. In particular, the compounds can be prepared according to the following synthesis methods.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase or chiral supercritical fluid chromatography (SFC). Said pure stereochemically isomeric forms may also be derived from the corresponding pure stereochemically isomeric forms of the appropriate starting materials, provided that the reaction occurs stereospecifically.

The absolute configuration of compounds of the invention reported herein was determined by analysis of the racemic mixture by supercritical fluid chromatography (SFC) followed by SFC comparison of the separate enantiomer(s) which were obtained by asymmetric synthesis or by chiral separation of mixtures, followed by vibrational circular dichroism (VCD) analysis of the particular enantiomer(s).

A. Preparation of the Final Compounds

Experimental Procedure 1

Final compounds according to Formula (I) can be prepared by a Goldberg coupling reaction of a compound of Formula (II) with an appropriate aryl halide of Formula (III) where X is halo, in particular bromo or iodo, according to conditions known to the skilled person. Such conditions include for example using a suitable copper(I) catalyst such as copper(I) iodide, in the presence of a ligand, such as N,N'-dimethylethylenediamine, in the presence of a base, such as inorganic carbonates, for example sodium carbonate (Na$_2$CO$_3$) or potassium carbonate (K$_2$CO$_3$), in a suitable solvent, such as toluene or a mixture of toluene and N,N-dimethylformamide (DMF), under suitable reaction conditions, such as at a convenient temperature, typically ranging between 100° C. and 140° C., in particular 110° C., for a period of time to ensure the completion of the reaction. A compound of Formula (III) can be obtained commercially or made according to procedures known in the art. In Reaction Scheme 1, all variables are defined as in Formula (I)

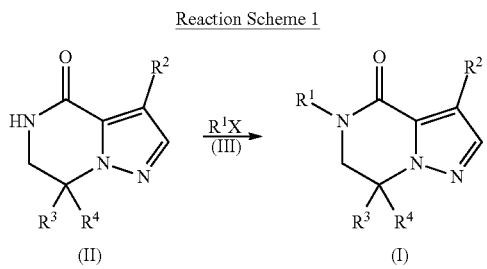

Reaction Scheme 1

Experimental Procedure 2

Alternatively, final compounds according to Formula (I) can be prepared by a Suzuki type coupling reaction of a compound of Formula (IVa) with a suitable boron species or a compound of Formula (IVb), wherein R$^{7a}$ and R$^{8a}$ may be each independently selected from H, C$_{1-4}$alkyl or R$^{7a}$ and R$^{8a}$ are taken together to form for example a bivalent radical of formula —CH$_2$CH$_2$—, —CH$_2$CH$_2$CH$_2$— or —C(CH$_3$)$_2$C(CH$_3$)$_2$—, with a suitable heteroaryl halide or aryl halide derivative in the presence of a palladium catalyst, according to reaction conditions known to the skilled person. Such reaction conditions include the use of a palladium catalyst, such as tetrakis(triphenylphosphine)palladium(0) or an alternative catalyst system prepared in situ from Pd(OAc)$_2$ and PPh$_3$, a suitable base, such as Na$_2$CO$_3$, K$_2$CO$_3$, NaOAc, NaHCO$_3$ or K$_3$PO$_4$, and in a suitable solvent, such as 1,4-dioxane, or a mixture of dimethoxyethane (DME) and water. Degassing the reaction mixture with an inert gas, such as N$_2$ or argon, and heating the reaction mixture to high temperatures, such as reflux temperature under classical heating or microwave irradiation, in particular 80° C., may enhance the reaction outcome. In Reaction Schemes 2a and 2b, all variables are defined as in Formula (I).

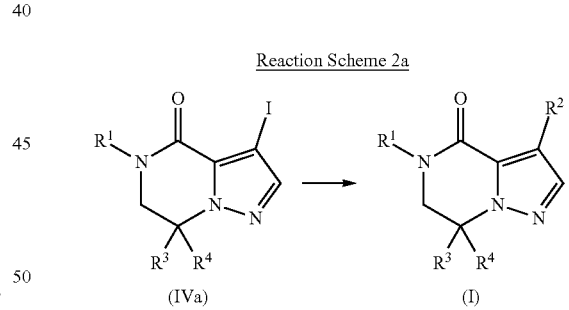

Reaction Scheme 2a

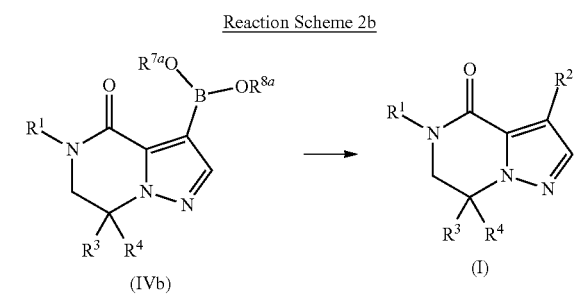

Reaction Scheme 2b

The suitable boron species may be selected for example from a boronic acid or a boronate ester, which may be conveniently represented as a compound of Formula (IIIa)

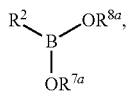

(IIIa)

wherein $R^2$ is as defined in Formula (I) herein and $R^{7a}$ and $R^{8a}$ may be each independently selected from H, $C_{1-4}$alkyl or $R^{7a}$ and $R^{8a}$ are taken together to form for example a bivalent radical of formula —$CH_2CH_2$—, —$CH_2CH_2CH_2$— or —$C(CH_3)_2C(CH_3)_2$—. A skilled person can envisage that the reaction under Reaction Scheme 2a can also be performed under similar conditions, when the compound of Formula (IVa) bears a bromo group in place of an iodo group. Such a reaction can be represented as in Reaction Scheme 2c, wherein the compound of Formula (IV), wherein $R^{2a}$ is halo, in particular bromo or iodo and all other variables are as defined in Formula (I), undergoes a Suzuki type coupling as described hereinbefore.

Reaction Scheme 2c

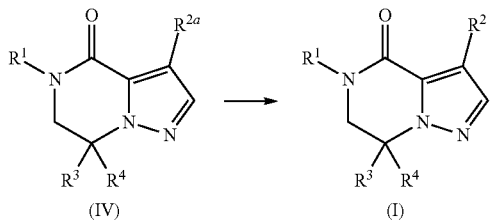

(IV)    (I)

Experimental Procedure 3

Alternatively, final compounds according to Formula (I), wherein $R^2$ is an optionally substituted 4-pyridinyl or 3-pyridinyl, hereby referred to as compounds of Formula (Ia) or Formula (Ib), respectively, can be prepared by a reaction of deprotection of a compound of Formula (Ia-1) or a compound of Formula (Ia-2) following art known procedures. A compound of Formula (Ia) or a compound Formula (Ib) can be obtained by removal of the protecting group such as for example a Boc protecting group in the compound of Formula (Ia-1) or compound of Formula (Ia-2), in the presence of acidic media, such as trifluoroacetic acid, in an inert solvent such as dichloromethane (DCM), under suitable reaction conditions, such as at a convenient temperature, typically rt, for a period of time to ensure the completion of the reaction. In Reaction Schemes 3a and 3b, all variables are defined as in Formula (I) and $R^{5a'}$ and $R^{6a'}$ include the residues indicated in the scope as $R^5$ and $R^6$ as well as their protected forms.

Reaction Scheme 3a

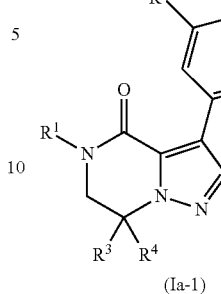

(Ia-1)

Deprotection

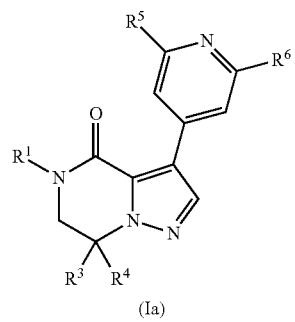

(Ia)

Reaction Scheme 3b

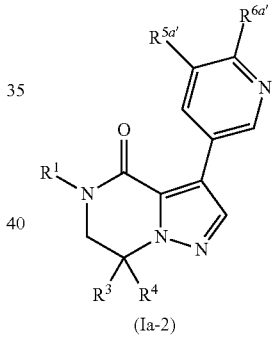

(Ia-2)

Deprotection

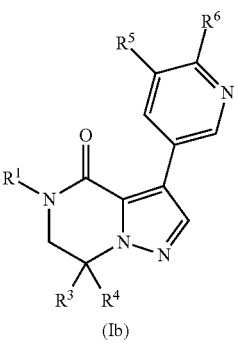

(Ib)

Experimental Procedure 4

Alternatively, final compounds according to Formula (Ia) and Formula (Ib) can be prepared by manipulation of a suitable precursor of Formula (Ib-1) and of Formula (Ib-2) respectively, bearing one or more functional groups which can be converted to the residues $R^5$ and $R^6$ by means of simple reactions known to the person skilled in the art, such as for example introduction of an alcohol or an amine in presence of a base and a suitable solvent or acylation with an acyl chloride in the presence of a base and a suitable solvent or reduction for example by using a suitable reducing agent such as sodium borohydride, in a suitable solvent or by means of cross coupling reactions known to the person skilled in the art, such as for example the Suzuki reaction with a suitable boron species or the Stille reaction with a suitable tin species. In Reaction Schemes 4a and 4b, all variables are defined as in Formula (I) and $R^{5b}$ and $R^{6b}$ include the residues indicated in the scope as $R^5$ and $R^6$ as well as their possible precursors. The person skilled in the art will recognize that suitable reaction conditions should be chosen for different $R^{5b}$ and $R^{6b}$ combinations, to avoid undesired side reactions.

of fluorination of a compound of Formula (Ic-1) and of Formula (Ic-2) wherein Y is N, CH or $CR^9c$ and one of $R^{5c}$, $R^{6c}$, $R^{3c}$, $R^{4c}$, $R^{9c}$ and $R^{10c}$ may be each independently selected from $C_{1-4}$alkyl-OH or $C_{1-3}$alkyl-CHO and herein referred to as a compound of Formula (Ic-1) and compound of Formula (Ic-2) respectively. A compound of Formula (Ic-1) or compound of Formula (Ic-2) can be treated in the presence of a fluorinating agent such as for example ®Deoxofluor ([Bis(2-methoxyethyl)amino]sulfur trifluoride) or (diethylamino)sulfur trifluoride in a suitable solvent such as, for example DCM, and stirring the reaction mixture at rt. In Reaction Schemes 5a and 5b, all variables are defined as in Formula (I) and $R^{5c}$, $R^{6c}$, $R^{3c}$, and $R^{4c}$ include the residues indicated in the scope of Formula (I) as $R^5$, $R^6$, $R^3$, $R^4$ as well as their possible precursors, and $R^{9c}$ and $R^{10c}$, when present, include the residues indicated in the scope of Formula (I) as substituents in $R^1$ as well as their possible precursors, wherein one of $R^{5c}$, $R^{6c}$, $R^{3c}$, $R^{4c}$, and $R^{9c}$ and $R^{10c}$ when present, is $C_{1-4}$alkyl-OH or $C_{1-3}$alkyl-CHO and in $(R^{10d})_n$, n=0-4.

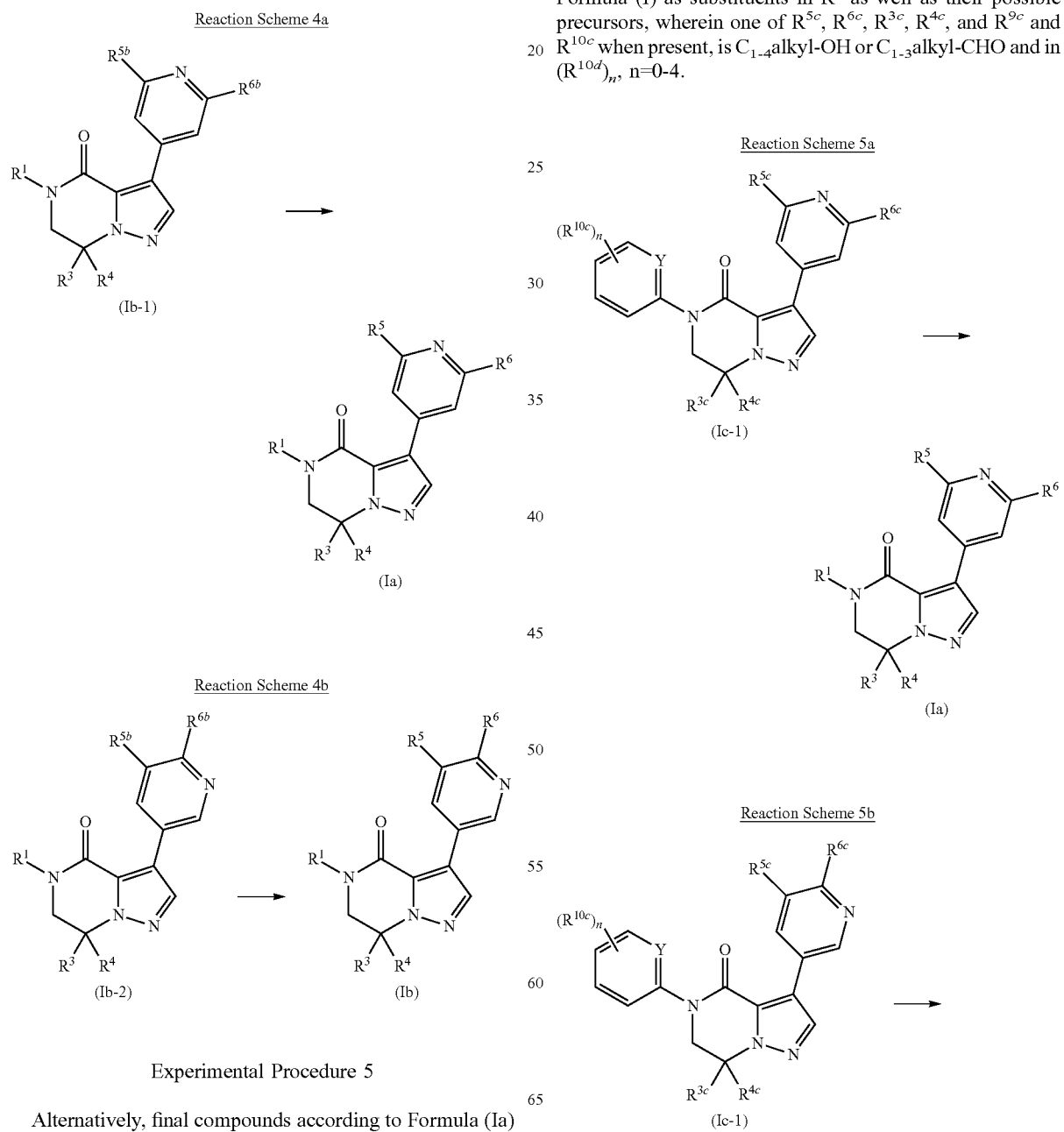

Experimental Procedure 5

Alternatively, final compounds according to Formula (Ia) and Formula (Ib) can be prepared respectively by a reaction

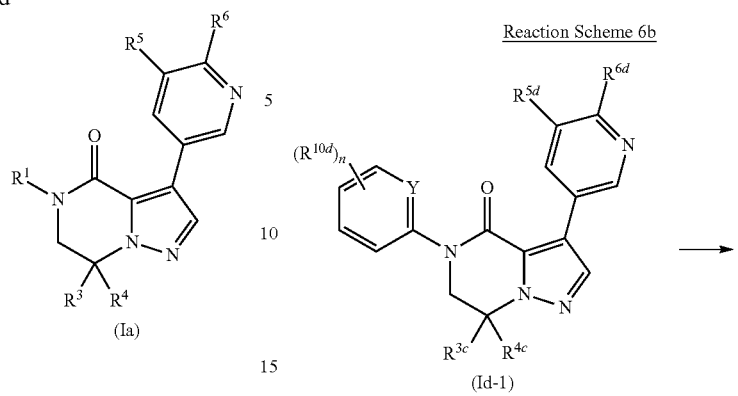

(Ia)

Experimental Procedure 6

Alternatively, final compounds according to Formula (Ia) and Formula (Ib) can be prepared by manipulation of a suitable precursor of Formula (Id-1) or of Formula (Id-2) respectively, wherein Y is N, CH or $CR^{9d}$, bearing one or more functional groups, $R^{5d}$, $R^{6d}$, $R^{9d}$ and $R^{10d}$, which can be converted to the residues $R^5$, $R^6$ and the substituents of $R^1$ as defined in Formula (I) by means of simple reactions known to the person skilled in the art, such as for example by reduction of a double bond to the corresponding saturated form, for example by means of catalytic hydrogenation. In Reaction Schemes 6a and 6b, all variables are defined as in Formula (I) and $R^{5d}$ and $R^{6d}$, include the residues indicated in the scope as $R^5$, $R^6$ as well as their possible precursors, and $R^{9d}$ and $R^{10d}$ when present include the substituents of $R^1$ as well as their possible precursors. The person skilled in the art will recognize that suitable reaction conditions should be chosen for different $R^{5d}$, $R^{6d}$, $R^{9d}$ and $R^{10d}$ combinations to avoid undesired side reactions and in $(R^{10d})_n$, n=0-4.

Reaction Scheme 6a

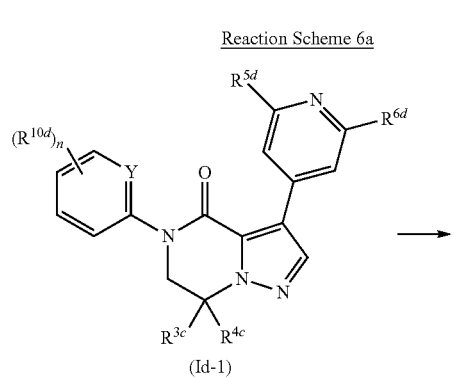

(Id-1)

Experimental Procedure 7

Alternatively, final compounds according to Formula (Id) can be prepared by means of an oxidation reaction of a compound of Formula (I) in the presence of an oxidant, such as for example 3-chloroperoxybenzoic acid and in a suitable solvent. In Reaction Scheme 7, all variables are defined as in Formula (I).

Reaction Scheme 7

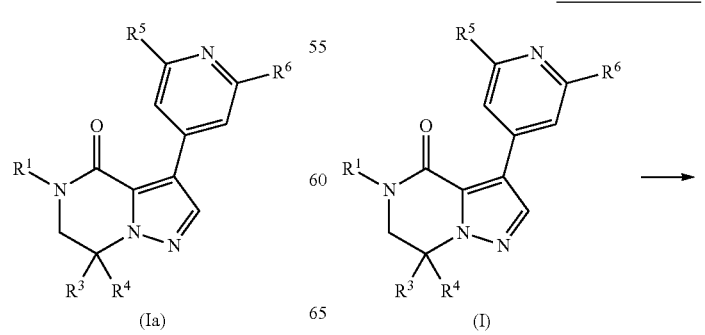

-continued

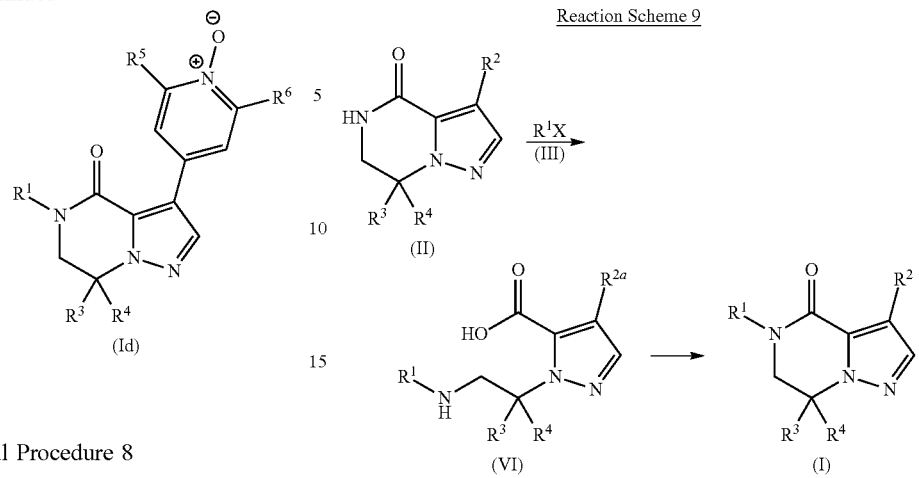

Experimental Procedure 8

Alternatively, final compounds according to Formula (I) can be prepared by intramolecular amidation starting from a compound of Formula (VI). Typically, amidation conditions can be applied, such as stirring the starting materials, dissolved in a suitable solvent, such as DMF, in the presence of a coupling agent, such as HATU (2-(7-aza-1H-benzotriazole-1-yl)-1,1,3,3-tetramethyluronium hexafluorophosphate) and in the presence of a base, such as TEA (triethylamine). In Reaction Scheme 8, all variables are defined as in Formula (I).

Reaction Scheme 8

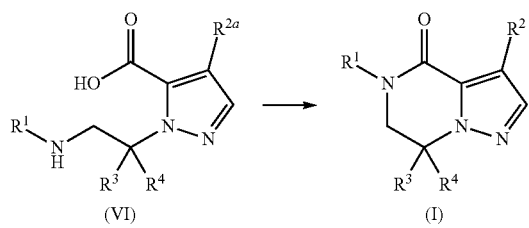

Experimental Procedure 9

Alternatively, final compounds according to Formula (I) can be prepared in one pot starting from a compound of Formula (II). First, a reaction of nucleophilic substitution of a compound of Formula (II) with an appropriate (hetero)aryl halide of Formula (III) where X is halo in the presence of a base such as for example sodium hydride in a suitable solvent such as for example DMF, followed by an intramolecular peptide type coupling of compound of Formula (VI) applying typical peptide type coupling conditions. Typically, peptide coupling conditions can be applied, such as stirring the starting materials, dissolved in a suitable solvent, such as DMF, in the presence of a peptide coupling agent, such as HATU and in the presence of a base, such as TEA. In Reaction Scheme 9, all variables are defined as in Formula (I).

Reaction Scheme 9

Alternatively, final compounds according to Formula (I) can be prepared in one pot starting from a compound of Formula (II). First by a coupling reaction of a compound of Formula (II) with an appropriate heteroaryl halide of Formula (III) where X is halo in the presence of a palladium catalyst, such as tetrakis(triphenylphosphine)palladium(0), in the presence of a ligand, such as 4,5-bis(diphenylphosphino)-9,9-dimethylxanthene, in the presence of a base, such as $Cs_2CO_3$ and in a suitable solvent, such as 1,4-dioxane, under suitable reaction conditions, such as at a convenient temperature, typically ranging between 100° C. and 140° C., for a period of time to ensure the completion of the reaction, followed by an intramolecular peptide type coupling of compound of Formula (VI) applying typical peptide type coupling conditions. Typically, peptide coupling conditions can be applied, such as stirring the starting materials, dissolved in a suitable solvent, such as DMF, in the presence of a peptide coupling agent, such as HATU and in the presence of a base, such as TEA. In Reaction Scheme 9, all variables are defined as in Formula (I).

B. Preparation of the Intermediate Compounds

Experimental Procedure 10

Intermediate compound according to Formula (II) (Reaction Scheme 10a) can be prepared following art known procedures, such as by subjecting an intermediate compound of Formula (Va) to a Suzuki type coupling reaction under conditions known to a skilled person. Such conditions include for example, reacting the intermediate compound of Formula (Va) with a suitable boron species, such as for example a boronic acid or a boronate ester, for example as described in Experimental procedure 2 hereinbefore, in the presence of a palladium catalyst, such as tetrakis(triphenylphosphine)palladium(0) or an alternative catalyst system prepared in situ from $Pd(OAc)_2$ and $PPh_3$, a suitable base, such as $Na_2CO_3$, $K_2CO_3$, $NaHCO_3$ and $K_3PO_4$, and in a suitable solvent, such as 1,4-dioxane, or a mixture of DME and water. Degassing the reaction mixture with an inert gas, such as $N_2$ or argon, and heating the reaction mixture to high temperatures, such as reflux temperature, in particular 80° C., may enhance the reaction outcome. In Reaction Scheme 10a, all variables are defined as in Formula (I).

Reaction Scheme 10a

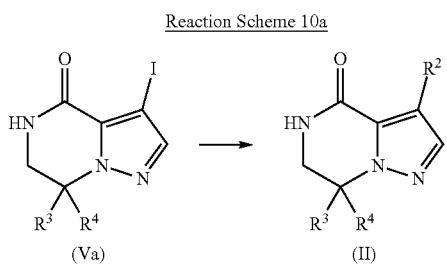

A skilled person can envisage that the reaction under Reaction Scheme 10a can also be performed under similar conditions, when the compound of Formula (Va) bears a bromo group in place of a iodo group. Such a reaction can be represented as in Reaction Scheme 10b, wherein the compound of Formula (V), wherein $R^{2a}$ is halo, in particular bromo or iodo and all other variables are as defined in Formula (I), undergoes a Suzuki type coupling as described hereinbefore.

Reaction Scheme 10b

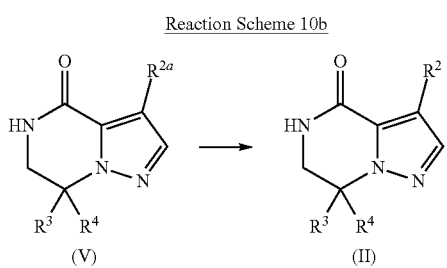

In particular aspect, the invention therefore relates to an intermediate compound of Formula (V), wherein $R^{2a}$ is halo, in particular Br or I

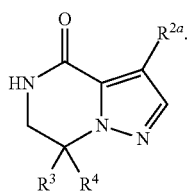

(V)

In a particular embodiment, the invention relates to an intermediate compound of Formula (V'), wherein $R^{2a}$ is halo, in particular, Br (referred to herein as compound (I-13a) or I (referred to herein as compound (I-13))

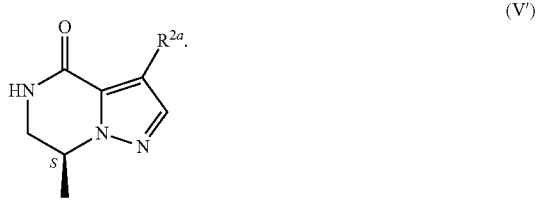

(V')

Experimental Procedure 11

Intermediate compound of Formula (Va) or of Formula (V) can be prepared by removal of the protecting group, for example a Boc group, in an intermediate of Formula (VIa) or of Formula (VIb), respectively, for example in the presence of acidic media, such as hydrochloric acid, in an inert solvent such as 1,4-dioxane or acetonitrile or ethyl acetate (EtOAc), under suitable reaction conditions, such as at a convenient temperature, such as from 15 to 80° C., typically 80° C. or from 15-30° C. depending on the solvent system, for a period of time to ensure the completion of the reaction followed by treatment with a base such as $Na_2CO_3$, $K_2CO_3$ or $NaHCO_3$, under suitable reaction conditions, such as at a convenient temperature, typically ranging between 0° C. and 40° C., in particular from 15 to 30° C., for a period of time to ensure the completion of the reaction. In Reaction Schemes 11a and 11b, $R^{2a}$ is halo, in particular bromo or iodo, $R^7$ is $C_{1-4}$alkyl, PG is a protecting group, for example Boc, and all other variables are defined as in Formula (I).

Reaction Scheme 11a

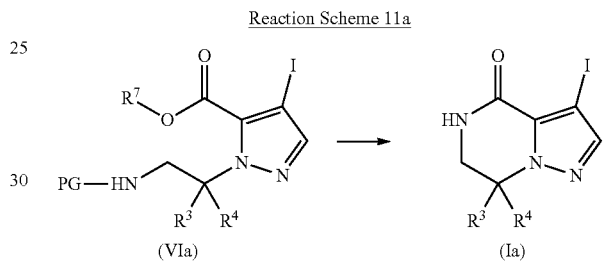

Reaction Scheme 11b

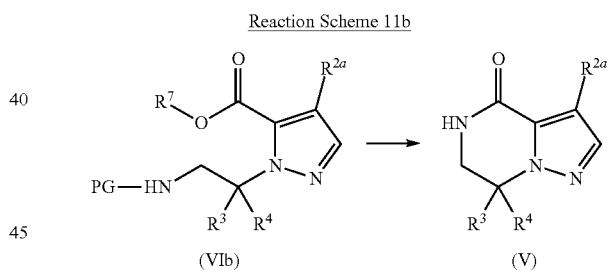

Experimental Procedure 12

Intermediate compound of Formula (VIa) or (VIb) wherein $R^7$ is $C_{1-4}$alkyl and PG is a protecting group, for example Boc, can be prepared by a Mitsunobu type reaction between an intermediate compound of Formula (VIIa) or (VII) respectively, and an appropriate alcohol of Formula (VIII), in the presence of a suitable triarylphosphine, such as triphenylphosphine typically 1.5 equivalents, or a suitable trialkylphosphine, and a suitable dialkyl azodicarboxylate reagent, such as di-tert-butyl azodicarboxylate or diethyl azodicarboxylate typically 1.5 equivalents, in a suitable inert solvent, such as tetrahydrofuran (THF), under suitable reaction conditions, such as at a convenient temperature, typically ranging 0° C. and rt, e.g. 20° C., for a period of time to ensure the completion of the reaction. An intermediate compound of Formula (VIII) can be obtained commercially or synthesized according to literature procedures.

Intermediate compound of Formula (VIIa) wherein $R^7$ is $C_{1-4}$alkyl, can be prepared via a reaction of halogenation of intermediate of Formula (IX) with a halogenating reagent such as N-iodosuccinimide, in an inert solvent such as dichloromethane, under suitable reaction conditions, such as at a convenient temperature, typically rt, for a period of time to ensure the completion of the reaction. Intermediate compound of Formula (VII), wherein $R^7$ is methyl and $R^{2a}$ is bromo, can be obtained commercially and is a particularly preferred material for use in the synthesis, including large scale, of a variety of final compounds of Formula (I) according to the general procedures described herein. An intermediate compound of Formula (IX) can be obtained commercially or synthesized according to literature procedures.

In Reaction Scheme 12a and 12b, $R^{2a}$ is halo, in particular bromo or iodo, $R^7$ is $C_{1-4}$alkyl, PG is a protecting group, such as for example Boc, and all other variables are defined as in Formula (I).

Experimental Procedure 13

Intermediate compound of Formula (IVb) can be prepared via a reaction of boronic ester or boronic acid formation starting from an intermediate of Formula (IVa) with a trans metallating agent such as for example BuLi or a Grignard reagent, a particular example of reagents includes isopropylmagnesium chloride lithium chloride complex solution and a boron species such as 2-isopropoxy-4,4,5,5-tetramethyl-1,3,2-dioxaborolane, in an inert solvent such as anhydrous THF, under suitable reaction conditions, such as at a convenient temperature, typically −25° C., for a period of time to ensure the completion of the reaction. Depending on reaction conditions, boronic ester or boronic acid are obtained. In Reaction Scheme 13, $R^{7a}$ and $R^{8a}$ are H or $C_{1-4}$ alkyl or $R^{7a}$ and $R^{8a}$ are taken together to form for example a bivalent radical of formula —CH$_2$CH$_2$—, —CH$_2$CH$_2$CH$_2$— or —C(CH$_3$)$_2$C(CH$_3$)$_2$—, and all other variables are defined as in Formula (I).

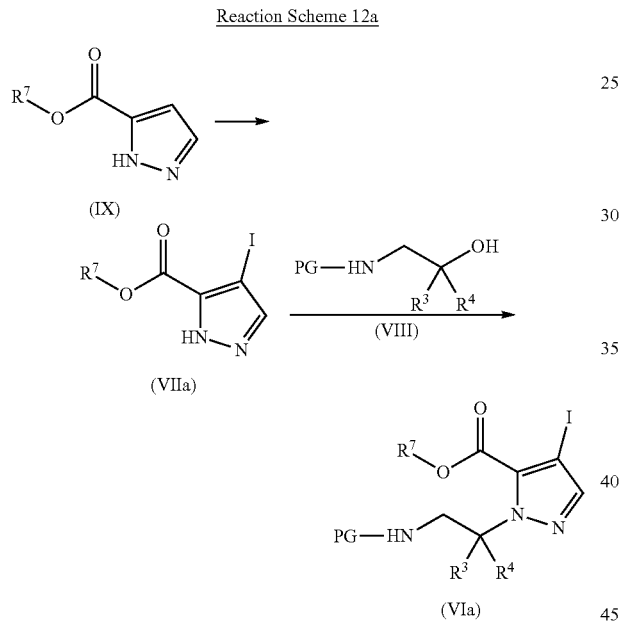

Reaction Scheme 12a

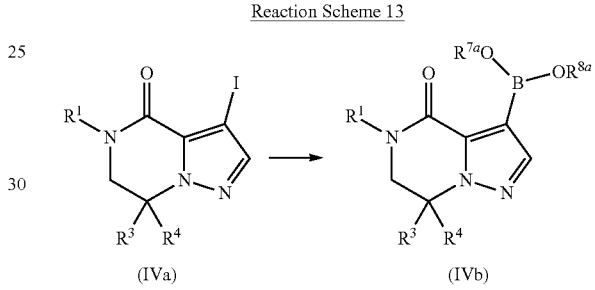

Reaction Scheme 13

Experimental Procedure 14

Intermediate compound of Formula (IVa) can be prepared via a reaction of halogenation of an intermediate of Formula (X) with a halogenating reagent such as iodine, in the presence of ammonium cerium(IV) nitrate and in an inert solvent such as acetonitrile, under suitable reaction conditions, such as at a convenient temperature, typically 70° C., for a period of time to ensure the completion of the reaction. In an analogous manner, intermediate compound of Formula (Va) can be prepared from intermediate of Formula (XI). In Reaction Schemes 14a and 14b, all variables are defined as in Formula (I).

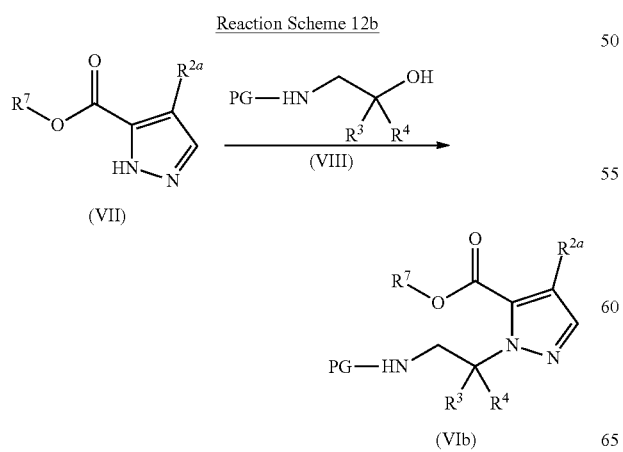

Reaction Scheme 12b

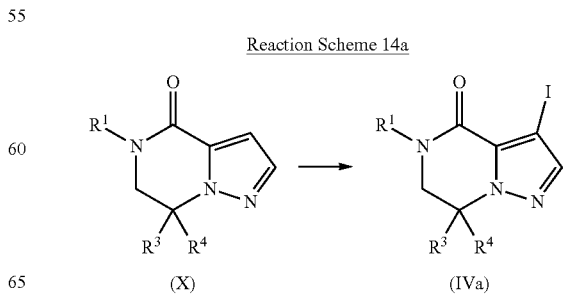

Reaction Scheme 14a

Reaction Scheme 14b

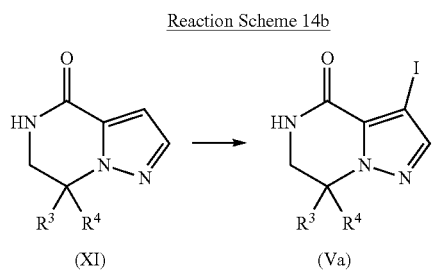

(XI) → (Va)

Experimental Procedure 15

Intermediate compound of Formula (X) can be prepared by a coupling reaction of an intermediate compound of Formula (XI) with an appropriate aryl/heteroaryl halide of Formula (III) where X is halo with a suitable copper(I) catalyst such as copper(I) iodide, in the presence of a ligand, such as N,N'-dimethylethylenediamine, in the presence of a base, such as $Na_2CO_3$, in a suitable solvent, such as toluene, under suitable reaction conditions, such as at a convenient temperature, typically ranging between 100° C. and 140° C., for a period of time to ensure the completion of the reaction. In an analogous manner, intermediate compound of Formula (IV) can be prepared from intermediate of Formula (V). An intermediate compound of Formula (III) can be obtained commercially. In Reaction Schemes 15a and 15b, all variables are defined as in Formula (I) and $R^{2a}$ is halo, in particular bromo or iodo.

Reaction Scheme 15a

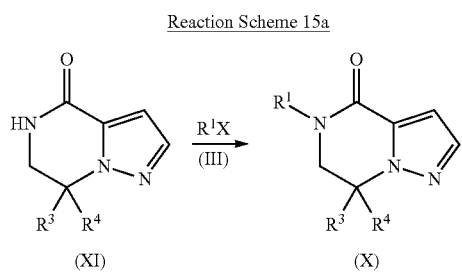

(XI) → (X)

Reaction Scheme 15b

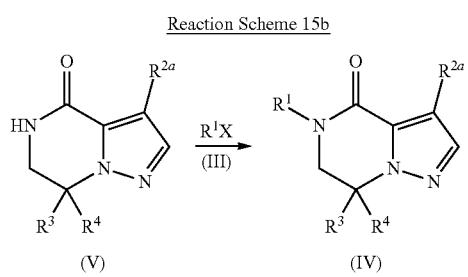

(V) → (IV)

Experimental Procedure 16

Intermediate compound of Formula (XI) can be prepared by removal of the protecting group in an intermediate of Formula (XII), for example in the presence of acidic media, such as hydrochloric acid, in an inert solvent such as 1,4-dioxane, under suitable reaction conditions, such as at a convenient temperature, typically 80° C., for a period of time to ensure the completion of the reaction followed by treatment with a base, such as $Na_2CO_3$ or $NaHCO_3$, under suitable reaction conditions, such as at a convenient temperature, typically ranging between 0° C. and 40° C., for a period of time to ensure the completion of the reaction. In an analogous manner, intermediate compound of Formula (V) can be prepared from intermediate of Formula (VIb). In Reaction Schemes 16a and 16b, $R^{2a}$ is halo, in particular bromo or iodo, $R^7$ is $C_{1-4}$alkyl, PG is a protecting group and all other variables are defined as in Formula (I).

Reaction Scheme 16a

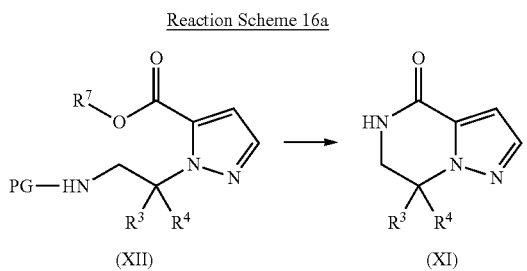

(XII) → (XI)

Reaction Scheme 16b

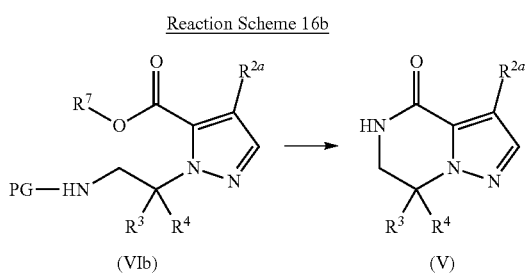

(VIb) → (V)

Experimental Procedure 17

Intermediate compound of Formula (XII) wherein $R^7$ is $C_{1-4}$alkyl and PG is a protecting group, can be prepared by a Mitsunobu type reaction between a compound of Formula (IX) and an appropriate alcohol of Formula (VIII), in the presence of a suitable triarylphosphine, such as triphenylphosphine, or a suitable trialkylphosphine, and a suitable dialkyl azodicarboxylate reagent, such as di-tert-butyl azodicarboxylate, in a suitable inert solvent, such as THF, under suitable reaction conditions, such as at a convenient temperature, typically rt, for a period of time to ensure the completion of the reaction. Intermediate compounds of Formula (IX) and of Formula (VIII) can be obtained commercially or synthesized according to literature procedures. In Reaction Scheme 17, $R^7$ is $C_{1-4}$alkyl, PG is a protecting group and all other variables are defined as in Formula (I).

Reaction Scheme 17

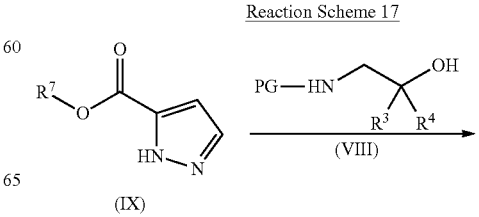

(IX) (VIII)

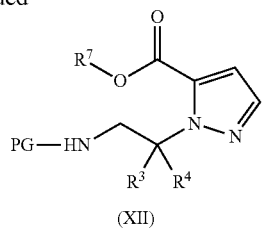

(XII)

Experimental Procedure 18

Intermediate compound of Formula (IX) wherein $R^7$ is $C_{1-4}$alkyl can be obtained by esterification of the commercially available intermediate compound of Formula (XIII), by methods known to the person skilled in the art, or may be commercially available. The reaction can be performed for example in the presence of an acidic agent, such as sulfuric acid, and an alcohol, such as EtOH, in a suitable solvent, such as EtOH, under suitable reaction conditions, such as at a convenient temperature, typically between 80° C. and 100° C., for a period of time to ensure the completion of the reaction. In Reaction Scheme 18, $R^7$ is $C_{1-4}$alkyl.

Reaction Scheme 18

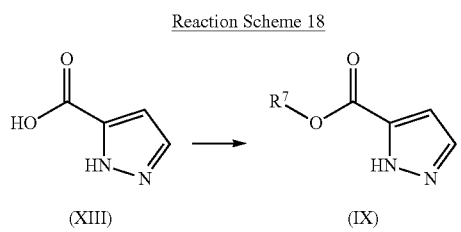

(XIII)        (IX)

Experimental Procedure 19

Intermediate compound of Formula (XI) wherein $R^3$ is H and $R^4$ is $CF_3$ herein referred to as compounds of Formula (XIa) can be prepared by hydrogenation of an intermediate of Formula (XIV) followed by one pot intramolecular cyclization, in the presence of a hydrogenation catalyst, such as Pd/C (palladium on carbon), under hydrogen atmosphere generated by using ammonium formate, in an inert solvent such as MeOH, under suitable reaction conditions, such as at a convenient temperature, typically 70° C., for a period of time to ensure the completion of the reaction. In Reaction Scheme 19, $R^7$ is $C_{1-4}$alkyl.

Reaction Scheme 19

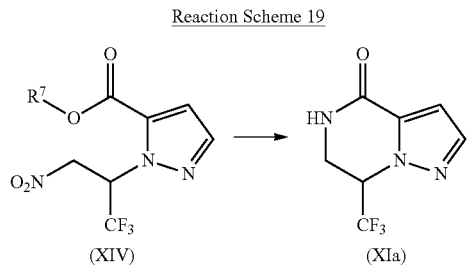

(XIV)        (XIa)

Experimental Procedure 20

Intermediate compound of Formula (XIV) wherein $R^7$ is $C_{1-4}$alkyl, can be prepared by an intermolecular reaction between an appropriate hydrazine of Formula (XV), in the presence of a suitable ketoester of Formula (XVI), such as ethyl pyruvate, in a suitable inert solvent, such as EtOH, under suitable reaction conditions, such as at a convenient temperature, typically rt, for a period of time to ensure the completion of the reaction. Intermediate compound of Formula (XVI) can be obtained commercially or synthesized according to literature procedures. In Reaction Scheme 20, $R^7$ is $C_{1-4}$alkyl.

Reaction Scheme 20

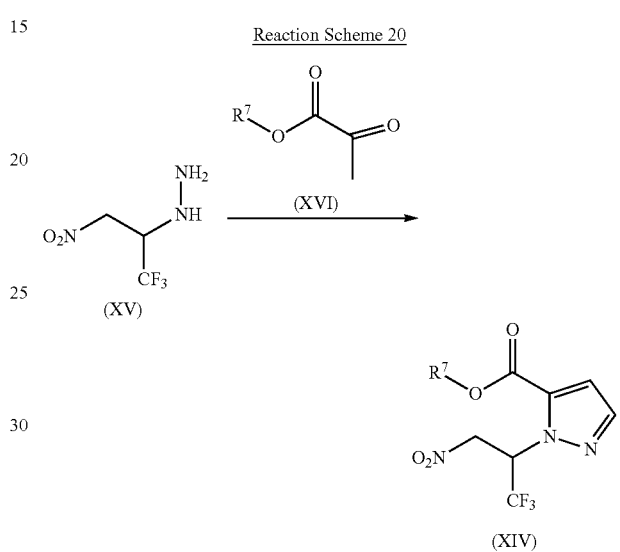

(XIV)

Experimental Procedure 21

Intermediate compound of Formula (XV) can be prepared by a reaction of deprotection of a compound of Formula (XVI) following art known procedures. A compound of Formula (XV) can be obtained by removal of the protecting group such as for example a Boc protecting group in the compound of Formula (XVI), in the presence of acidic media, such as hydrochloric acid, in an inert solvent such as MeOH, under suitable reaction conditions, such as at a convenient temperature, typically rt, for a period of time to ensure the completion of the reaction.

Intermediate compound of Formula (XVI) can be obtained by addition of a protected hydrazine of Formula (XVIII) to 3,3,3-trifluoro-1-nitro-prop-1-ene (XVII) (prepared as described in J. Fluorine Chem. 2008, 767-774). In Reaction Scheme 21, PG is a protecting group, for example BOC.

Reaction Scheme 21

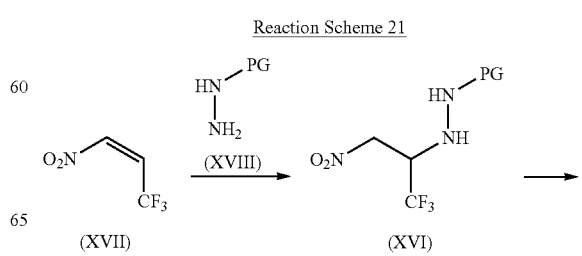

(XVII)        (XVI)

-continued

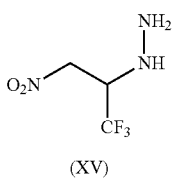

(XV)

In order to obtain the HCl salt forms of the compounds, several procedures known to those skilled in the art can be used. In a typical procedure, for example, the free base can be dissolved in DIPE or Et$_2$O and subsequently, a 6N HCl solution in 2-propanol, 4N HCl solution in dioxane, or a 1N HCl solution in Et$_2$O can be added dropwise. The mixture typically is stirred for 10 minutes after which the product can be filtered off. The HCl salt usually is dried in vacuo.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

The compounds provided in this invention are negative allosteric modulators (NAMs) of metabotropic glutamate receptors, in particular they are negative allosteric modulators of mGluR2. The compounds of the present invention do not appear to bind to the glutamate recognition site, the orthosteric ligand site, but instead to an allosteric site within the seven transmembrane region of the receptor. In the presence of glutamate, the compounds of this invention decrease the mGluR2 response. The compounds provided in this invention are expected to have their effect at mGluR2 by virtue of their ability to decrease the response of such receptors to glutamate, attenuating the response of the receptor.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

Hence, the present invention relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof for use as a medicament.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of negative allosteric modulators of mGluR2.

Also, the present invention relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of negative allosteric modulators of mGluR2.

In particular, the neurological and psychiatric disorders associated with glutamate dysfunction, include one or more of the following central nervous system conditions or diseases: mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

In particular, the central nervous system disorder is a psychotic disorder selected from the group of schizophrenia (in particular in antipsychotic-stabilized patients), schizophreniform disorder, schizoaffective disorder, delusional disorder, brief psychotic disorder, and substance-induced psychotic disorder.

In particular, the central nervous system disorder is a substance-related disorder selected from the group of alcohol dependence, alcohol abuse, amphetamine dependence, amphetamine abuse, caffeine dependence, caffeine abuse, cannabis dependence, cannabis abuse, cocaine dependence, cocaine abuse, hallucinogen dependence, hallucinogen abuse, nicotine dependence, nicotine abuse, opioid dependence, opioid abuse, phencyclidine dependence, and phencyclidine abuse.

In particular, the central nervous system disorder is a mood disorder selected from the group of major depressive disorder, depression, treatment resistant depression, dysthymic disorder, cyclothymic disorder, and substance-induced mood disorder.

In particular, the central nervous system disorder is a disorder usually first diagnosed in infancy, childhood, or adolescence selected from mental retardation, learning disorder, motor skills disorder, communication disorder, attention-deficit and disruptive behaviour disorders (such as Attention-Deficit/Hyperactivity Disorder (ADHD)). An additional disorder usually first diagnosed in infancy, childhood, or adolescence is autistic disorder.

In particular, the central nervous system disorder is a cognitive disorder selected from the group of dementia, in particular, dementia of the Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, and substance-induced persisting dementia.

In particular, the central nervous system disorder is an amnestic disorder, such as substance-induced persisting amnestic disorder.

As already mentioned hereinabove, the term "treatment" does not necessarily indicate a total elimination of all symptoms, but may also refer to symptomatic treatment in any of the disorders mentioned above. In particular, symptoms that may be treated include but are not limited to, memory impairment in particular in dementia or in major depressive disorder, age-related cognitive decline, mild cognitive impairment, and depressive symptoms.

Of the disorders mentioned above, the treatment of dementia, major depressive disorder, depression, treatment resistant depression, attention-deficit/hyperactivity disorder and schizophrenia, in particular in antipsychotic-stabilized patients, are of particular importance.

The fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

A skilled person will be familiar with alternative nomenclatures, nosologies, and classification systems for the diseases or conditions referred to herein. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, cannabis use disorder, cocaine use disorder, other hallucinogen use disorder, tobacco use disorder, opiod use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; somatic symptom disorders; hypersomnolence disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder. In particular, the disorder is autism. Specifiers associated with ASD include those where the individual has a genetic disorder, such as in Rett syndrome or Fragile X syndrome.

Therefore, the invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in the treatment of any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in treating any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the treatment or prevention, in particular treatment, of any one of the diseases mentioned hereinbefore.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof, or an N-oxide thereof, or a pharmaceutically acceptable salt or solvate thereof, in particular, a compound of Formula (I) or a stereoisomeric form thereof, or a pharmaceutically acceptable salt or a solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a subject in need thereof.

One skilled in the art will recognize that a therapeutically effective amount of the NAMs of the present invention is the amount sufficient to modulate the activity of the mGluR2 and that this amount varies inter alia, depending on the type of disease, the concentration of the compound in the therapeutic formulation, and the condition of the patient. Generally, an amount of NAM to be administered as a therapeutic agent for treating diseases in which modulation of the mGluR2 is beneficial, such as the disorders described herein, will be determined on a case by case by an attending physician.

Generally, a suitable dose is one that results in a concentration of the NAM at the treatment site in the range of 0.5 nM to 200 µM, and more usually 5 nM to 50 µM.

To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone. Examples of such combinations include the compounds of the invention in combination with antipsychotic(s), NMDA receptor antagonists (e.g. memantine), NR2B antagonists, acetylcholinesterase inhibitors (e.g. donepezil, galantamine, physostigmine and rivastigmine) and/or antidepressant neurotransmitter reuptake inhibitors. Particular combinations include the compounds of the invention in combination with antipsychotics, or the compounds of the invention in combination with memantine and/or NR2B antagonists.

Pharmaceutical Compositions

The present invention also provides compositions for preventing or treating diseases in which modulation of the mGluR2 receptor is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), an N-oxide, a pharmaceutically acceptable salt thereof, a solvate thereof or a stereochemically isomeric form thereof, more in particular, a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the N-oxides thereof, the pharmaceutically acceptable salts thereof, the solvates and the stereochemically isomeric forms thereof, more in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-3-cyclodextrin or sulfobutyl-3-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility. The use of such a composition for the manufacture of a medicament as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an additional drug selected from the group of antipsychotics; NMDA receptor antagonists (e.g. memantine); NR2B antagonists; acetylcholinesterase inhibitors (e.g. donepezil, galantamine, physostigmine and rivastigmine) and/or antidepressant neurotransmitter reuptake inhibitors. In particular, the present invention also relates to a combination of a compound according to the present invention and antipsychotic(s), or to a combination of a compound according to the present invention and memantine and/or an NR2B antagonist. The present invention also relates to such a combination for use as a medicine. The present invention also relates to a product comprising (a) a compound according to the present invention, an N-oxide thereof, a pharmaceutically acceptable salt thereof or a solvate thereof, in particular, a pharmaceutically acceptable salt thereof or a solvate thereof, and (b) an additional component selected from antipsychotics, NMDA receptor antagonists (e.g. memantine), NR2B antagonists, acetylcholinesterase inhibitors and/or antidepressant neurotransmitter reuptake inhibitor(s), as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular negative mGluR2 allosteric modulators. More in particular the additional component (b) is selected from antipsychotic(s) or memantine and/or an NR2B antagonist. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "Boc" or "BOC" means tert-Butyloxycarbonyl; "CI" means chemical ionisation; "DAD" means diode-array detector; "THF" means tetrahydrofuran; "TEA" means triethylamine; "DIPE" means diisopropylether; "DMF" means N,N-dimethylformamide; "Et$_{20}$" means diethylether; "EtOAc" means ethyl acetate; "DCM" means dichloromethane; "DMSO" means dimethylsulfoxide; "L" means liter; "LRMS" means low-resolution mass spectrometry/spectra; "HATU" means 2-(7-aza-1H-benzotriazole-1-yl)-1,1,3,3-tetramethyluronium hexafluorophosphate; "HPLC" means high performance liquid chromatography; "HRMS" means high-resolution mass spectrometry/spectra; "mL" or "ml" means milliliter; "NH$_4$Ac" means ammonium acetate; "EtOH" means ethanol; "ES" means electrospray; "iPrOH" means isopropanol; "iPrNH$_2$" means isopropylamine; "MeOH" means methanol; "eq" means equivalent(s); "RP" means Reverse Phase; "rt" means room temperature; "M.p." means melting point; "min" means minutes; "h" means hour(s); "s" means second(s); "TOF" means time of flight; "QTOF" means Quadrupole-Time of Flight; "sat." means saturated; "SFC" means supercritical fluid chromatography; "sol." means solution.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques.

Automated flash column chromatography was performed using ready-to-connect cartridges, on irregular silica gel, particle size 15-40 μm (normal phase disposable flash columns) on different flash systems: either a SPOT or LAFLASH systems from Armen Instrument, or PuriFlash® 430evo systems from Interchim, or 971-FP systems from Agilent, or Isolera 1SV systems from Biotage.

Nuclear Magnetic Resonance (NMR): For a number of compounds, $^1$H NMR spectra were recorded either on a Bruker Avance III, on a Bruker DPX-400 or on a Bruker AV-500 spectrometer with standard pulse sequences, operating at 400 MHz and 500 MHz, respectively. Chemical shifts (δ) are reported in parts per million (ppm) downfield from tetramethylsilane (TMS), which was used as internal standard.

Synthesis of Intermediate Compounds

Intermediate 1 (I-1)

2H-Pyrazole-3-carboxylic acid ethyl ester (I-1)

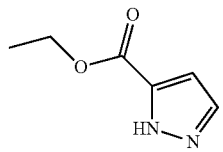

Sulfuric acid (10 mL, 187.6 mmol) was added to a solution of 1-H-pyrazole-3-carboxylic acid (1.93 g, 17.22 mmol) in EtOH (20 mL). The mixture was stirred at 90° C. for 15 h. Then it was allowed to cool to rt and the solvents were evaporated in vacuo. The residue was poured into water and the solution basified with K$_2$CO$_3$ and extracted with EtOAc. The organic layer was separated, dried (MgSO$_4$), filtered and the solvent evaporated in vacuo to yield intermediate compound I-1 as a white solid (2.28 g, 93% purity, 94%) which was used in the following step without further purification.

Intermediate 2 (I-2)

4-Iodo-2H-pyrazole-3-carboxylic acid ethyl ester (I-2)

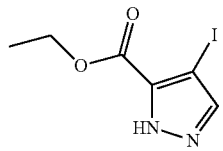

Intermediate I-1 (100 g, 0.68 mol), N-iodosuccinimide (213.5 g, 0.95 mol) were dissolved in DCM (2 L). The mixture was stirred at rt for 24 h. The mixture was treated with a sat. sol. of Na$_2$S$_2$O$_3$ and a sat. sol. of Na$_2$CO$_3$ and extracted with DCM. The organic layer was separated, dried (MgSO$_4$), filtered and the solvent evaporated in vacuo to yield intermediate compound I-2 as a white solid (160 g, 85%).

Intermediate 3 (I-3)

(2R-Hydroxy-propyl)-carbamic acid tert-butyl ester (I-3)

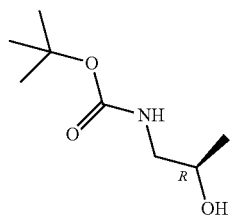

Di-tert-butyl dicarbonate (58.1 g, 266.3 mmol) in DCM (50 mL) was added to a stirred solution of (R)-(−)-1-amino-2-propanol in DCM (50 mL) at 0° C. under nitrogen. The mixture was stirred at rt for 2 h. The mixture was diluted with cooled water and extracted with DCM. The organic layer was separated, dried (Na$_2$SO$_4$), filtered and the solvents evaporated in vacuo to yield intermediate I-3 as a colorless oil (47 g, quant.). The product was used in the next step without further purification.

Intermediate 4 (I-4)

(2S-Hydroxy-propyl)-carbamic acid tert-butyl ester (I-4)

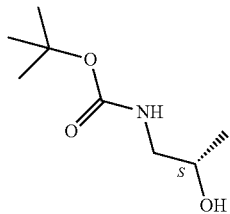

Intermediate compound I-4 was synthesized following a similar approach described for intermediate I-3. Starting from (S)-(−)-1-amino-2-propanol (3 mL, 38.1 mmol), intermediate compound I-4 was obtained as a colorless oil (6.13 g, 89% purity, 82%), that solidified upon standing at rt.

Intermediate 5 (I-5)

(2-Hydroxy-propyl)-carbamic acid tert-butyl ester (I-5)

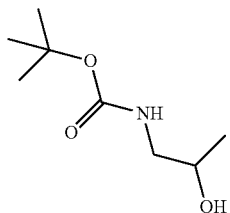

Intermediate compound I-5 was synthesized following a similar approach described for intermediate I-3. Starting from 1-amino-2-propanol (3 mL, 38.1 mmol), intermediate compound I-5 was obtained as a colorless oil (6.69 g, 98%).

Intermediate 6 (I-6)

2-(2-tert-Butoxycarbonylamino-1S-methyl-ethyl)-4-iodo-2H-pyrazole-3-carboxylic

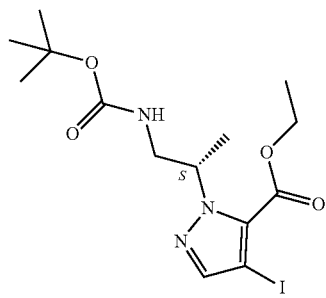

Di-tert-butyl azodicarboxylate (4.67 g, 20.3 mmol) was added to a stirred solution of intermediate I-2 (3 g, 11.28 mmol), intermediate I-3 (4.44 g, 22.55 mmol) and triphenylphosphine (5.32 g, 20.3 mmol) in THF (56 mL) under nitrogen. The mixture was stirred at rt for 5 h. The solvent was evaporated in vacuo and the crude product was triturated with DIPE. The solid was filtered and the filtrate was evaporated in vacuo. The crude product was purified by flash column chromatography (silica; EtOAc in Heptane 0/100 to 30/70). The desired fractions were collected and the solvents evaporated in vacuo to give intermediate compound I-6 as a colorless oil (4.9 g, 91% purity, 93%).

Intermediate 7 (I-7)

2-(2-tert-Butoxycarbonylamino-1R-methyl-ethyl)-4-iodo-2H-pyrazole-3-carboxylic acid ethyl ester (I-7)

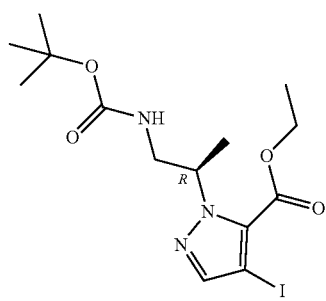

Intermediate compound I-7 was synthesized following a similar approach described for intermediate I-6. Starting from intermediate I-2 (1.18 g, 4.44 mmol) and intermediate I-4 (1.75 g, 8.87 mmol), intermediate compound I-7 was obtained as a white solid as two fractions (790 mg, 41%) and (900 mg, 86% purity, 41%).

Intermediate 8 (I-8)

2-(2-tert-Butoxycarbonylamino-1-methyl-ethyl)-4-iodo-2H-pyrazole-3-carboxylic acid ethyl ester (I-8)

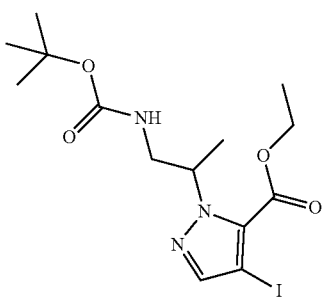 [SMILES: CCOC(=O)c1c(I)cnn1C(C)CNC(=O)OC(C)(C)C]

Intermediate compound I-8 was synthesized following a similar approach described for intermediate I-6. Starting from intermediate I-2 (2.87 g, 10.79 mmol) and intermediate I-5 (3.78 g, 21.6 mmol), intermediate compound I-8 was obtained as a colorless oil (3.46 g, 75%).

Intermediate 9 (I-9)

2-(2-tert-Butoxycarbonylamino-ethyl)-4-iodo-2H-pyrazole-3-carboxylic acid ethyl ester (I-9)

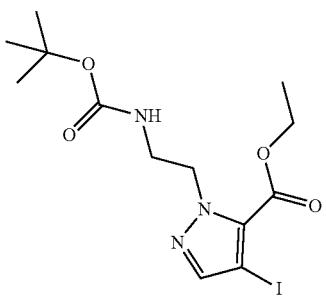 [SMILES: CCOC(=O)c1c(I)cnn1CCNC(=O)OC(C)(C)C]

Intermediate compound I-9 was synthesized following a similar approach described for intermediate I-6. Starting from intermediate I-2 (3.18 g, 11.95 mmol) and N-(tert-butoxycarbonyl)ethanolamine (3.78 g, 23.9 mmol), intermediate compound I-9 was obtained as a colorless oil (3.46 g, 75%).

Intermediate 10 (I-10)

2-(2-tert-Butoxycarbonylamino-1S-methyl-ethyl)-2H-pyrazole-3-carboxylic acid ethyl ester (I-10)

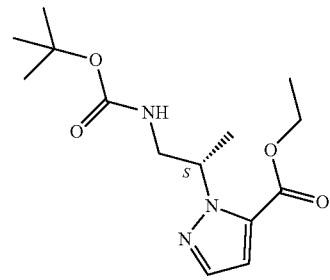

Intermediate compound I-10 was synthesized following a similar approach described for intermediate I-6. Starting from intermediate I-1 (25.82 g, 184.25 mmol) and intermediate I-3 (47.16 g, 239.5 mmol), intermediate compound I-10 was obtained as a yellow oil (123 g, quant) which was used in the following step without further purification.

Intermediate 11 (I-11)

2-(2-Amino-1S-methyl-ethyl)-4-iodo-2H-pyrazole-3-carboxylic acid ethyl ester hydrochloride salt (I-11)

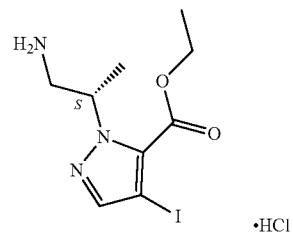

A 4M solution of HCl in 1,4-dioxane (10 mL, 40 mmol) was added to a solution of intermediate I-6 (4.2 g, 9.63 mmol) in acetonitrile (20 mL). The mixture was stirred at 80° C. for 2 h. The solvent was evaporated in vacuo to yield intermediate compound I-11 (3.5 g, 97%).

Intermediate 12 (I-12)

2-(2-Amino-1S-methyl-ethyl)-2H-pyrazole-3-carboxylic acid ethyl ester hydrochloride salt (I-12)

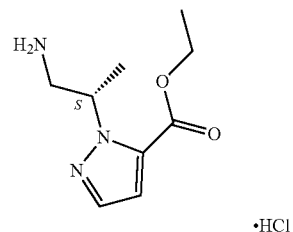

Intermediate compound I-12 was synthesized following a similar approach described for intermediate I-11. Starting from intermediate I-10 (54.79 g, 184.25 mmol) and a 4M solution of HCl in 1,4-dioxane (415 mL, 1.66 mol), intermediate compound I-12 was obtained as a white solid (32.5 g, 82% purity, 75%) which was used in the following step without further purification.

Intermediate 13 (I-13)

3-Iodo-7S-methyl-6,7-dihydro-5H-pyrazolo[1,5-a]pyrazin-4-one (I-13)

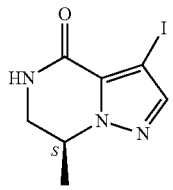

Intermediate I-11 as HCl salt (180 g, 350.4 mmol) was dissolved in a sat. sol. of NaHCO$_3$ (2 L). The mixture was stirred at rt for 12 h. The mixture was diluted with water and extracted with DCM. The organic layers were separated, dried (Na$_2$SO$_4$), filtered and the solvents evaporated in vacuo. Then the residue was washed with tert-butyl methyl ether to yield intermediate compound I-13 (92 g, 90%), mp 182.6-186.1° C. $^1$H NMR (500 MHz, DMSO-d$_6$) δ ppm 1.42 (d, J=6.65 Hz, 3H) 3.26-3.35 (m, 1H) 3.57-3.71 (m, 1H) 4.44-4.60 (m, 1H) 7.68 (s, 1H) 8.26 (br. s., 1H). LC-HRMS (ESI+) Calculated for C$_7$H$_8$IN$_3$O (M+H)$^+$: 277.9790, Found: m/z 277.9796 (+0.6 mDa), Rt=0.76 min (Method 13, see table 2). [α]=+11.7° (589 nm, c 1.00 w/v %, CH$_3$OH, 25° C.).

Intermediate 13a (I-13a)

(7S)-3-Bromo-7-methyl-6,7-dihydro-5H-pyrazolo[1,5-a]pyrazin-4-one (I-13a)

Intermediate 13a was prepared in 71% yield according to the following general description of a synthesis performed at a large scale:

A mixture of methyl 4-bromo-1H-pyrazole-5-carboxylate (referred to as "pyrazole SM" herein) (1 eq.), triphenyl phosphine (1.2 eq.), I-3 (1.2 eq.) and anhydrous THF (15 mL/g pyrazole SM) under nitrogen was cooled to 5-10° C. Di-tert-butyl azodicarboxylate (1.2 eq.) was added in portions at 5-15° C. under nitrogen. The solution was heated to 20-30° C. and stirred at 20-30° C. for 2-3 h. The obtained solution was concentrated and co-evaporated with isopropyl acetate to remove THF to afford a solution of crude 4-bromo-1-[(1S)-1-[[(1,1-dimethylethoxy)carbonyl]amino]ethyl]-1H-pyrazole-5-carboxylic acid methyl ester I-6a in isopropyl acetate (20 mL/g pyrazole SM). To the solution of I-6a was bubbled HCl gas at 15-30° C. until cleavage of the Boc protecting group was completed. The suspension was bubbled with nitrogen gas to remove most of the HCl gas. The suspension was concentrated to a volume of about 5 mL/g pyrazole SM below 50° C., and then isopropyl acetate (15 mL/g pyrazole SM) was added to the residue. Water (10 mL/g pyrazole SM) was added at 10-20° C. The mixture was stirred at 10-20° C. for 20-30 min. The mixture was filtered and the aqueous layer was separated. The organic layer was extracted with water (2 mL/g pyrazole SM). The combined aqueous layers were washed with isopropyl acetate (2×10 mL/g pyrazole SM) to remove residual triphenylphosphine oxide. I-11a was obtained as an aqueous solution (6.25 mL/g pyrazole SM). To the aqueous solution of I-11a was added potassium carbonate (~1 g/g pyrazole SM) to adjust to pH=8-9 at 10-25° C. The mixture was stirred at 10-25° C. for 5-6 h and solid I-13a precipitated. The suspension was cooled to 5-10° C. and stirred at 5-10° C. for 2-3 h, it was then filtered and washed with water (1 mL/g pyrazole SM) and heptanes (1 mL/g pyrazole SM), then dried in vacuo at 40-45° C. to afford I-13a as a white solid, mp. 196.12° C. $^1$H NMR (500 MHz, CDCl$_3$) δ ppm 1.61 (d, J=6.36 Hz, 3H) 3.48 (ddd, J=12.72, 7.22, 2.60 Hz, 1H) 3.75-3.84 (m, 1H) 4.49-4.59 (m, 1H) 6.54 (br. s., 1H) 7.56 (s, 1H). LC-HRMS (ESI+) Calculated for C$_7$H$_8$BrN$_3$O (M+H)$^+$: 229.9929, Found: m/z 229.9931 (+0.2 mDa), Rt=0.62 min (Method 13, see table 2). [u]=+25.2° (589 nm, c 0.53 w/v %, DMF, 20° C.).

Intermediate 14 (I-14)

7S-Methyl-6,7-dihydro-5H-pyrazolo[1,5-a]pyrazin-4-one (I-14)

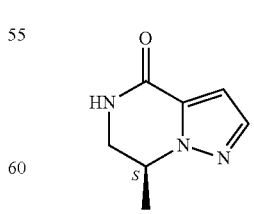

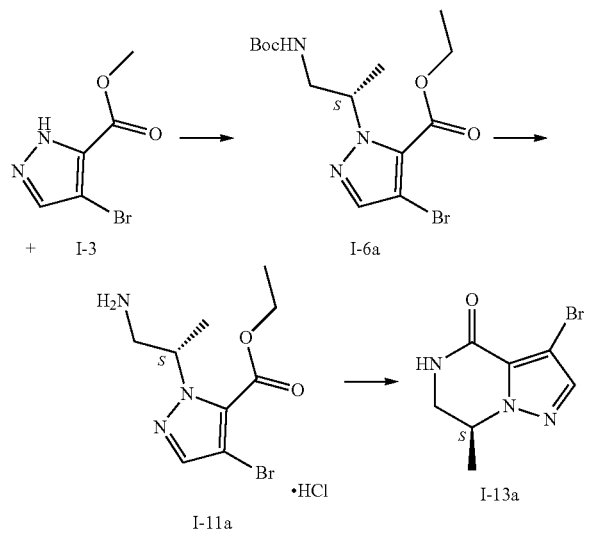

Intermediate compound I-14 was synthesized following a similar approach described for intermediate I-13. Starting from intermediate I-12 (32.5 g, 139.1 mmol), intermediate compound I-14 was obtained as a solid (14.8 g, 70%).

Intermediate 15 (I-15)

3-Iodo-7R-methyl-6,7-dihydro-5H-pyrazolo[1,5-a]pyrazin-4-one (I-15)

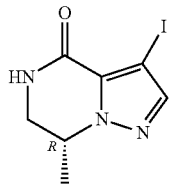

A 4M solution of HCl in 1,4-dioxane (2.3 mL, 9.2 mmol) was added to a solution of intermediate I-7 (0.78 g, 1.84 mmol) in CH₃CN (8.3 mL). The mixture was stirred at 80° C. for 7 h. After Boc deprotection was complete, part of the solvent was evaporated in vacuo and the solution was basified with a sat. sol. of NaHCO₃. The mixture was stirred for 16 h at rt. Then the mixture was diluted with water and extracted with DCM. The organic layers were separated, dried (MgSO₄), filtered and the solvents evaporated in vacuo. The solid was triturated with DIPE to yield intermediate compound I-15 as a white solid (0.42 g, 82%).

Intermediate 16 (I-16)

3-Iodo-7-methyl-6,7-dihydro-5H-pyrazolo[1,5-a]pyrazin-4-one (I-16)

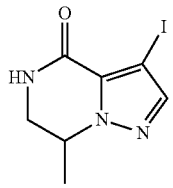

Intermediate compound I-16 was synthesized following a similar approach described for intermediate I-15. Starting from intermediate I-8 (3.46 g, 8.17 mmol), intermediate compound I-16 was obtained as a white solid (1.87 g, 82%).

Intermediate 17 (I-17)

3-Iodo-6,7-dihydro-5H-pyrazolo[1,5-a]pyrazin-4-one (I-17)

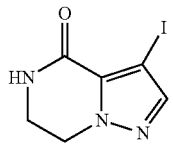

Intermediate compound I-17 was synthesized following a similar approach described for intermediate I-15. Starting from intermediate I-9 (4.89 g, 11.95 mmol), intermediate compound I-17 was obtained as a white solid (1.87 g, 59%).

Intermediate 18 (I-18)

7S-Methyl-3-(2-methyl-pyridin-4-yl)-6,7-dihydro-5H-pyrazolo[1,5-a]pyrazin-4-one (I-18)

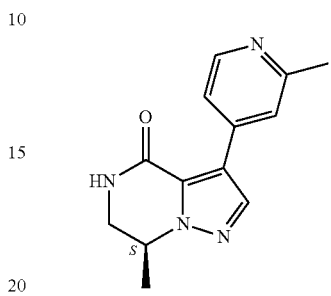

Pd(PPh₃)₄ (0.33 g, 0.29 mmol) was added to a stirred suspension of intermediate I-13 (1.6 g, 5.77 mmol) and 2-picoline-4-boronic acid (0.95 g, 6.93 mmol) in 1,4-dioxane (8 mL) and a sat. sol. of NaHCO₃ (4 mL) in a sealed tube under nitrogen. The mixture was stirred at 100° C. for 16 h. Then the mixture was diluted with H₂O and extracted with DCM. The organic layer was separated, dried (Na₂SO₄), filtered and the solvent evaporated in vacuo. The crude product was purified by flash column chromatography (silica; MeOH in DCM 0/100 to 6/94). The desired fractions were collected and the solvents evaporated in vacuo to yield intermediate compound I-18 as a white solid (1 g, 71%), mp 173.20° C. $^1$H NMR (500 MHz, CDCl₃) δ ppm 1.67 (d, J=6.65 Hz, 3H) 2.60 (s, 3H) 3.52 (ddd, J=12.79, 7.15, 2.89 Hz, 1H) 3.84 (dt, J=12.72, 4.00 Hz, 1H) 4.57-4.66 (m, 1H) 6.10 (br. s., 1H) 7.51 (dd, J=5.20, 1.44 Hz, 1H) 7.55 (s, 1H) 7.78 (s, 1H) 8.50 (d, J=5.20 Hz, 1H). LC-HRMS (ESI+) Calculated for $C_{13}H_{14}IN_4O$ (M+H)$^+$: 243.1246, Found: m/z 243.1250 (+0.4 mDa), Rt=0.82 min (Method 13, see table 2). [α]=+32.8° (589 nm, c 0.52 w/v %, DMF, 20° C.).

Intermediate I-18 was alternatively prepared in 70% yield according to the following general description of a synthesis performed at a large scale: A mixture of I-13a (1 eq.), 2-methyl-4-(4,4,5,5-tetramethyl-1,3,2-dioxaborolan-2-yl)-pyridine (1.1 eq.), anhydrous potassium phosphate (2 eq.), DME (7.5 mL/g I-13a) and purified water (2.5 mL/g I-13a) was evacuated and backfilled with nitrogen 3 times. Triphenyl phosphine (0.261 eq.) and palladium (II) acetate (0.131 eq.) were added in one portion under nitrogen. The mixture was evacuated and backfilled with nitrogen 3 times again, it was heated to 75-80° C. and stirred at 75-80° C. for 12-15 h under nitrogen. The aqueous layer was separated at 60-70° C. and discarded, and then water (8 mL/g I-13a) was added to the organic layer. DME was removed by concentration below 40° C. Isopropyl acetate (15 mL/g I-13a) was added, the pH of the mixture was adjusted to 1-2 with conc. HCl. The mixture was filtered and the filter cake was washed with water (1 mL/g I-13a), the aqueous layer was separated and the organic layer was extracted with water (2 mL/g I-13a). The combined aqueous layers were washed with Isopropyl acetate (2×15 mL/g I-13a). The aqueous layer was concentrated to remove residual DME and isopropyl acetate. MTBE (2 mL/g I-13a) was added and the mixture was cooled to 0-5° C., stirred at 0-5° C. for 2-3 h. I-18 was filtered, washed with cooled water (1 mL/g I-13a), and dried in vacuum at 45-50° C. to afford I-18 as an off-white solid.

Intermediate 19 (I-19)

7R-Methyl-3-(2-methyl-pyridin-4-yl)-6,7-dihydro-5H-pyrazolo[1,5-a]pyrazin-4-one (I-19)

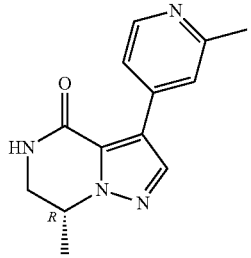

Intermediate compound I-19 was synthesized following a similar approach described for intermediate I-18. Starting from intermediate I-15 (0.62 g, 2.24 mmol), intermediate compound I-19 was obtained as a white solid (0.38 g, 70%).

Intermediate 20 (I-20)

7-Methyl-3-(2-methyl-pyridin-4-yl)-6,7-dihydro-5H-pyrazolo[1,5-a]pyrazin-4-one (I-20)

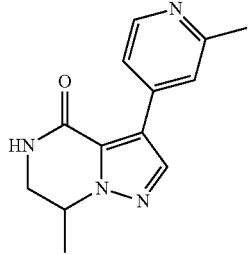 [SMILES: Cc1cc(-c2cnn3c2C(=O)NCC3C)ccn1]

Intermediate compound I-20 was synthesized following a similar approach described for intermediate I-18. Starting from intermediate I-16 (846 mg, 3.05 mmol), intermediate compound I-20 was obtained as a yellowish solid (585 mg, 79%).

Intermediate 18 (I-18) and Intermediate 19 (I-19)

7S-Methyl-3-(2-methyl-pyridin-4-yl)-6,7-dihydro-5H-pyrazolo[1,5-a]pyrazin-4-one (I-18) and 7R-Methyl-3-(2-methyl-pyridin-4-yl)-6,7-dihydro-5H-pyrazolo[1,5-a]pyrazin-4-one (I-19).

(I-18)

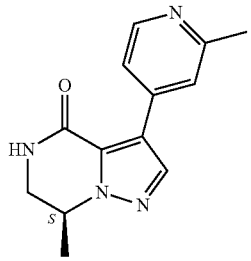

(I-19)

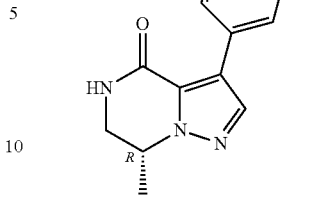

Intermediate I-20 (975 mg, 4.02 mmol) was purified by RP HPLC (Stationary phase: irregular bare silica 40 g), Mobile phase: 0.5% NH$_4$OH, 95% DCM, 5% MeOH) then by chiral SFC ((Stationary phase: CHIRALCELR OD-H 5 m 250×20 mm), (Mobile phase: 75% CO$_2$, 25% iPrOH (0.3% iPrNH$_2$)) to yield intermediate compound I-18 (390 mg) and intermediate compound I-19 (395 mg).

Intermediate 21 (I-21)

3-(2-Methyl-pyridin-4-yl)-6,7-dihydro-5H-pyrazolo[1,5-a]pyrazin-4-one (I-21)

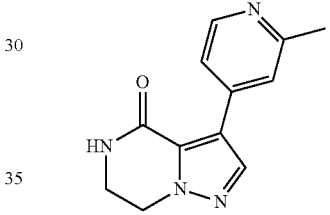

Intermediate compound I-21 was synthesized following a similar approach described for intermediate I-18. Starting from intermediate I-17 (908 mg, 3.45 mmol), intermediate compound I-21 was obtained as a white solid (0.5 g, 63%).

Intermediate 22 (I-22)

7S-Methyl-5-(4-trifluoromethyl-phenyl)-6,7-dihydro-5H-pyrazolo[1,5-a]pyrazin-4-one (I-22)

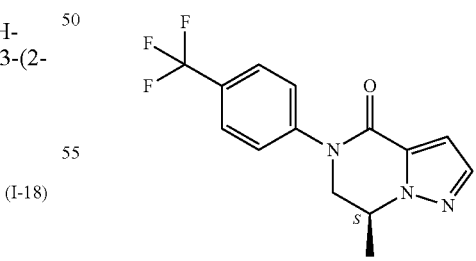

A mixture of intermediate I-14 (5 g, 33.01 mmol), copper (I) iodide (3.78 g, 19.85 mmol) and K$_2$CO$_3$ (9.14 g, 66.15 mmol) in toluene (150 mL) was nitrogen flushed for a few min. Then 4-bromobenzotrifluoride (9.3 mL, 66.1 mmol) and N,N'-dimethylethylenediamine (2.1 mL, 19.8 mmol) were added. The mixture was stirred under nitrogen at rt for 10 min and then stirred at 100° C. for 16 h. Then, DMF (20 mL) was added and the mixture was stirred at 100° C. for 8 h. Then water, a conc. sol. of ammonia and DCM were added. The organic layer was separated, dried (Na$_2$SO$_4$), filtered and the solvents evaporated in vacuo. The crude product was purified by flash column chromatography (silica; EtOAc in DCM 0/100 to 50/50). The desired fractions were collected and the solvents evaporated in vacuo to yield intermediate compound I-22 as a pale yellow oil (9.6 g, 98%).

Intermediate 23 (I-23)

3-Iodo-7S-methyl-5-(4-trifluoromethyl-phenyl)-6,7-dihydro-5H-pyrazolo[1,5-a]pyrazin-4-one (I-23)

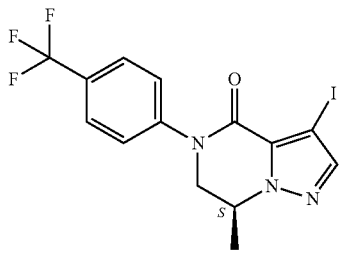

Iodine (11.55 g, 45.5 mmol) was added to a solution of intermediate I-22 (19.2 g, 65.0 mmol) and ammonium cerium(IV) nitrate (24.95 g, 45.5 mmol) in acetonitrile (350 mL). The mixture was stirred at 70° C. for 1 h. Then the mixture was diluted with EtOAc and washed with a sat. sol. of Na$_2$S$_2$O$_3$ and brine. The organic layer was separated, dried (Na$_2$SO$_4$), filtered and the solvents evaporated in vacuo. The residue was precipitated with DIPE and then was purified by short column chromatography (silica, DCM) then by flash column chromatography (silica; DCM in heptane 50/50 to 100/0). The desired fractions were collected and the solvents evaporated in vacuo to yield intermediate compound I-23 as a solid (24.8 g, 90%).

Intermediate 24 (I-24)

2-Amino-pyridine-4-boronic acid (I-24)

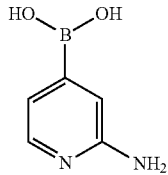

2-Amino-4-chloropyridine (3 g, 23.34 mmol) was added to a mixture of bis(pinacolato)diboron (17.78 g, 70.01 mmol), 2-dicyclohexylphosphino-2',6'-dimethoxybiphenyl (0.38 g, 0.93 mmol), tris(dibenzylideneacetone)dipalladium (0) (0.21 g, 0.23 mmol) and potassium acetate (3.89 g, 39.67 mmol) in 1,4-dioxane (78 mL) under nitrogen atmosphere. The resulting mixture was stirred at 100° C. for 3 h. The hot reaction mixture was filtered through diatomaceous earth and washed with EtOAc. The organic layer was evaporated in vacuo. The residue was precipitated with DIPE to yield intermediate compound I-24 as a white solid (5.84 g, quant.) that was used in the next reaction step without further purification.

Intermediate 25 (I-25)

3-(2-Methoxy-pyridin-4-yl)-7S-methyl-6,7-dihydro-5H-pyrazolo[1,5-a]pyrazin-4-one (I-25)

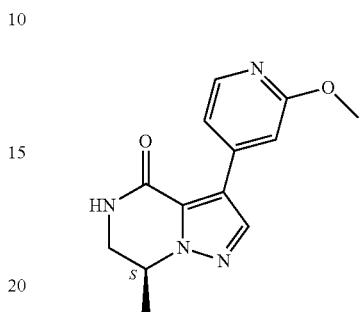

Pd(PPh$_3$)$_4$ (0.42 g, 0.36 mmol) was added to a stirred suspension of intermediate I-13 (2 g, 7.22 mmol) and 2-methoxypyridine-4-boronic acid (1.77 g, 11.55 mmol) in 1,4-dioxane (16 mL) and a sat. sol. of NaHCO$_3$ (8 mL) in a sealed tube under nitrogen atmosphere. The mixture was stirred at 100° C. for 3 days. Then the mixture was diluted with H$_2$O and extracted with DCM. The organic layer was separated, dried (Na$_2$SO$_4$), filtered and the solvent evaporated in vacuo. The crude product was purified by flash column chromatography (silica; MeOH in DCM 0/100 to 6/94). The desired fractions were collected and the solvents evaporated in vacuo to yield intermediate compound I-25 as a pale brown solid (1.6 g, 86%).

Intermediate 26 and Final Compound 215 (I-26 and Co. No. 215)

3-(2-Chloro-pyridin-4-yl)-7S-methyl-5-(4-trifluoromethyl-phenyl)-6,7-dihydro-5H-pyrazolo[1,5-a]pyrazin-4-one I-26 and Co. No. 215)

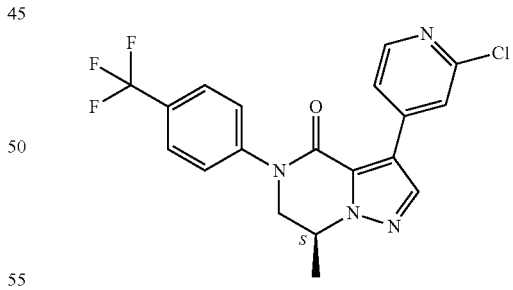

This reaction was divided in four batches to a combined total amount indicated herein and combined for workup and purification. Pd(PPh$_3$)$_4$ (401 mg, 0.35 mmol) was added to a stirred suspension of intermediate I-23 (2.92 g, 6.94 mmol) and 2-chloropyridine-4-boronic acid (1.42 g, 9.02 mmol) in 1,4-dioxane (39 mL) and a sat. sol. of NaHCO$_3$ (19.5 mL). The mixture was stirred at 150° C. for 10 min under microwave irradiation. Then the mixture was diluted with H$_2$O and extracted with DCM. The organic layer was separated, dried (Na$_2$SO$_4$), filtered and the solvent evaporated in vacuo. The crude product was purified by flash column chromatography (silica; EtOAc in DCM 0/100 to 20/80). The desired fractions were collected and the solvents evaporated in vacuo to yield intermediate compound I-26 as a yellow solid (1.84 g, 65%).

Intermediate 27 (I-27)

7S-Methyl-5-(4-trifluoromethyl-phenyl)-3-(2-vinyl-pyridin-4-yl)-6,7-dihydro-5H-pyrazolo[1,5-a]pyrazin-4-one (I-27)

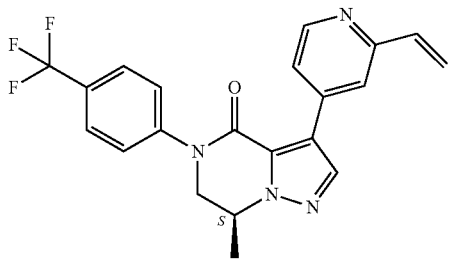

Pd(PPh$_3$)$_4$ (51 mg, 0.044 mmol) was added to a stirred suspension of intermediate I-26 (600 mg, 1.48 mmol) and vinylboronic acid pinacolester (0.325 mL, 1.92 mmol) in 1,4-dioxane (10 mL) and a sat. sol. of NaHCO$_3$ (5 mL). The mixture was stirred at 150° C. for 15 min under microwave irradiation. Then the mixture was diluted with H$_2$O and extracted with DCM. The organic layer was separated, dried (Na$_2$SO$_4$), filtered and the solvent evaporated in vacuo. The crude product was purified by flash column chromatography (silica; EtOAc in DCM 0/100 to 30/70). The desired fractions were collected and the solvents evaporated in vacuo to yield intermediate compound I-27 as a yellow oil (0.53 g, 90%).

Intermediate 28 (I-28)

Ethyl 2-[1-[(tert-butoxycarbonylamino)methyl]-2-[tert-butyl(dimethyl)silyl]oxy-ethyl]-4-iodo-pyrazole-3-carboxylate (I-28)

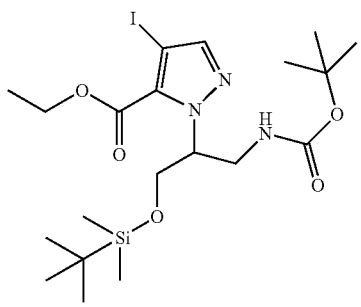 [SMILES: CCOC(=O)c1c(I)cnn1C(CNC(=O)OC(C)(C)C)CO[Si](C)(C)C(C)(C)C]

Di-tert-butyl azodicarboxylate (1.97 g, 8.53 mmol) was added to a stirred solution of 4-iodo-1H-pyrazole-3-carboxylic acid ethyl ester (1.26 g, 4.74 mmol), [3-(tert-butyldimethylsilanyloxy)-2-hydroxypropyl]carbamic acid tert-butyl ester (2.90 g, 9.48 mmol) and triphenylphosphine (2.24 g, 8.53 mmol) in THF (23.6 mL) under nitrogen atmosphere. The mixture was stirred at rt for 2.5 h. The solvent was evaporated and the residue was treated with DIPE. The solid (Ph$_3$PO) was filtered off and the filtrate was evaporated in vacuo. The crude product was purified by flash column chromatography (silica; DCM in Heptane 50/50 to 100/0 then EtOAc in DCM 0/100 to 3/97). The desired fractions were collected and concentrated in vacuo to yield intermediate compound I-28 (2.57 g, 98%) as a colorless oil.

Intermediate 29 (I-29)

Ethyl 2-[1-(aminomethyl)-2-hydroxy-ethyl]-4-iodo-pyrazole-3-carboxylate hydrochloride salt (I-29)

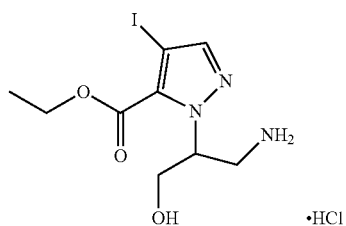 [SMILES: CCOC(=O)c1c(I)cnn1C(CN)CO ; Cl]

Hydrochloric acid (4 M in 1,4-dioxane, 5.80 mL, 23.21 mmol) was added to a stirred solution of intermediate I-28 (2.57 g, 4.64 mmol) in CH$_3$CN (21 mL). The mixture was stirred at rt for 1 h. The mixture was concentrated in vacuo to yield intermediate compound I-29 (1.69 g) as a beige solid which was used in the next step without any further purification.

Intermediate 30 (I-30)

7-(Hydroxymethyl)-3-iodo-6,7-dihydro-5H-pyrazolo[1,5-a]pyrazin-4-one (I-30)

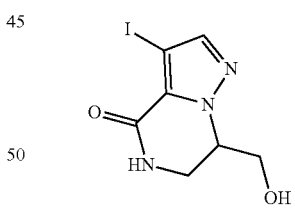

TEA (1.38 mL, 9.93 mmol) was added to a stirred solution of intermediate I-29 (1.68 g, 4.48 mmol) in DMF (16.8 mL). The mixture was stirred at rt for 3 h. The mixture was treated with a sat. sol. of NaHCO$_3$ and EtOAc and filtered. The filtrate was partitioned between water and EtOAc and extracted with EtOAc and EtOAc/THF. The organic layer was separated, dried (Na$_2$SO$_4$), filtered and concentrated in vacuo. The crude product was purified by flash column chromatography (silica; MeOH in DCM 0/100 to 20/80). The desired fractions were collected and concentrated in vacuo to yield intermediate compound I-30 (0.88 g, 67%) as a white solid.

Intermediate 31 (I-31)

7-(Hydroxymethyl)-3-(2-methyl-4-pyridyl)-6,7-dihydro-5H-pyrazolo[1,5-a]pyrazin-4-one (I-31)

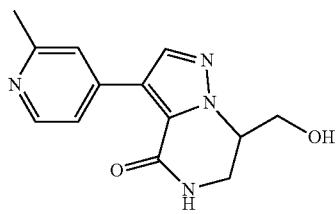 [SMILES: Cc1cc(-c2cnn3c2C(=O)NCC3CO)ccn1]

Pd(PPh₃)₄ (134 mg, 0.12 mmol) was added to a stirred suspension of intermediate I-30 (0.88 g, 3.00 mmol) and 2-picoline-4-boronic acid (658 mg, 3.00 mmol) in 1,4-dioxane (15.4 mL) and a sat. aq. NaHCO₃ (10 mL) under nitrogen atmosphere. The mixture was stirred at 90° C. for 16 h. Then additional 2-picoline-4-boronic acid (263 mg, 1.20 mmol) and Pd(PPh₃)₄ (35 mg, 0.03 mmol) were added at rt and under nitrogen. The mixture was stirred at 100° C. for 7 h. Then the mixture was diluted with water and extracted with EtOAc. The organic layer was separated, dried (Na₂SO₄), filtered and the solvents evaporated in vacuo. The crude product was purified by flash column chromatography (silica; MeOH in DCM 0/100 to 10/90). The desired fractions were collected and concentrated in vacuo to yield intermediate compound I-31 (347 mg, 45%) as pale orange solid.

Intermediate 32 (I-32)

7-(Hydroxymethyl)-6,7-dihydro-5H-pyrazolo[1,5-a]pyrazin-4-one (I-32)

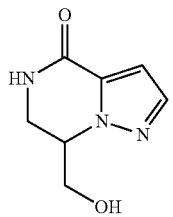 [SMILES: O=C1NCC(CO)n2nccc21]

Palladium 10% on charcoal (907 mg, 0.0.853 mmol) was added to a solution of intermediate I-30 (2.5 g, 8.53 mmol) and TEA (4.74 mL, 34.12 mmol) in DMF (125 mL) under nitrogen atmosphere. The mixture was hydrogenated (at atmospheric pressure) at rt for 16 h. The mixture was filtered through a pad of diatomaceous earth and the residue was washed with MeOH and 7M solution of ammonia in MeOH. The filtrate was concentrated in vacuo and the residue was treated with a small amount of water and extracted with EtOAc/THF. The organic layer was separated, dried (Na₂SO₄), filtered and concentrated in vacuo to yield intermediate compound I-32 (1.4 g, quant.) as a brown oil.

Intermediate 33a (I-33a) and Intermediate 33b (I-33b)

(7S)-7-methyl-3-(4,4,5,5-tetramethyl-1,3,2-dioxaborolan-2-yl)-5-[4-(trifluoromethyl)phenyl]-6,7-dihydropyrazolo[1,5-a]pyrazin-4-one (I-33a) and [(7S)-7-methyl-4-oxo-5-[4-(trifluoromethyl)phenyl]-6,7-dihydropyrazolo-[1,5-a]pyrazin-3-yl]boronic acid (I-33b)

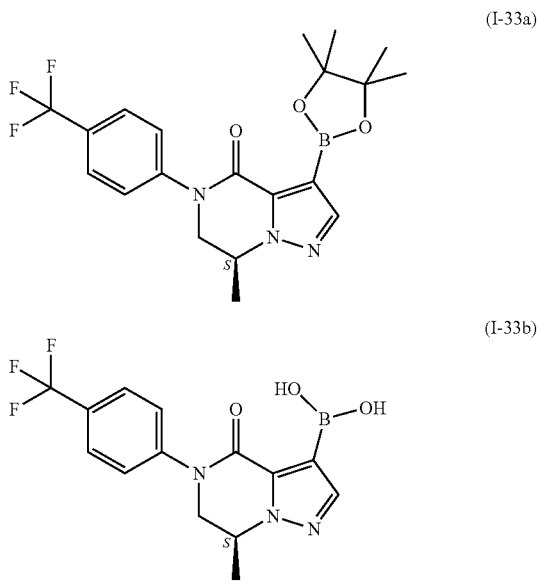

Isopropylmagnesium chloride lithium chloride complex (1.3M solution, 32.9 mL, 42.7 mmol) was added dropwise to a stirred solution of intermediate I-23 (10 g, 23.7 mmol) and 2-isopropoxy-4,4,5,5-tetramethyl-1,3,2-dioxaborolane (9.7 mL, 47.5 mmol) in anhydrous THF (100 mL) at −25° C. under nitrogen atmosphere. The mixture was stirred for 30 min at −25° C. Then the reaction was quenched with a 10% NH₄C₁ aq sol. and extracted with EtOAc. The organic layer was separated, dried (Na₂SO₄), filtered and the solvents evaporated in vacuo. The crude product was purified by flash column chromatography (silica; MeOH in DCM 0/100 to 3/97). The desired fractions were collected and the solvents evaporated in vacuo. The crude product was triturated with DIPE, filtered and dried to yield intermediate compound I-33a (6.4 g, 64%) as a white solid. The solution and impure fractions from the column purification were combined and repurified by flash column chromatography (silica, EtOAc in Heptane 30/70 to 70/30). The desired fractions were collected and the solvents evaporated in vacuo. The product was triturated in DIPE/Heptane, filtered and dried to yield intermediate compound I-33b (1 g, 10%) as a white solid.

Intermediates I-34 to I-37

The following intermediates were synthesized by following an analogous synthetic procedure as reported for intermediate 22.

| Structure | Intermediate number | Starting materials |
|---|---|---|
| 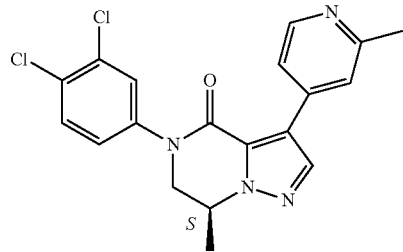 | I-34 | I-18<br>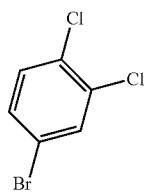 |
| 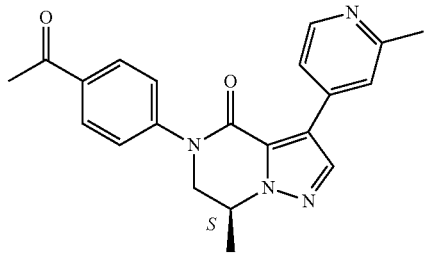 | I-35 | I-18<br>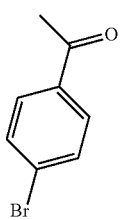 |
| 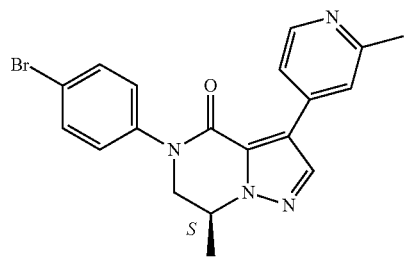 | I-36 | I-18<br> |

| Structure | Intermediate number | Starting materials |
|---|---|---|
| 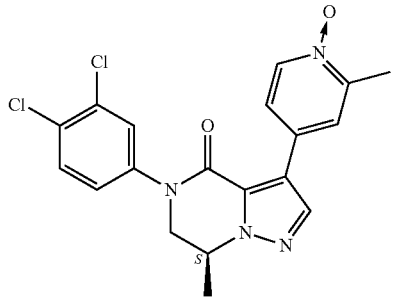 | I-37 | I-32 |

Intermediate 38 and Final Compound 170

(7S)-5-(3,4-dichlorophenyl)-7-methyl-3-(2-methyl-1-oxido-pyridin-1-ium-4-yl)-6,7-dihydropyrazolo[1,5-a]pyrazin-4-one (I-38 and Co. No. 170

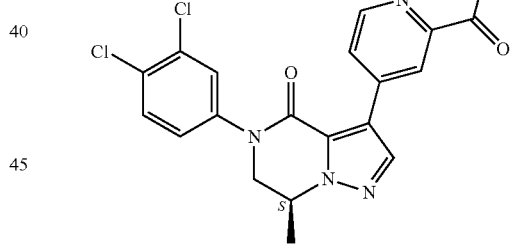

3-Chloroperoxybenzoic acid (2.03 g, 11.77 mmol) was added to a stirred solution of intermediate I-34 (2.28 g, 5.88 mmol) in DCM (37 mL) at 0° C. The mixture was allowed to reach rt and stirred at rt for 2 h. The mixture was treated with a sat sol. of Na₂CO₃ and diluted with DCM. The organic layer was separated, dried (Na₂SO₄), filtered and the solvents evaporated in vacuo to yield intermediate compound I-38 (1.84 g, 77%) that was used in the next step without any further purification.

Intermediate 39 (I-39)

4-[(7S)-5-(3,4-dichlorophenyl)-7-methyl-4-oxo-6,7-dihydropyrazolo[1,5-a]pyrazin-3-yl]pyridine-2-carbaldehyde (I-39)

Manganese dioxide (2.39 g, 27.57 mmol) was added to a solution of final compound 125 (E-14) (1.11 g, 2.75 mmol) in chloroform (11.7 mL). The mixture was stirred at rt for 16 h, at 60° C. for 5 h and then at rt for 16 h. Then, the mixture was filtered through a pad of diatomaceous earth and washed with DCM. The solvent was evaporated in vacuo. The crude product was purified by flash column chromatography (silica; EtOAc in DCM 0/100 to 50/50). The desired fractions were collected and evaporated in vacuo to yield intermediate compound I-39 (537 mg, 48%) as a pale yellow solid.

Intermediate 40 (I-40)

The following intermediate was synthesized by following an analogous synthetic procedure as reported for intermediate 39.

| Structure | Intermediate number | Starting material |
|---|---|---|
| 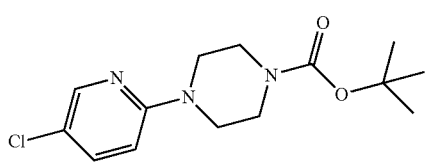 [SMILES: CC(C)(C)OC(=O)N1CCN(c2ccc(Cl)cn2)CC1] | I-40 | I-37 |

Intermediate 41 (I-41)

tert-Butyl 4-(5-chloro-2-pyridyl)piperazine-1-carboxylate (I-41)

A mixture of 2-bromo-5-chloropyridine (1.5 g, 7.79 mmol), 1-BOC-piperazine (2.18 g, 11.69 mmol), sodium tert-butoxide (1.49 g, 15.59 mmol), 9,9-dimethyl-4,5-bis(diphenylphosphino)xanthene (0.451 g, 0.78 mmol) and tris(dibenzylideneacetone)dipalladium(0) (0.357 g, 0.390 mmol) in toluene (25 mL) was stirred at 120° C. for 16 h. The mixture was poured into water, and extracted with EtOAc. The mixture was filtered through a short pad of diatomaceous earth. The organic layer was separated, washed with water and brine, dried (MgSO$_4$) and evaporated in vacuo. The crude product was purified by flash column chromatography (silica, EtOAc in DCM 0/100 to 20/80). The desired fractions were collected and evaporated in vacuo to yield intermediate compound I-41 (0.888 g, 38%) as an orange solid.

Intermediate 42 (I-42)

tert-Butyl 4-[5-[(7S)-7-methyl-4-oxo-5-[4-(trifluoromethyl)phenyl]-6,7-dihydropyrazolo[1,5-a]pyrazin-3-yl]-2-pyridyl]piperazine-1-carboxylate (I-42)

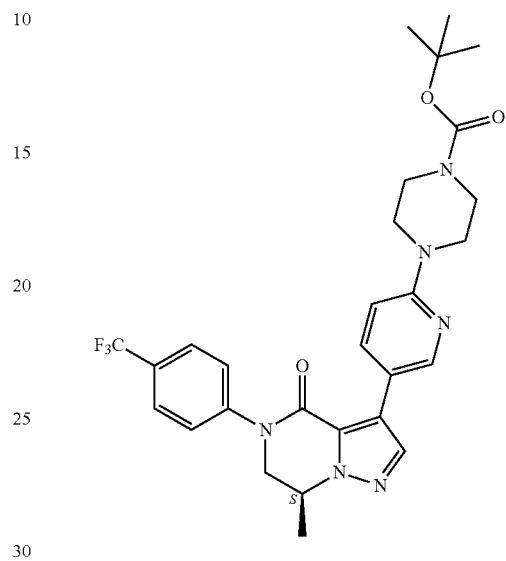

A suspension of intermediate I-41 (478 mg, 1.60 mmol), intermediate I-33a (653 mg, 1.55 mmol), palladium(II) acetate (7 mg, 0.032 mmol), 2-dicyclohexylphosphino-2',6'-dimethoxybiphenyl (26 mg, 0.064 mmol) and K$_2$CO$_3$ (554 mg, 4.013 mmol) in CH$_3$CN (1.6 mL) and H$_2$O (2.5 mL) was flushed with nitrogen for a few minutes and the mixture was stirred at 80° C. for 24 h. Then the mixture was diluted with H$_2$O and extracted with EtOAc. The organic layer was separated, dried (Na$_2$SO$_4$), filtered and the solvent evaporated in vacuo. The crude product was purified by flash column chromatography (silica; EtOAc in DCM 0/100 to 50/50). The desired fractions were collected and evaporated in vacuo to yield intermediate compound I-42 (663 mg, 74%) as a yellow oil.

Intermediate 43 and Final Compound 188

(7S)-5-[6-chloro-5-(trifluoromethyl)-2-pyridyl]-7-methyl-3-(2-methyl-4-pyridyl)-6,7-dihydropyrazolo[1,5-a]pyrazin-4-one (I-43 and Co. No. 188)

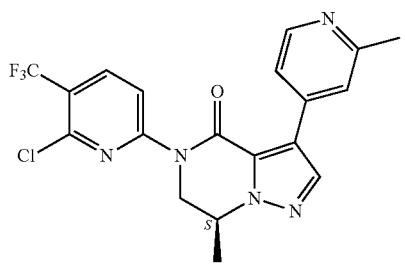

Pd(PPh$_3$)$_4$ (47 mg, 0.041 mmol) was added to a stirred suspension of intermediate I-18 (100 mg, 0.413 mmol), 2,6-dichloro-3-(trifluoromethyl)pyridine (86 μL, 0.620 mmol), 4,5-bis(diphenylphosphino)-9,9-dimethylxanthene (47 mg, 0.082 mmol), Cs$_2$CO$_3$ (269 mg, 0.825 mmol) in 1,4-dioxane (3 mL) in a sealed tube and under nitrogen. The mixture was stirred at 120° C. for 4 h. The mixture was filtered through a pad of diatomaceous earth and washed with DCM. The filtrate was evaporated in vacuo. The crude product was purified by flash column chromatography (silica, EtOAc in DCM 0/100 to 30/70). The desired fractions were collected and concentrated in vacuo. Then the product was triturated with Et$_2$O and filtered to yield intermediate compound I-43 (71 mg, 40%) as a white solid.

Intermediate 44 (I-44)

7-(Difluoromethyl)-5-[4-(trifluoromethyl)phenyl]pyrazolo[1,5-a]pyrazin-4-one (I-44)

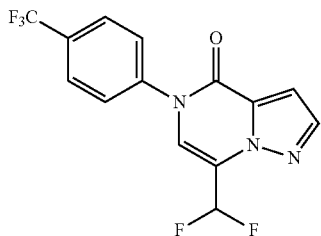 [SMILES: O=c1c2ccnn2c(C(F)F)cn1-c1ccc(C(F)(F)F)cc1]

Diethylaminosulfur trifluoride (0.373 mL, 3.866 mmol) was added to a stirred solution of intermediate I-40 (297 mg, 0.966 mmol) in DCM (33 mL) at 0° C. The mixture was allowed to warm to rt and stirred for 5 h. Then additional diethylaminosulfur trifluoride (0.355 mL, 2.9 mmol) was added at 0° C. and the mixture was stirred at rt for 20 h. The mixture was treated with water and extracted with DCM. The organic layer was separated, dried (Na$_2$SO$_4$), filtered and concentrated in vacuo. The crude product was purified by flash column chromatography (silica; DCM). The desired fractions were collected and concentrated in vacuo to yield intermediate compound I-44 (258 mg, 81%) as a colorless oil.

Intermediate 45 (I-45)

The following intermediate was synthesized by following an analogous synthetic procedure as reported for intermediate 23.

| Structure | Intermediate number | Starting materials |
|---|---|---|
| ![structure] | I-45 | I-44 |

Intermediate 46 (I-46)

The following intermediate was synthesized by following an analogous synthetic procedure as reported for intermediate 18.

| Structure | Intermediate number | Starting materials |
|---|---|---|
| ![structure] | I-46 | I-45 |

Intermediates 47 and 48 (I-47 and I-48)

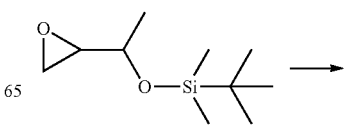

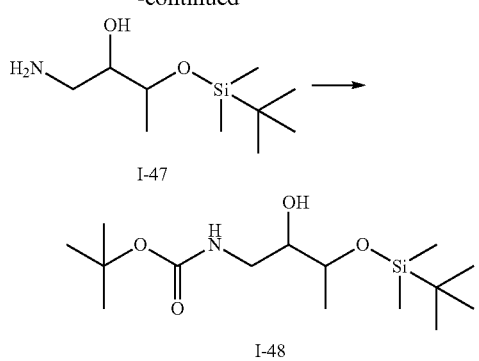

i) NH₃ (28% in water, 54 mL) was added over 2-[1-[[(1,1-dimethylethyl)dimethylsilyl]oxy]ethyl]-oxirane (4.73 g, 23.373 mmol) and the mixture was stirred at 120° C. for 40 min under microwave irradiation. The solvent was then concentrated in vacuo to yield intermediate compound I-47 as an orange oil (3.298 g, 64%).

ii) Intermediate I-48 was synthesized following an analogous synthetic procedure as reported for intermediate I-3. Starting from intermediate I-47 (3.269 g, 14.9 mmol), intermediate compound I-48 was obtained as a colorless oil (4.642 g, 97.5%).

Intermediates 49-52 (I-49 to I-52)

The following intermediates were synthesized by following an analogous synthetic procedure as reported for intermediate 6.

| Structure | Intermediate number | Starting materials |
|---|---|---|
| 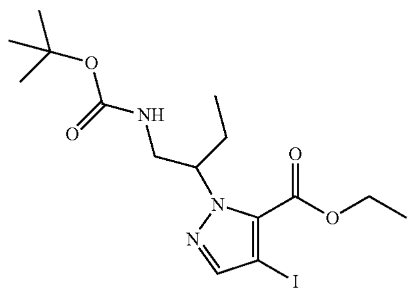 [SMILES: CCOC(=O)c1c(I)cnn1C(CC)CNC(=O)OC(C)(C)C] | I-49 | I-2 |
| | | N-(2-hydroxybutyl)-carbamic acid 1,1-dimethylethyl ester |
| 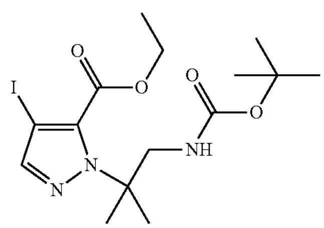 [SMILES: CCOC(=O)c1c(I)cnn1C(C)(C)CNC(=O)OC(C)(C)C] | I-50 | I-2 |
| | | N-(2-hydroxy-2-methylpropyl)-carbamic acid 1,1-dimethylethyl ester |
| 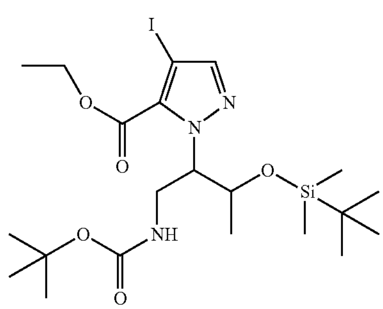 [SMILES: CCOC(=O)c1c(I)cnn1C(CNC(=O)OC(C)(C)C)C(C)O[Si](C)(C)C(C)(C)C] | I-51 | I-2 |
| | | I-48 |

-continued

| Structure | Intermediate number | Starting materials |
|---|---|---|
| 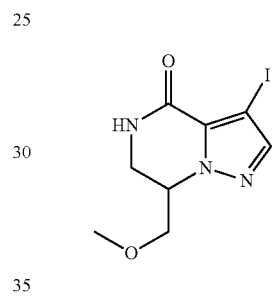 | I-52 | I-2 |
| | | tert-butyl N-(2-hydroxy-3-methoxypropyl)carbamate |

Intermediate 53 (I-53)

The following intermediate was synthesized following the procedure for the synthesis of intermediate I-29, followed by the procedure for the synthesis of intermediate I-30.

| Structure | Intermediate number | Starting materials |
|---|---|---|
| 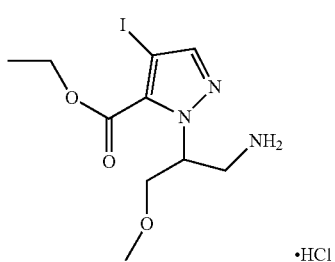 [SMILES: CCOC(=O)c1c(I)cnn1C(CN)COC ; Cl] | I-53 | I-51 |

Intermediate 54 (I-54)

Ethyl 2-[1-(aminomethyl)-2-methoxy-ethyl]-4-iodo-pyrazole-3-carboxylate (I-54)

HCl (4 M in dioxane, 2.2 mL, 8.82 mmol) was added to a solution of intermediate I-52 (0.8 g, 1.765 mmol) in CH$_3$CN (8 mL). The mixture was stirred at rt for 1 h and then the solvent was concentrated in vacuo to give intermediate compound I-54 (700 mg, 87%) as a cream solid.

Intermediate 55 (I-55)

3-Iodo-7-(methoxymethyl)-6,7-dihydro-5H-pyrazolo[5-a]pyrazin-4-one (I-55)

Et$_3$N (0.55 mL, 3.98 mmol) was added to a solution of intermediate I-54 (0.7 g, 1.80 mmol) in DMF (6.7 mL). The mixture was stirred at rt for 3 h then neutralized with a sat. sol. of NaHCO$_3$ and extracted with DCM. The organic layer was separated, dried (Na$_2$SO$_4$), filtered and the solvents evaporated in vacuo to give intermediate compound I-55 (440 mg, 80%) as a white solid.

Intermediates 56 and 57 (I-56 and I-57) The following intermediates were synthesized by following an analogous synthetic procedure as that reported for intermediate 15.

| Structure | Intermediate number | Starting material |
|---|---|---|
| 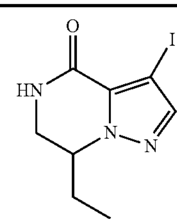 | I-56 | I-49 |
| 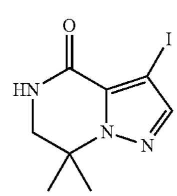 | I-57 | I-50 |

Intermediates 58-61 (I-58 to I-61)

The following intermediates were synthesized by following an analogous synthetic procedure as reported for intermediate 25.

| Structure | Intermediate number | Starting materials |
|---|---|---|
| 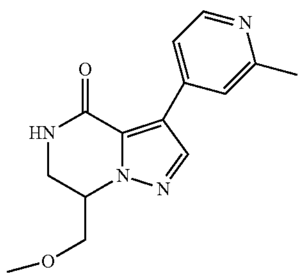 | I-58 | I-55<br>2-picoline-4-boronic acid |
| 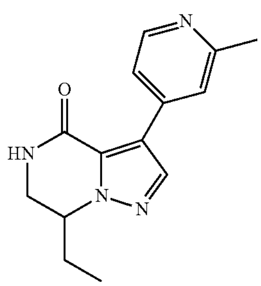 [SMILES: CCC1CNC(=O)c2c(-c3ccnc(C)c3)cnn21] | I-59 | I-56<br>2-picoline-4-boronic acid |
| 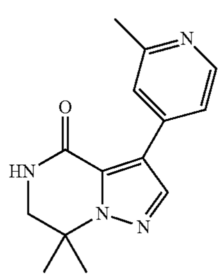 [SMILES: Cc1cc(-c2cnn3c2C(=O)NCC3(C)C)ccn1] | I-60 | I-57<br>2-picoline-4-boronic acid |
| 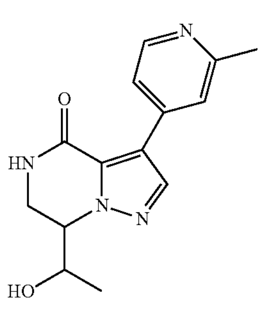 [SMILES: Cc1cc(-c2cnn3c2C(=O)NCC3C(C)O)ccn1] | I-61 | I-53<br>2-picoline-4-boronic acid |

Intermediate 62 (I-62)

2-[(1S)-2-(3,4-dichloroanilino)-1-methyl-ethyl]-4-(2-methyl-4-pyridyl)pyrazole-3-carboxylic acid (I-62)

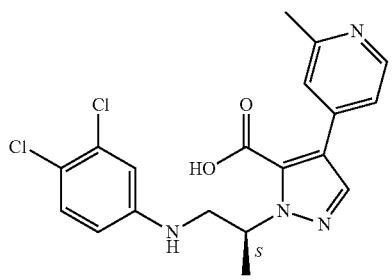

Sodium hydride (60% dispersion in mineral oil, 20 mg, 0.344 mmol) was added to a solution of compound Co. No. 6a (200 mg, 0.516 mmol) in DMF (4 mL) and the mixture was stirred at 60° C. for 24 h. Then more sodium hydride (60% dispersion in mineral oil, 11 mg, 0.172 mmol) was added and the mixture was stirred at 60° C. for 3 h. Then, the mixture was quenched with a $NH_4Cl$ sat. sol. and extracted with EtOAc. The organic layer was separated, dried ($MgSO_4$), filtered and the solvents evaporated in vacuo to give intermediate compound I-62 (230 mg, quantitative) as a solid which was used in the next step without further purification.

Intermediate 63 (I-63)

2-[(1S)-2-(4,5-dichloro-2-iodo-anilino)-1-methyl-ethyl]-4-(2-methyl-4-pyridyl)pyrazole-3-carboxylic acid (I-63a) and 2-[(1S)-2-(3,4-dichloro-2-iodo-anilino)-1-methyl-ethyl]-4-(2-methyl-4-pyridyl)pyrazole-3-carboxylicacid (I-63b)

(I-63a)
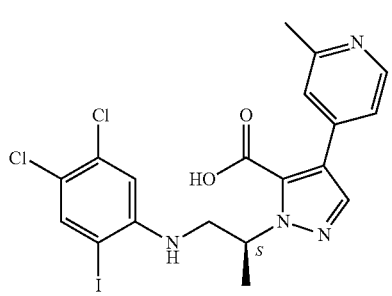

(I-63b)
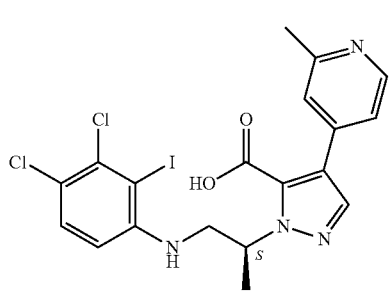

N-iodosuccimide (124 mg, 0.552 mmol) was added to a solution of intermediate compound I-62 (224 mg, 0.5523 mmol) in chloroform (5 mL) and the mixture was stirred at rt for 3 h. Then more N-iodosuccimide (62 mg, 0.277 mmol) was added and the mixture was stirred at rt for 18 h. Then the reaction was quenched with a sat. sol. of Na₂SO₃ and extracted with DCM. The organic layer was separated, dried (MgSO₄), filtered and the solvent evaporated in vacuo to give a mixture of intermediates compounds I-63a and I-63b (240 mg, 41%) which was used in next step without further purification.

Intermediate 64 (I-64)

tert-Butyl N-[[2,2,2-trifluoro-1-nitromethyl)ethyl]amino]carbamate (I-64)

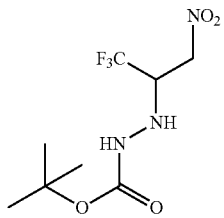 [SMILES: CC(C)(C)OC(=O)NNC(C[N+](=O)[O-])C(F)(F)F]

tert-Butyl carbazate (281 mg, 2.13 mmol) was added to a stirred solution of 3,3,3-trifluoro-1-nitro-prop-1-ene (prepared as described in J. Fluorine Chem. 2008, 767-774) (73 µL, 0.709 mmol) in MeOH (3.1 mL) at rt. The mixture was stirred for 1 h and the solvents evaporated in vacuo. The crude product was purified by flash column chromatography (silica, EtOAc in Heptane 40/60 to 60/40) to yield intermediate compound I-64 (200 mg, quant.)

Intermediate 65 (I-65)

[2,2,2-Trifluoro-1-(nitromethyl)ethyl]hydrazine hydrochloride salt (I-65)

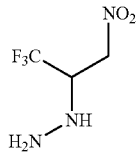

HCl (6M in 1,4-dioxane, 10.5 mL, 42 mmol) was added to a solution of intermediate I-64 (1.15 g, 4.2 mmol) in MeOH (10 mL) at rt. The mixture was stirred for 2 h and the solvents were evaporated in vacuo to yield intermediate compound I-65 (880 mg, quant.) that was used in the next step without further purification.

Intermediate 66 (I-66)

Ethyl 2-[2,2,2-trifluoro-1-(nitromethyl)ethyl]pyrazole-3-carboxylate (I-66a) and ethyl 1-[2,2,2-trifluoro-1-(nitromethyl)ethyl]pyrazole-3-carboxylate (I-66b)

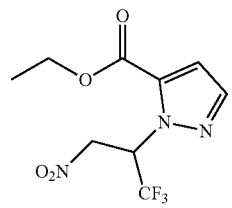

I-66a

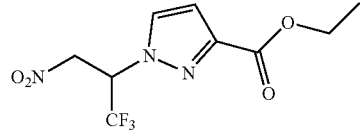

I-66b

Ethyl pyruvate (77 µL, 0.692 mmol) and N,N-dimethylformamide dimethyl acetal (92 µL, 0.692 mmol) were stirred at rt for 16 h. The dark red/brown solution was added to a solution of intermediate I-65 (145 mg, 0.692 mmol) in EtOH (2 mL). The mixture was stirred at 85° C. for 3 h. The solvent was concentrated in vacuo. The crude product was purified by flash column chromatography (silica; EtOAc in Heptane 30/70 to 60/40) to yield intermediate compounds I-66a (78 mg, 40%) and I-66b (54 mg, 28%).

Intermediate 67 (I-67)

7-Methyl-6,7-dihydro-5H-pyrazolo[1,5-a]pyrazin-4-one (I-67)

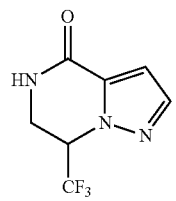 [SMILES: O=C1NCC(C(F)(F)F)n2nccc21]

Pd (10% on charcoal, 100 mg, 0.094 mmol) and ammonium formate (112 mg, 1.78 mmol) were added to a stirred solution of intermediate I-66 (100 mg, 0.355 mmol) in MeOH (3.3 mL). The mixture was stirred in a sealed tube at 70° C. for 2 h. The solvent was concentrated in vacuo to yield intermediate compound I-67 (70 mg, 96%) that was used in the following step without further purification.

101

Intermediate 68 (I-68)

3-Iodo-7-(trifluoromethyl)-5-[4-(trifluoromethyl)phenyl]-6,7-dihydropyrazolo[1,5-a]pyrazin-4-one (I-68)

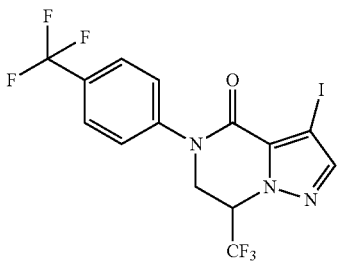 [SMILES: O=C1c2c(I)cnn2C(C(F)(F)F)CN1c1ccc(C(F)(F)F)cc1]

Intermediate compound I-68 was synthesized by following the sequence of an analogous synthetic procedure as reported for intermediate I-22 starting from intermediate I-67 and 4-bromobenzotrifluoride, followed by the procedure for intermediate I-23.

Final Compounds

Example 1

(7S)-7-Methyl-3-(2-methylpyridin-4-yl)-5-[4-(trifluoromethyl)phenyl]-6,7-dihydropyrazolo[1,5-a]pyrazin-4(5H)-one (E-1, Co. No. 1

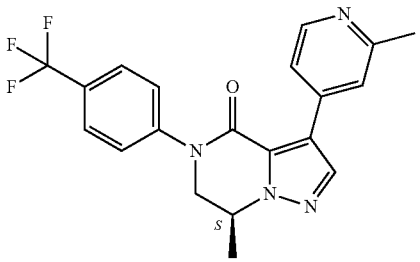

Procedure A: Copper(I) iodide (872 mg, 4.58 mmol) was added to a stirred suspension of intermediate I-18 (1.85 g, 7.64 mmol), 4-bromobenzotrifluoride (2.14 mL, 15.27 mmol), $K_2CO_3$ (2.11 g, 15.27 mmol) and N,N-dimethylethylenediamine (0.492 mL, 4.58 mmol) in toluene (70 mL) in a sealed tube and under nitrogen. The mixture was stirred at 100° C. for 16 h. Then DMF (10 mL) was added and the mixture was stirred at 100° C. for additional 8 h. The mixture was filtered through diatomaceous earth and washed with EtOAc. The organic layer was washed with diluted $NH_4OH$ sol, dried ($Na_2SO_4$), filtered and the solvents evaporated in vacuo. The crude product was purified by flash column chromatography (silica; EtOAc in Heptane 20/80 to 50/50). The desired fractions were collected and the solvents evaporated in vacuo. The product was precipitated with heptane, filtered and dried in vacuo to yield final product compound 1 as a white solid (2.32 g, 78%). $^1$H NMR (500 MHz, $CDCl_3$) δ ppm 1.75 (d, J=6.4 Hz, 3H), 2.57 (s, 3H), 4.02 (dd, J=12.7, 7.2 Hz, 1H), 4.30 (dd, J=12.6, 4.2 Hz, 1H), 4.75-4.84 (m, 1H), 7.44 (d, J=5.2 Hz, 1H), 7.49 (d, J=3.8 Hz, 2H), 7.51 (s, 1H), 7.71 (d, J=8.4 Hz, 2H), 7.80 (s, 1H), 8.48 (d, J=5.2 Hz, 1H).

102

Procedure B: Copper(I) iodide (94 mg, 0.495 mmol) was added to a stirred suspension of intermediate I-18 (200 mg, 0.825 mmol), 4-bromobenzotrifluoride (0.231 mL, 1.651 mmol), $K_2CO_3$ (228 mg, 1.65 mmol) and N,N-dimethylethylenediamine (53 μL) in toluene (7.5 mL) in a sealed tube and under nitrogen. The mixture was stirred at 100° C. overnight. The mixture was filtered through a pad of diatomaceous earth and washed with DCM. The organic layer was separated, dried ($MgSO_4$), filtered and the solvents evaporated in vacuo. The crude product was purified by flash column chromatography (silica, EtOAc in Heptane 0/100 to 70/30). The desired fractions were collected and concentrated in vacuo to yield compound 1 (283 mg, 89%) as a pinkish solid.

Procedure C: $Pd(PPh_3)_4$ (384 mg, 0.332 mmol) was added to a stirred suspension of intermediate I-23 (2 g, 4.74 mmol) and 2-methylpyridine-4-boronic acid pinacol ester (1.66 g, 7.60 mmol) in 1,4-dioxane (10 mL) and a sat. sol. of $Na_2CO_3$ (5 mL) in a sealed tube under nitrogen. The mixture was stirred at 100° C. for 16 h. Then the mixture was diluted with $H_2O$ and extracted with DCM and DCM with a small amount of EtOH. The organic layer was dried ($Na_2SO_4$), filtered and the solvent evaporated in vacuo. The crude product was purified by flash column chromatography (silica; 7M solution of ammonia in MeOH in DCM 0/100 to 3/97 then EtOAc in Heptane 0/100 to 100/0). The desired fractions were collected and evaporated in vacuo to yield compound 1 as a white solid (480 mg, 26%). (1.31 g of starting material was recovered).

Procedure D; general description of a synthesis performed at a large scale by which Co. No. 1 was isolated in 90% yield before purification: A mixture of I-18 (1 eq.), potassium carbonate (2 eq.), copper(I) iodide (0.3 eq.), 4-bromobenzotrifluoride (1.3 eq.), N,N'-Dimethyl ethylenediamine (0.35 eq.), DMF (5 mL/g I-18) and toluene (8 mL/g I-18) was evacuated and backfilled with nitrogen 3 times. It was heated to 100-110° C. and stirred at 100-110° C. for 7-8 h under nitrogen.

The reaction solution was concentrated to remove toluene below 50° C. Isopropyl acetate (15 mL/g I-18) was added. The mixture was washed with 5% $NH_4OH$ aqueous solution (3×7 mL/g I-18), and then 5% N-acetyl-L-cysteine and 5% $K_2CO_3$ aqueous solution (2×7 mL/g I-18) at 10-25° C. Finally, it was washed with 5% NaCl aqueous solution (5 mL/g I-18). The obtained solution was concentrated and co-evaporated with MTBE to remove isopropyl acetate. The resulting solid was filtered and dried in vacuo at 45-50° C. Co. No. 1 was obtained as an off-white solid which was further purified as follows:

Co. No. 1 was dissolved in a solvent mixture of IPA (4 mL/g Co. No. 1) and water (1 mL/g Co. No. 1) at 48-55° C. The solution was filtered and cooled to 0-5° C. An IPA/water mixture (0.5 mL/g Co. No. 1, 4/1 v/v) was used to rinse. Water (650 μL/g Co. No. 1) was added drop-wise and seeding with Co. No. 1 was performed. The mixture was stirred at 0-5° C. for 3-4 h. Water (14 mL/g Co. No. 1) was added drop-wise at 0-5° C. for 3-4 h, and then the suspension was stirred at 0-5° C. for 5-6 h. The wet product was filtered and rinsed with water (2 mL/g Co. No. 1), then dried in vacuo at 45-50° C. for 16 h to afford Co. No. 1 as a white solid.

For compound 1 (DSC mp=155.35° C.), the hydrochloride salt (.HCl) (DSC mp=decomposes above 200° C.); the sulfate salt (.H$_2$SO$_4$) (DSC mp=decomposes above 200° C.); the methane sulfonate salt (.CH$_3$SO$_3$H) (DSC mp=252° C.); and the maleate salt (.HO$_2$CCH=CHCO$_2$H-cis) (DSC mp=163° C.); wherein the mp were determined by DSC (Mettler Toledo Q2000 MDSC, heating from 25 to 350° C. at 10° C./min) were obtained following the procedure described below:

Compound 1 (1.5 g) in 9 mL of IPA or acetone (hydrochloride and sulfate salts were generated in acetone; methanesulfonate and maleate salts were generated in IPA) were stirred at 50° C. until all the solid was dissolved. The acid (1.1 mol equivalents) was added to the solution and the reaction mixture was further stirred for 2 h at 50° C., then cooled to 20° C. in 1 h and further stirred for 30 h at 20° C. The suspension was filtered and the solids were dried at 50° C. in a vacuum oven overnight.

Example 2

(7S)-7-Methyl-3-pyridin-4-yl-5-[4-(trifluoromethyl)phenyl]-6,7-dihydropyrazolo[1,5-a]pyrazin-4(5H)-one (E-2, Co. No. 2)

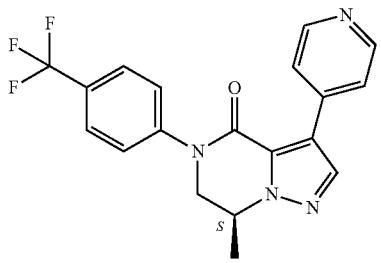

Pd(PPh$_3$)$_4$ (41 mg, 0.036 mmol) was added to a stirred suspension of intermediate I-23 (300 mg, 0.71 mmol) and pyridine-4-boronic acid (114 mg, 0.93 mmol) in 1,4-dioxane (3.3 mL) and a sat. sol. of NaHCO$_3$ (1.5 mL). The mixture was stirred at 150° C. for 10 min under microwave irradiation. Then the mixture was diluted with H$_2$O and extracted with DCM. The organic layer was separated, dried (Na$_2$SO$_4$), filtered and the solvent evaporated in vacuo. The crude product was purified by flash column chromatography (silica; MeOH in DCM 0/100 to 6/94). The desired fractions were collected and the solvents evaporated in vacuo. The residue was purified by ion exchange chromatography using an ISOLUTE® SCX2 cartridge eluting first with MeOH and then with 7M solution of ammonia in MeOH. The desired fractions contained in the 7M solution of ammonia in MeOH were collected and the solvents evaporated in vacuo. The residue was precipitated with DIPE to yield compound 2 as a white solid (215 mg, 81%). $^1$H NMR (400 MHz, CDCl$_3$) δ ppm 1.76 (d, J=6.5 Hz, 3H), 4.03 (dd, J=12.7, 7.2 Hz, 1H), 4.31 (dd, J=12.7, 4.2 Hz, 1H), 4.81 (qdd, J=6.7, 6.7, 6.7, 6.5, 4.3 Hz, 1H), 7.51 (d, J=8.1 Hz, 2H), 7.65 (dd, J=4.4, 1.6 Hz, 2H), 7.71 (d, J=8.3 Hz, 2H), 7.83 (s, 1H), 8.60 (dd, J=4.6, 1.8 Hz, 2H).

Example 3

(7S)-3-(2-Aminopyridin-4-yl)-7-methyl-5-[4-(trifluoromethyl)phenyl]-6,7-dihydropyrazolo[1,5-a]pyrazin-4(5H)-one (E-3, Co. No. 71

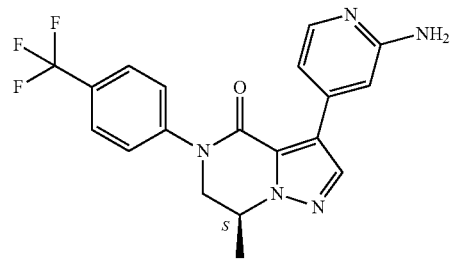

Pd(PPh$_3$)$_4$ (96 mg, 0.083 mmol) was added to a stirred suspension of intermediate I-23 (700 mg, 1.66 mmol) and intermediate I-24 (458 mg, 3.32 mmol) in 1,4-dioxane (10 mL) and a sat. sol. of NaHCO$_3$ (5 mL). The mixture was stirred at 150° C. for 10 min under microwave irradiation. Then the mixture was diluted with H$_2$O and extracted with DCM. The organic layer was separated, dried (Na$_2$SO$_4$), filtered and the solvent evaporated in vacuo. The crude product was purified by flash column chromatography (silica; MeOH in DCM 0/100 to 10/90). The desired fractions were collected and the solvents evaporated in vacuo and the residue was purified by RP HPLC (RP C18 XBridge™ 30×100 mm 5 um), mobile phase (gradient from 67% 0.1% NH$_4$CO$_3$H/NH$_4$OH pH 9 solution in Water, 33% CH$_3$CN to 50% 0.1% NH$_4$CO$_3$H/NH$_4$OH pH 9 solution in Water, 50% CH$_3$CN). The residue was purified by ion exchange chromatography using an ISOLUTE® SCX2 cartridge eluting first with MeOH and then with 7M solution of ammonia in MeOH. The desired fractions contained in the 7M solution of ammonia in MeOH were collected and the solvents evaporated in vacuo to yield final product compound 71 as a white solid (163 mg, 25%). $^1$H NMR (500 MHz, CDCl$_3$) δ ppm 1.74 (d, J=6.4 Hz, 3H) 4.01 (dd, J=12.6, 7.1 Hz, 1H) 4.29 (dd, J=12.6, 4.2 Hz, 1H) 4.43 (br. s., 2H) 4.78 (quind, J=6.6, 4.3 Hz, 1H) 6.94 (dd, J=5.5, 1.4 Hz, 1H) 6.98 (s, 1H) 7.51 (br. d, J=8.4 Hz, 2H) 7.71 (br. d, J=8.4 Hz, 2H) 7.79 (s, 1H) 8.06 (d, J=4.9 Hz, 1H).

Example 4

(7S)-3-[2-(Ethylamino)-4-pyridyl]-7-methyl-5-[4-(trifluoromethyl)phenyl]-6,7-dihydropyrazolo[1,5-a]pyrazin-4-one (E-4, Co. No. 44)

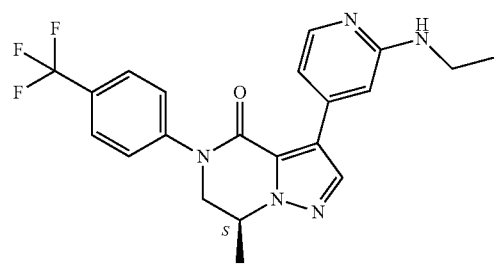

Sodium triacetoxyborohydride (246 mg, 1.16 mmol) was added to a stirred solution of compound 71 (300 mg, 0.77 mmol) and acetaldehyde (0.048 mL, 0.85 mmol) in 1,2-dichloroethane (3 mL). The mixture was stirred at rt for 16 h. Then the mixture was diluted with a sat. sol. of NaHCO$_3$ and extracted with DCM. The organic layer was separated, dried (Na$_2$SO$_4$), filtered and the solvent evaporated in vacuo. The crude product was purified by flash column chromatography (silica; EtOAc in heptane 0/100 to 40/60). The desired fractions were collected and the solvents evaporated in vacuo. The residue was purified by ion exchange chromatography using an ISOLUTE® SCX2 cartridge eluting first with MeOH and then with 7M solution of ammonia in MeOH. The desired fractions contained in the 7M solution of ammonia in MeOH were collected and the solvents evaporated in vacuo and the residue was purified by RP HPLC (RP C18 XBridge™ 30×100 mm 5 um), mobile phase (gradient from 60% 0.1% NH$_4$CO$_3$H/NH$_4$OH pH 9 solution in Water, 40% CH$_3$CN to 43% 0.1% NH$_4$CO$_3$H/NH$_4$OH pH 9 solution in Water, 57% CH$_3$CN). The residue was precipitated with DIPE to yield compound 44 as a white solid (28 mg, 9%). $^1$H NMR (500 MHz, CDCl$_3$) δ ppm 1.24 (t, J=7.2 Hz, 3H) 1.74 (d, J=6.4 Hz, 3H) 3.29-3.37 (m, 2H) 4.00 (dd, J=12.6, 7.1 Hz, 1H) 4.29 (dd, J=12.6, 4.2 Hz, 1H) 4.42 (br. t, J=4.6 Hz, 1H) 4.74-4.82 (m, 1H) 6.83 (s, 1H) 6.84 (dd, J=5.3, 1.3 Hz, 1H) 7.51 (br. d, J=8.7 Hz, 2H) 7.70 (br. d, J=8.7 Hz, 2H) 7.79 (s, 1H) 8.07 (d, J=5.5 Hz, 1H).

Example 5

(7S)-3-(2-Methoxy-4-pyridyl)-7-methyl-5-[4-(trifluoromethyl)phenyl]-6,7-dihydropyrazolo[1,5-a]pyrazin-4-one (E-5, Co. No. 45)

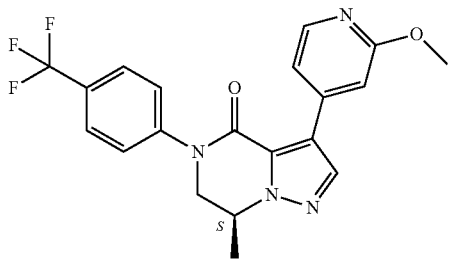

Copper(I) iodide (66 mg, 0.348 mmol) was added to a stirred suspension of intermediate I-25 (150 mg, 0.58 mmol), 4-bromobenzotrifluoride (209 mg, 0.93 mmol), K$_2$CO$_3$ (161 mg, 1.16 mmol) and N,N-dimethylethylenediamine (0.037 mL, 0.348 mmol) in toluene (3.75 mL) in a sealed tube and under nitrogen. The mixture was stirred at 100° C. for 24 h. Then, more 4-bromobenzotrifluoride (131 mg, 0.58 mmol) was added and the mixture was stirred at 100° C. for additional 16 h. The mixture was filtered through diatomaceous earth and washed with DCM. The organic layer was evaporated in vacuo. The crude product was purified by flash column chromatography (silica; EtOAc in Heptane 0/100 to 20/80). The desired fractions were collected and the solvents evaporated in vacuo. The product was precipitated with Et$_2$O. The solid was purified by RP HPLC (RP C18 XBridge™ 30×100 mm 5 um), mobile phase (gradient from 60% 0.1% NH$_4$CO$_3$H/NH$_4$OH pH 9 solution in Water, 40% CH$_3$CN to 43% 0.1% NH$_4$CO$_3$H/NH$_4$OH pH 9 solution in Water, 57% CH$_3$CN) to yield compound 45 as a white solid (130 mg, 56%). %). $^1$H NMR (500 MHz, CDCl$_3$) δ ppm 1.75 (d, J=6.6 Hz, 3H) 3.94 (s, 3H) 4.02 (dd, J=12.7, 7.2 Hz, 1H) 4.30 (dd, J=12.6, 4.2 Hz, 1H) 4.75-4.83 (m, 1H) 7.09 (s, 1H) 7.23 (dd, J=5.5, 1.2 Hz, 1H) 7.50 (br. d, J=8.7 Hz, 2H) 7.70 (br. d, J=8.7 Hz, 2H) 7.79 (s, 1H) 8.14 (d, J=5.5 Hz, 1H).

Example 6

(7S)-3-(2-Ethyl-4-pyridyl)-7-methyl-5-[4-(trifluoromethyl)phenyl]-6,7-dihydropyrazolo[1,5-a]pyrazin-4-one (E-6, Co. No. 46)

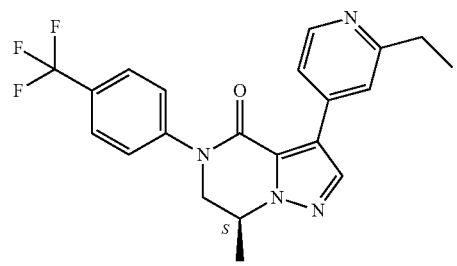

A solution of intermediate I-27 (114 mg, 0.29 mmol) in EtOH (5.7 mL) was hydrogenated in a H-CubeR reactor (1 mL/min, 30 mm Pd(OH)$_2$/C 20% cartridge, full H$_2$ mode, rt, 1 cycle). Then, the solvent was evaporated in vacuo. The crude product was purified by RP HPLC (RP C18 XBridge™ 30×100 mm 5 um), mobile phase (gradient from 60% 0.1% NH$_4$CO$_3$H/NH$_4$OH pH 9 solution in Water, 40% CH$_3$CN to 43% 0.1% NH$_4$CO$_3$H/NH$_4$OH pH 9 solution in Water, 57% CH$_3$CN) to yield compound 46 as a white solid (84 mg, 73%). $^1$H NMR (400 MHz, CDCl$_3$) δ ppm 1.32 (t, J=7.6 Hz, 3H) 1.75 (d, J=6.7 Hz, 3H) 2.85 (q, J=7.6 Hz, 2H) 4.02 (dd, J=12.7, 7.2 Hz, 1H) 4.31 (dd, J=12.7, 4.2 Hz, 1H) 4.80 (quind, J=6.7, 4.2 Hz, 1H) 7.46 (dd, J=5.1, 1.6 Hz, 1H) 7.48 (br. s, 1H) 7.51 (br. d, J=8.3 Hz, 2H) 7.71 (br. d, J=8.3 Hz, 2H) 7.81 (s, 1H) 8.51 (dd, J=5.3, 0.7 Hz, 1H).

Example 7

7-(Hydroxymethyl)-3-(2-methyl-4-pyridyl)-5-[4-(trifluoromethyl)phenyl]-6,7-dihydropyrazolo[1,5-a]pyrazin-4-one (E-7, Co. No. 87)

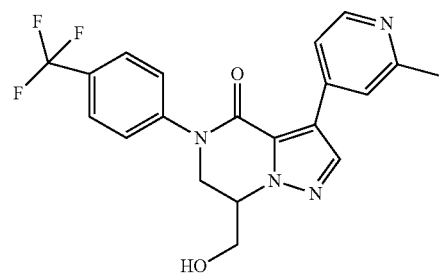 [SMILES: Cc1cc(-c2cnn3c2C(=O)N(c2ccc(C(F)(F)F)cc2)CC3CO)ccn1]

Copper(I) iodide (0.135 g, 0.709 mmol) was added to a stirred suspension of intermediate I-31 (305 mg, 1.18 mmol), 4-bromobenzotrifluoride (298 μL, 2.12 mmol), K₂CO₃ (330 mg, 2.36 mmol) and N,N'-dimethylethylenediamine (76 μL, 0.71 mmol) in toluene (7.63 mL) in a sealed tube and under nitrogen. The mixture was stirred at 100° C. for 18 h. Then additional K₂CO₃ (160 mg, 1.18 mmol), copper(I) iodide (0.067 g, 0.354 mmol), N,N'-dimethylethylenediamine (38 μL, 0.35 mmol) and 4-bromobenzotrifluoride (132 μL, 0.95 mmol) were added under nitrogen and the mixture was stirred at 100° C. for 5 h. The mixture was filtered through a pad of diatomaceous earth and washed with DCM. The organic layer was separated, dried (Na₂SO₄), filtered and concentrated in vacuo. The crude product was purified by flash column chromatography (silica; methanol in DCM 0/100 to 7/93). The desired fractions were collected and concentrated in vacuo to yield compound 87 (321 mg, 68%) as yellow oil that precipitated upon standing at rt.

Example 8

7-(Fluoromethyl)-3-(2-methyl-4-pyridyl)-5-[4-(trifluoromethyl)phenyl]-6,7-dihydropyrazolo[1,5-a]pyrazin-4-one (E-8, Co. No. 52)

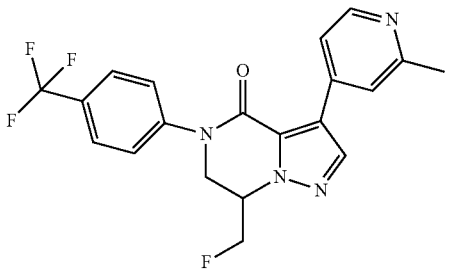 [SMILES: Cc1cc(-c2cnn3c2C(=O)N(c2ccc(C(F)(F)F)cc2)CC3CF)ccn1]

(Diethylamino)sulfur trifluoride (23 μL, 0.185 mmol) was added to a stirred solution of compound 87 (50 mg, 0.124 mmol) in DCM (2.4 mL) at −10° C. The mixture was allowed to warm to rt and stirred for 18 h. The mixture was treated with water and extracted with DCM. The organic layer was separated, dried (Na₂SO₄), filtered and concentrated in vacuo. The crude product was purified by flash column chromatography (silica; EtOAc in DCM 0/100 to 100/0 and MeOH in EtOAc 0/100 to 1/99). The desired fractions were collected and concentrated in vacuo. Then the compound was triturated with DIPE to yield compound 52 (14.5 mg, 29%) as a white solid. ¹H NMR (500 MHz, CDCl₃) δ ppm 2.58 (s, 3H) 4.31 (dd, J=13.1, 4.8 Hz, 1H) 4.47-4.53 (m, 1H) 4.86-5.07 (m, 3H) 7.45 (br. d, J=4.6 Hz, 1H) 7.51 (br. d, J=8.7 Hz, 2H) 7.50 (s, 1H) 7.72 (br. d, J=8.7 Hz, 2H) 7.85 (s, 1H) 8.49 (d, J=5.2 Hz, 1H).

Example 9

(7S)-5-[4-Fluoro-3-(trifluoromethyl)phenyl]-7-methyl-3-(2-methyl-4-pyridyl)-6,7-dihydropyrazolo[1,5-a]pyrazin-4-one (E-9, Co. No. 67)

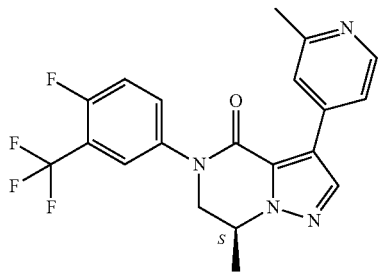

Compound 67 was obtained starting from intermediate I-18 (160 mg, 0.66 mmol), 5-bromo-2-fluorobenzotrifluoride (149 μL, 1.06 mmol), N,N'-dimethylethylenediamine (42 μL, 0.396 mmol), copper(I) iodide (75 mg, 0.396 mmol), K₂CO₃ (182 mg, 1.32 mmol) in toluene (4.27 mL), following a procedure similar to that described in E-1, yielding compound 67 (224 mg, 84%) as a pale yellow solid. ¹H NMR (500 MHz, CDCl₃) δ ppm 1.76 (d, J=6.4 Hz, 3H) 2.58 (s, 3H) 3.98 (dd, J=12.7, 7.2 Hz, 1H) 4.25 (dd, J=12.6, 4.2 Hz, 1H) 4.80 (quind, J=6.6, 4.3 Hz, 1H) 7.29 (d, J=9.5 Hz, 1H) 7.43 (dd, J=5.2, 1.2 Hz, 1H) 7.48 (s, 1H) 7.54-7.61 (m, 2H) 7.80 (s, 1H) 8.49 (d, J=5.2 Hz, 1H).

Example 10

(7S)-5-[4-(2-Fluoroethoxy)-3-(trifluoromethyl)phenyl]-7-methyl-3-(2-methyl-4-pyridyl)-6,7-dihydropyrazolo[1,5-a]pyrazin-4-one (E-10, Co. No. 77)

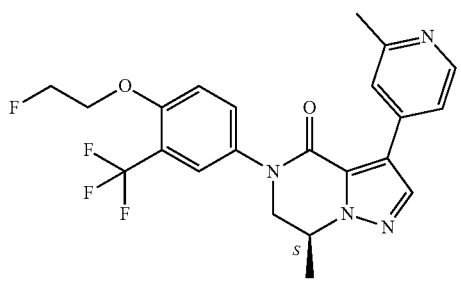

Sodium hydride (60% dispersion in mineral oil, 22 mg, 0.544 mmol) was added to a solution of 2-fluoroethanol (453 μL, 0.495 mmol) in DMF (4.5 mL) at 0° C. and the mixture was stirred at rt for 10 minutes. Then compound 67 (200 mg, 0.495 mmol) was added. The mixture was stirred at 110° C. for 23 h. The reaction mixture was cooled to rt and a solution of 2-fluoroethanol (227 μL, 0.247 mmol) and Sodium hydride (60% dispersion in mineral oil, 12 mg, 0.297 mmol) in DMF (0.5 ml) was added. The resulting mixture was stirred at 110° C. for 16 h. The mixture was quenched with water and extracted with EtOAc. The organic layer was separated, dried (Na₂SO₄) and the solvents were evaporated in vacuo. The crude product was purified by flash column chromatography (silica; 7M solution of ammonia in MeOH in DCM/DCM 0/100 to 2/98). The desired fractions were collected and the solvents evaporated in vacuo to afford 164 mg of compound 77, which was further purified by RP HPLC (Stationary phase: C18 XBridge™ 30×100 mm 5 um), mobile phase: Gradient from 67% 0.1% NH$_4$CO$_3$H/NH$_4$OH pH 9 solution in Water, 33% CH$_3$CN to 50% 0.1% NH$_4$CO$_3$H/NH$_4$OH pH 9 solution in Water, 50% CH$_3$CN), yielding 125 mg of compound 77, which was further purified by RP HPLC (Stationary phase: C18 XBridge™ 30×100 mm 5 um), mobile phase: Gradient from 67% 0.1% NH$_4$CO$_3$H/NH$_4$OH pH 9 solution in Water, 33% CH$_3$CN to 50% 0.1% NH$_4$CO$_3$H/NH$_4$OH pH 9 solution in Water, 50% CH$_3$CN), yielding 117 mg of compound 77 which was further purified by RP HPLC (Stationary phase: C18 XBridge™ 30×100 mm 5 μm), mobile phase: Gradient from 47% 0.1% NH$_4$CO$_3$H/NH$_4$OH pH 9 solution in Water, 53% MeOH to 30% 0.1% NH$_4$CO$_3$H/NH$_4$OH pH 9 solution in Water, 70% MeOH), yielding compound 77 (39 mg, 18%), also recovering 38 mg of starting material, compound 67. For compound 77: $^1$H NMR (400 MHz, CDCl$_3$) δ ppm 1.75 (d, J=6.5 Hz, 3H) 2.57 (s, 3H) 3.96 (dd, J=12.8, 7.3 Hz, 1H) 4.24 (dd, J=12.7, 4.4 Hz, 1H) 4.28-4.38 (m, 2H) 4.70-4.87 (m, 2H) 4.75-4.83 (m, 1H) 7.08 (d, J=8.6 Hz, 1H) 7.44 (dd, J=5.2, 1.3 Hz, 1H) 7.48-7.57 (m, 3H) 7.79 (s, 1H) 8.47 (dd, J=5.3, 0.5 Hz, 1H).

Example 11

(7S)-5-(4-Ethoxyphenyl)-7-methyl-3-(2-methyl-4-pyridyl)-6,7-dihydropyrazolo[1,5-a]pyrazin-4-one hydrochloride salt (E-11, Co. No. 81)

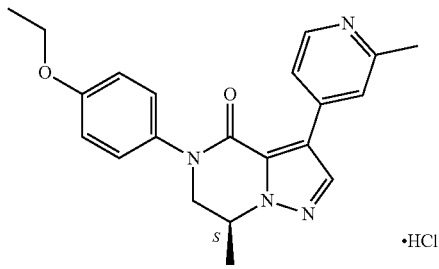

Copper(I) iodide (47 mg, 0.247 mmol) was added to a stirred suspension of intermediate I-18 (0.1 g, 0.413 mmol), 4-iodophenetole (0.164 g, 0.661 mmol), K$_2$CO$_3$ (114 mg, 0.825 mmol) and N,N'-dimethylethylenediamine (26 μL, 0.211 mmol) in toluene (6 mL) in a sealed tube and under nitrogen. The mixture was stirred at 100° C. for 24 h. The mixture was filtered through a pad of diatomaceous earth and washed with DCM. The organic layer was evaporated in vacuo. The crude product was purified by flash column chromatography (silica; EtOAc in DCM 0/100 to 40/60). The desired fractions were collected and concentrated in vacuo to yield compound 81 as an oil. The residue was dissolved in EtOAc and HCl (4N) (103 μL, 0.413 mmol) was added. The residue was triturated from DIPE, filtered and dried in vacuo to yield compound 81 (163 mg, 99%) as a white solid. Free base: $^1$H NMR (300 MHz, CDCl$_3$) δ ppm 1.35 (t, J=6.9 Hz, 3H) 1.65 (d, J=6.5 Hz, 3H) 2.50 (s, 3H) 3.84 (dd, J=12.9, 7.0 Hz, 1H) 3.97 (q, J=7.0 Hz, 2H) 4.16 (dd, J=12.9, 4.3 Hz, 1H) 4.60-4.76 (m, 1H) 6.87 (br. d, J=8.8 Hz, 2H) 7.18 (br. d, J=8.7 Hz, 2H) 7.43 (br. d, J=4.8 Hz, 1H) 7.48 (br. s, 1H) 7.72 (s, 1H) 8.39 (br. d, J=4.3 Hz, 1H); HCl salt: $^1$H NMR (300 MHz, DMSO-d$_6$) δ ppm 1.34 (t, J=6.9 Hz, 3H) 1.60 (d, J=6.3 Hz, 3H) 2.68 (s, 3H) 3.38 (br. s., 1H) 3.90-4.14 (m, 3H) 4.28 (dd, J=13.0, 4.1 Hz, 1H) 4.78-4.94 (m, 1H) 7.00 (br. d, J=8.9 Hz, 2H) 7.35 (br. d, J=8.8 Hz, 2H) 8.23-8.42 (m, 3H) 8.69 (d, J=6.3 Hz, 1H).

Example 12

4-[(7S)-7-Methyl-4-oxo-5-[4-(trifluoromethyl)phenyl]-6,7-dihydropyrazolo[1,5-a]pyrazin-3-yl]pyridine-2-carbonitrile (E-12, Co. No. 127)

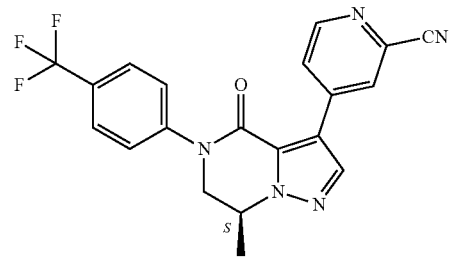

Pd(PPh$_3$)$_4$ (42 mg, 0.036 mmol) was added to a stirred suspension of intermediate I-33a (250 mg, 0.593 mmol) and 4-bromopyridine-2-carbonitrile (162 mg, 0.884 mmol) in 1,4-dioxane (4 mL) and a sat. sol. of Na$_2$CO$_3$ (2 mL). The mixture was stirred at 150° C. for 10 min under microwave irradiation. Then the mixture was diluted with H$_2$O and extracted with DCM. The organic layer was dried (Na$_2$SO$_4$), filtered and the solvent evaporated in vacuo. The crude product was purified by flash column chromatography (silica; EtOAc in DCM 0/100 to 50/50). The desired fractions were collected and evaporated in vacuo. The residue was precipitated with DIPE. The solid was filtered to yield compound 127 as a white solid. $^1$H NMR (500 MHz, CDCl$_3$) δ ppm 1.77 (d, J=6.4 Hz, 3H) 4.05 (dd, J=12.9, 7.4 Hz, 1H) 4.32 (dd, J=12.7, 4.0 Hz, 1H) 4.79-4.88 (m, 1H) 7.51 (br. d, J=8.4 Hz, 2H) 7.74 (br. d, J=8.4 Hz, 2H) 7.86 (s, 1H) 7.92 (dd, J=5.2, 1.7 Hz, 1H) 8.04-8.14 (m, 1H) 8.67 (d, J=5.2 Hz, 1H).

Example 13

(7S)-3-(2-Isopropyl-4-pyridyl)-7-methyl-5-[4-(trifluoromethyl)phenyl]-6,7-dihydropyrazolo[1,5-a]pyrazin-4-one (E-13, Co. No. 126)

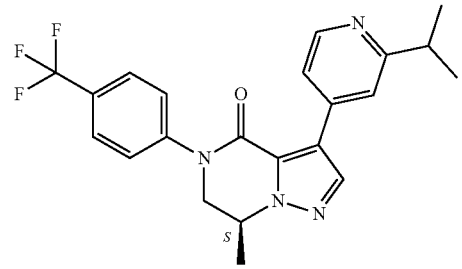

Pd(PPh$_3$)$_4$ (26 mg, 0.022 mmol) was added to a stirred suspension of intermediate I-33b (150 mg, 0.442 mmol) and 4-bromo-2-isopropyl-pyridine (prepared as described in WO2009/118292) (97 mg, 0.486 mmol) in a sat. aq. sol. NaHCO₃ (1 mL) and 1,4-dioxane (1 mL). The mixture was stirred at 120° C. for 10 min under microwave irradiation. The mixture was filtered through diatomaceous earth and washed with DCM. The organic layer was washed with water, separated, dried (Na₂SO₄), filtered and concentrated in vacuo. The crude product was purified by flash column chromatography ((silica; 7N solution of ammonia in MeOH in DCM 0/100 to 10/90) then (silica, EtOAc in DCM 0/100 to 30/70)) then by RP HPLC (Stationary phase: C18 XSelect™ 19×100 mm 5 μm, Mobile phase: Gradient from 80% 0.1% NH₄CO₃H/NH₄OH pH 9 solution in Water, 20% CH₃CN to 0% 0.1% NH₄CO₃H/NH₄OH pH 9 solution in Water, 100% CH₃CN)). The desired fractions were collected and evaporated in vacuo to yield compound 126 as a white solid. ¹H NMR (400 MHz, CDCl₃) δ ppm 1.32 (d, J=6.9 Hz, 6H) 1.75 (d, J=6.7 Hz, 3H) 3.08 (spt, J=6.9 Hz, 1H) 4.02 (dd, J=12.7, 7.2 Hz, 1H) 4.31 (dd, J=12.6, 4.0 Hz, 1H) 4.80 (quind, J=6.7, 4.3 Hz, 1H) 7.45-7.48 (m, 2H) 7.51 (br. d, J=8.3 Hz, 2H) 7.71 (br. d, J=8.6 Hz, 2H) 7.81 (s, 1H) 8.50-8.55 (m, 1H)

Example 14

(7S)-5-(3,4-Dichlorophenyl)-3-[2-(hydroxymethyl)-4-pyridyl]-7-methyl-6,7-dihydropyrazolo[1,5-a]pyrazin-4-one (E-14, Co. No. 125)

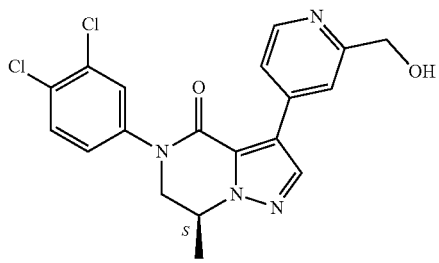

A suspension of intermediate I-34 (1.09 g, 4.56 mmol) in acetic anhydride (8 mL) was stirred at 100° C. for 2 h. The mixture was cooled to rt, and poured into water (15 mL) and EtOAc (30 mL). The organic layer was separated, washed with a sat. NaHCO₃ sol., dried (Na₂SO₄), filtered and concentrated in vacuo. The resultant oil was stirred with lithium hydroxide (259 mg, 10.81 mmol) in MeOH (5.45 mL) and H₂O (2.72 mL) at rt for 30 min. Then, EtOAc was added and the organic layer was washed with water, brine, dried (Na₂SO₄), filtered and concentrated in vacuo. The crude product was purified by flash column chromatography (silica; 7M solution of ammonia in MeOH in DCM 0/100 to 3/97). The desired fractions were collected and evaporated in vacuo to yield compound 125 (670 mg, 61%).

Crude compound 125 (100 mg) was purified by RP HPLC (Stationary phase: C18 XBridge 30×100 mm 5 um), Mobile phase: Gradient from 54% 0.1% NH₄CO₃H/NH₄OH pH 9 solution in Water, 46% CH₃CN to 64% 0.1% NH₄CO₃H/NH₄OH pH 9 solution in Water, 36% CH₃CN), yielding 72 mg compound 125. ¹H NMR (500 MHz, CDCl₃) δ ppm 1.74 (d, J=6.4 Hz, 3H) 3.73 (br. s., 1H) 3.96 (dd, J=12.7, 7.2 Hz, 1H) 4.24 (dd, J=12.7, 4.3 Hz, 1H) 4.72-4.83 (m, 3H) 7.23 (dd, J=8.7, 2.3 Hz, 1H) 7.49 (d, J=2.3 Hz, 1H) 7.51 (d, J=8.7 Hz, 1H) 7.55 (d, J=4.9 Hz, 1H) 7.59 (s, 1H) 7.82 (s, 1H) 8.54 (d, J=4.9 Hz, 1H).

Example 15

(7S)-5-(3,4-Dichlorophenyl)-3-[2-(1-hydroxyethyl)-4-pyridyl]-7-methyl-6,7-dihydropyrazolo[1,5-a]pyrazin-4-one (E-15, Co. No. 111)

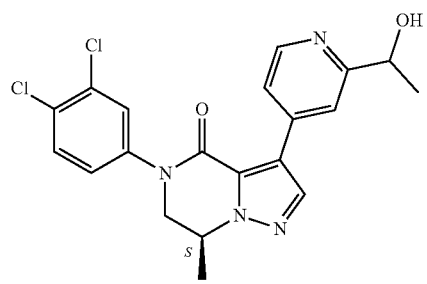

Methylmagnesium chloride 3M in THF (249 μL, 0.747 mmol) was added dropwise to a solution of intermediate I-39 (150 mg, 0.374 mmol) in THF (1.24 mL) at −78° C. and under nitrogen. The mixture was stirred at −78° C. for 2 h. Then, more methylmagnesium chloride 3M in THF (125 μL, 0.374 mmol) was added and the mixture was stirred at −78° C. for 1 h. Then, it was quenched at −78° C. with a sat. NH₄C₁ sol. and allowed to reach rt. The mixture was extracted with EtOAc. The organic layer was separated, dried (MgSO₄), filtered and the solvents evaporated in vacuo. The crude product was purified by flash column chromatography (silica; MeOH in DCM 0/100 to 5/95). The desired fractions were collected and evaporated in vacuo. The residue was precipitated with Ether/Heptane to yield compound 111 as a pale yellow solid. ¹H NMR (400 MHz, CDCl₃) δ ppm 1.52 (dd, J=6.6, 0.8 Hz, 3H) 1.74 (dd, J=6.5, 2.3 Hz, 3H) 3.91-4.02 (m, 1H) 4.13-4.31 (m, 2H) 4.72-4.84 (m, 1H) 4.92 (q, J=6.5 Hz, 1H) 7.23 (dd, J=8.6, 2.5 Hz, 1H) 7.49 (d, J=2.3 Hz, 1H) 7.51 (d, J=8.6 Hz, 1H) 7.56 (br. d, J=5.3 Hz, 1H) 7.59-7.63 (m, 1H) 7.82 (s, 1H) 8.52 (dd, J=5.1, 0.7 Hz, 1H)

Example 16

(7S)-7-Methyl-3-(2-methyl-1-oxido-pyridin-1-ium-4-yl)-5-[4-(trifluoromethyl)phenyl]-6,7-dihydropyrazolo[1,5-a]pyrazin-4-one (E-16, Co. No. 140)

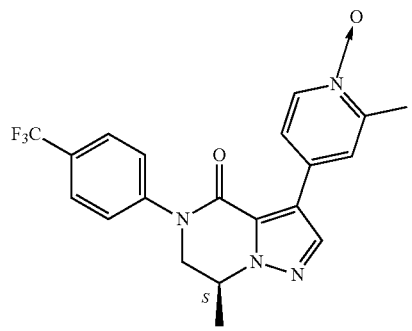

3-Chloroperoxybenzoic acid (2.96 g, 17.18 mmol) was added to a stirred solution of final compound E-1 (3.32 g, 8.59 mmol) in DCM (133 mL) at 0° C. The mixture was allowed to reach rt and stirred at rt for 3 h. The mixture was treated with Na$_2$CO$_3$ sat sol. and diluted with DCM. The organic layer was separated, dried (Na$_2$SO$_4$), filtered and the solvents evaporated in vacuo to yield compound 140 (3.4 g, 98%) as a pale yellow solid.

A small fraction (350 mg) was purified by flash column chromatography (silica; MeOH in DCM 0/100 to 5/95). The desired fractions were collected and evaporated in vacuo. The residue was precipitated with Et$_2$O and filtered to yield pure compound 140 (290 mg, 8%). $^1$H NMR (500 MHz, CDCl$_3$) δ ppm 1.75 (d, J=6.4 Hz, 3H) 2.53 (s, 3H) 4.02 (dd, J=12.7, 7.2 Hz, 1H) 4.30 (dd, J=12.7, 4.0 Hz, 1H) 4.75-4.85 (m, 1H) 7.50 (d, J=8.4 Hz, 2H) 7.63 (dd, J=6.8, 2.5 Hz, 1H) 7.67-7.77 (m, 3H) 7.81 (s, 1H) 8.21 (d, J=6.6 Hz, 1H).

Example 17

(7S)-5-[4-(1-Hydroxyethyl)phenyl]-7-methyl-3-(2-methyl-4-pyridyl)-6,7-dihydropyrazolo[1,5-a]pyrazin-4-one (E-17, Co. No. 149)

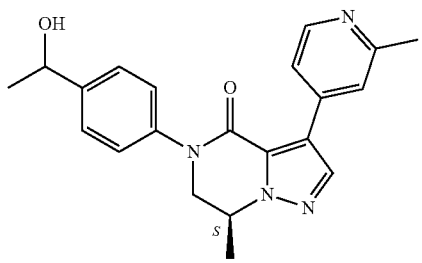

Sodium borohydride (6 mg, 0.166 mmol) was added to a stirred solution of intermediate I-35 (60 mg, 0.166 mmol) in MeOH (5 mL) at 0° C. The mixture was stirred at rt for 16 h. The solvent was concentrated in vacuo. The residue was dissolved with DCM and washed with a sat. Na$_2$CO$_3$ sol. The organic layer was separated, dried (MgSO$_4$), filtered and the solvents evaporated in vacuo. The crude product was purified by flash column chromatography (silica; MeOH in DCM 0/100 to 100/0). The desired fractions were collected and concentrated in vacuo to yield compound 149 (40 mg, 66%). $^1$H NMR (300 MHz, CDCl$_3$) δ ppm 1.52 (d, J=6.5 Hz, 3H) 1.73 (d, J=6.5 Hz, 3H) 2.31 (br. s., 1H) 2.57 (s, 3H) 3.97 (dd, J=12.8, 6.9 Hz, 1H) 4.16-4.39 (m, 1H) 4.60-4.86 (m, 1H) 4.95 (q, J=6.4 Hz, 1H) 7.35 (br. d, J=8.2 Hz, 2H) 7.42-7.59 (m, 4H) 7.81 (s, 1H) 8.37-8.49 (m, 1H).

Example 18

(7S)-5-(4-Cyclopropylphenyl)-7-methyl-3-(2-methyl-4-pyridyl)-6,7-dihydropyrazolo[1,5-a]pyrazin-4-one (E-18, Co. No. 156)

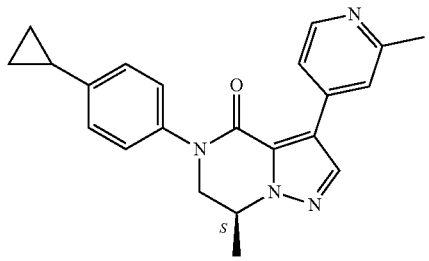

Pd(PPh$_3$)$_4$ (37 mg, 0.032 mmol) was added to a stirred suspension of intermediate I-36 (255 mg, 0.642 mmol), cyclopropylboronic acid (165 mg, 1.92 mmol) and K$_2$CO$_3$ (177 mg, 1.28 mmol) in CH$_3$CN (5 mL) and H$_2$O (2 mL). The mixture was stirred at 150° C. for 10 min under microwave irradiation. Then more cyclopropylboronic acid (165 mg, 1.92 mmol) and Pd(PPh$_3$)$_4$ (37 mg, 0.032 mmol) were added. The mixture was stirred at 150° C. for another 10 min under microwave irradiation. Then the mixture was diluted with H$_2$O and extracted with DCM. The organic layer was dried (MgSO$_4$), filtered and the solvent evaporated in vacuo. The crude product was purified by flash column chromatography (silica; EtOAc in Heptane 0/100 to 75/25) and by RP HPLC (Stationary phase: C18 XBridge™ 30×100 mm 5 um, Mobile phase: Gradient from 67% 0.1% NH$_4$CO$_3$H/NH$_4$OH pH 9 solution in Water, 33% CH$_3$CN to 50% 0.1% NH$_4$CO$_3$H/NH$_4$OH pH 9 solution in Water, 50% CH$_3$CN). The desired fractions were collected and concentrated in vacuo to yield compound 156 (80 mg, 24%) as a solid. $^1$H NMR (400 MHz, CDCl$_3$) δ ppm 0.62-0.77 (m, 2H) 0.91-1.06 (m, 2H) 1.72 (d, J=6.7 Hz, 3H) 1.91 (tt, J=8.5, 5.1 Hz, 1H) 2.56 (s, 3H) 3.93 (dd, J=12.9, 6.9 Hz, 1H) 4.25 (dd, J=12.9, 4.2 Hz, 1H) 4.75 (quind, J=6.6, 4.4 Hz, 1H) 7.09-7.18 (m, 2H) 7.18-7.25 (m, 2H) 7.48 (dd, J=5.1, 1.2 Hz, 1H) 7.53 (s, 1H) 7.79 (s, 1H) 8.45 (d, J=5.1 Hz, 1H)

Example 19

(7S)-7-Methyl-3-(6-piperazin-1-yl-3-pyridyl)-5-[4-(trifluoromethyl)phenyl]-6,7-dihydropyrazolo[1,5-a]pyrazin-4-one (E-19, Co. No. 176)

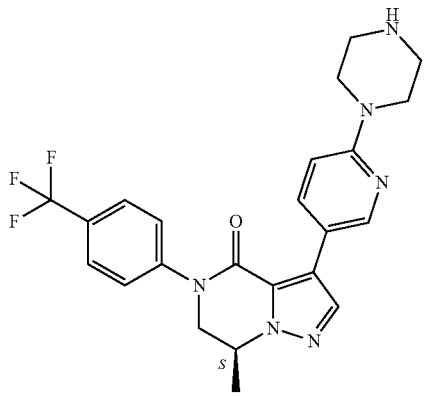

Trifluoroacetic acid (0.911 mL, 11.91 mmol) was added to a stirred solution of intermediate I-42 (663 mg, 1.19 mmol) in DCM (1.9 mL). The mixture was stirred at rt for 1 h. The solvent was concentrated in vacuo. The crude product was purified by flash column chromatography (silica; MeOH in DCM 0/100 to 20/80). The desired fractions were collected and evaporated in vacuo. The residue was precipitated with Et$_2$O and filtrated a solid that was purified by RP HPLC (Stationary phase: C18 XBridge™ 50×100 5 μm, Mobile phase: Gradient from 53% 0.1% NH$_4$CO$_3$H/NH$_4$OH pH 9 solution in Water, 43% CH$_3$CN to 40% 0.1% NH$_4$CO$_3$H/NH$_4$OH pH 9 solution in Water, 60% CH$_3$CN), to yield compound 176 (151 mg, 28%) as a solid. $^1$H NMR (500 MHz, CDCl$_3$) δ ppm 1.73 (d, J=6.6 Hz, 3H) 1.76 (br. s., 1H) 2.92-3.02 (m, 4H) 3.50-3.57 (m, 4H) 4.00 (dd, J=12.4, 7.2 Hz, 1H) 4.27 (dd, J=12.4, 4.0 Hz, 1H) 4.70-4.82 (m, 1H)

6.63 (d, J=8.7 Hz, 1H) 7.50 (br. d, J=8.7 Hz, 2H) 7.68 (br. d, J=8.7 Hz, 2H) 7.71 (s, 1H) 7.96 (dd, J=9.0, 2.3 Hz, 1H) 8.42 (d, J=2.3 Hz, 1H)

Example 20

(7S)-7-Methyl-3-(2-methyl-4-pyridyl)-5-[6-(trifluoromethyl)-3-pyridyl]-6,7-dihydropyrazolo[1,5-a]pyrazin-4-one (E-20 Co. No. 186)

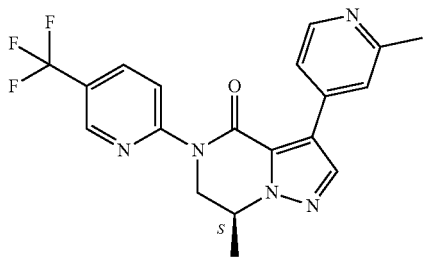

Pd(PPh$_3$)$_4$ (155 mg, 0.134 mmol) was added to a stirred suspension of intermediate I-18 (325 mg, 1.341 mmol), 2-chloro-5-(trifluoromethyl)pyridine (365 mg, 2.012 mmol), 4,5-bis(diphenylphosphino)-9,9-dimethylxanthene (155 mg, 0.268 mmol), Cs$_2$CO$_3$ (874 mg, 2.683 mmol) in 1,4-dioxane (10 mL) in a sealed tube and under nitrogen. The mixture was stirred at 120° C. for 7 h. The mixture was filtered through a pad of diatomaceous earth and washed with DCM. The filtrate was evaporated in vacuo and the crude product was purified by flash column chromatography (silica, EtOAc in DCM 0/100 to 30/70). The desired fractions were collected and concentrated in vacuo. The residue was purified by ion exchange chromatography using an (ISOLUTE® SCX2 cartridge) eluting first with MeOH then with 7M solution of ammonia in MeOH. The desired fractions contained in the 7M solution of ammonia in MeOH were collected and the solvents evaporated in vacuo. The residue was triturated with Et$_2$O to yield compound 186 (415 mg, 80%) as a white solid. $^1$H NMR (500 MHz, CDCl$_3$) δ ppm 1.73 (d, J=6.4 Hz, 3H) 2.60 (s, 3H) 4.35-4.44 (m, 1H) 4.68-4.80 (m, 2H) 7.41 (dd, J=5.2, 1.2 Hz, 1H) 7.45 (s, 1H) 7.78 (s, 1H) 7.94 (dd, J=8.8, 2.2 Hz, 1H) 8.24 (d, J=9.0 Hz, 1H) 8.52 (d, J=5.2 Hz, 1H) 8.69-8.73 (m, 1H).

Example 21

(7S)-7-Methyl-3-(2-methyl-4-pyridyl)-5-[6-methyl-5-(trifluoromethyl)-2-pyridyl]-6,7-dihydropyrazolo[1,5-a]pyrazin-4-one (E-21, Co. No. 192)

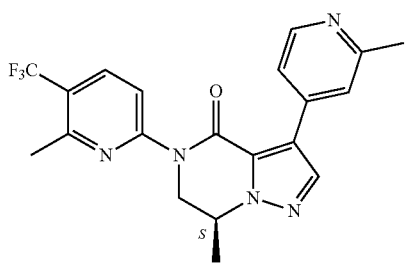

Tetramethyltin (32 μL, 0.231 mmol) was added to a mixture of intermediate I-43 (65 mg, 0.154 mmol), lithium chloride (13 mg, 0.308 mmol) and bis(triphenylphosphine)palladium(II) dichloride (6 mg, 0.007 mmol) in degassed DMF (2.4 mL), in a sealed tube under nitrogen. The mixture was stirred at 110° C. for 5 h. The mixture was diluted with a sat. sol. of NaHCO$_3$ and extracted with EtOAc. The organic layer was separated, dried (Na$_2$SO$_4$), filtered and the solvents evaporated in vacuo. The crude product was purified by flash column chromatography (silica; EtOAc in DCM 0/100 to 30/70). The desired fractions were collected and concentrated in vacuo. Then the product was triturated with Et$_2$O to yield compound 192 (26 mg, 42%) as a white solid. $^1$H NMR (400 MHz, CDCl$_3$) δ ppm 1.73 (d, J=6.5 Hz, 3H) 2.60 (s, 3H) 2.69 (br. d, J=1.6 Hz, 3H) 4.34-4.46 (m, 1H) 4.66-4.80 (m, 2H) 7.41 (dd, J=5.1, 1.2 Hz, 1H) 7.44 (s, 1H) 7.78 (s, 1H) 7.90 (d, J=8.8 Hz, 1H) 8.02 (d, J=8.6 Hz, 1H) 8.52 (d, J=4.9 Hz, 1H).

Example 22a (7S)-5-[6-Ethoxy-5-(trifluoromethyl)-2-pyridyl]-7-methyl-3-(2-methyl-4-pyridyl)-6,7-dihydropyrazolo[1,5-a]pyrazin-4-one (E-22a, Co. No. 189)

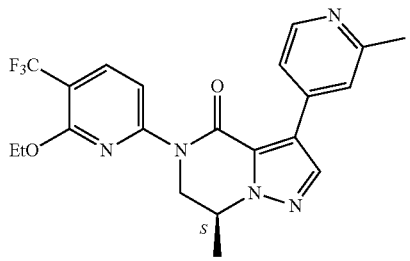

EtOH (114 μL, 1.95 mmol) was added to a stirred suspension of sodium hydride (60% dispersion in mineral oil) (78 mg, 1.95 mmol) in DMF (5 mL) at 0° C. The mixture was stirred at rt for 10 min. Then, a solution of 2-chloro-4-iodo-5-(trifluoromethyl)pyridine (0.5 g, 1.62 mmol) in DMF (5 mL) was added at 0° C. and the mixture was stirred at rt for 18 h. Then, more sodium hydride (60% dispersion in mineral oil) (26 mg, 0.65 mmol) and EtOH (38 μL, 0.65 mmol) were added at 0° C. and the mixture was stirred at rt for 2 h. Intermediate I-18 (157 mg, 0.65 mmol) was then added and the mixture was cooled to 0° C. More sodium hydride (60% dispersion in mineral oil) (52 mg, 1.301 mmol) was added and the mixture was stirred at rt for 1 h and at 80° C. for 16 h. Then more sodium hydride (60% dispersion in mineral oil) (13 mg, 0.325 mmol) was added at rt and the mixture was stirred at 80° C. for 2 h more. The mixture was treated with a 10% NH$_4$C$_1$ sol. and extracted with EtOAc/THF. The organic layer was separated, dried (Na$_2$SO$_4$), filtered and the solvents evaporated in vacuo. The residue was dissolved in DMF (10 mL). TEA (0.226 mL, 1.626 mmol) and HATU (0.247 g, 0.605 mmol) were added. The mixture was stirred at rt for 1 h. The mixture was treated with a sat. NaHCO$_3$ sol./brine at 0° C. and extracted with EtOAc. The organic layer was separated, dried (Na$_2$SO$_4$), filtered and the solvents evaporated in vacuo. The crude product was purified by flash column chromatography (silica; EtOAc in DCM 0/100 to 100/0). The desired fractions were collected and concentrated in vacuo. Then the residue was repurified by RP HPLC (Stationary phase: C18

XBridge™ 30×100 mm 5 um, Mobile phase: Gradient from 54% 0.1% NH$_4$CO$_3$H/NH$_4$OH pH 9 solution in Water, 46% CH$_3$CN to 64% 0.1% NH$_4$CO$_3$H/NH$_4$OH pH 9 solution in Water, 36% CH$_3$CN) to yield compound 189 (27 mg, 4%) as a beige solid. $^1$H NMR (500 MHz, CDCl$_3$) δ ppm 1.46 (t, J=6.9 Hz, 3H) 1.71 (d, J=6.6 Hz, 3H) 2.60 (s, 3H) 4.15-4.27 (m, 2H) 4.39 (dd, J=13.3, 7.2 Hz, 1H) 4.65-4.80 (m, 2H) 7.40 (dd, J=5.2, 1.2 Hz, 1H) 7.43 (s, 1H) 7.77 (s, 1H) 7.82 (s, 1H) 8.47 (s, 1H) 8.52 (d, J=5.2 Hz, 1H).

Example 22b (7S)-5-[4-Chloro-5-(trifluoromethyl)-2-pyridyl]-7-methyl-3-(2-methyl-4-pyridyl)-6,7-dihydropyrazolo[1,5-a]pyrazin-4-one (E-22b, Co. No. 204)

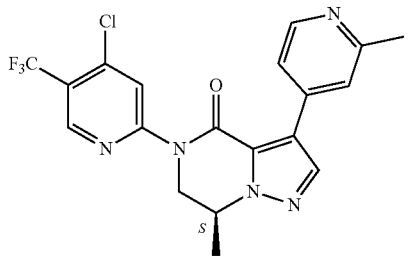

Pd(PPh$_3$)$_4$ (47 mg, 0.041 mmol) and 2,4-dichloro-5-(trifluoromethyl)pyridine (134 mg, 0.619 mmol) were added to a stirred suspension of intermediate I-18 (100 mg, 0.413 mmol), 4,5-bis(diphenylphosphino)-9,9-dimethylxanthene (48 mg, 0.082 mmol) and Cs$_2$CO$_3$ (269 mg, 0.082 mmol) in 1,4-dioxane (2.5 mL) in a sealed tube and under nitrogen. The mixture was stirred at 110° C. for 4 h and at 100° C. for 2 days. The mixture was filtered through a pad of diatomaceous earth and washed with DCM. The filtrate was evaporated in vacuo. The residue was dissolved in DMF (7 mL) and TEA (57 µL, 0.413 mmol) then HATU (157 mg, 0.413 mmol) were added. The mixture was stirred at rt for 2 h. The mixture was treated at 0° C. with a sat. sol. NaHCO$_3$/brine then EtOAc was added. The mixture was filtered through a pad of diatomaceous earth. The organic layer was separated, dried (Na$_2$SO$_4$), filtered and the solvents evaporated in vacuo. The crude product was purified by flash column chromatography (silica; EtOAc in DCM 0/100 to 100/0). The desired fractions were collected and concentrated in vacuo. The residue was repurified by RP HPLC (Stationary phase: C18 XBridge™ 30×100 mm 5 um, Mobile phase: Gradient from 54% 0.1% NH$_4$CO$_3$H/NH$_4$OH pH 9 solution in Water, 46% CH$_3$CN to 64% 0.1% NH$_4$CO$_3$H/NH$_4$OH pH 9 solution in Water, 36% CH$_3$CN) to yield compound 204 (27 mg, 15%) as a white solid. $^1$H NMR (500 MHz, CDCl$_3$) δ ppm 1.72 (d, J=6.4 Hz, 3H) 2.61 (s, 3H) 4.36-4.45 (m, 1H) 4.68-4.79 (m, 2H) 7.39 (dd, J=5.2, 1.7 Hz, 1H) 7.43 (s, 1H) 7.78 (s, 1H) 8.42 (s, 1H) 8.54 (d, J=5.2 Hz, 1H) 8.68 (s, 1H).

Example 23

(7S)-3-(2-Iodo-4-pyridyl)-7-methyl-5-[4-(trifluoromethyl)phenyl]-6,7-dihydropyrazolo[1,5-a]pyrazin-4-one (E-23, Co. No. 225)

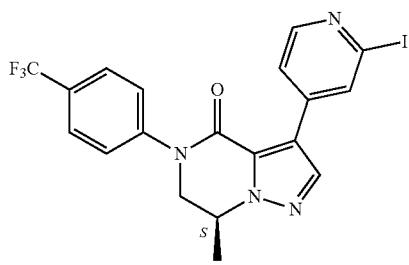

Acetyl chloride (84 µL, 1.18 mmol) was added to a stirred suspension of intermediate I-26 (320 mg, 0.786 mmol) and NaI (1.18 g, 7.866 mmol) in CH$_3$CN (12.8 mL) at rt. The mixture was stirred at 120° C. for 30 min under MW irradiation. Then the mixture was diluted with EtOAc and washed with a sat. sol. of Na$_2$S$_2$O$_3$ and brine. The organic layer was separated, dried (Na$_2$SO$_4$), filtered and the solvents evaporated in vacuo. The crude product was purified by flash column chromatography (silica; EtOAc in Heptane 0/100 to 60/40). The desired fractions were collected and evaporated in vacuo to yield compound 225 (289 mg, 74%). $^1$H NMR (400 MHz, CDCl$_3$) δ ppm 1.75 (d, J=6.5 Hz, 3H) 4.02 (dd, J=12.8, 7.3 Hz, 1H) 4.30 (dd, J=12.7, 4.2 Hz, 1H) 4.80 (quind, J=6.7, 4.2 Hz, 1H) 7.50 (br. d, J=8.3 Hz, 2H) 7.67 (dd, J=5.1, 1.6 Hz, 1H) 7.72 (br. d, J=8.3 Hz, 2H) 7.80 (s, 1H) 8.03-8.05 (m, 1H) 8.32 (dd, J=5.2, 0.6 Hz, 1H)

Example 24

(7S)-7-Methyl-3-(2-piperazin-1-yl-4-pyridyl)-5-[4-(trifluoromethyl)phenyl]-6,7-dihydropyrazolo[1,5-a]pyrazin-4-one hydrochloride salt (E-24, Co. No. 175)

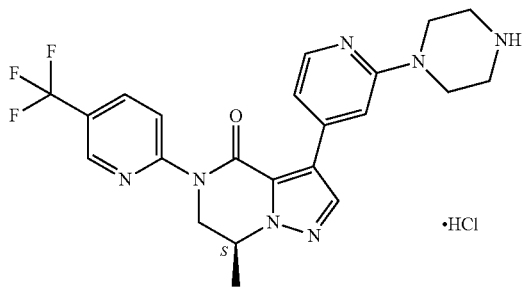

Compound 175 was obtained starting from intermediate I-33a (200 mg, 0.474 mmol), 1-(4-bromo-2-pyridyl)piperazine (CAS: 1201643-59-5, 157 mg, 0.649 mmol, 1.06 mmol), Pd(PPh$_3$)$_4$ (34 mg, 0.029 mmol) in 1,4-dioxane (4 mL) and a sat. sol. of Na$_2$CO$_3$ (2 mL), following a procedure similar to that described in E-12, then treatment with a solution of HCl 5N in iPrOH, yielded compound 175 (224 mg, 84%) as a pale yellow solid. $^1$H NMR (400 MHz, DMSO-d$_6$) δ ppm 1.59 (d, J=6.5 Hz, 3H) 3.22 (br. s., 4H) 3.83 (br. s., 4H) 4.10 (dd, J=12.9, 7.4 Hz, 1H) 4.39 (dd, J=12.9, 4.2 Hz, 1H) 4.81-4.92 (m, 1H) 7.29 (br. d, J=4.4 Hz, 1H) 7.56 (br. s., 1H) 7.69 (br. d, J=8.6 Hz, 2H) 7.84 (br. d, J=8.6 Hz, 2H) 8.11 (d, J=5.8 Hz, 1H) 8.19 (br. s, 1H) 9.20 (br. s., 2H).

Example 25

(7S)-3-[2-(4-Acetylpiperazin-1-yl)-4-pyridyl]-7-methyl-5-[4-(trifluoromethyl)phenyl]-6,7-dihydropyrazolo[1,5-a]pyrazin-4-one (E-25, Co. No. 106)

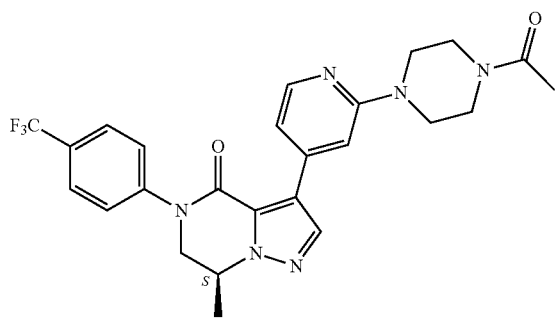

Acetyl chloride (4 μL, 0.060 mmol) was added to a solution of compound 175 (25 mg, 0.054 mmol) and TEA (16 μL, 0.115 mmol) in DCM (1 mL) under nitrogen. The mixture was stirred at rt for 5 h. Then the mixture was diluted with HCl 0.1N and extracted with DCM. The organic layer was separated, dried (MgSO₄), filtered and the solvent evaporated in vacuo. The crude product was purified by flash column chromatography (silica; MeOH in DCM 0/100 to 05/95). The desired fractions were collected and concentrated in vacuo to yield compound 106 (17 mg, 62%) as a solid. ¹H NMR (400 MHz, CDCl₃) δ ppm 1.75 (d, J=6.5 Hz, 3H) 2.13 (s, 3H) 3.49-3.55 (m, 2H) 3.55-3.61 (m, 2H) 3.61-3.67 (m, 2H) 3.70-3.77 (m, 2H) 4.01 (dd, J=12.7, 6.9 Hz, 1H) 4.30 (dd, J=12.7, 4.2 Hz, 1H) 4.79 (quind, J=6.6, 4.4 Hz, 1H) 6.94 (dd, J=5.2, 1.3 Hz, 1H) 7.17 (br. s, 1H) 7.46-7.55 (m, 2H) 7.66-7.76 (m, 2H) 7.80 (s, 1H) 8.19 (dd, J=5.2, 0.6 Hz, 1H).

Example 26

7-(Difluoromethyl)-3-(2-methyl-4-pyridyl)-5-[4-(trifluoromethyl)phenyl]-6,7-dihydropyrazolo[1,5-a]pyrazin-4-one (E-26, Co. No. 181)

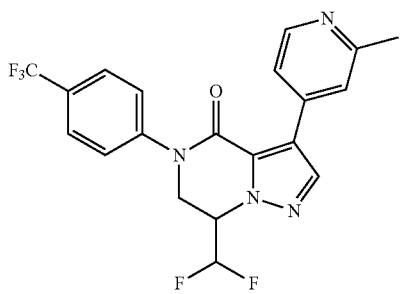 [SMILES: Cc1cc(-c2cnn3c2C(=O)N(c2ccc(C(F)(F)F)cc2)CC3C(F)F)ccn1]

Compound 181 was obtained starting from intermediate I-46 (71 mg, 0.169 mmol) using Pd/C 10% (36 mg, 0.033 mmol) in EtOH (3 mL) under H₂ atmosphere pressure, following a procedure similar to that described in E-6, yielding compound 181 (13 mg, 19%) as a white solid. ¹H NMR (400 MHz, CDCl₃) δ ppm 2.58 (s, 3H) 4.36 (dd, J=13.6, 3.2 Hz, 1H) 4.61 (ddd, J=13.6, 5.0, 1.3 Hz, 1H) 4.88-4.99 (m, 1H) 6.21-6.55 (m, 1H) 7.45 (dd, J=5.2, 1.3 Hz, 1H) 7.47-7.54 (m, 3H) 7.73 (br. d, J=8.3 Hz, 2H) 7.89 (s, 1H) 8.50 (d, J=5.1 Hz, 1H).

Example 27

(7S)-7-Methyl-3-[2-(methylamino)-4-pyridyl]-5-[4-(trifluoromethyl)phenyl]-6,7-dihydropyrazolo[1,5-a]pyrazin-4-one (E-27, Co. No. 147)

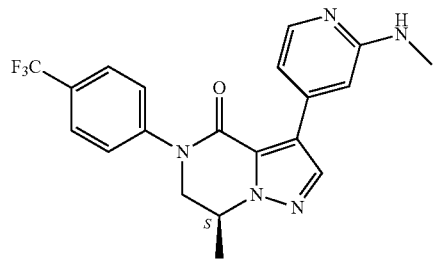

Compound 147 was obtained starting from intermediate I-33a (1.5 g, 3.561 mmol), 4-bromo-N-methyl-pyridin-2-amine (799 mg, 4.273 mmol, 1.06 mmol), Pd(PPh₃)₄ (206 mg, 0.178 mmol) in 1,4-dioxane (8.1 mL) and a sat. sol. of Na₂CO₃ (8.2 mL), following a procedure similar to that described in E-12, yielding compound 147 (1.14 g, 80%) as a white solid. ¹H NMR (500 MHz, CDCl₃) δ ppm 1.74 (d, J=6.4 Hz, 3H) 2.93 (d, J=5.2 Hz, 3H) 4.00 (dd, J=12.6, 7.1 Hz, 1H) 4.29 (dd, J=12.7, 4.0 Hz, 1H) 4.54 (br. d, J=3.2 Hz, 1H) 4.73-4.82 (m, 1H) 6.84 (s, 1H) 6.86 (d, J=5.2 Hz, 1H) 7.50 (br. d, J=8.4 Hz, 2H) 7.70 (br. d, J=8.4 Hz, 2H) 7.79 (s, 1H) 8.09 (d, J=5.2 Hz, 1H).

Example 28

(7S)-5-[4-Iodo-5-(trifluoromethyl)-2-pyridyl]-7-methyl-3-(2-methyl-4-pyridyl)-6,7-dihydropyrazolo[1,5-a]pyrazin-4-one (E-28, Co. No. 212)

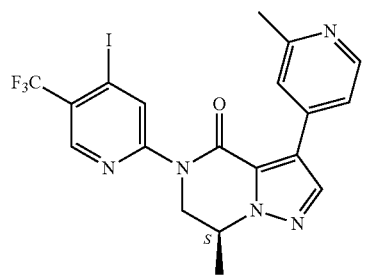

Intermediate I-18 (320 mg, 1.32 mmol) was added portionwise to a stirred suspension of sodium hydride (60% dispersion in mineral oil, 78 mg, 1.98 mmol) in DMF (5 mL) at rt. The mixture was stirred at rt for 15 min and a solution of 2-chloro-4-iodo-5-(trifluoromethyl)pyridine (446 mg, 1.453 mmol) in DMF (5 mL) was added at rt. The mixture was stirred at 80° C. for 16 h. Then more sodium hydride (60% dispersion in mineral oil, 27 mg, 0.66 mmol) was added at rt and the mixture was stirred at 80° C. for 1 h. The mixture was treated with 10% $NH_4Cl$ sol./brine and extracted with EtOAc. The organic layer was separated, washed with brine, dried ($Na_2SO_4$), filtered and the solvents evaporated in vacuo. The crude product was purified by flash column chromatography (silica; EtOAc in DCM 0/100 to 100/0). The desired fractions were collected and the solvents concentrated in vacuo to yield compound 212 (220 mg, 32%) as a white foam.

Example 29

(7S)-5-(3,4-Dichloro-2-iodo-phenyl)-7-methyl-3-(2-methyl-4-pyridyl)-6,7-dihydropyrazolo[1,5-a]pyrazin-4-one (Co. No. 220) and (7S)-5-(3,4-dichloro-6-iodo-1-methyl-cyclohexa-1,3,5-trien-1-yl)-7-methyl-3-(2-methyl-4-pyridyl)-6,7-dihydropyrazolo[1,5-a]pyrazin-4-one (Co. No. 221) (E-29, Co. No. 220 and Co. No. 221)

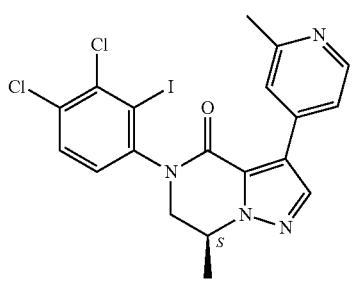

220

-continued

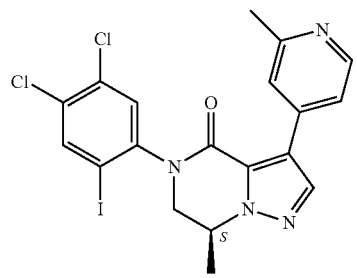

221

HATU (89 mg, 0.235 mmol) was added to a stirred solution of mixture intermediate compounds I-63a and I-63b (250 mg, 0.235 mmol) and TEA (65 µL, 0.471 mmol) in DMF (3 mL). The mixture was stirred at rt for 2 h. The mixture was treated with a sat. sol. of $NH_4Cl$ and a sat. sol. of $NaHCO_3$ and extracted with EtOAc. The organic layer was separated, dried ($MgSO_4$), filtered and the solvents evaporated in vacuo. The crude product was purified by flash column chromatography (silica; EtOAc in Heptane 0/100 to 90/10). The desired fractions were collected and the solvents concentrated in vacuo to give two fractions that were triturated with DCM/Heptane to yield compound 220 (55 mg, 45%) and compound 221 (20 mg, 16%) as solids. Compound 220: $^1$H NMR (500 MHz, $CDCl_3$) δ ppm 1.78 (d, J=6.4 Hz, 2H) 1.85 (d, J=6.6 Hz, 1H) 2.58 (s, 3H) 3.82 (dd, J=12.7, 9.2 Hz, 0.65H) 3.97 (dd, J=12.7, 7.2 Hz, 0.35H) 4.00-4.07 (m, 1H) 4.76-4.84 (m, 0.35H) 4.92-5.00 (m, 0.65H) 7.39 (s, 0.35H) 7.40 (s, 0.65H) 7.48 (br. d, J=5.2 Hz, 1H) 7.52-7.56 (m, 1H) 7.82 (s, 1H) 8.03 (s, 0.35H) 8.03 (s, 0.65H) 8.48 (d, J=5.2 Hz, 1H); compound 221: $^1$H NMR (500 MHz, $CDCl_3$) δ ppm 1.78 (d, J=6.6 Hz, 2H) 1.85 (d, J=6.6 Hz, 1H) 2.57 (s, 3H) 3.81 (dd, J=12.7, 9.0 Hz, 0.65H) 3.98 (dd, J=12.7, 4.6 Hz, 0.35H) 4.02-4.11 (m, 1H) 4.76-4.84 (m, 0.35H) 4.95-5.04 (m, 0.65H) 7.16 (d, J=8.7 Hz, 0.35H) 7.17 (d, J=8.7 Hz, 0.65H) 7.49 (br. d, J=5.2 Hz, 1H) 7.52-7.61 (m, 2H) 7.83 (s, 0.65H) 7.83 (s, 0.35H) 8.47 (d, J=5.2 Hz, 1H).

The following final compounds were synthesized by following an analogous synthetic procedure as reported for compound 1 (E-1) followed by the procedure for intermediates I-18 and I-19 when needed.

| Structure | Compound number | Starting material |
|---|---|---|
| ![structure] | Co. No. 70 | I-59 |

-continued
| Structure | Compound number | Starting material |
|---|---|---|
| 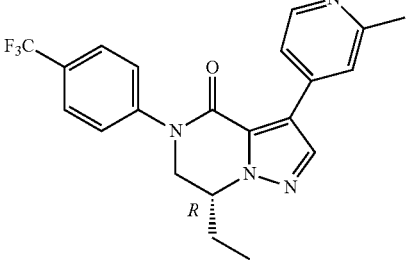 | Co. No. 129 | Co. No. 70 |
| 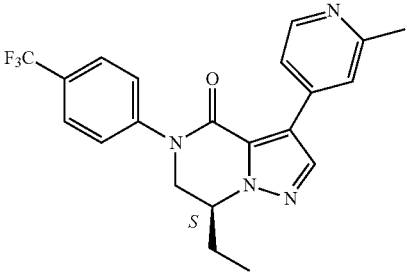 | Co. No. 130 | |
| 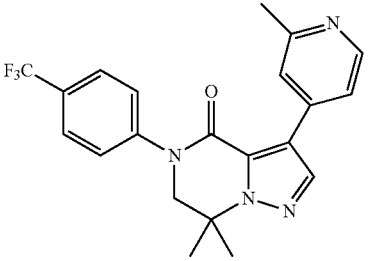 [SMILES: Cc1cc(-c2cnn3c2C(=O)N(c2ccc(C(F)(F)F)cc2)CC3(C)C)ccn1] | Co. No. 171 | I-60 |
| 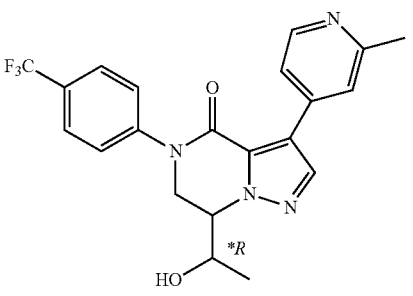 | Co. No. 216 | I-61 |
| 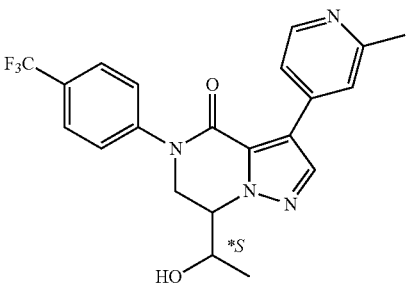 | Co. No. 217 | |

| Structure | Compound number | Starting material |
|---|---|---|
| 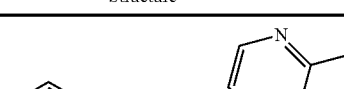 | Co. No. 120 | I-58 |
| 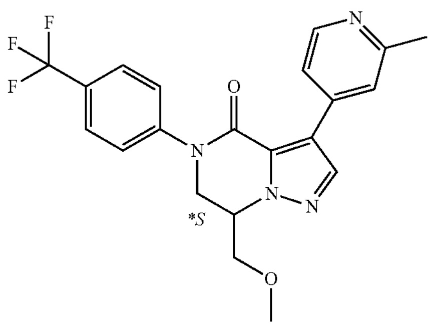 | Co. No. 121 | |

The following compound was synthesized by following the sequence of an analogous synthetic procedure as reported for intermediate I-22 starting from intermediate I-14 and 1-bromo-3,4-dichlorobenzene, followed by the procedure for intermediates I-23 then following an analogous synthetic procedure as reported for compound 2 (E-2) using 2-methyl-4-(4,4,5,5-tetramethyl-1,3,2-dioxaborolan-2-yl)pyridine.

| Structure | Intermediate number | Starting material |
|---|---|---|
| 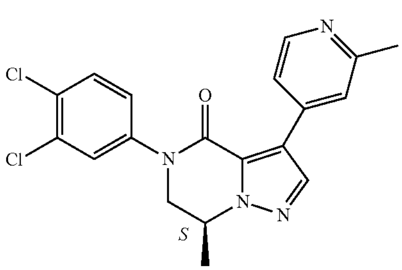 | Co. No. 6a | I-14 |

Example 30

3-(2-Methyl-4-pyridyl)-7-(trifluoromethyl)-5-[4-(trifluoromethyl)phenyl]-6,7-dihydropyrazolo[1,5-a]pyrazin-4-one (Co. No. 238)

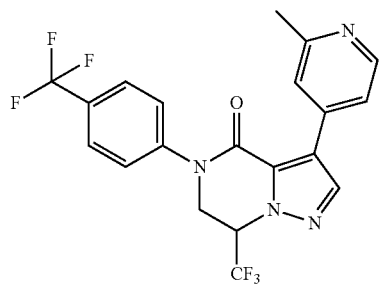 [SMILES: Cc1cc(-c2cnn3c2C(=O)N(c2ccc(C(F)(F)F)cc2)CC3C(F)(F)F)ccn1]

Compound 238 (E-30) was obtained starting from intermediate I-68 (20 mg, 0.042 mmol), 2-picoline-4-boronic acid (8 mg, 0.059 mmol), Pd(PPh$_3$)$_4$ (2 mg, 0.002 mmol) in 1,4-dioxane (0.4 mL) and a sat. sol. of NaHCO$_3$ (0.4 mL) following a procedure similar to that described in E-12 and purified by RP HPLC ((Stationary phase: C18 XBridge 30×100 5 um), (Mobile phase: Gradient from 60% 0.1% NH$_4$CO$_3$H/NH$_4$OH pH 9 solution in Water, 40% CH$_3$CN to 43% 0.1% NH$_4$CO$_3$H/NH$_4$OH pH 9 solution in Water, 57% CH$_3$CN)), yielding compound 238 (14 mg, 75%). $^1$H NMR (500 MHz, CDCl$_3$) δ ppm 2.53 (s, 3H) 4.23 (dd, J=14.0, 1.3 Hz, 1H) 4.67-4.74 (m, 1H) 5.07-5.14 (m, 1H) 7.38-7.43 (m, 3H) 7.47 (s, 1H) 7.67 (br. d, J=8.4 Hz, 2H) 7.87 (s, 1H) 8.44 (d, J=5.2 Hz, 1H).

Tables 1a (compounds I-87) and 1b (with an alternative representation for compounds I-87) below list additional compounds of Formula (I).

Tables 1a and 1b.

The following compounds were prepared following the methods exemplified in the Experimental Part (Ex. No.). Compounds exemplified and described in the experimental part are marked with an asterisk *. The work-up for compounds synthesized by an analogous procedure to E1 can be performed either by filtration through a pad of diatomaceous earth or by extraction with an organic solvent, washing with aqueous ammonia. The coupling agent used in the synthesis of compounds synthesized by an analogous procedure to E2 was either a boronic acid or a boronic ester. For some compounds the stereochemical configuration has been designated as *R or *S when the absolute stereochemistry is undetermined although the compound itself has been isolated as a single stereoisomer and is enantiomerically pure.

TABLE 1a

| Co. No. | Ex. No. | R$^1$ | R$^2$ | R$^4$ | R$^3$ | Salt form |
|---|---|---|---|---|---|---|
| 1 | E1* | 4-CF$_3$-phenyl | 2-methyl-4-pyridyl | —Me (S) | —H | |
| 1a | | | | | | .HCl |
| 1b | | | | | | .H$_2$SO$_4$ |
| 1c | | | | | | .CH$_3$SO$_3$H |
| 1d | | | | | | .HO$_2$CCH=CHCO$_2$H-cis |
| 2 | E2* | 4-CF$_3$-phenyl | 4-pyridyl | —Me (S) | —H | |
| 3 | E1 | 2-Cl-4-CF$_3$-phenyl | 2-methyl-4-pyridyl | —Me (S) | —H | |
| 4 | E1 | 4-SF$_5$-phenyl | 2-methyl-4-pyridyl | —Me (S) | —H | |

TABLE 1a-continued
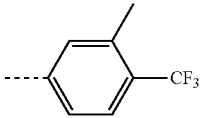
| Co. No. | Ex. No. | R¹ | R² | R⁴ | R³ | Salt form |
|---|---|---|---|---|---|---|
| 5 | E1 | 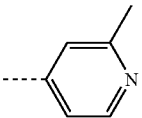 | 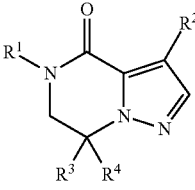 | —Me (S) | —H | .HCl |
| 6 | E1 | 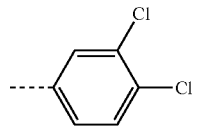 | 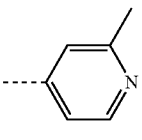 | —Me (S) | —H | .HCl |
| 6a | E1 | 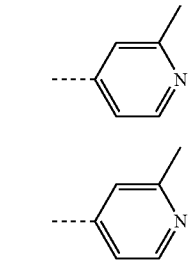 | 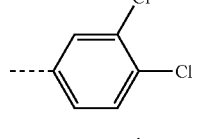 | —Me (S) | —H | |
| 7 | E1 | 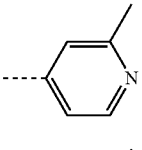 | 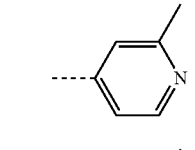 | —Me (S) | —H | |
| 8 | E1 | 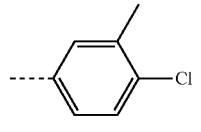 | 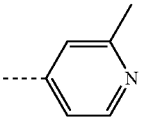 | —Me (S) | —H | |
| 9 | E1 | 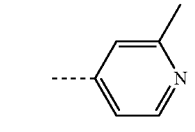 | 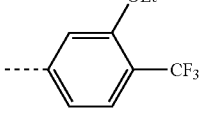 | —Me (S) | —H | |
| 10 | E1 | 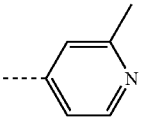 | 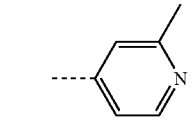 | —Me (S) | —H | |
| 11 | E1 | 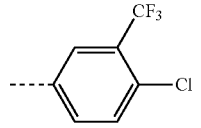 | 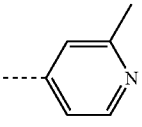 | —Me | —H | |
| 12 | E1 | 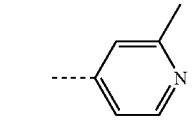 | 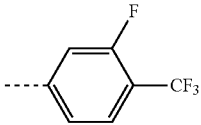 | —Me (S) | —H | .HCl |
| 13 | E1 | 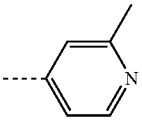 | 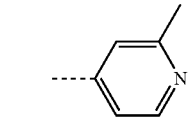 | —Me (S) | —H | |

TABLE 1a-continued
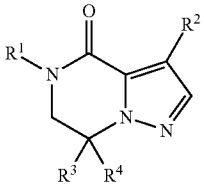
| Co. No. | Ex. No. | R¹ | R² | R⁴ | R³ | Salt form |
|---|---|---|---|---|---|---|
| 14 | E2 | 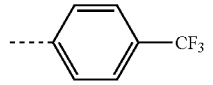 | 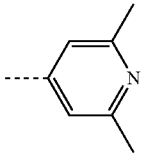 | —Me (S) | —H | |
| 15 | E1 | 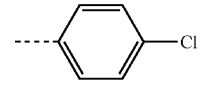 | 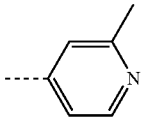 | —Me (S) | —H | .HCl |
| 16 | E1 | 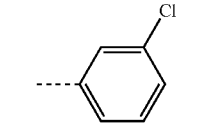 | 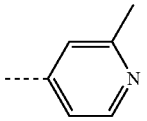 | —Me (S) | —H | |
| 17 | E1 | 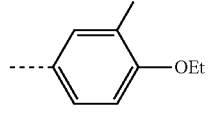 | 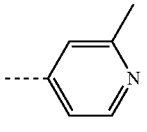 | —Me (S) | —H | .HCl |
| 18 | E1 | 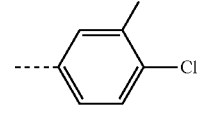 | 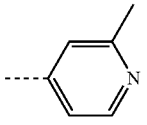 | —Me (S) | —H | |
| 19 | E1 | 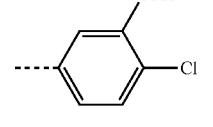 | 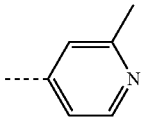 | —Me (S) | —H | |
| 20 | E1 | 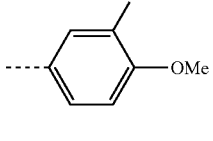 | 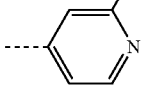 | —Me (S) | —H | .HCl |
| 21 | E1 | 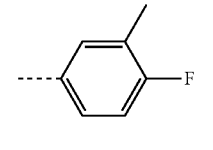 | 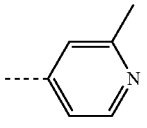 | —Me (S) | —H | |
| 22 | E2 | 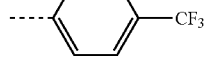 | 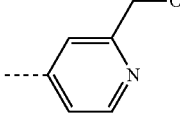 | —Me (S) | —H | .HCl |

TABLE 1a-continued

| Co. No. | Ex. No. | R¹ | R² | R⁴ | R³ | Salt form |
|---|---|---|---|---|---|---|
| 23 | E1 | 3-(CF₃)phenyl | pyridin-4-yl (2-position to N) | —Me (S) | —H | |
| 24 | E2 | 4-(CF₃)phenyl | pyridin-3-yl | —Me (S) | —H | |
| 25 | E1 | 3,4-difluorophenyl | pyridin-4-yl | —Me (S) | —H | .HCl |
| 26 | E1 | 4-(CF₃)phenyl | pyridin-4-yl | —Me (R) | —H | |
| 27 | E1 | 4-(OCHF₂)phenyl | pyridin-4-yl | —Me (S) | —H | |
| 28 | E1 | 4-fluorophenyl | pyridin-4-yl | —Me (S) | —H | .HCl |
| 29 | E2 | 4-(CF₃)phenyl | 2,3-dimethylpyridin-5-yl | —Me (S) | —H | |
| 30 | E1 | 3-fluoro-4-chlorophenyl | pyridin-4-yl | —Me (S) | —H | |
| 31 | E1 | 3-OEt-2-(CF₃)phenyl | pyridin-4-yl | —Me (R) | —H | |
| 32 | E2 | 4-(CF₃)phenyl | pyridin-3-yl | —Me (S) | —H | |

TABLE 1a-continued
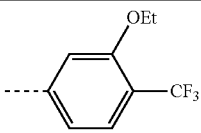
| Co. No. | Ex. No. | R¹ | R² | R⁴ | R³ | Salt form |
|---|---|---|---|---|---|---|
| 33 | E1 | 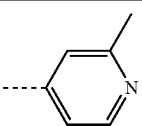 | 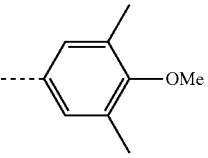 | —H | —H | |
| 34 | E1 | 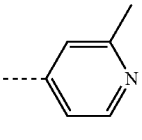 | 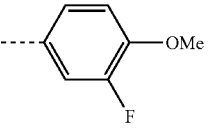 | —Me (S) | —H | |
| 35 | E1 | 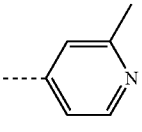 | 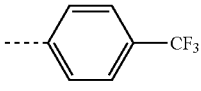 | —Me (S) | —H | .HCl |
| 36 | E2 | 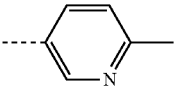 | 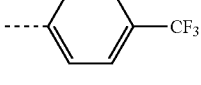 | —Me (S) | —H | |
| 37 | E2 | 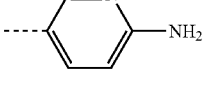 | 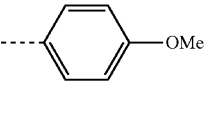 | —Me (S) | —H | |
| 38 | E1 | 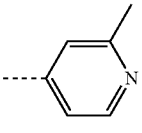 | 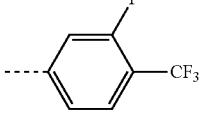 | —Me (S) | —H | .HCl |
| 39 | E1 | 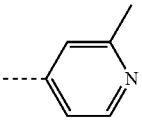 | 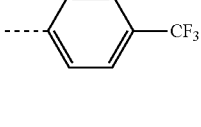 | —H | —H | |
| 40 | E1 | 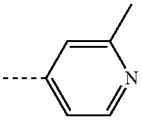 | 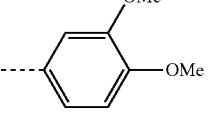 | —H | —H | |
| 41 | E1 | 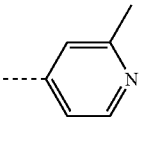 | 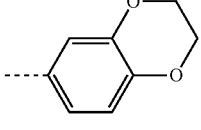 | —Me (S) | —H | |
| 42 | E1 | 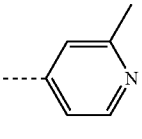 | | —Me (S) | —H | |

TABLE 1a-continued

| Co. No. | Ex. No. | R¹ | R² | R⁴ | R³ | Salt form |
|---|---|---|---|---|---|---|
| 43 | E1 | 3-Cl, 4-CF₃-phenyl | 2,6-dimethylpyridin-4-yl | —Me (S) | —H | |
| 44 | E4* | 4-CF₃-phenyl | 2-(ethylamino)pyridin-4-yl | —Me (S) | —H | |
| 45 | E5* | 4-CF₃-phenyl | 2-methoxypyridin-4-yl | —Me (S) | —H | |
| 46 | E6* | 4-CF₃-phenyl | 2-ethylpyridin-4-yl | —Me (S) | —H | |
| 47 | E1 | 3,4-dichlorophenyl | 2,6-dimethylpyridin-4-yl | —Me (S) | —H | |
| 48 | E1 | 3-(2-fluoroethoxy), 4-CF₃-phenyl | 2-methylpyridin-4-yl | —Me (S) | —H | |
| 49 | E1 | 3-ethoxy, 4-CF₃-phenyl | 2,6-dimethylpyridin-4-yl | —Me (S) | —H | |
| 50 | E1 | 3-Cl, 4-CF₃-phenyl | pyridin-4-yl | —Me (S) | —H | |
| 51 | E1 | 3-methoxy, 4-CF₃-phenyl | 2,6-dimethylpyridin-4-yl | —Me (S) | —H | |

TABLE 1a-continued

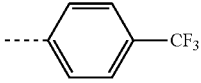

| Co. No. | Ex. No. | R¹ | R² | R⁴ | R³ | Salt form |
|---|---|---|---|---|---|---|
| 52 | E8* | 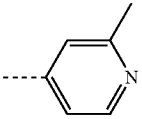 4-CF₃-phenyl | 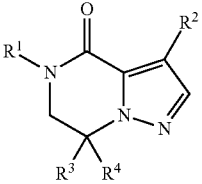 2-methylpyridin-4-yl | —CH₂F | —H | |
| 53 | E1 | 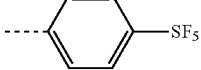 4-SF₅-phenyl | 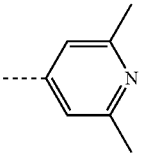 2,6-dimethylpyridin-4-yl | —Me (S) | —H | |
| 54 | E1 | 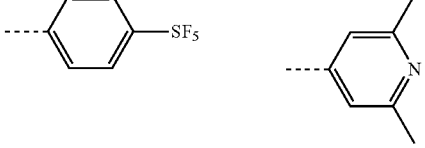 3-CF₃-4-Cl-phenyl | 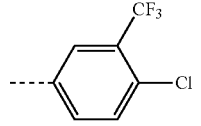 2,6-dimethylpyridin-4-yl | —Me (S) | —H | |
| 55 | E1 | 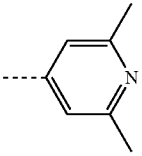 3-OEt-4-CF₃-phenyl | 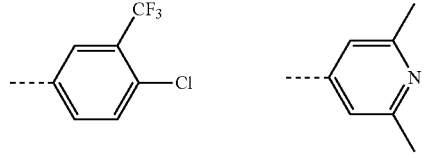 pyridin-4-yl | —Me (S) | —H | |
| 56 | E1 | 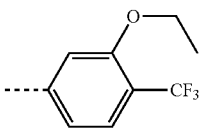 4-SF₅-phenyl | 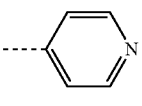 pyridin-4-yl | —Me (S) | —H | |
| 57 | E1 | 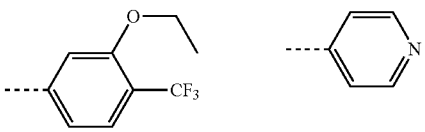 3,4-dichlorophenyl | 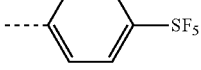 pyridin-4-yl | —Me (S) | —H | |
| 58 | E1 | 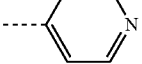 3-OCF₃-phenyl | 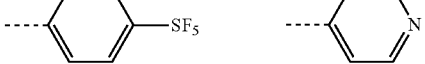 2-methylpyridin-4-yl | —Me (S) | —H | .HCl |
| 59 | E1 | 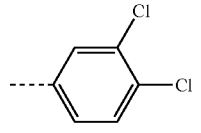 3-CN-4-CF₃-phenyl | 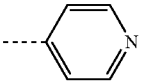 2,6-dimethylpyridin-4-yl | —Me (S) | —H | |
| 60 | E1 |  3-F-4-CF₃-phenyl | 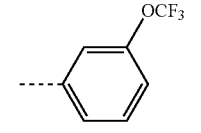 pyridin-4-yl | —Me (S) | —H | |

TABLE 1a-continued
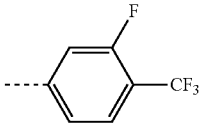
| Co. No. | Ex. No. | R¹ | R² | R⁴ | R³ | Salt form |
|---|---|---|---|---|---|---|
| 61 | E1 | 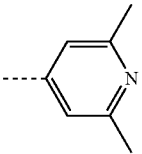 | 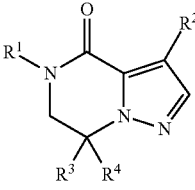 | —Me (S) | —H | |
| 62 | E1 | 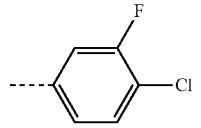 | 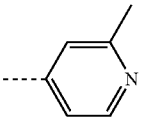 | —Me (S) | —H | |
| 63 | E1 | 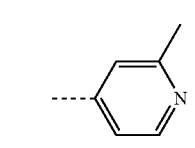 | 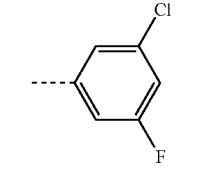 | —Me (S) | —H | .HCl |
| 64 | E1 | 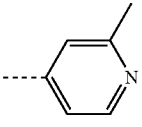 | 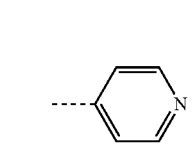 | —Me (S) | —H | |
| 65 | E1 | 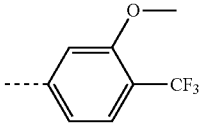 | 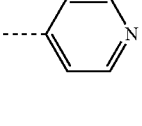 | —Me (S) | —H | .HCl |
| 66 | E1 | 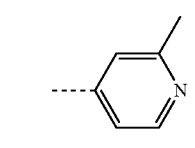 | 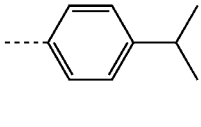 | —Me (S) | —H | .HCl |
| 67 | E9* | 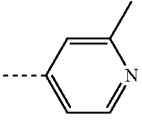 | 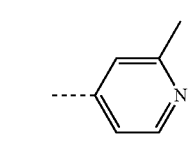 | —Me (S) | —H | |
| 68 | E1 | 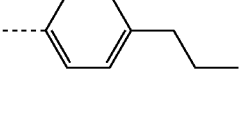 | 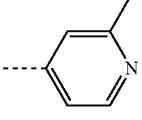 | —Me (S) | —H | |
| 69 | E1 | 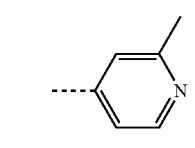 | 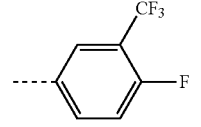 | —Me (S) | —H | .HCl |

TABLE 1a-continued

| Co. No. | Ex. No. | R¹ | R² | R⁴ | R³ | Salt form |
|---|---|---|---|---|---|---|
| 70 | E1 | 4-(CF₃)phenyl | 2-methylpyridin-4-yl | —CH₂CH₂ | —H | |
| 71 | E3* | 4-(CF₃)phenyl | 2-aminopyridin-4-yl | —Me (S) | —H | |
| 72 | E1 | 4-Cl-phenyl | 2,6-dimethylpyridin-4-yl | —Me (S) | —H | |
| 73 | E1 | 4-Cl-phenyl | pyridin-4-yl | —Me (S) | —H | |
| 74 | E1 | 3-ethoxy-2-(CF₃)phenyl | 2-methylpyridin-4-yl | —CH₂OH | —H | |
| 75 | E1 | 3-fluoro-4-cyanophenyl | 2-methylpyridin-4-yl | —Me (S) | —H | |
| 76 | E1 | 3-fluoro-4-methylphenyl | 2-methylpyridazin-4-yl | —Me (S) | —H | |
| 77 | E10* | 3-(CF₃)-4-(2-fluoroethoxy)phenyl | 2-methylpyridin-4-yl | —Me (S) | —H | |
| 78 | E1 | 4-methylphenyl | 2-methylpyridin-4-yl | —Me (S) | —H | |

TABLE 1a-continued
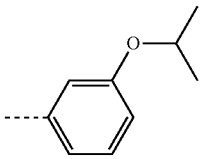
| Co. No. | Ex. No. | R¹ | R² | R⁴ | R³ | Salt form |
|---|---|---|---|---|---|---|
| 79 | E1 | 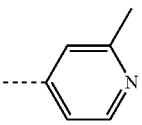 | 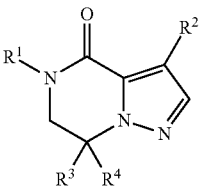 | —Me (S) | —H | .HCl |
| 80 | E1 | 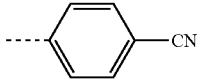 | 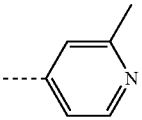 | —Me (S) | —H | |
| 81 | E11* | 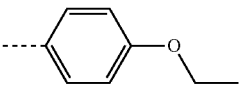 | 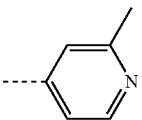 | —Me (S) | —H | .HCl |
| 82 | E1 | 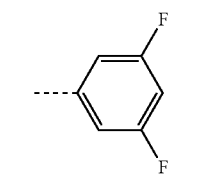 | 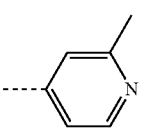 | —Me (S) | —H | |
| 83 | E1 | 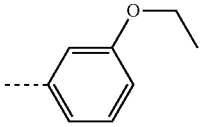 | 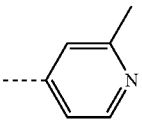 | —Me (S) | —H | |
| 84 | E1 | 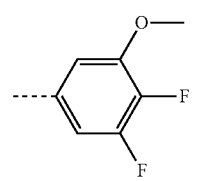 | 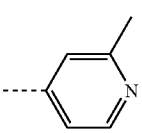 | —Me (S) | —H | |
| 85 | E1 | 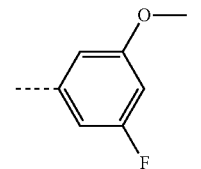 | 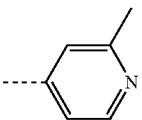 | —Me (S) | —H | |
| 86 | E1 | 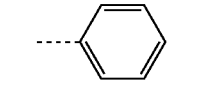 | 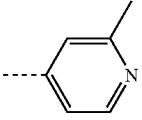 | —Me (S) | —H | |

TABLE 1a-continued
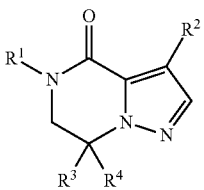
| Co. No. | Ex. No. | R¹ | R² | R⁴ | R³ | Salt form |
|---|---|---|---|---|---|---|
| 87 | E7* | 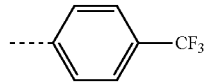 | 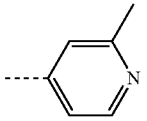 | —CH₂OH | —H | |
TABLE 1b
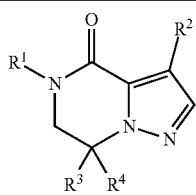
| Co. No. | Ex. No. | R¹ | R² | CR³R⁴ | Salt form |
|---|---|---|---|---|---|
| 1<br>1a<br>1b<br>1c<br>1d | E1* | 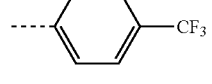 | 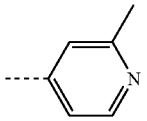 | CH(CH₃)<br>(S) | •HCl<br>•H₂SO₄<br>•CH₃SO₃H<br>•HO₂CCH=CHCO₂H-cis |
| 2 | E2* | 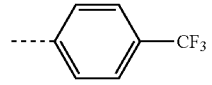 | 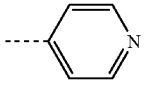 | CH(CH₃)<br>(S) | |
| 3 | E1 | 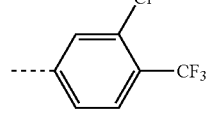 | 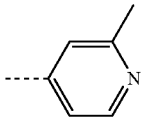 | CH(CH₃)<br>(S) | |
| 4 | E1 | 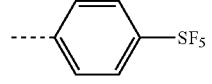 | 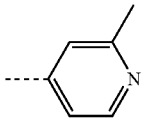 | CH(CH₃)<br>(S) | |
| 5 | E1 | 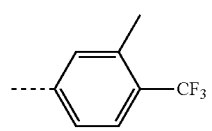 | 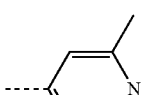 | CH(CH₃)<br>(S) | •HCl |
| 6 | E1 | 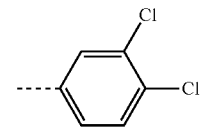 | 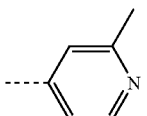 | CH(CH₃)<br>(S) | •HCl |

TABLE 1b-continued
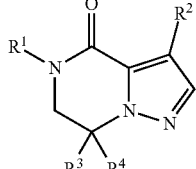
| Co. No. | Ex. No. | R¹ | R² | CR³R⁴ | Salt form |
|---|---|---|---|---|---|
| 6a | E1 | 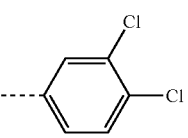 | 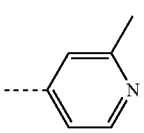 | CH(CH₃) (S) | |
| 7 | E1 | 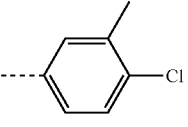 | 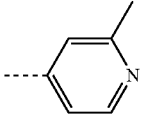 | CH(CH₃) (S) | |
| 8 | E1 | 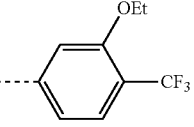 | 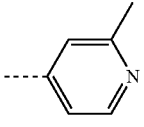 | CH(CH₃) (S) | |
| 9 | E1 | 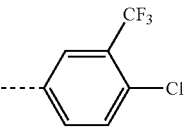 | 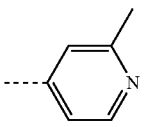 | CH(CH₃) (S) | |
| 10 | E1 | 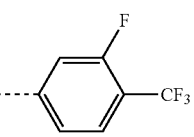 | 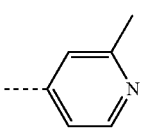 | CH(CH₃) (S) | |
| 11 | E1 | 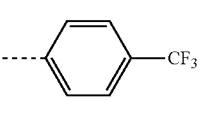 | 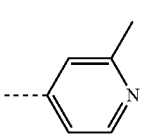 | CH(CH₃) | |
| 12 | E1 | 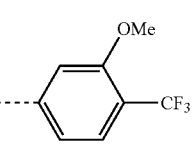 | 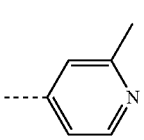 | CH(CH₃) (S) | •HCl |
| 13 | E1 | 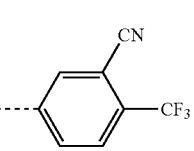 | 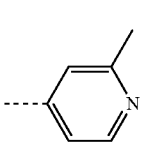 | CH(CH₃) (S) | |
| 14 | E2 | 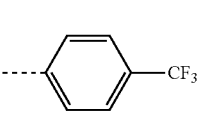 | 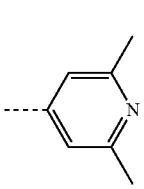 | CH(CH₃) (S) | |

TABLE 1b-continued

| Co. No. | Ex. No. | R¹ | R² | CR³R⁴ | Salt form |
|---|---|---|---|---|---|
| 15 | E1 | 4-Cl-phenyl | 2-methyl-pyridin-4-yl | CH(CH₃) (S) | •HCl |
| 16 | E1 | 3-Cl-phenyl | 2-methyl-pyridin-4-yl | CH(CH₃) (S) | |
| 17 | E1 | 3-Cl-4-OEt-phenyl | 2-methyl-pyridin-4-yl | CH(CH₃) (S) | •HCl |
| 18 | E1 | 3-OEt-4-Cl-phenyl | 2-methyl-pyridin-4-yl | CH(CH₃) (S) | |
| 19 | E1 | 3-OMe-4-Cl-phenyl | 2-methyl-pyridin-4-yl | CH(CH₃) (S) | |
| 20 | E1 | 3-Cl-4-OMe-phenyl | 2-methyl-pyridin-4-yl | CH(CH₃) (S) | •HCl |
| 21 | E1 | 3-methyl-4-F-phenyl | 3-methyl-pyrazolo-pyridinyl | CH(CH₃) (S) | |
| 22 | E2 | 4-CF₃-phenyl | 2-(methoxymethyl)pyridin-4-yl | CH(CH₃) (S) | •HCl |
| 23 | E1 | 3-CF₃-phenyl | 2-methyl-pyridin-4-yl | CH(CH₃) (S) | |
| 24 | E2 | 4-CF₃-phenyl | 5-methyl-pyridin-3-yl | CH(CH₃) (S) | |

TABLE 1b-continued

Structure: pyrazolo-pyrazinone core with R¹ on N, R² at 3-position, R³ and R⁴ on CR³R⁴ carbon.

| Co. No. | Ex. No. | R¹ | R² | CR³R⁴ | Salt form |
|---|---|---|---|---|---|
| 25 | E1 | 3,4-difluorophenyl | 2-methylpyridin-4-yl | CH(CH₃) (S) | ·HCl |
| 26 | E1 | 4-(trifluoromethyl)phenyl | 2-methylpyridin-4-yl | CH(CH₃) (R) | |
| 27 | E1 | 4-(difluoromethoxy)phenyl | 2-methylpyridin-4-yl | CH(CH₃) (S) | |
| 28 | E1 | 4-fluorophenyl | 2-methylpyridin-4-yl | CH(CH₃) (S) | ·HCl |
| 29 | E2 | 4-(trifluoromethyl)phenyl | 2,3-dimethylpyridin-5-yl | CH(CH₃) (S) | |
| 30 | E1 | 3-fluoro-4-chlorophenyl | 2-methylpyridin-4-yl | CH(CH₃) (S) | |
| 31 | E1 | 3-ethoxy-4-(trifluoromethyl)phenyl | 2-methylpyridin-4-yl | CH(CH₃) (R) | |
| 32 | E2 | 4-(trifluoromethyl)phenyl | pyridin-3-yl | CH(CH₃) (S) | |
| 33 | E1 | 3-ethoxy-4-(trifluoromethyl)phenyl | 2-methylpyridin-4-yl | CH₂ | |

TABLE 1b-continued
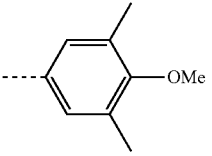
| Co. No. | Ex. No. | R¹ | R² | CR³R⁴ | Salt form |
|---|---|---|---|---|---|
| 34 | E1 | 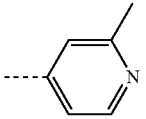 | 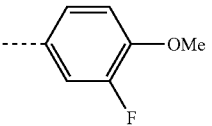 | CH(CH₃) (S) | |
| 35 | E1 | 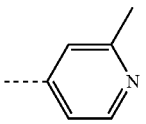 | 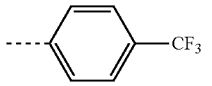 | CH(CH₃) (S) | •HCl |
| 36 | E2 | 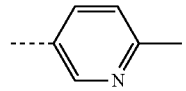 | 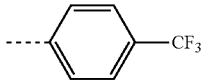 | CH(CH₃) (S) | |
| 37 | E2 | 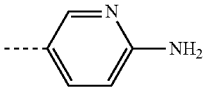 | 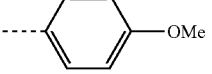 | CH(CH₃) (S) | |
| 38 | E1 | 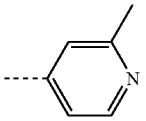 | 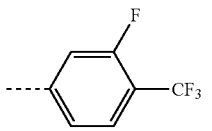 | CH(CH₃) (S) | •HCl |
| 39 | E1 | 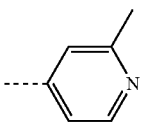 | 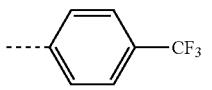 | CH₂ | |
| 40 | E1 | 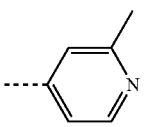 | 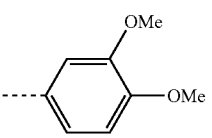 | CH₂ | |
| 41 | E1 | 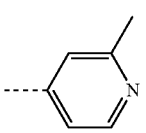 | 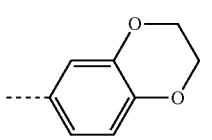 | CH(CH₃) (S) | |
| 42 | E1 | 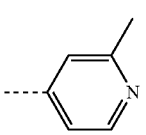 | 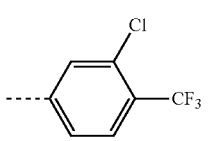 | CH(CH₃) (S) | |
| 43 | E1 | 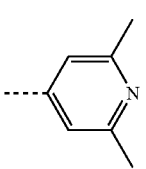 | | CH(CH₃) (S) | |

TABLE 1b-continued
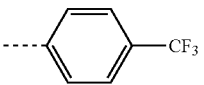
| Co. No. | Ex. No. | R¹ | R² | CR³R⁴ | Salt form |
|---|---|---|---|---|---|
| 44 | E4* | 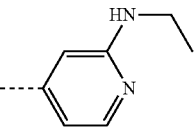 | 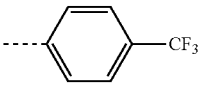 | CH(CH₃) (S) | |
| 45 | E5* | 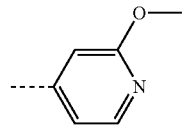 | 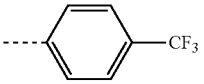 | CH(CH₃) (S) | |
| 46 | E6* | 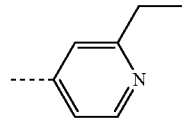 | 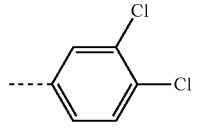 | CH(CH₃) (S) | |
| 47 | E1 | 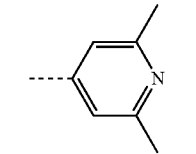 | 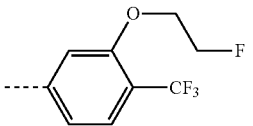 | CH(CH₃) (S) | |
| 48 | E1 | 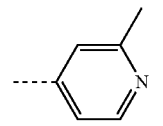 | 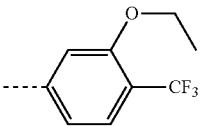 | CH(CH₃) (S) | |
| 49 | E1 | 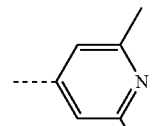 | 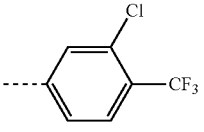 | CH(CH₃) (S) | |
| 50 | E1 | 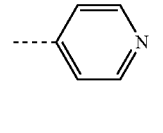 | 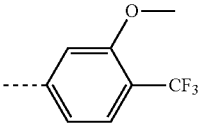 | CH(CH₃) (S) | |
| 51 | E1 | 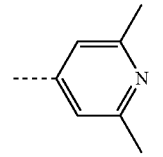 | 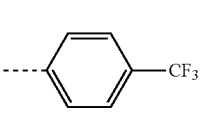 | CH(CH₃) (S) | |
| 52 | E8* | 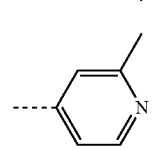 | | CH(CH₂F) | |

TABLE 1b-continued

| Co. No. | Ex. No. | R¹ | R² | CR³R⁴ | Salt form |
|---|---|---|---|---|---|
| 53 | E1 | 4-SF₅-phenyl | 2,6-dimethylpyridin-4-yl | CH(CH₃) (S) | |
| 54 | E1 | 3-CF₃-4-Cl-phenyl | 2,6-dimethylpyridin-4-yl | CH(CH₃) (S) | |
| 55 | E1 | 3-ethoxy-4-CF₃-phenyl | pyridin-4-yl | CH(CH₃) (S) | |
| 56 | E1 | 4-SF₅-phenyl | pyridin-4-yl | CH(CH₃) (S) | |
| 57 | E1 | 3,4-dichlorophenyl | pyridin-4-yl | CH(CH₃) (S) | |
| 58 | E1 | 3-OCF₃-phenyl | 2-methylpyridin-4-yl | CH(CH₃) (S) | ·HCl |
| 59 | E1 | 3-CN-4-CF₃-phenyl | 3,6-dimethylpyridazin-4-yl | CH(CH₃) (S) | |
| 60 | E1 | 3-F-4-CF₃-phenyl | pyridin-4-yl | CH(CH₃) (S) | |
| 61 | E1 | 3-F-4-CF₃-phenyl | 2,6-dimethylpyridin-4-yl | CH(CH₃) (S) | |

TABLE 1b-continued
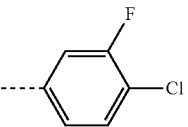
| Co. No. | Ex. No. | R¹ | R² | CR³R⁴ | Salt form |
|---|---|---|---|---|---|
| 62 | E1 | 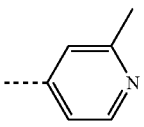 | 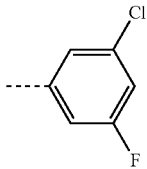 | CH(CH₃) (S) | |
| 63 | E1 | 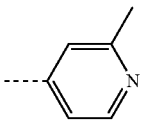 | 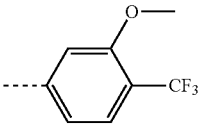 | CH(CH₃) (S) | •HCl |
| 64 | E1 | 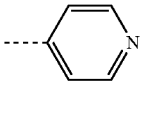 | 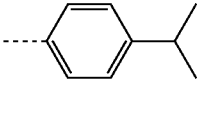 | CH(CH₃) (S) | |
| 65 | E1 | 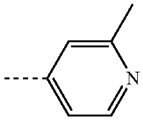 | 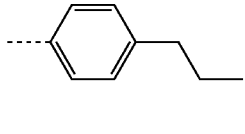 | CH(CH₃) (S) | •HCl |
| 66 | E1 | 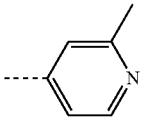 | 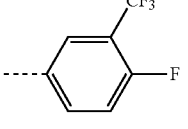 | CH(CH₃) (S) | •HCl |
| 67 | E9* | 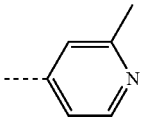 | 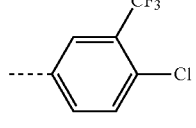 | CH(CH₃) (S) | |
| 68 | E1 | 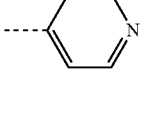 | 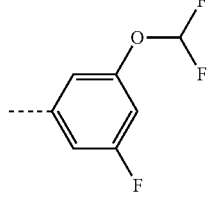 | CH(CH₃) (S) | |
| 69 | E1 | 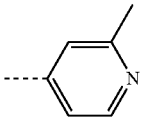 | 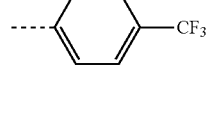 | CH(CH₃) (S) | •HCl |
| 70 | E1 | 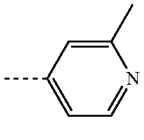 |  | CH(CH₂CH₃) | |

TABLE 1b-continued

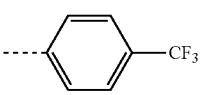

| Co. No. | Ex. No. | R¹ | R² | CR³R⁴ | Salt form |
|---|---|---|---|---|---|
| 71 | E3* | 4-CF₃-phenyl | 2-amino-pyridin-4-yl | CH(CH₃) (S) | |
| 72 | E1 | 4-Cl-phenyl | 2,6-dimethyl-pyridin-4-yl | CH(CH₃) (S) | |
| 73 | E1 | 4-Cl-phenyl | pyridin-4-yl | CH(CH₃) (S) | |
| 74 | E1 | 3-ethoxy-4-CF₃-phenyl | 2-methyl-pyridin-4-yl | CH(CH₂OH) | |
| 75 | E1 | 3-F-4-CN-phenyl | 2-methyl-pyridin-4-yl | CH(CH₃) (S) | |
| 76 | E1 | 3-F-4-methyl-phenyl | 2-methyl-pyridin-4-yl | CH(CH₃) (S) | |
| 77 | E10* | 3-CF₃-4-(2-fluoroethoxy)-phenyl | 3-methyl-pyridazin-5-yl | CH(CH₃) (S) | |
| 78 | E1 | 4-methyl-phenyl | 2-methyl-pyridin-4-yl | CH(CH₃) (S) | |
| 79 | E1 | 3-isopropoxy-phenyl | 2-methyl-pyridin-4-yl | CH(CH₃) (S) | •HCl |

TABLE 1b-continued

| Co. No. | Ex. No. | R¹ | R² | CR³R⁴ | Salt form |
|---|---|---|---|---|---|
| 80 | E1 | 4-cyanophenyl | pyridin-4-yl | CH(CH₃) (S) | |
| 81 | E11* | 4-ethoxyphenyl | pyridin-4-yl | CH(CH₃) (S) | •HCl |
| 82 | E1 | 3,5-difluorophenyl | pyridin-4-yl | CH(CH₃) (S) | |
| 83 | E1 | 3-ethoxyphenyl | pyridin-4-yl | CH(CH₃) (S) | |
| 84 | E1 | 3-methoxy-4,5-difluorophenyl | pyridin-4-yl | CH(CH₃) (S) | |
| 85 | E1 | 3-methoxy-5-fluorophenyl | pyridin-4-yl | CH(CH₃) (S) | |
| 86 | E1 | phenyl | pyridin-4-yl | CH(CH₃) (S) | |
| 87 | E7* | 4-(trifluoromethyl)phenyl | pyridin-4-yl | CH(CH₂OH) | |
| 88 | E3 | 3-cyano-4-(trifluoromethyl)phenyl | 2-methoxypyridin-4-yl | CH(CH₃) (S) | |

TABLE 1b-continued

| Co. No. | Ex. No. | R¹ | R² | CR³R⁴ | Salt form |
|---|---|---|---|---|---|
| 89 | E3 | 4-Cl-phenyl | 2-methoxy-pyridin-4-yl | CH(CH₃) (S) | |
| 90 | E8 | 3,4-dichloro-phenyl | 2-(dimethylamino)pyridin-4-yl | CH(CH₂F) (*R) | |
| 91 | E8 | 3,4-dichloro-phenyl | 2-(dimethylamino)pyridin-4-yl | CH(CH₂F) (*S) | |
| 92 | E13 | 3-Cl-4-CF₃-phenyl | 2-(3-fluoroazetidin-1-yl)pyridin-4-yl | CH(CH₃) (S) | |
| 93 | E8 | 3,4-dichloro-phenyl | 2-(methylamino)pyridin-4-yl | CH(CH₂F) | |
| 94 | E13 | 4-CF₃-phenyl | 2-(3-fluoroazetidin-1-yl)pyridin-4-yl | CH(CH₃) (S) | |
| 95 | E13 | 3-Cl-4-CF₃-phenyl | 6-cyano-2-(methylamino)pyridin-4-yl | CH(CH₃) (S) | |

TABLE 1b-continued
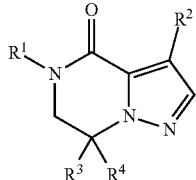
| Co. No. | Ex. No. | R¹ | R² | CR³R⁴ | Salt form |
|---|---|---|---|---|---|
| 96 | E1 | 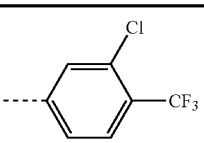 | 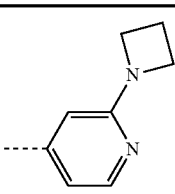 | CH(CH₃) (S) | |
| 97 | E13 | 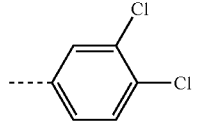 | 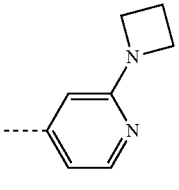 | CH(CH₃) (S) | |
| 98 | E8 | 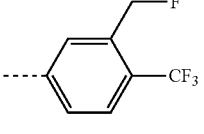 | 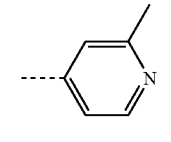 | CH(CH₃) (S) | |
| 99 | E13 | 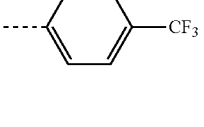 | 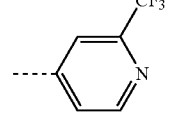 | CH(CH₃) (S) | |
| 100 | E13 | 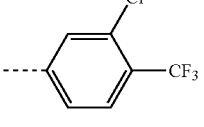 | 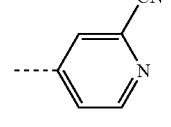 | CH(CH₃) (S) | |
| 101 | E12 | 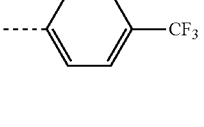 | 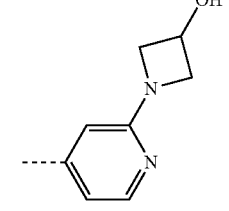 | CH(CH₃) (S) | |
| 102 | E12 | 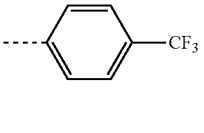 | 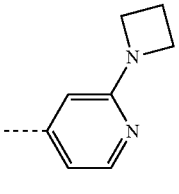 | CH(CH₃) (S) | |
| 103 | E3 | 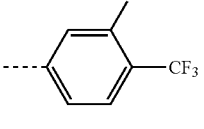 | 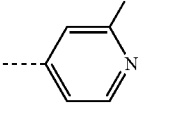 | CH(CH₃) (S) | |

TABLE 1b-continued

| Co. No. | Ex. No. | R¹ | R² | CR³R⁴ | Salt form |
|---|---|---|---|---|---|
| 104 | E3 | 3-Cl,4-CF₃-phenyl | 2-methoxypyridin-4-yl | CH(CH₃) (S) | |
| 105 | E12 | 4-CF₃-phenyl | 2-(pyrrolidin-1-yl)pyridin-4-yl | CH(CH₃) (S) | |
| 106 | E25* | 4-CF₃-phenyl | 2-(4-acetylpiperazin-1-yl)pyridin-4-yl | CH(CH₃) (S) | |
| 107 | E12 | 4-CF₃-phenyl | 2-(piperidin-1-yl)pyridin-4-yl | CH(CH₃) (S) | ·HCl |
| 108 | E12 | 4-CF₃-phenyl | 2-(morpholin-4-yl)pyridin-4-yl | CH(CH₃) (S) | |
| 109 | E12 | 3,4-diCl-phenyl | 2-cyanopyridin-4-yl | CH(CH₃) (S) | |
| 110 | E13 | 3,4-diCl-phenyl | 2-(methylamino)pyridin-4-yl | CH(CH₃) (S) | |

TABLE 1b-continued

| Co. No. | Ex. No. | R¹ | R² | CR³R⁴ | Salt form |
|---|---|---|---|---|---|
| 111 | E15* | 3,4-diCl-phenyl | 1-hydroxyethyl-pyridin-4-yl | CH(CH₃) (S) | |
| 112 | E8 | 4-CF₃-phenyl | 2-(fluoromethyl)pyridin-4-yl | CH(CH₃) (S) | |
| 113 | E6 | 4-(1,1,1-trifluoropropan-2-yl)phenyl | 2-methylpyridin-4-yl | CH(CH₃) (S) | |
| 114 | E8 | 3,4-diCl-phenyl | 2-(difluoromethyl)pyridin-4-yl | CH(CH₃) (S) | |
| 115 | E8 | 3,4-diCl-phenyl | 2-methylpyridin-4-yl | CH(CH₂F) (*S) | |
| 116 | E8 | 3,4-diCl-phenyl | 2-methylpyridin-4-yl | CH(CH₂F) (*R) | |
| 117 | E8 | 3,4-diCl-phenyl | 2-(fluoromethyl)pyridin-4-yl | CH(CH₃) (S) | |
| 118 | E1 | 3,4-diCl-phenyl | 2-methylpyridin-4-yl | CH(CH₂OMe) (*S) | |
| 119 | E1 | 3,4-diCl-phenyl | 2-methylpyridin-4-yl | CH(CH₂OMe) (*R) | |

TABLE 1b-continued

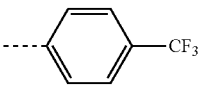

| Co. No. | Ex. No. | R¹ | R² | CR³R⁴ | Salt form |
|---|---|---|---|---|---|
| 120 | E1 | 4-CF₃-phenyl | 2-methyl-pyridin-4-yl | CH(CH₂OMe) (*R) | |
| 121 | E1 | 4-CF₃-phenyl | 2-methyl-pyridin-4-yl | CH(CH₂OMe) (*S) | |
| 122 | E13 | 3,4-diCl-phenyl | 2-cyclopropyl-pyridin-4-yl | CH(CH₃) (S) | •2 HCl |
| 123 | E2 | 4-CF₃-phenyl | 2-ethoxy-pyridin-4-yl | CH(CH₃) (S) | |
| 124 | E13 | 3,4-diCl-phenyl | 2-isopropyl-pyridin-4-yl | CH(CH₃) (S) | |
| 125 | E14* | 3,4-diCl-phenyl | 2-(hydroxymethyl)-pyridin-4-yl | CH(CH₃) (S) | |
| 126 | E13* | 4-CF₃-phenyl | 2-isopropyl-pyridin-4-yl | CH(CH₃) (S) | |
| 127 | E12* | 4-CF₃-phenyl | 2-cyano-pyridin-4-yl | CH(CH₃) (S) | |
| 128 | E14 | 4-CF₃-phenyl | 2-(1-hydroxyethyl)-pyridin-4-yl | CH(CH₃) (S) | |

TABLE 1b-continued

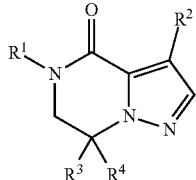

| Co. No. | Ex. No. | R¹ | R² | CR³R⁴ | Salt form |
|---|---|---|---|---|---|
| 129 | E1 | 4-CF₃-phenyl | 2-methylpyridin-4-yl | CH(CH₂CH₃) (R) | |
| 130 | E1 | 4-CF₃-phenyl | 2-methylpyridin-4-yl | CH(CH₂CH₃) (S) | |
| 131 | E8 | 4-CF₃-phenyl | 2-(difluoromethyl)pyridin-4-yl | CH(CH₃) (S) | |
| 132 | E1 | 3,5-difluoro-4-CF₃-phenyl | 2-methylpyridin-4-yl | CH(CH₃) (S) | |
| 133 | E2 | 3,4-dichlorophenyl | 2-ethoxypyridin-4-yl | CH(CH₃) (S) | •HCl |
| 134 | E6 | 3,4-dichlorophenyl | 2-ethylpyridin-4-yl | CH(CH₃) (S) | |
| 135 | E17 | 4-CF₃-phenyl | 2-(hydroxymethyl)pyridin-4-yl | CH(CH₃) (S) | |
| 136 | E1 | 4-(1-CF₃-cyclopropyl)phenyl | 2-methylpyridin-4-yl | CH(CH₃) (S) | |
| 137 | E2 | 3,4-dichlorophenyl | 2-isopropoxypyridin-4-yl | CH(CH₃) (S) | •HCl |

TABLE 1b-continued
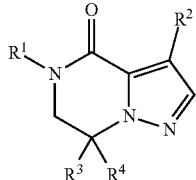
| Co. No. | Ex. No. | R¹ | R² | CR³R⁴ | Salt form |
|---|---|---|---|---|---|
| 138 | E2 | 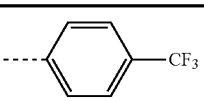 | 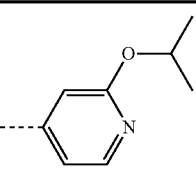 | CH(CH₃) (S) | ·HCl |
| 139 | E1 | 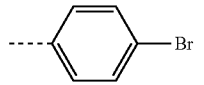 | 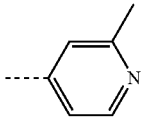 | CH(CH₃) (S) | |
| 140 | E16* | 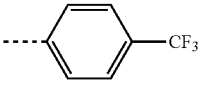 | 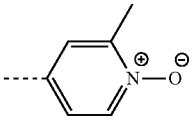 | CH(CH₃) (S) | |
| 141 | E1 | 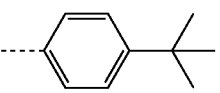 | 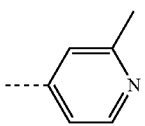 | CH(CH₃) (S) | |
| 142 | E3 | 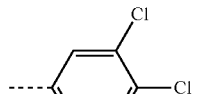 | 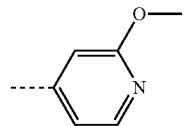 | CH(CH₃) (S) | |
| 143 | E1 | 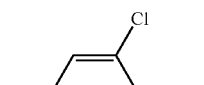 | 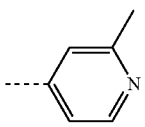 | CH(CH₂OMe) | |
| 144 | E1 | 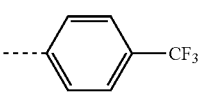 | 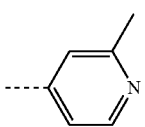 | CH(CH₂OMe) | |
| 145 | E2 | 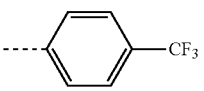 | 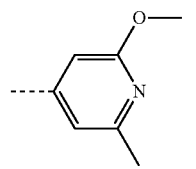 | CH(CH₃) (S) | |
| 146 | E2 | 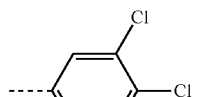 | 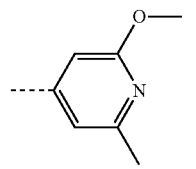 | CH(CH₃) (S) | |

TABLE 1b-continued
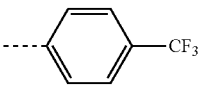
| Co. No. | Ex. No. | R¹ | R² | CR³R⁴ | Salt form |
|---|---|---|---|---|---|
| 147 | E27* | 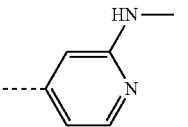 | 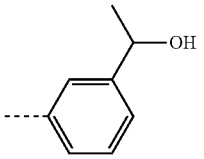 | CH(CH₃) (S) | |
| 148 | E1 | 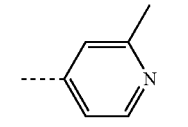 | 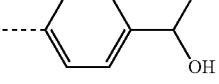 | CH(CH₃) (S) | |
| 149 | E17* | 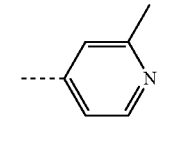 | 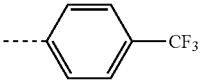 | CH(CH₃) (S) | |
| 150 | E3 | 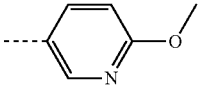 | 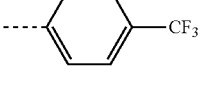 | CH(CH₃) (S) | |
| 151 | E2 | 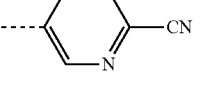 | 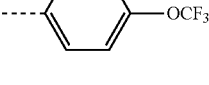 | CH(CH₃) (S) | |
| 152 | E1 | 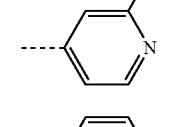 | 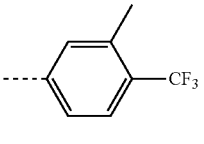 | CH(CH₃) (S) | |
| 153 | E1 | 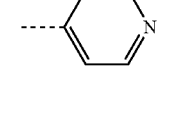 | 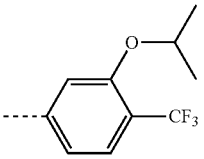 | CH(CH₃) (S) | |
| 154 | E1 | 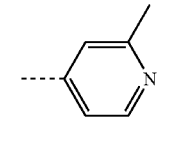 | 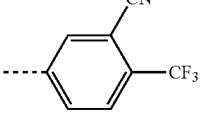 | CH(CH₃) (S) | |
| 155 | E1 | 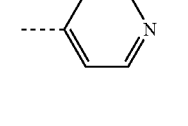 | 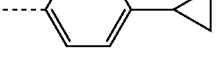 | CH(CH₃) (S) | |
| 156 | E18* | 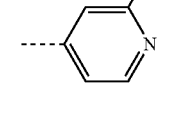 | | CH(CH₃) (S) | |

TABLE 1b-continued
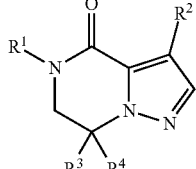
| Co. No. | Ex. No. | R¹ | R² | CR³R⁴ | Salt form |
|---|---|---|---|---|---|
| 157 | E1 | 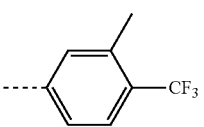 | 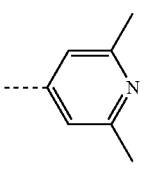 | CH(CH₃) (S) | |
| 158 | E1 | 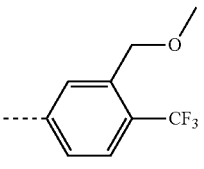 | 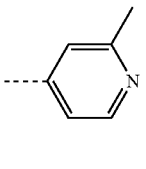 | CH(CH₃) (S) | |
| 159 | E1 | 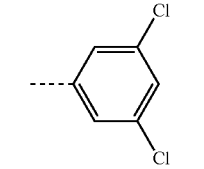 | 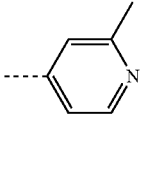 | CH(CH₃) (S) | |
| 160 | E1 | 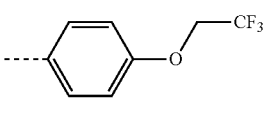 | 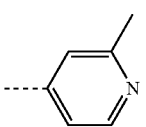 | CH(CH₃) (S) | |
| 161 | E1 | 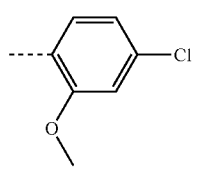 | 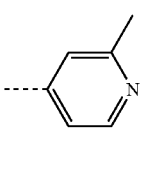 | CH(CH₃) (S) | |
| 162 | E1 | 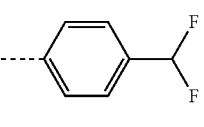 | 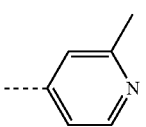 | CH(CH₃) (S) | |
| 163 | E1 | 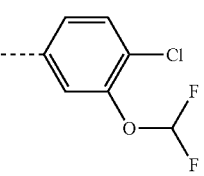 | 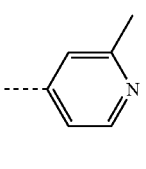 | CH(CH₃) (S) | |
| 164 | E3 | 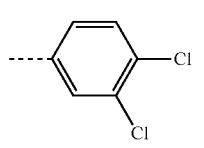 | 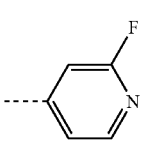 | CH(CH₃) (S) | |

TABLE 1b-continued

| Co. No. | Ex. No. | R¹ | R² | CR³R⁴ | Salt form |
|---|---|---|---|---|---|
| 165 | E1 | 4-(1-(CF₃)ethoxy)phenyl | 2-methylpyridin-4-yl | CH(CH₃) (S) | |
| 166 | E13 | 4-(CF₃)phenyl | 2-(N,N-dimethylamino)pyridin-4-yl | CH(CH₃) (S) | |
| 167 | E1 | 2,4-dichlorophenyl | 2-methylpyridin-4-yl | CH(CH₃) (S) | |
| 168 | E1 | 3-chloro-4-(difluoromethoxy)phenyl | 2-methylpyridin-4-yl | CH(CH₃) (S) | |
| 169 | E1 | 4-chloro-3-(trifluoromethoxy)phenyl | 2-methylpyridin-4-yl | CH(CH₃) (S) | |
| 170 | I-38* E16 | 3,4-dichlorophenyl | 2-methylpyridin-4-yl 1-oxide | CH(CH₃) (S) | |
| 171 | E1 | 4-(CF₃)phenyl | 2-methylpyridin-4-yl | C(CH₃)₂ | |
| 172 | E1 | 4-chloro-3-methylphenyl | 2-methylpyridin-4-yl | CH(CH₃) (S) | |
| 173 | E13 | 4-(CF₃)phenyl | 2-cyclopropylpyridin-4-yl | CH(CH₃) (S) | ·HCl |

TABLE 1b-continued
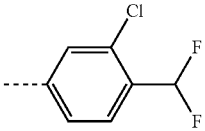
| Co. No. | Ex. No. | R¹ | R² | CR³R⁴ | Salt form |
|---|---|---|---|---|---|
| 174 | E1 | 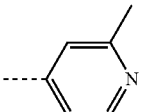 | 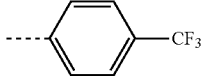 | CH(CH₃) (S) | |
| 175 | E24* | 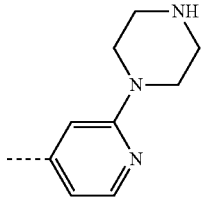 | 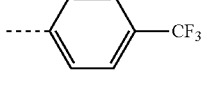 | CH(CH₃) (S) | ·HCl |
| 176 | E19* | 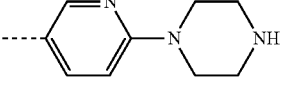 | 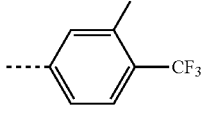 | CH(CH₃) (S) | |
| 177 | E10 | 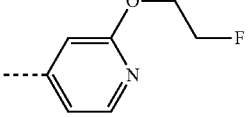 |  | CH(CH₃) (S) | |
| 178 | E3 | 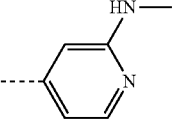 | 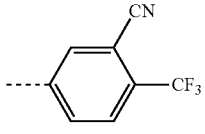 | CH(CH₃) (S) | |
| 179 | E3 | 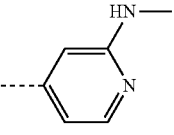 | 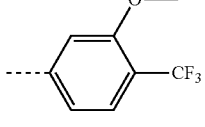 | CH(CH₃) (S) | |
| 180 | E3 | 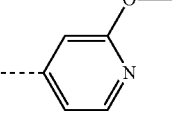 | 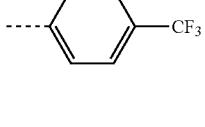 | CH(CH₃) (S) | |
| 181 | E26* | 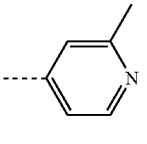 | 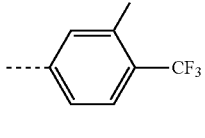 | CH(CHF₂) | |
| 182 | E3 | 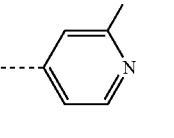 |  | CH(CH₃) (S) | |

TABLE 1b-continued
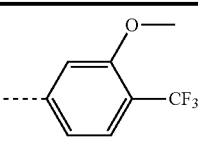
| Co. No. | Ex. No. | R¹ | R² | CR³R⁴ | Salt form |
|---|---|---|---|---|---|
| 183 | E3 | 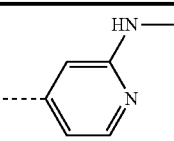 | 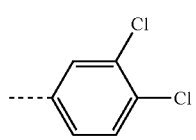 | CH(CH₃) (S) | |
| 184 | E8 | 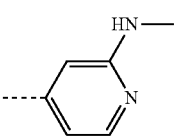 | 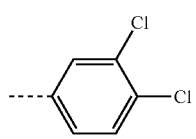 | CH(CH₂F) (*R) | |
| 185 | E8 | 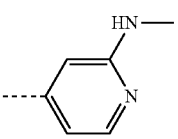 | 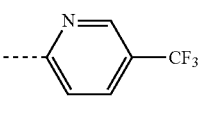 | CH(CH₂F) (*S) | |
| 186 | E20* | 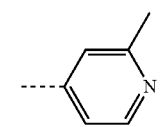 | 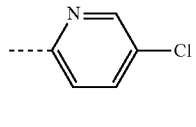 | CH(CH₃) (S) | |
| 187 | E1 | 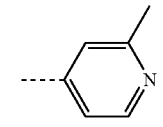 | 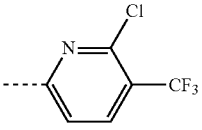 | CH(CH₃) (S) | |
| 188 | I-43* E20 | 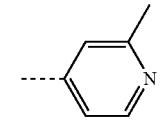 | 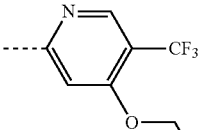 | CH(CH₃) (S) | |
| 189 | E22a* | 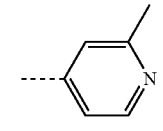 | 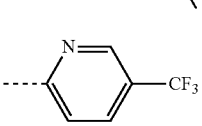 | CH(CH₃) (S) | |
| 190 | E20 | 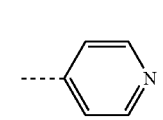 | 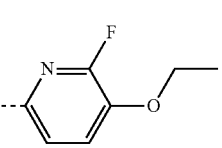 | CH(CH₃) (S) | |
| 191 | E1 | 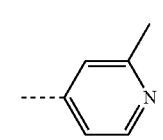 | 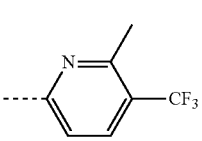 | CH(CH₃) (S) | |
| 192 | E21* | 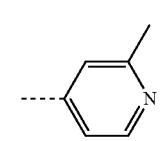 | | CH(CH₃) (S) | |

TABLE 1b-continued
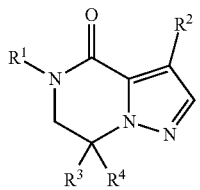
| Co. No. | Ex. No. | R¹ | R² | CR³R⁴ | Salt form |
|---|---|---|---|---|---|
| 193 | E21 | 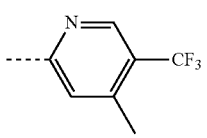 | 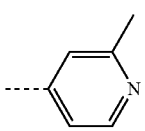 | CH(CH₃) (S) | |
| 194 | E20 | 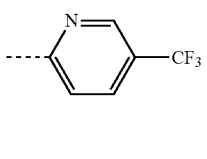 | 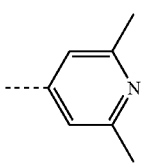 | CH(CH₃) (S) | |
| 195 | E20 | 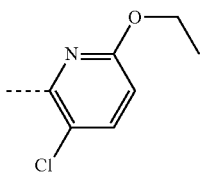 | 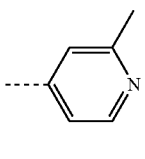 | CH(CH₃) (S) | |
| 196 | E20 | 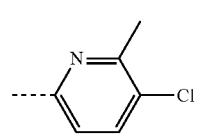 | 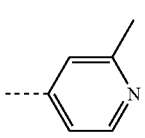 | CH(CH₃) (S) | |
| 197 | E3 | 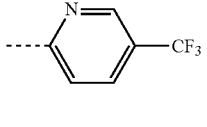 | 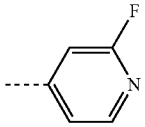 | CH(CH₃) (S) | |
| 198 | E18 | 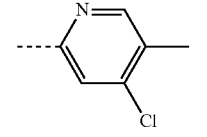 | 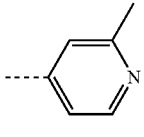 | CH(CH₃) (S) | |
| 199 | E20 | 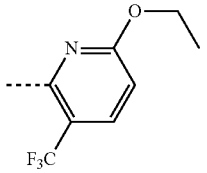 | 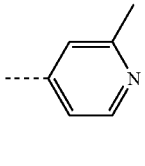 | CH(CH₃) (S) | |
| 200 | E20 | 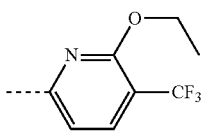 | 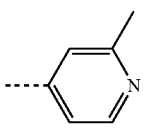 | CH(CH₃) (S) | |

TABLE 1b-continued

| Co. No. | Ex. No. | R¹ | R² | CR³R⁴ | Salt form |
|---|---|---|---|---|---|
| 201 | E20 | 2-ethoxy-3-chloropyridin-6-yl | 2-methylpyridin-4-yl | CH(CH₃) (S) | |
| 202 | E20 | 2,3-dichloropyridin-6-yl | 2-methylpyridin-4-yl | CH(CH₃) (S) | |
| 203 | E20 | 3,4-dichloropyridin-6-yl | 2-methylpyridin-4-yl | CH(CH₃) (S) | |
| 204 | E22b* | 3-trifluoromethyl-4-chloropyridin-6-yl | 2-methylpyridin-4-yl | CH(CH₃) (S) | |
| 205 | E20 | 2-ethoxy-3-trifluoromethylpyridin-6-yl | 2,6-dimethylpyridin-4-yl | CH(CH₃) (S) | |
| 206 | E20 | 2-methoxy-3-chloropyridin-6-yl | 2-methylpyridin-4-yl | CH(CH₃) (S) | |
| 207 | E20 | 2-methoxy-3-trifluoromethylpyridin-6-yl | 2-methylpyridin-4-yl | CH(CH₃) (S) | |
| 208 | E20 | 2-ethoxy-3-trifluoromethylpyridin-6-yl | pyridin-4-yl | CH(CH₃) (S) | |
| 209 | E1 | 2-methoxy-3-trifluoromethylpyridin-6-yl | 2-(azetidin-1-yl)pyridin-5-yl | CH(CH₃) (S) | |

TABLE 1b-continued

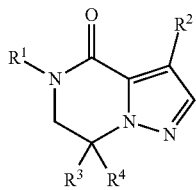

| Co. No. | Ex. No. | R¹ | R² | CR³R⁴ | Salt form |
|---|---|---|---|---|---|
| 210 | E3 | 5-CF₃-pyridin-2-yl | 2-(methylamino)pyridin-4-yl | CH(CH₃) (S) | |
| 211 | E1 | 5-CF₃-pyridin-2-yl | 2-methylpyridin-4-yl | CH₂ | |
| 212 | E28* | 5-CF₃-4-I-pyridin-2-yl | 2-methylpyridin-4-yl | CH(CH₃) (S) | |
| 213 | E28 | 5-I-4-Cl-pyridin-2-yl | 2-methylpyridin-4-yl | CH(CH₃) (S) | |
| 214 | E13 | 4-CF₃-phenyl | 2-(methylamino)pyridine 1-oxide-4-yl | CH(CH₃) (S) | |
| 215 | I-26* E3 | 4-CF₃-phenyl | 2-chloropyridin-4-yl | CH(CH₃) (S) | |
| 216 | E1 | 4-CF₃-phenyl | 2-methylpyridin-4-yl | CH(CH(OH)CH₃) *R | |
| 217 | E1 | 4-CF₃-phenyl | 2-methylpyridin-4-yl | CH(CH(OH)CH₃) *S | |
| 218 | E3 | 3,4-dichlorophenyl | 2-chloropyridin-4-yl | CH(CH₃) (S) | |

TABLE 1b-continued

| Co. No. | Ex. No. | R¹ | R² | CR³R⁴ | Salt form |
|---|---|---|---|---|---|
| 219 | E2 | 3,4-dichlorophenyl | 2-methylpyridin-4-yl | CH(CH₂OH) | |
| 220 | E29* | 3,4-dichloro-5-iodophenyl | 2-methylpyridin-4-yl | CH(CH₃) (S) | |
| 221 | E29* | 3,4-dichloro-2-iodophenyl | 2-methylpyridin-4-yl | CH(CH₃) (S) | |
| 222 | E8 | 3,4-dichlorophenyl | 2-methylpyridin-4-yl | CH(CH₂F) | |
| 223 | E2 | 4-(trifluoromethyl)phenyl | 2-bromopyridin-4-yl | CH(CH₃) (S) | |
| 224 | E3 | 3,4-dichlorophenyl | 2-fluoropyridin-4-yl | CH(CH₂OH) | |
| 225 | E23* | 4-(trifluoromethyl)phenyl | 2-iodopyridin-4-yl | CH(CH₃) (S) | |
| 226 | E3 | 3,4-dichlorophenyl | 2-fluoropyridin-4-yl | CH(CH₂OH) (*S) | |
| 227 | E3 | 3,4-dichlorophenyl | 2-fluoropyridin-4-yl | CH(CH₂OH) (*R) | |

TABLE 1b-continued
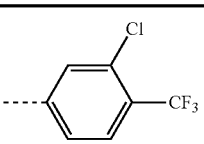
| Co. No. | Ex. No. | R¹ | R² | CR³R⁴ | Salt form |
|---|---|---|---|---|---|
| 228 | E3 | 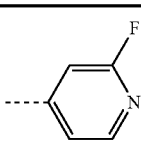 | 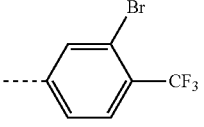 | CH(CH₃) (S) | |
| 229 | E1 | 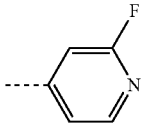 | 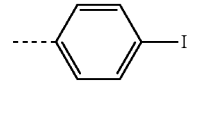 | CH(CH₃) (S) | |
| 230 | E1 | 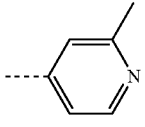 | 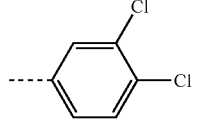 | CH(CH₃) (S) | |
| 231 | E10 | 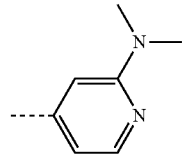 | 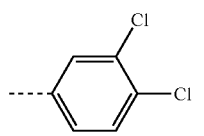 | CH(CH₂OH) (*S) | |
| 232 | E10 | 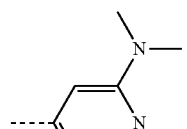 | 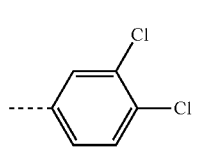 | CH(CH₂OH) (*R) | |
| 233 | E10 | 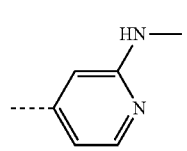 | 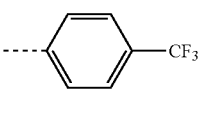 | CH(CH₂OH) | |
| 234 | E3 | 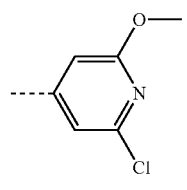 | 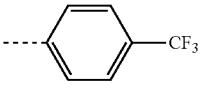 | CH(CH₃) (S) | |
| 235 | E13 | 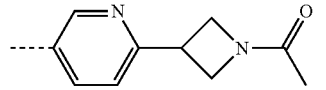 | 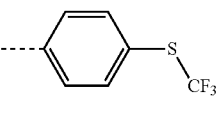 | CH(CH₃) (S) | |
| 236 | E1 | 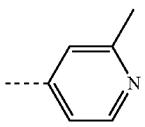 |  | CH(CH₃) (S) | ·HCl |

TABLE 1b-continued
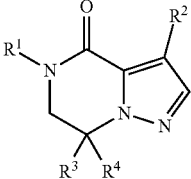
| Co. No. | Ex. No. | R¹ | R² | CR³R⁴ | Salt form |
|---|---|---|---|---|---|
| 237 | E3 | 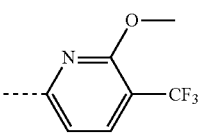 | 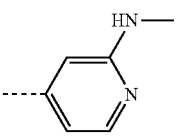 | CH(CH₃) (S) | |
| 238 | E30* | 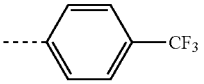 | 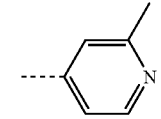 | CH(CF₃) | |
| 239 | E1 | 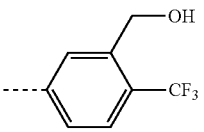 | 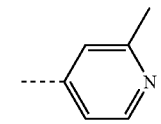 | CH(CH₃) (S) | |
| 240 | E3 | 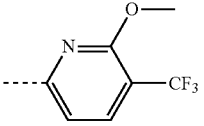 | 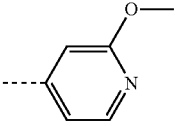 | CH(CH₃) (S) | |
| 241 | E3 | 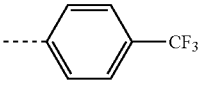 | 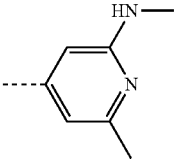 | CH(CH₃) (S) | |
| 242 | E2 | 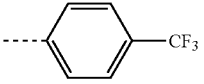 | 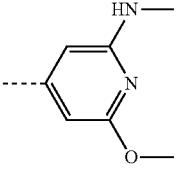 | CH(CH₃) (S) | |
| 243 | E2 | 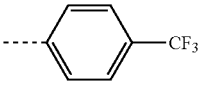 | 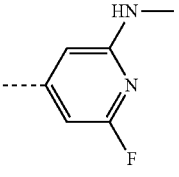 | CH(CH₃) (S) | |
| 244 | E1 | 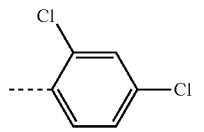 | 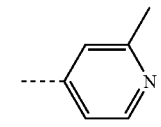 | CH₂ | |

TABLE 1b-continued
| Co. No. | Ex. No. | R¹ | R² | CR³R⁴ | Salt form |
|---|---|---|---|---|---|
| 245 | E1 | 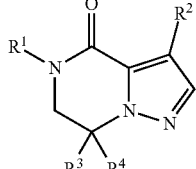 | 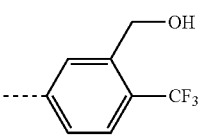 | CH(CH₃) (S) | |
| 246 | E8 | 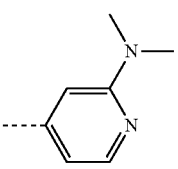 | 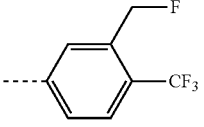 | CH(CH₃) (S) | |
| 247 | E13 | 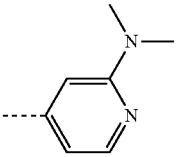 | 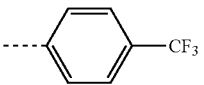 | CH(CH₃) (S) | |
| 248 | E12 | 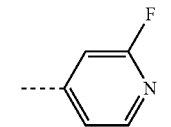 | 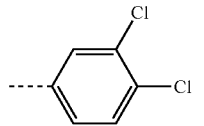 | CH(CH₃) (S) | |
| 249 | E1 | 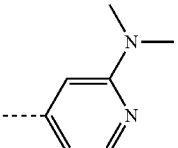 | 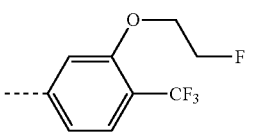 | CH(CH₃) (S) | |
| 250 | E20 | 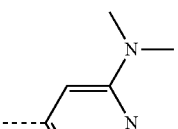 | 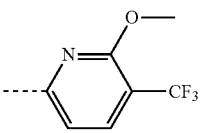 | CH(CH₃) (S) | |
| 251 | E12 | 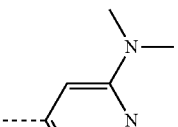 | 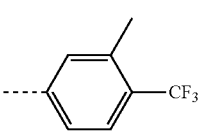 | CH(CH₃) (S) | |
| 252 | E16 | 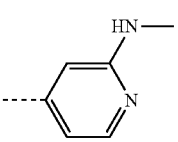 | 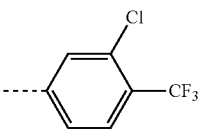 | CH(CH₃) (S) | |

TABLE 1b-continued
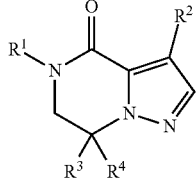
| Co. No. | Ex. No. | R¹ | R² | CR³R⁴ | Salt form |
|---|---|---|---|---|---|
| 253 | E13 | 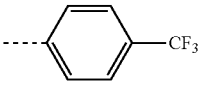 | 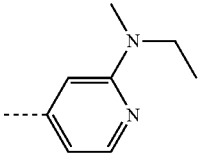 | CH(CH₃) (S) | |
| 254 | E4 | 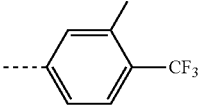 | 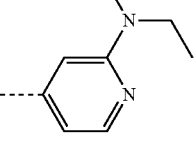 | CH(CH₃) (S) | |
| 255 | E13 | 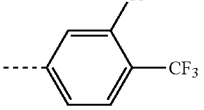 | 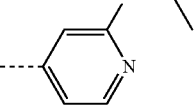 | CH(CH₃) (S) | |
| 256 | E12 | 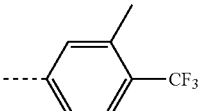 | 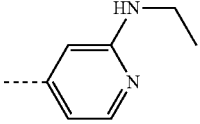 | CH(CH₃) (S) | |
| 257 | E13 | 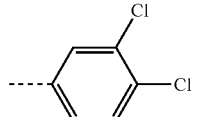 | 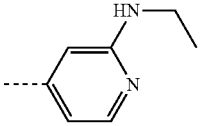 | CH(CH₃) (S) | |
| 258 | E12 | 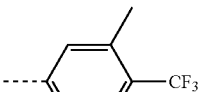 | 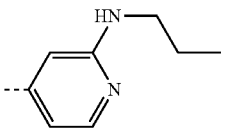 | CH(CH₃) (S) | |
| 259 | E13 | 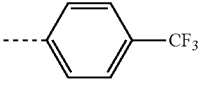 | 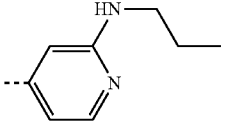 | CH(CH₃) (S) | |
| 260 | E12 | 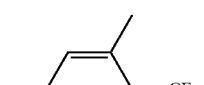 | 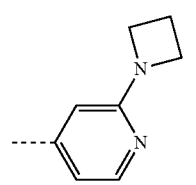 | CH(CH₃) (S) | |

TABLE 1b-continued

| Co. No. | Ex. No. | R¹ | R² | CR³R⁴ | Salt form |
|---|---|---|---|---|---|
| 261 | E12 | 3,4-diCl-phenyl | 2-(isopropylamino)pyridin-4-yl | CH(CH₃) (S) | |
| 262 | E12 | 3-Cl-4-CF₃-phenyl | 2-(isopropylamino)pyridin-4-yl | CH(CH₃) (S) | |
| 263 | E12 | 3,4-diCl-phenyl | 2-(propylamino)pyridin-4-yl | CH(CH₃) (S) | |
| 264 | E12 | 3-Cl-4-CF₃-phenyl | 2-(propylamino)pyridin-4-yl | CH(CH₃) (S) | |
| 265 | E8 | 3-Cl-4-CF₃-phenyl | 2-(fluoromethyl)pyridin-4-yl | CH(CH₃) (S) | |
| 266 | E13 | 4-CF₃-phenyl | 2-(isopropylamino)pyridin-4-yl | CH(CH₃) (S) | |
| 267 | E12 | 3-methyl-4-CF₃-phenyl | 2-(isopropylamino)pyridin-4-yl | CH(CH₃) (S) | |

The values of salt stoichiometry or acid content in the compounds as provided herein, are those obtained experimentally and may vary when using different analytical methods. The content of hydrochloric acid reported herein was determined by ¹H NMR integration and/or elemental analysis. For compound 1 the salt stoichiometry was determined by ion chromatography (hydrochloride and sulfate salts) and by NMR (methanesulfonate and maleate salts).

Analytical Part

Melting Points

Values are peak values, and are obtained with experimental uncertainties that are commonly associated with this analytical method.

Mettler FP 62 (A):

For a number of compounds, melting points were determined in open capillary tubes on a Mettler FP62 apparatus. Melting points were measured with a temperature gradient of 3 or 10° C./minute. Maximum temperature was 300° C. The melting point was read from a digital display.

Mettler FP 62 (A1):

Melting points (m.p.) were determined in open capillary tubes on a Mettler FP62 apparatus. Melting points were measured with a temperature ranging from 50° C. to 300° C., using a gradient of 10° C./minute. The melting point value was read from a digital display.

Mettler FP 81HT/FP90 (B):

For a number of compounds, melting points were determined in open capillary tubes on a FP 81HT/FP90 apparatus (Mettler-Toledo). Melting points were measured with a temperature gradient of 1, 3, 5 or 10° C./minute. Maximum temperature was 300° C. The melting point was read from a digital display.

Mettler Toledo MP50 (C):

For a number of compounds, melting points were determined in open capillary tubes on a Mettler Toledo MP50. Melting points were measured with a temperature gradient of 10° C./minute. Maximum temperature was 300° C. The melting point data was read from a digital display and checked from a video recording system.

DSC823e (D):

For a number of compounds, melting points (m.p.) were determined with a DSC823e (Mettler-Toledo). Melting points were measured with a temperature gradient of 30° C./minute. Maximum temperature was 400° C. Peak values were recorded.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, $[M+CH_3COO]^-$ etc. . . . ). For molecules with multiple isotopic patterns (Br, Cl.), the reported value is the one obtained for the lowest isotope mass. All results were obtained with experimental uncertainties that are commonly associated with the method used.

Hereinafter, "LCT" means LC-Time of Flight, "SQD" Single Quadrupole Detector, "MSD" Mass Selective Detector, "QTOF" Quadrupole-Time of Flight, "RT" room temperature, "BEH" bridged ethylsiloxane/silica hybrid, "DAD" Diode Array Detector.

TABLE 2

LC-MS Methods (Flow expressed in mL/min; column temperature (T) in ° C; Run time in minutes).

| Method | Instrument | Column | Mobile phase | Gradient | Flow Col T | Run time |
|---|---|---|---|---|---|---|
| 1 | Waters: Acquity ® UPLC ® - DAD and SQD | Agilent: Eclipse Plus C18 RRHD (1.8 µm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 50 | 5 |
| 2 | Agilent: HP1100-DAD, Waters: SQD | Agilent: Eclipse Plus C18 (3.5 µm, 2.1 × 30 mm) | A: 95% $CH_3COONH_4$ 6.5 mM + 5% $CH_3CN$, B: 1/1 $CH_3CN$/$CH_3OH$ | 95% A kept for 0.2 min, to 0% A in 2.8 min, held for 0.15 min, back to 95% A in 0.15 min, held for 1.7 min | 1 60 | 5 |
| 3 | Agilent 1100 - DAD-MSD G1956A | YMC-pack ODS-AQ C18 (50 × 4.6 mm, 3 µm) | A: 0.1% HCOOH in $H_2O$ B: $CH_3CN$ | From 95% A to 5% A in 4.8 min, held for 1.0 min, to 95% A in 0.2 min. | 2.6 35 | 6.0 |
| 4 | Waters: Acquity ® UPLC ® - DAD/SQD | Agilent: Eclipse Plus C18 RRHD (1.8 µm, 2.1 × 50 mm) | A: 95% $CH_3COONH_4$ 6.5 mM + 5% $CH_3CN$, B: $CH_3CN$ | From 95% A to 5% A in 1.8 min, held for 0.2 min | 1 50 | 2 |
| 5 | Waters: Acquity ® UPLC ® - DAD/SQD | Waters: CSH ™ C18 (1.7 µm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 50 | 5 |
| 6 | Agilent: HP1100-DAD, MSD G1956B | Agilent: Eclipse Plus C18 (3.5 µm, 2.1 × 30 mm) | A: 95% $CH_3COONH_4$ 6.5 mM + 5% $CH_3CN$, B: $CH_3CN$ | 95% A for 0.2 min, to 0% A in 2.8 min, held for 0.15 min, back to 95% A in 0.15 min, | 1 −60 | 5 |

TABLE 2-continued

LC-MS Methods (Flow expressed in mL/min; column temperature (T) in °C; Run time in minutes).

| Method | Instrument | Column | Mobile phase | Gradient | Flow Col T | Run time |
|---|---|---|---|---|---|---|
| 7 | Waters: Acquity ® UPLC ® - DAD/SQD | Waters: CSH ™ C18 (1.7 µm, 2.1 × 50 mm) | A: 95% CH$_3$COONH$_4$ 6.5 mM + 5% CH$_3$CN, B: CH$_3$CN | held for 1.7 min From 95% A to 40% A in 1.2 min, to 5% A in 0.6 min, held for 0.2 min | 1 −50 | 2 |
| 8 | Waters: Acquity UPLC ® - DAD/ Quattro Micro ™ | Waters: BEH C18 (1.7 µm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 −40 | 6.2 |
| 9 | Agilent: HP1100-DAD, Waters: LCT | Agilent: Eclipse Plus C18 (3.5 µm, 2.1 × 30 mm) | A: 95% CH$_3$COONH$_4$ 6.5 mM + 5% CH$_3$CN, B: CH$_3$CN/CH$_3$OH, 1/1 | From 95% A to 0% A in 5.0 min, held for 0.15 min, back to 95% A in 0.15 min, held for 1.7 min | 1 −60 | 7 |
| 10 | Agilent: HP1100-DAD, Waters: SQD | Agilent: Eclipse Plus C18 (3.5 µm, 2.1 × 30 mm) | A: 95% CH$_3$COONH$_4$ 6.5 mM + 5% CH$_3$CN, B: CH$_3$CN/ CH$_3$OH, 1/1 | From 95% A to 0% A in 5.0 min, held for 0.15 min, back to 95% A in 0.15 min, held for 1.7 min | 1 −60 | 7 |
| 11 | Waters: Acquity ® UPLC ® - DAD/SQD | Agilent: Eclipse Plus C18 RRHD (1.8 µm, 2.1 × 50 mm) | A: 95% CH$_3$COONH$_4$ 6.5 mM + 5% CH$_3$CN, B: CH$_3$CN | From 95% A to 40% A in 1.2 min, to 5% A in 0.6 min, held for 0.2 min | 1 50 | 2 |
| 12 | Waters: Acquity ® UPLC ® - DAD/ QTOF G2-S | Waters: CSH ™ C18 (1.7 µm, 2.1 × 50 mm) | A: 95% CH3COONH4 6.5 mM + 5% CH3CN, B: CH3CN | From 95% A to 40% A in 1.2 min, to 5% A in 0.6 min, held for 0.2 min | 1 −50 | 2 |
| 13 | Waters: Acquity ® UPLC ® - DAD/ QTOF G2-S | Waters: CSH ™ C18 (1.7 µm, 2.1 × 50 mm) | A: 95% CH3COONH4 6.5 mM + 5% CH3CN, B: CH3CN | From 95% A to 5% A in 4.6 min, held for 0.4 min | 1 −50 | 5 |

TABLE 3a

Analytical data - melting point (M.p.) and LCMS: [M + H]$^+$ means the protonated mass of the free base of the compound, [M − H]$^-$ means the deprotonated mass of the free base of the compound or the type of adduct specified [M + CH$_3$COO]$^-$). R$_t$ means retention time (in min). For some compounds, exact mass was determined.

| Co. No. | M.p. (° C.) | [M + H]$^+$ | [M − H]$^-$ or adduct | R$_t$ | LCMS Method |
|---|---|---|---|---|---|
| 1 | 152.6 (B) | 387 | 445 (M + CH$_3$COO)$^-$ | 2.73 | 2 |
| 2 | 181.9 (A) | 373 | 431 (M + CH$_3$COO)$^-$ | 2.07 | 1 |
| 3 | 103.3 (B) | 421 | 479 (M + CH$_3$COO)$^-$ | 2.48 | 1 |
| 4 | 247.0 (A) | 445 | 503 (M + CH$_3$COO)$^-$ | 2.4 | 1 |
| 5 | >300 (A) | 401 | 459 (M + CH$_3$COO)$^-$ | 2.42 | 1 |
| 6 | >300 (A) | 387 | 445 (M + CH$_3$COO)$^-$ | 2.29 | 1 |
| 7 | 126.7 (B) | 367 | 425 (M + CH$_3$COO)$^-$ | 2.25 | 1 |
| 8 | 126.1 (B) | 431 | 489 (M + CH$_3$COO)$^-$ | 2.5 | 1 |
| 9 | 143.6 (B) | 421 | 479 (M + CH$_3$COO)$^-$ | 2.44 | 1 |
| 10 | 85.1 (B) | 405 | 463 (M + CH$_3$COO)$^-$ | 2.32 | 1 |

TABLE 3a-continued

Analytical data - melting point (M.p.) and LCMS: [M + H]⁺ means the protonated mass of the free base of the compound, [M − H]⁻ means the deprotonated mass of the free base of the compound or the type of adduct specified [M + CH₃COO]⁻). $R_t$ means retention time (in min). For some compounds, exact mass was determined.

| Co. No. | M.p. (° C.) | [M + H]⁺ | [M − H]⁻ or adduct | $R_t$ | LCMS Method |
|---|---|---|---|---|---|
| 11 | 159.3 (B) | 387 | 445 (M + CH₃COO)⁻ | 2.19 | 1 |
| 12 | 269.9 (A) | 417 | 475 (M + CH₃COO)⁻ | 2.22 | 1 |
| 13 | 128.9 (B) | 412 | 470 (M + CH₃COO)⁻ | 2.12 | 1 |
| 14 | 201.1 (B) | 401 | 459 (M + CH₃COO)⁻ | 2.33 | 1 |
| 15 | >300 (A) | 353 | 411 (M + CH₃COO)⁻ | 1.96 | 1 |
| 17 | >300 (B) | 397 | 455 (M + CH₃COO)⁻ | 2.25 | 1 |
| 18 | 98.5 (B) | 397 | 455 (M + CH₃COO)⁻ | 2.28 | 1 |
| 19 | 137 (B) | 383 | 441 (M + CH₃COO)⁻ | 2.01 | 1 |
| 20 | 293.6 (B) | 383 | 441 (M + CH₃COO)⁻ | 1.98 | 1 |
| 21 | 219.2 (A) | 351 | 409 (M + CH₃COO)⁻ | 1.99 | 1 |
| 22 | 282.3 (B) | 417 | 475 (M + CH₃COO)⁻ | 2.19 | 1 |
| 23 | 139.2 (A) | 387 | 445 (M + CH₃COO)⁻ | 2.18 | 1 |
| 24 | 119.6 (B) | 387 | 445 (M + CH₃COO)⁻ | 2.29 | 1 |
| 26 | 153.6 (B) | 387 | 445 (M + CH₃COO)⁻ | 2.73 | 2 |
| 27 | 137.1 (A) | 385 | 443 (M + CH₃COO)⁻ | 1.96 | 1 |
| 29 | 140.8 (B) | 401 | 459 (M + CH₃COO)⁻ | 2.41 | 1 |
| 30 | 78.6 (B) | 371 | 429 (M + CH₃COO)⁻ | 2.07 | 1 |
| 31 | 112.8 (B) | 431 | 489 (M + CH₃COO)⁻ | 2.49 | 1 |
| 32 | n.d. | 373 | 431 (M + CH₃COO)⁻ | 2.05 | 1 |
| 33 | 162.8 (B) | 417 | 475 (M + CH₃COO)⁻ | 2.26 | 1 |
| 34 | >300 (B) | 377 | 435 (M + CH₃COO)⁻ | 2.1 | 1 |
| 36 | 128.2 (B) | 387 | 445 (M + CH₃COO)⁻ | 2.25 | 1 |
| 37 | 254.0 (B) | 388 | 446 (M + CH₃COO)⁻ | 1.89 | 1 |
| 38 | 294.0 (B) | 349 | 407 (M + CH₃COO)⁻ | 1.71 | 1 |
| 39 | 185.2 (B) | 391 | 449 (M + CH₃COO)⁻ | 2.08 | 1 |
| 40 | 137.0 (B) | 373 | 431 (M + CH₃COO)⁻ | 1.97 | 1 |
| 41 | 166.9 (B) | 379 | 437 (M + CH₃COO)⁻ | 1.56 | 1 |
| 43 | 203.9 (B) | 435 | 493 (M + CH₃COO)⁻ | 2.59 | 1 |
| 44 | >300 (B) | 416 | 474 (M + CH₃COO)⁻ | 2.21 | 5 |
| 45 | 143.9 (A1) | 403 | 461 (M + CH₃COO)⁻ | 2.51 | 1 |
| 46 | 124.6 (B) | 401 | 459 (M + CH₃COO)⁻ | 2.46 | 1 |
| 47 | 185.6 (B) | 401 | 459 (M + CH₃COO)⁻ | 2.3 | 5 |
| 49 | 183.9 (B) | 445 | 503 (M + CH₃COO)⁻ | 2.61 | 1 |
| 50 | 146.8 (B) | 407 | 465 (M + CH₃COO)⁻ | 2.23 | 1 |
| 51 | 93 (B) | 431 | 489 (M + CH₃COO)⁻ | 2.4 | 1 |
| 52 | >300 (B) | 405 | 463 (M + CH₃COO)⁻ | 1.99 | 5 |
| 53 | 233.1 (B) | 459 | 517 (M + CH₃COO)⁻ | 2.37 | 5 |
| 54 | 205.1 (B) | 435 | 493 (M + CH₃COO)⁻ | 2.39 | 5 |
| 55 | 104.2 (B) | 417 | 475 (M + CH₃COO)⁻ | 2.29 | 5 |
| 56 | 199 (B) | 431 | 489 (M + CH₃COO)⁻ | 2.17 | 5 |
| 57 | 153.2 (B) | 373 | 431 (M + CH₃COO)⁻ | 2.04 | 5 |
| 59 | 214.1 (B) | 426 | 484 (M + CH₃COO)⁻ | 2.1 | 5 |
| 60 | 163.8 (B) | 391 | 449 (M + CH₃COO)⁻ | 2.07 | 5 |
| 61 | 73.3 (B) | 419 | 477 (M + CH₃COO)⁻ | 2.29 | 5 |
| 62 | 141.7 (B) | 371 | 429 (M + CH₃COO)⁻ | 2.09 | 1 |
| 64 | 273.9 (B) | 403 | 461 (M + CH₃COO)⁻ | 2.03 | 5 |
| 68 | >300 (B) | 407 | 465 (M + CH₃COO)⁻ | 2.19 | 5 |
| 70 | n.d. | 401 | 459 (M + CH₃COO)⁻ | 2.29 | 5 |
| 71 | 218.9 (B) | 388 | 446 (M + CH₃COO)⁻ | 1.88 | 1 |
| 72 | 88 (B) | 367 | 425 (M + CH₃COO)⁻ | 2.15 | 1 |
| 73 | 144.3 (B) | 339 | 397 (M + CH₃COO)⁻ | 1.77 | 5 |
| 74 | 99.1 (B) | 447 | 505 (M + CH₃COO)⁻ | 2.03 | 1 |
| 77 | 60.8 (A, Temp. grad.: 3° C./min) | 449 | 507 (M + CH₃COO)⁻ | 2.19 | 1 |
| 88 | 157.75° C. (D) | 428 | 486 (M + CH₃COO)⁻ | 2.29 | 5 |
| 92 | n.d. | 480 | 538 (M + CH₃COO)⁻ | 2.48 | 5 |
| 93 | n.d. | 420 | 478 (M + CH₃COO)⁻ | 2.00 | 5 |
| 94 | n.d. | 446 | 504 (M + CH₃COO)⁻ | 2.28 | 5 |
| 95 | 210.61° C. (D) | 461 | 519 (M + CH₃COO)⁻ | 2.62 | 5 |
| 97 | n.d. | 428 | 486 (M + CH₃COO)⁻ | 2.39 | 5 |
| 99 | 126.4° C. (B) | 441 | 499 (M + CH₃COO)⁻ | 2.63 | 5 |
| 100 | 144.9° C. (B) | 432 | 490 (M + CH₃COO)⁻ | 2.56 | 5 |
| 101 | >300° C. (B) | 444 | 502 (M + CH₃COO)⁻ | 1.91 | 5 |
| 102 | 129.8° C. (B) | 428 | 486 (M + CH₃COO)⁻ | 2.33 | 5 |
| 103 | 164.7° C. (B) | 436 | 494 (M + CH₃COO)⁻ | 2.25 | 5 |
| 104 | 183° C. (B) | 437 | 495 (M + CH₃COO)⁻ | 2.66 | 5 |
| 105 | 124° C. (B) | 442 | 500 (M + CH₃COO)⁻ | 2.61 | 5 |
| 106 | n.d. | 499 | 557 (M + CH₃COO)⁻ | 2.04 | 5 |
| 107 | 294° C. (B) | 456 | 514 (M + CH₃COO)⁻ | 2.92 | 5 |
| 108 | 128.1° C. (B) | 458 | 516 (M + CH₃COO)⁻ | 2.27 | 5 |
| 109 | 149.8° C. (B) | 398 | 456 (M + CH₃COO)⁻ | 2.38 | 5 |

TABLE 3a-continued

Analytical data - melting point (M.p.) and LCMS: [M + H]⁺ means the protonated mass of the free base of the compound, [M − H]⁻ means the deprotonated mass of the free base of the compound or the type of adduct specified [M + CH₃COO]⁻). $R_t$ means retention time (in min). For some compounds, exact mass was determined.

| Co. No. | M.p. (° C.) | [M + H]⁺ | [M − H]⁻ or adduct | $R_t$ | LCMS Method |
|---|---|---|---|---|---|
| 110 | 257.9° C. (B) | 402 | 460 (M + CH₃COO)⁻ | 2.09 | 5 |
| 111 | >300° C. (B) | 417 | 475 (M + CH₃COO)⁻ | 1.96 | 5 |
| 113 | n.d. | 415 | 473 (M + CH₃COO)⁻ | 2.29 | 11 |
| 114 | 177.6° C. (B) | 423 | 481 (M + CH₃COO)⁻ | 2.94 | 2 |
| 115 | n.d. | 405 | 463 (M + CH₃COO)⁻ | 2.79 | 8 |
| 116 | n.d. | 405 | 463 (M + CH₃COO)⁻ | 2.79 | 8 |
| 118 | n.d. | 417 | 475 (M + CH₃COO)⁻ | 2.87 | 8 |
| 119 | n.d. | 417 | 475 (M + CH₃COO)⁻ | 2.87 | 8 |
| 120 | n.d. | 417 | 475 (M + CH₃COO)⁻ | 2.78 | 8 |
| 121 | n.d. | 417 | 475 (M + CH₃COO)⁻ | 2.78 | 8 |
| 122 | n.d. | 413 | 471 (M + CH₃COO)⁻ | 2.55 | 5 |
| 123 | 189.5° C. (B) | 417 | 475 (M + CH₃COO)⁻ | 3.92 | 10 |
| 124 | 62.4° C. (B) | 415 | 473 (M + CH₃COO)⁻ | 2.57 | 5 |
| 125 | 105.4 (A, temp. grad.: 3° C./min) | 403 | 461 (M + CH₃COO)⁻ | 1.81 | 5 |
| 126 | 70.5° C. (B) | 415 | 473 (M + CH₃COO)⁻ | 2.49 | 5 |
| 127 | 155.1° C. (B) | 398 | 456 (M + CH₃COO)⁻ | 2.29 | 5 |
| 128 | 139.8° C. (B) | 417 | 475 (M + CH₃COO)⁻ | 1.87 | 5 |
| 129 | 135.1° C. (B) | 401.3 | 459 (M + CH₃COO)⁻ | 2.92 | 8 |
| 130 | 134.4° C. (B) | 401.3 | 459 (M + CH₃COO)⁻ | 2.92 | 8 |
| 131 | 134.7° C. (B) | 423 | 481 (M + CH₃COO)⁻ | 2.36 | 5 |
| 132 | 148° C. (B) | 423 | 481 (M + CH₃COO)⁻ | 2.33 | 5 |
| 133 | 191.5° C. (B) | 417 | 475 (M + CH₃COO)⁻ | 2.70 | 5 |
| 134 | n.d. | 401 | 459 (M + CH₃COO)⁻ | 2.40 | 5 |
| 135 | 76.8° C. (B) | 403 | 461 (M + CH₃COO)⁻ | 1.76 | 5 |
| 136 | 126.2° C. (B) | 427 | 485 (M + CH₃COO)⁻ | 2.38 | 5 |
| 137 | 193.8° C. (B) | 431 | 489 (M + CH₃COO)⁻ | 2.90 | 5 |
| 138 | 173.9° C. (B) | 431 | 489 (M + CH₃COO)⁻ | 2.78 | 5 |
| 140 | 231.5° C. (B) | 403 | 461 (M + CH₃COO)⁻ | 1.62 | 5 |
| 143 | >300° C. (B) | 417 | 475 (M + CH₃COO)⁻ | 2.17 | 5 |
| 144 | 133.2° C. (B) | 417 | 475 (M + CH₃COO)⁻ | 2.06 | 5 |
| 145 | 57.5° C. (B) | 417 | 475 (M + CH₃COO)⁻ | 2.59 | 5 |
| 146 | 166.8° C. (B) | 417 | 475 (M + CH₃COO)⁻ | 2.67 | 5 |
| 147 | 85.9° C. (B) | 402 | 460 (M + CH₃COO)⁻ | 2.01 | 5 |
| 150 | >300° C. (B) | 403 | 461 (M + CH₃COO)⁻ | 2.39 | 5 |
| 151 | 157.6° C. (B) | 398 | 456 (M + CH₃COO)⁻ | 2.28 | 5 |
| 152 | 105.4° C. (B) | 403 | 461 (M + CH₃COO)⁻ | 2.13 | 5 |
| 153 | 162° C. (B) | 387 | 445 (M + CH₃COO)⁻ | 2.15 | 5 |
| 154 | 169.5° C. (B) | 445 | 503 (M + CH₃COO)⁻ | 2.52 | 5 |
| 155 | 101.8° C. (B) | 398 | 456 (M + CH₃COO)⁻ | 1.86 | 5 |
| 157 | 158.9° C. (B) | 415 | 473 (M + CH₃COO)⁻ | 2.37 | 5 |
| 158 | 48.2° C. (B) | 431 | 489 (M + CH₃COO)⁻ | 2.15 | 5 |
| 159 | 71.5° C. (B) | 387 | 445 (M + CH₃COO)⁻ | 2.27 | 5 |
| 160 | 129.5° C. (B) | 417 | 475 (M + CH₃COO)⁻ | 2.04 | 5 |
| 162 | 185.9° C. (B) | 369 | 427 (M + CH₃COO)⁻ | 1.78 | 5 |
| 163 | n.d. | 419 | 477 (M + CH₃COO)⁻ | 2.08 | 5 |
| 164 | 170.3° C. (A, temp. grad.: 3° C./min) | 391 | 389 | 3.75 | 9 |
| 165 | n.d. | 431 | 489 (M + CH₃COO)⁻ | 2.22 | 5 |
| 166 | 99.8° C. (B) | 416 | 474 (M + CH₃COO)⁻ | 2.33 | 5 |
| 168 | 108.5° C. (B) | 419 | 417 | 2.09 | 5 |
| 169 | 64.7° C. (B) | 437 | 495 (M + CH₃COO)⁻ | 2.39 | 5 |
| 171 | 158.8° C. (B) | 401 | 459 (M + CH₃COO)⁻ | 2.32 | 5 |
| 173 | n.d. | 413 | 471 (M + CH₃COO)⁻ | 2.44 | 5 |
| 174 | 127.5° C. (B) | 403 | 461 (M + CH₃COO)⁻ | 2.12 | 5 |
| 175 | 220.8° C. (B) | 457 | 515 (M + CH₃COO)⁻ | 1.70 | 5 |
| 176 | >300° C. (B) | 457 | 515 (M + CH₃COO)⁻ | 1.78 | 5 |
| 179 | n.d. | 427 | 485 (M + CH₃COO)⁻ | 1.93 | 5 |
| 180 | 76.8° C. (A) | 433 | 491 (M + CH₃COO)⁻ | 2.41 | 5 |
| 181 |  | 423 | 481 (M + CH₃COO)⁻ | 2.08 | 5 |
| 182 | 67.8° C. (B) | 420 | 478 (M + CH₃COO)⁻ | 2.11 | 5 |
| 183 | 125.6° C. (B) | 432 | 490 (M + CH₃COO)⁻ | 2.07 | 5 |
| 184 | n.d. | 420 | 478 (M + CH₃COO)⁻ | 2.73 | 8 |
| 185 | n.d. | 420 | 478 (M + CH₃COO)⁻ | 2.73 | 8 |
| 188 | 161.4° C. (B) | 422 | 480 (M + CH₃COO)⁻ | 2.50 | 5 |
| 189 | 142.4° C. (B) | 432 | 490 (M + CH₃COO)⁻ | 2.46 | 5 |
| 200 | 122.3° C. (A) | 432 | 490 (M + CH₃COO)⁻ | 2.81 | 1 |
| 201 | 119.7° C. (B) | 398 | 456 (M + CH₃COO)⁻ | 2.44 | 5 |
| 204 | 292.8° C. (B) | 422 | 480 (M + CH₃COO)⁻ | 2.51 | 5 |
| 205 | 179.2° C. (B) | 446 | 504 (M + CH₃COO)⁻ | 2.77 | 5 |

TABLE 3a-continued

Analytical data - melting point (M.p.) and LCMS: [M + H]+ means the protonated mass of the free base of the compound, [M − H]− means the deprotonated mass of the free base of the compound or the type of adduct specified [M + CH$_3$COO]−). R$_t$ means retention time (in min). For some compounds, exact mass was determined.

| Co. No. | M.p. (° C.) | [M + H]+ | [M − H]− or adduct | R$_t$ | LCMS Method |
|---|---|---|---|---|---|
| 207 | 147.6° C. (B) | 418 | 476 (M + CH$_3$COO)− | 2.44 | 5 |
| 208 | 141.3° C. (B) | 418 | 476 (M + CH$_3$COO)− | 2.60 | 5 |
| 210 | 125.66° C. (D) | 403 | 461 (M + CH$_3$COO)− | 2.09 | 5 |
| 214 | n.d. | 418 | 476 (M + CH$_3$COO)− | 1.67 | 5 |
| 216 | n.d. | 417 | 415 | 2.59 | 2 |
| 217 | 255.5° C. (B) | 417 | 415 | 2.61 | 2 |
| 219 | n.d. | 403 | 401 | 1.72 | 5 |
| 220 | n.d. | 513 | 572 (M + CH$_3$COO)− | 2.48 | 5 |
| 222 | >300° C. (B) | 405 | 463 (M + CH$_3$COO)− | 2.10 | 5 |
| 225 | n.d. | 499 | 557 (M + CH$_3$COO)− | 1.38 | 7 |
| 226 | n.d. | 407 | 405 | 1.10 | 7 |
| 227 | n.d. | 407 | 405 | 1.10 | 7 |
| 229 | n.d. | 465 | 523 (M + CH$_3$COO)− | 2.40 | 5 |
| 235 | 93 (B) | 470 | 528 (M + CH$_3$COO)− | 1.84 | 5 |
| 236 | >300 (B) | 419 | 477 (M + CH$_3$COO)− | 2.37 | 5 |
| 237 | 125.82 (D) | 433 | 431 | 2.34 | 5 |
| 238 | n.d. | | 439.0995 | 2.32 | 13 |
| 240 | 107.87 (D) | 434 | 492 (M + CH$_3$COO)− | 2.73 | 5 |
| 241 | n.d. | 416 | 474 (M + CH$_3$COO)− | 2.04 | 5 |
| 248 | n.d. | 416 | 474 (M + CH$_3$COO)− | 1.35 | 7 |
| 249 | n.d. | | 478.1874 | 2.47 | 13 | n.d. = not determined

TABLE 3b

Analytical data - melting point (M.p.) and LCMS: [M + H]+ means the protonated mass of the free base of the compound, R$_t$ means retention time (in min), method refers to the method used for LCMS.

| Co. No. | M.p. (° C.) | [M + H]+ | R$_t$ | LCMS Method |
|---|---|---|---|---|
| 16 | 174.0 (A) | 353 | 2.00 | 1 |
| 25 | >300 (A) | 355 | 1.87 | 1 |
| 28 | >300 (A) | 337 | 1.74 | 1 |
| 35 | >300 (A) | 367 | 1.79 | 1 |
| 42 | 250.1 (A) | 377 | 1.71 | 1 |
| 48 | 75.2 (A) | 449 | 2.27 | 1 |
| 58 | 281.9 (C) | 403 | 2.51 | 3 |
| 63 | >300 (C) | 371 | 2.369 | 3 |
| 65 | n.d. | 361 | 2.626 | 3 |
| 66 | 281.8 (C) | 361 | 2.68 | 3 |
| 67 | 138.0 (C) | 405 | 1.16 | 4 |
| 69 | n.d. | 403 | 2.438 | 3 |
| 75 | 186.5 (C) | 362 | 2.087 | 3 |
| 76 | 124.5 (C) | 351 | 2.327 | 3 |
| 78 | 91.1 (B) | 333 | 2.149 | 3 |
| 79 | 266.7 (C) | 377 | 2.314 | 3 |
| 80 | n.d. | 344 | 1.902 | 3 |
| 81 | 288.4 (C) | 363 | 2.241 | 3 |
| 82 | 144.2 (B) | 355 | 2.178 | 3 |
| 83 | 94.5 (A) (10° C./min) | 363 | 2.178 | 3 |
| 84 | 101.2 (A) (10° C./min) | 385 | 2.263 | 3 |
| 85 | 133.0 (A) (10° C./min) | 367 | 2.278 | 3 |
| 86 | 137.9° C. (A) | 319.2 | 2 | 3 |
| 87 | n.d. | 403 | 0.99 | 1 |
| 89 | 136.75 (D) | 369 | 2.17 | 5 |
| 90 | 93.7 (A, temp. grad.: 3° C./min) | 434 | 2.33 | 5 |
| 91 | 86 (A, temp. grad.: 3° C./min) | 434 | 2.34 | 5 |
| 96 | 262.88 (D) | 462 | 2.85 | 6 |
| 98 | n.d. | 419 | 2.15 | 5 |
| 112 | 154.9 (A, temp. grad.: 3° C./min) | 405 | 2.16 | 5 |
| 117 | n.d. | 405 | 2.26 | 5 |
| 139 | 182.3 (B) | 397 | 1.97 | 5 |
| 141 | 93.5 (B) | 375 | 2.51 | 5 |
| 142 | >300 (B) | 403 | 2.45 | 5 |
| 148 | 149.7 (A1, 10° C./min) | 363.2 | 1.79 | 3 |
| 149 | 197.7 (C) | 363 | 0.36 | 3 |
| 156 | 123.7 (B) | 359 | 2.06 | 5 |
| 161 | 82.7 (B) | 383 | 1.92 | 5 |
| 167 | 96.7 (B) | 387 | 2.10 | 5 |
| 170 | 276.2 (B) | 403 | 1.70 | 5 |
| 172 | 124.7 (B) | 367 | 2.02 | 5 |
| 177 | 174.13 (D) | 469 | 2.72 | 5 |
| 178 | n.d. | 368 | 1.81 | 5 |
| 186 | >300 (A) | 388 | 2.28 | 1 |
| 187 | 131.4 (B) | 354 | 2.02 | 1 |
| 190 | 117.6 (B) | 374 | 2.02 | 5 |
| 191 | 60.7 (A, temp. grad.: 3° C./min) | 382 | 1.97 | 5 |
| 192 | 155.9 (B) | 402 | 2.43 | 5 |
| 193 | 58 (B) | 402 | 2.31 | 5 |
| 194 | >300 (B) | 402 | 2.26 | 5 |
| 195 | 75.9 (B) | 398 | 2.08 | 5 |
| 196 | 136.9 (B) | 368 | 2.18 | 5 |
| 197 | 146.6 (A, temp. grad.: 3° C./min) | 392 | 2.37 | 5 |
| 198 | 112.8 (B) | 368 | 2.09 | 5 |
| 199 | 112.8 (A) | 432 | 2.37 | 1 |
| 202 | 255.8 (B) | 388 | 2.35 | 5 |
| 203 | 131.8 (B) | 388 | 2.31 | 5 |
| 206 | n.d. | 384 | 2.21 | 5 |

TABLE 3b-continued

Analytical data - melting point (M.p.) and LCMS: [M + H]$^+$ means the protonated mass of the free base of the compound, $R_t$ means retention time (in min), method refers to the method used for LCMS.

| Co. No. | M.p. (° C.) | [M + H]$^+$ | $R_t$ | LCMS Method |
|---|---|---|---|---|
| 209 | 138.26 (D) | 459 | 2.91 | 6 |
| 211 | n.d. | 374 | 1.99 | 1 |
| 212 | n.d. | 514 | 1.44 | 11 |
| 213 | n.d. | 480 | 1.32 | 7 |
| 215 | n.d. | 407 | 1.33 | 7 |
| 218 | 167.3 (A, temp. grad.: 3° C./min) | 407 | 2.50 | 5 |
| 221 | n.d. | 513 | 2.40 | 5 |
| 223 | n.d. | 451 | 2.97 | 2 |
| 224 | n.d. | 407 | 2.80 | 2 |
| 228 | n.d. | 425 | 1.40 | 7 |
| 230 | n.d. | 445 | 1.25 | 12 |
| 231 | n.d. | 432 | 1.12 | 7 |
| 232 | n.d. | 432 | 1.11 | 7 |
| 233 | n.d. | 418 | 0.96 | 7 |
| 234 | n.d. | 437 | 2.88 | 13 |
| 239 | n.d. | 417 | 0.99 | 7 |
| 242 | n.d. | 432 | 2.44 | 5 |
| 243 | 72.44 (D) | 420.1455 | 2.38 | 13 |
| 244 | 188.41 (D) | 373.0626 (+0.3 mDa) | 1.11 | 12 |
| 245 | n.d. | 446.1820 | 2.0 | 13 |
| 246 | n.d. | 448.1765 (+0.5 mDa) | 2.43 | 13 |
| 247 | 155.12 (D) | 391.1184 (+0.2 mDa) | 2.33 | 13 |
| 250 | 158.03 (D) | 447.1756 (0.0 mDa) | 2.78 | 13 |
| 251 | 151.45 (D) | 416.1698 (−0.0 mDa) | 2.29 | 13# |
| 252 | n.d. | 437.0994 (+0.2 mDa) | 1.94 | 13 |
| 253 | n.d. | 430.1857 (+0.3 mDa) | 2.63 | 13 |
| 254 | n.d. | 464.1469 (+0.4 mDa) | 2.88 | 13 |
| 255 | 136.39 (D) | 450.1310 (+0.2 mDa) | 2.52 | 13 |
| 256 | 153.60 (D) | 430.1855 (+0.1 mDa) | 2.48 | 13 |
| 257 | n.d. | 416.1046 (+0.1 mDa) | 2.38 | 13 |
| 258 | 121.41 (D) | 444.2012 (+0.1 mDa) | 2.7 | 13 |
| 259 | 115.50 (D) | 430.1856 (+0.2 mDa) | 2.49 | 13 |
| 260 | 141.74 (D) | 442.1852 (−0.2 mDa) | 2.56 | 13 |
| 261 | n.d. | 430.1202 (+0.1 mDa) | 2.54 | 13 |
| 262 | 116.12. | 464.1463 (−0.2 mDa) | 2.71 | 13 |
| 263 | n.d. | 430.1199 (−0.2 mDa) | 2.55 | 13 |
| 264 | n.d. | 464.1465 (+0.0 mDa) | 2.72 | 13 |
| 265 | n.d. | 439.0951 (+0.2 mDa) | 2.50 | 13 |
| 266 | 173.08 | 430.1853 (−0.1 mDa) | 2.51 | 13 |
| 267 | 131.30 | 444.2012 (+0.1 mDa) | 2.69 | 13 | n.d. = not determined

General Procedure

The SFC measurement was performed using Analytical system from Berger instrument comprising a FCM-1200 dual pump fluid control module for delivering carbon dioxide ($CO_2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 ta, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

TABLE 4

Analytical SFC-MS Methods (Flow expressed in mL/min; column temperature (T) in ° C.; Pressure in Mpa).

| Method | Column | Mobile Phase | Flow | T | Pressure |
|---|---|---|---|---|---|
| 1 | Chiralcel OD-H 250 × 4.6 mm, 5 μm Daicel | $CO_2$/EtOH (0.3% IPrNH$_2$) 70/30 | 3 | 35 | 100 |
| 2 | Chiralpak IC 250 × 4.6 mm 5 μm Daicel | $CO_2$/EtOH (0.3% IPrNH$_2$) 70/30 | 3 | 35 | 100 |
| 3 | Chiralpak IC 250 × 4.6 mm 5 μm Daicel | $CO_2$/EtOH (0.3% IPrNH$_2$) 60/40 | 3 | 35 | 100 |
| 4 | Chiralpak IC 250 × 4.6 mm, 5 μm Daicel | $CO_2$/MeOH (0.3% IPrNH$_2$)/ iPrOH (0.3% IPrNH$_2$) 80/10/10 | 3 | 35 | 100 |
| 5 | Chiralpak AD-H 150 × 4.6 mm, 5 μm Daicel | $CO_2$/MeOH (0.3% IPrNH$_2$)/ iPrOH (0.3% IPrNH$_2$) 60/20/20 | 3 | 35 | 100 |

TABLE 5

Analytical SFC data-$R_t$ means retention time (in minutes), [M + H]$^+$ means the protonated mass of the compound, method refers to the method used for SFC/MS analysis of enantiomerically pure compounds. The measurement was compared against the mixture.

| Co. No. | $R_t$ | [M + H]$^+$ | UV Area % | Isomer Elution Order | Method |
|---|---|---|---|---|---|
| 130 | 2.65 | 401 | 100 | A | 1 |
| 129 | 3.84 | 401 | 100 | B | 1 |
| 120 | 3.28 | 417 | 100 | A | 2 |
| 121 | 4.40 | 417 | 100 | B | 2 |
| 119 | 4.86 | 417 | 100 | A | 3 |
| 118 | 6.86 | 417 | 100 | B | 3 |
| 116 | 3.74 | 405 | 100 | A | 4 |
| 115 | 5.24 | 405 | 100 | B | 4 |
| 184 | 3.62 | 420 | 100 | A | 5 |
| 185 | 5.22 | 420 | 100 | B | 5 |

Optical Rotations

Optical rotations were measured on a Perkin-Elmer 341 polarimeter with a sodium lamp and reported as follows: [u]° (λ, c g/100 ml, solvent, T° C.). $[\alpha]_\lambda^T = (100a)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 6

| Optical Rotation data. | | | | | |
|---|---|---|---|---|---|
| Co. No. | $\alpha_D$ (°) | Wavelength (nm) | Concentration w/v % | Solvent | Temp. (° C.) |
| 1 | +21.2 | 589 | 0.59 | DMF | 20 |
| 3 | +26.4 | 589 | 1.26 | DMF | 20 |
| 4 | +16.8 | 589 | 0.48 | DMF | 20 |
| 7 | +16.9 | 589 | 0.56 | DMF | 20 |
| 8 | +21.5 | 589 | 0.54 | DMF | 20 |
| 9 | +19.8 | 589 | 0.40 | DMF | 20 |

TABLE 6-continued

Optical Rotation data.

| Co. No. | $\alpha_D$ (°) | Wavelength (nm) | Concentration w/v % | Solvent | Temp. (° C.) |
|---|---|---|---|---|---|
| 10 | +21.6 | 589 | 0.82 | DMF | 20 |
| 12 | +18.8 | 589 | 0.56 | DMF | 20 |
| 13 | +22.4 | 589 | 0.52 | DMF | 20 |
| 14 | +19.9 | 589 | 0.54 | DMF | 20 |
| 16 | +25.8 | 589 | 0.49 | DMF | 20 |
| 18 | +19.1 | 589 | 0.54 | DMF | 20 |
| 19 | +22.5 | 589 | 0.49 | DMF | 20 |
| 21 | +18.6 | 589 | 0.53 | DMF | 20 |
| 23 | +23.5 | 589 | 0.63 | DMF | 20 |
| 24 | +18.6 | 589 | 0.54 | DMF | 20 |
| 26 | −22.5 | 589 | 0.59 | DMF | 20 |
| 27 | +16.6 | 589 | 0.61 | DMF | 20 |
| 28 | +20.7 | 589 | 0.68 | DMF | 20 |
| 29 | +18.6 | 589 | 0.52 | DMF | 20 |
| 30 | +14.9 | 589 | 0.54 | DMF | 20 |
| 31 | −22.9 | 589 | 0.52 | DMF | 20 |
| 34 | +18.1 | 589 | 0.64 | DMF | 20 |
| 36 | +19.6 | 589 | 0.48 | DMF | 20 |
| 37 | +17.7 | 589 | 0.49 | DMF | 20 |
| 42 | +18.2 | 589 | 0.59 | DMF | 20 |
| 43 | +25.1 | 589 | 0.54 | DMF | 20 |
| 44 | +22.9 | 589 | 0.48 | DMF | 20 |
| 45 | +20.5 | 589 | 0.68 | DMF | 20 |
| 46 | +22.3 | 589 | 0.49 | DMF | 20 |
| 47 | +26.0 | 589 | 0.50 | DMF | 20 |
| 48 | +17.0 | 589 | 0.54 | DMF | 20 |
| 49 | +21.1 | 589 | 0.50 | DMF | 20 |
| 50 | +27.4 | 589 | 0.50 | DMF | 20 |
| 51 | +19.9 | 589 | 0.52 | DMF | 20 |
| 53 | +23.7 | 589 | 0.40 | DMF | 20 |
| 54 | +26.7 | 589 | 0.50 | DMF | 20 |
| 55 | +24.8 | 589 | 0.65 | DMF | 20 |
| 56 | +16.1 | 589 | 0.50 | DMF | 20 |
| 57 | +24.1 | 589 | 0.58 | DMF | 20 |
| 59 | +27.9 | 589 | 0.42 | DMF | 20 |
| 60 | +20.7 | 589 | 0.57 | DMF | 20 |
| 61 | +23.1 | 589 | 0.52 | DMF | 20 |
| 62 | +23.0 | 589 | 0.55 | DMF | 20 |
| 64 | +20.4 | 589 | 0.58 | DMF | 20 |
| 68 | +24.1 | 589 | 0.59 | DMF | 20 |
| 71 | +24.9 | 589 | 0.50 | DMF | 20 |
| 72 | +22.7 | 589 | 0.48 | DMF | 20 |
| 73 | +22.9 | 589 | 0.58 | DMF | 20 |
| 77 | +16.4 | 589 | 0.48 | DMF | 20 |
| 88 | +20.3 | 589 | 1.0 | DMF | 20 |
| 90 | −2.1 | 589 | 0.53 | DMF | 20 |
| 91 | +3.0 | 589 | 0.51 | DMF | 20 |
| 92 | +24.7 | 589 | 0.50 | DMF | 20 |
| 94 | +22.3 | 589 | 0.60 | DMF | 20 |
| 95 | +26.1 | 589 | 1.00 | DMF | 20 |
| 96 | +45.1 | 589 | 0.60 | DMF | 25 |
| 97 | +32.6 | 589 | 1.50 | DMF | 20 |
| 98 | +22.5 | 589 | 0.45 | DMF | 20 |
| 99 | +18.7 | 589 | 1.45 | DMF | 20 |
| 100 | +26.4 | 589 | 0.49 | DMF | 20 |
| 101 | +20.3 | 589 | 0.50 | DMF | 20 |
| 102 | +21.2 | 589 | 0.51 | DMF | 20 |
| 103 | +27.1 | 589 | 0.88 | DMF | 20 |
| 104 | +25.2 | 589 | 0.50 | DMF | 20 |
| 105 | +21.2 | 589 | 0.55 | DMF | 20 |
| 107 | +18.8 | 589 | 0.55 | DMF | 20 |
| 108 | +19.4 | 589 | 0.55 | DMF | 20 |
| 109 | +26.1 | 589 | 0.51 | DMF | 20 |
| 110 | +22.6 | 589 | 0.52 | DMF | 20 |
| 112 | +20.7 | 589 | 0.49 | DMF | 20 |
| 113 | +15.6 | 589 | 0.53 | DMF | 20 |
| 114 | +20.0 | 589 | 0.49 | DMF | 20 |
| 115 | +3.9 | 589 | 0.52 | DMF | 20 |
| 116 | −2.5 | 589 | 0.56 | DMF | 20 |
| 117 | +26.4 | 589 | 0.48 | DMF | 20 |
| 118 | −33.8 | 589 | 0.61 | DMF | 20 |
| 119 | +38.8 | 589 | 0.58 | DMF | 20 |
| 120 | +44.2 | 589 | 0.63 | DMF | 20 |
| 121 | −45.9 | 589 | 0.61 | DMF | 20 |
| 123 | +18.8 | 589 | 0.62 | DMF | 20 |
| 124 | +23.2 | 589 | 0.53 | DMF | 20 |
| 125 | +23.6 | 589 | 0.52 | DMF | 20 |
| 126 | +17.5 | 589 | 0.58 | DMF | 20 |
| 127 | +25.7 | 589 | 0.58 | DMF | 20 |
| 129 | +12.2 | 589 | 0.54 | DMF | 20 |
| 130 | −12.6 | 589 | 0.52 | DMF | 20 |
| 131 | +21.5 | 589 | 0.51 | DMF | 20 |
| 132 | +21.1 | 589 | 0.6 | DMF | 20 |
| 133 | +18.7 | 589 | 0.71 | DMF | 20 |
| 135 | +19.5 | 589 | 0.55 | DMF | 25 |
| 136 | +15.9 | 589 | 0.53 | DMF | 20 |
| 137 | +17.6 | 589 | 0.50 | DMF | 20 |
| 138 | +11.9 | 589 | 0.51 | DMF | 20 |
| 139 | +21.6 | 589 | 0.57 | DMF | 20 |
| 140 | +20.3 | 589 | 0.57 | DMF | 20 |
| 141 | +17.2 | 589 | 0.45 | DMF | 20 |
| 142 | +25.0 | 589 | 0.49 | DMF | 20 |
| 145 | +18.6 | 589 | 0.54 | DMF | 20 |
| 146 | +21.5 | 589 | 0.61 | DMF | 20 |
| 147 | +21.1 | 589 | 0.51 | DMF | 20 |
| 150 | +20.3 | 589 | 0.49 | DMF | 20 |
| 151 | +19.8 | 589 | 0.59 | DMF | 20 |
| 152 | +15.6 | 589 | 0.50 | DMF | 20 |
| 153 | −30.9 | 589 | 0.58 | DMF | 20 |
| 154 | +20.7 | 589 | 0.51 | DMF | 20 |
| 155 | +19.9 | 589 | 0.51 | DMF | 20 |
| 156 | +14.5 | 589 | 0.48 | DMF | 20 |
| 157 | +22.6 | 589 | 0.52 | DMF | 20 |
| 158 | +27.9 | 589 | 0.60 | DMF | 20 |
| 159 | +14.0 | 589 | 0.51 | DMF | 20 |
| 160 | +16.1 | 589 | 0.62 | DMF | 20 |
| 161 | −16.8 | 589 | 0.46 | DMF | 20 |
| 162 | −33.9 | 589 | 0.54 | DMF | 20 |
| 163 | +20.4 | 589 | 0.50 | DMF | 20 |
| 164 | +27.2 | 589 | 0.50 | DMF | 20 |
| 166 | +21.8 | 589 | 0.50 | DMF | 20 |
| 167 | +12.4 | 589 | 0.41 | DMF | 20 |
| 168 | +22.2 | 589 | 0.61 | DMF | 20 |
| 169 | +21.7 | 589 | 0.77 | DMF | 20 |
| 171 | −0.7 | 589 | 0.74 | DMF | 20 |
| 172 | +16.7 | 589 | 0.64 | DMF | 20 |
| 174 | +25.8 | 589 | 0.52 | DMF | 20 |
| 175 | +15.4 | 589 | 0.51 | DMF | 20 |
| 176 | +13.3 | 589 | 0.50 | DMF | 20 |
| 177 | +19.2 | 589 | 0.49 | DMF | 20 |
| 178 | +11.5 | 589 | 0.49 | DMF | 20 |
| 179 | +13.0 | 589 | 0.49 | DMF | 20 |
| 180 | +15.5 | 589 | 0.45 | DMF | 20 |
| 182 | +18.3 | 589 | 0.40 | DMF | 20 |
| 183 | +19.7 | 589 | 0.40 | DMF | 20 |
| 184 | +0.5 | 589 | 0.47 | DMF | 20 |
| 185 | −4.9 | 589 | 0.51 | DMF | 20 |
| 186 | +11.1 | 589 | 0.46 | DMF | 20 |
| 187 | +30.5 | 589 | 0.49 | DMF | 20 |
| 188 | −16.8 | 589 | 0.59 | DMF | 20 |
| 189 | +42.8 | 589 | 0.53 | DMF | 20 |
| 190 | +29.4 | 589 | 0.54 | DMF | 20 |
| 191 | +28.3 | 589 | 0.53 | DMF | 20 |
| 195 | −55.0 | 589 | 0.53 | DMF | 20 |
| 196 | +26.8 | 589 | 0.62 | DMF | 20 |
| 197 | +33.7 | 589 | 0.54 | DMF | 20 |
| 198 | +35.2 | 589 | 0.52 | DMF | 20 |
| 199 | −16.0 | 589 | 0.48 | DMF | 20 |
| 200 | +0.8 | 589 | 0.46 | DMF | 20 |
| 201 | −5.3 | 589 | 1.00 | DMF | 20 |
| 202 | +24.2 | 589 | 0.54 | DMF | 20 |
| 203 | +39.4 | 589 | 0.52 | DMF | 20 |
| 204 | +46.3 | 589 | 0.84 | DMF | 20 |
| 205 | +3.2 | 589 | 0.50 | DMF | 20 |
| 206 | −2.2 | 589 | 0.49 | DMF | 20 |
| 207 | +33.1 | 589 | 0.58 | DMF | 20 |
| 208 | +1.3 | 589 | 0.54 | DMF | 25 |
| 209 | +5.9 | 589 | 1.40 | DMF | 20 |
| 210 | +28.5 | 589 | 0.51 | DMF | 20 |
| 218 | +17.6 | 589 | 0.49 | DMF | 25 |

TABLE 6-continued

Optical Rotation data.

| Co. No. | $\alpha_D$ (°) | Wavelength (nm) | Concentration w/v % | Solvent | Temp. (° C.) |
|---|---|---|---|---|---|
| 235 | +18.6 | 589 | 0.60 | DMF | 25 |
| 237 | +10.5 | 589 | 0.50 | DMF | 20 |
| 240 | +2.2 | 589 | 0.55 | DMF | 20 |
| 241 | +20.3 | 589 | 0.50 | DMF | 20 |
| 242 | +21.5 | 589 | 0.50 | DMF | 20 |
| 243 | +19.0 | 589 | 0.51 | DMF | 20 |
| 250 | +2.3 | 589 | 0.48 | DMF | 20 |
| 253 | +16.2 | 589 | 0.69 | DMF | 20 |
| 255 | +25.0 | 589 | 0.54 | DMF | 20 |
| 257 | +16.4 | 589 | 0.40 | DMF | 20 |
| 258 | +23.7 | 589 | 0.80 | DMF | 20 |
| 259 | +21.3 | 589 | 0.57 | DMF | 20 |
| 260 | +19.4 | 589 | 0.49 | DMF | 20 |
| 261 | +21.4 | 589 | 0.54 | DMF | 20 |
| 262 | 25.9 | 589 | 0.51 | DMF | 20 |
| 263 | 19.2 | 589 | 0.52 | DMF | 20 |
| 264 | 23.3 | 589 | 0.49 | DMF | 20 |
| 266 | 20.3 | 589 | 0.53 | DMF | 20 |
| 267 | 20.3 | 589 | 0.51 | DMF | 20 |

NMR

Co. No. 237: $^1$H NMR (500 MHz, CDCl$_3$) δ ppm 1.72 (d, J=6.6 Hz, 3H) 2.96 (d, J=5.2 Hz, 3H) 4.05 (s, 3H) 4.42 (dd, J=13.7, 7.1 Hz, 1H) 4.53-4.59 (m, 1H) 4.64 (dd, J=13.6, 4.0 Hz, 1H) 4.70-4.78 (m, 1H) 6.76 (s, 1H) 6.84 (d, J=5.2 Hz, 1H) 7.78 (d, J=8.7 Hz, 1H) 7.77 (s, 1H) 7.88 (d, J=8.4 Hz, 1H) 8.13 (d, J=5.2 Hz, 1H)

Pharmacological Examples

The compounds provided in the present invention are negative allosteric modulators of mGluR2. These compounds appear to inhibit glutamate responses by binding to an allosteric site other than the glutamate binding site. The response of mGluR2 to a concentration of glutamate is decreased when compounds of Formula (I) are present. Compounds of Formula (I) are expected to have their effect substantially at mGluR2 by virtue of their ability to reduce the function of the receptor. The effects of negative allosteric modulators tested at mGluR2 using the [$^{35}$S]GTPγS binding assay method described below and which is suitable for the identification of such compounds, and more particularly the compounds according to Formula (I), are shown in Table 7.

1) [$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein a subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the antagonist can be determined. mGlu2 receptors are shown to be preferentially coupled to Gαl-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the negative allosteric modulation (NAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with an Ultra Turrax homogenizer. The suspension was centrifuged at 12,400 RPM (Sorvall F14S-6×250Y) for 10 minutes and the supernatant discarded. The pellet was homogenized in 5 mM Tris-HCl, pH 7.4 using an Ultra Turrax homogenizer and centrifuged again (13,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 negative allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM MgCl$_2$ and 10 µM GDP. Human mGlu2 receptor-containing membranes were thawed on ice and diluted in assay buffer supplemented with 18 µg/ml saponin. Membranes were pre-incubated with compound together with a predefined (~EC$_{80}$) concentration of glutamate (60 µM) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 µg of membrane protein in 10 mM HEPES acid, 10 mM HEPES salt, pH 7.4, 100 mM NaCl, 3 mM MgCl$_2$, 10 µM GDP and 10 µg/ml saponin. Total reaction volume was 200 µl. Reactions were terminated by rapid filtration through Unifilter-96 GF/B plates (Perkin Elmer, Massachusetts, USA) using a 96-well filtermate universal harvester. Filters were washed 6 times with ice-cold 10 mM NaH$_2$PO$_4$/10 mM Na$_2$HPO$_4$, pH 7.4. Filters were then air-dried, and 30 µl of liquid scintillation cocktail (Microscint-O) was added to each well. Membrane-bound radioactivity was counted in a Topcount.

Data Analysis

The concentration-response curves of representative compounds of the present invention were generated using the Lexis software interface (developed at J&J). Data were calculated as % of the control glutamate response, defined as the response that is generated upon addition of an EC$_{80}$-equivalent concentration of glutamate. Sigmoid concentration-response curves plotting these percentages versus the log concentration of the test compound were analyzed using non-linear regression analysis. The concentration producing half-maximal inhibition was calculated as the IC$_{50}$. The pIC$_{50}$ values were calculated as the −log IC$_{50}$, when the IC$_{50}$ is expressed in M. E$_{max}$ is defined as the relative maximal effect (i.e. maximal % inhibition relative to the control glutamate response).

TABLE 7

Pharmacological data for compounds according to the invention.

| Co. No. | GTPγS-hmGluR2 anGT pIC$_{50}$ | GTPγS-hmGluR2 anGT Emax |
|---|---|---|
| 1 | 8.05 | 106 |
| 2 | 7.65 | 104 |
| 3 | 8.75 | 106 |
| 4 | 8.48 | 104 |
| 5 | 8.29 | 105 |
| 6 | 8.3 | 106 |
| 6a | 8.32 | 112 |
| 7 | 8.12 | 102 |
| 8 | 8.23 | 105 |
| 9 | 7.98 | 103 |
| 10 | 7.93 | 104 |
| 11 | 7.72 | 103 |
| 12 | 7.71 | 104 |
| 13 | 7.53 | 103 |
| 14 | 7.62 | 104 |
| 15 | 7.58 | 103 |
| 16 | 7.29 | 102 |
| 17 | 7.32 | 104 |
| 18 | 7.28 | 102 |
| 19 | 7.16 | 105 |
| 20 | 7.06 | 104 |
| 21 | 7.21 | 107 |
| 22 | 7.16 | 104 |
| 23 | 6.96 | 104 |
| 24 | 6.92 | 104 |
| 25 | 6.84 | 103 |
| 26 | 6.76 | 105 |
| 27 | 6.86 | 104 |
| 28 | 6.62 | 105 |
| 29 | 6.64 | 102 |
| 30 | 6.59 | 104 |
| 31 | 6.36 | 107 |
| 32 | 6.25 | 101 |
| 33 | 6.24 | 99 |
| 34 | 6.25 | 100 |
| 35 | 6.22 | 100 |
| 36 | 6.08 | 100 |
| 37 | 6.01 | 99 |
| 38 | 6.02 | 103 |
| 39 | 5.79 | 100 |
| 40 | 5.83 | 105 |
| 41 | 5.45 | 95 |
| 42 | 5.51 | 102 |
| 43 | 8.54 | 107 |
| 44 | 8.21 | 105 |
| 45 | 8 | 104 |
| 46 | 8.2 | 105 |
| 47 | 8.19 | 105 |
| 48 | 8.11 | 100 |
| 49 | 8.06 | 103 |
| 50 | 8.02 | 103 |
| 51 | 7.96 | 104 |
| 52 | 7.98 | 107 |
| 53 | 8.01 | 102 |
| 54 | 7.98 | 105 |
| 55 | 7.79 | 104 |
| 56 | 7.79 | 102 |
| 57 | 7.89 | 104 |
| 58 | 7.66 | 107 |
| 59 | 7.45 | 98 |
| 60 | 7.5 | 101 |
| 61 | 7.55 | 106 |
| 62 | 7.48 | 105 |
| 63 | 7.47 | 105 |
| 64 | 7.58 | 103 |
| 65 | 7.35 | 106 |
| 66 | 7.39 | 107 |
| 67 | 7.2 | 104 |
| 68 | 7.15 | 100 |
| 69 | 7.27 | 103 |
| 70 | 7.1 | 106 |
| 71 | 7.01 | 103 |
| 72 | 6.97 | 103 |
| 73 | 6.89 | 102 |
| 74 | 6.67 | 100 |
| 75 | 6.56 | 100 |
| 76 | 6.55 | 100 |
| 77 | 6.41 | 101 |
| 78 | 6.32 | 103 |
| 79 | 6.29 | 104 |
| 80 | 6.29 | 107 |
| 81 | 6.27 | 103 |
| 82 | 6.2 | 101 |
| 83 | 6.1 | 104 |
| 84 | 6.09 | 104 |
| 85 | 6.02 | 101 |
| 86 | 6 | 102 |
| 87 | n.t. | |
| 88 | 7.39 | 102 |
| 89 | 7.38 | 104 |
| 90 | 8.51 | 103 |
| 91 | 7.25 | 103 |
| 92 | 8.53 | 107 |
| 93 | 7.74 | 105 |
| 94 | 7.26 | 108 |
| 95 | 8.75 | 110 |
| 96 | 8.91 | 108 |
| 97 | 8.78 | 104 |
| 98 | 8.19 | 111 |
| 99 | 7.84 | 108 |
| 100 | 8.16 | 109 |
| 101 | 6.39 | 109 |
| 102 | 8.08 | 107 |
| 103 | 8.55 | 107 |
| 104 | 8.43 | 108 |
| 105 | 7.56 | 108 |
| 106 | 6.22 | 109 |
| 107 | 7.75 | 114 |
| 108 | 6.91 | 108 |
| 109 | 7.73 | 107 |
| 110 | 8.29 | 108 |
| 111 | 6.53 | 108 |
| 112 | 7.45 | 103 |
| 113 | 7.04 | 103 |
| 114 | 8.15 | 104 |
| 115 | 8.15 | 108 |
| 116 | 6.25 | 105 |
| 117 | 8.12 | 109 |
| 118 | 7.71 | 105 |
| 119 | 5.6 | 100 |
| 120 | 7.19 | 106 |
| 121 | 4.79 | 75 |
| 122 | 8.43 | 108 |
| 123 | 8.18 | 107 |
| 124 | 8.52 | 108 |
| 125 | 6.75 | 105 |
| 126 | 8.24 | 108 |
| 127 | 7.56 | 103 |
| 128 | 6.23 | 104 |
| 129 | 6.16 | 100 |
| 130 | 7.77 | 102 |
| 131 | 7.61 | 105 |
| 132 | 7.62 | 103 |
| 133 | 8.08 | 104 |
| 134 | 8.49 | 104 |
| 135 | 6.19 | 103 |
| 136 | 7.36 | 102 |
| 137 | 7.74 | 107 |
| 138 | 7.17 | 105 |
| 139 | 7.44 | 106 |
| 140 | 6.29 | 104 |
| 141 | 7.21 | 102 |
| 142 | 8.18 | 105 |
| 143 | 7.61 | 104 |

TABLE 7-continued

Pharmacological data for compounds according to the invention.

| Co. No. | GTPγS-hmGluR2 anGT pIC$_{50}$ | GTPγS-hmGluR2 anGT Emax |
|---|---|---|
| 144 | 7.02 | 103 |
| 145 | 7.73 | 105 |
| 146 | 7.78 | 105 |
| 147 | 8.24 | 106 |
| 148 | 5.25 | 100 |
| 149 | <4.3 | 49 |
| 150 | 6.33 | 103 |
| 151 | 5.92 | 103 |
| 152 | 8 | 105 |
| 153 | 7.84 | 103 |
| 154 | 7.7 | 104 |
| 155 | 7.09 | 103 |
| 156 | 7.25 | 106 |
| 157 | 8.06 | 104 |
| 158 | 7.6 | 106 |
| 159 | 7.87 | 104 |
| 160 | 6.97 | 106 |
| 161 | 4.81 | 76 |
| 162 | 6.89 | 102 |
| 163 | 7.96 | 103 |
| 164 | 8.26 | 107 |
| 165 | 7.71 | 102 |
| 166 | 8.6 | 102 |
| 167 | 6.12 | 105 |
| 168 | 7.6 | 106 |
| 169 | 8.22 | 105 |
| 170 | 7.14 | 107 |
| 171 | 4.77 | 94 |
| 172 | 5.98 | 105 |
| 173 | 8.36 | 106 |
| 174 | 8 | 105 |
| 175 | 5.87 | 102 |
| 176 | 5.2 | 85 |
| 177 | 8.03 | 105 |
| 178 | 7.62 | 107 |
| 179 | 7.44 | 103 |
| 180 | 7.88 | 106 |
| 181 | 6.38 | 103 |
| 182 | 8.08 | 106 |
| 183 | 7.64 | 103 |
| 184 | 6.56 | 105 |
| 185 | 8.22 | 104 |
| 186 | 7.42 | 102 |
| 187 | 6.49 | 108 |
| 188 | 8.39 | 108 |
| 189 | 7.39 | 102 |
| 190 | 6.68 | 105 |
| 191 | 5.97 | 109 |
| 192 | 8.13 | 106 |
| 193 | 7.72 | 103 |
| 194 | 6.86 | 107 |
| 195 | 5.39 | 92 |
| 196 | 7.3 | 107 |
| 197 | 6.82 | 104 |
| 198 | 7.04 | 104 |
| 199 | 4.59 | 67 |
| 200 | 8.23 | 105 |
| 201 | 8.08 | 105 |
| 202 | 7.99 | 103 |
| 203 | 8.17 | 105 |
| 204 | 8.31 | 107 |
| 205 | 7.99 | 102 |
| 206 | 7.75 | 111 |
| 207 | 8.42 | 109 |
| 208 | 7.65 | 107 |
| 209 | 8.19 | 104 |
| 210 | 7.63 | 105 |
| 211 | 5.43 | 92 |
| 212 | n.t. | |
| 213 | n.t. | |
| 214 | n.t. | |
| 215 | n.t. | |
| 216 | n.t. | |
| 217 | 5.35 | 97 |
| 218 | n.t. | |
| 219 | n.t. | |
| 220 | n.t. | |
| 221 | n.t. | |
| 222 | n.t. | |
| 223 | n.t. | |
| 224 | n.t. | |
| 225 | n.t. | |
| 226 | n.t. | |
| 227 | n.t. | |
| 228 | n.t. | |
| 229 | n.t. | |
| 230 | n.t. | |
| 231 | n.t. | |
| 232 | n.t. | |
| 233 | n.t. | |
| 234 | n.t. | |
| 235 | 5.9 | 102 |
| 236 | 8.14 | 105 |
| 237 | 8.5 | 111 |
| 238 | 5.67 | 103 |
| 239 | n.t. | |
| 240 | 8.17 | 109 |
| 241 | 7.74 | 109 |
| 242 | 7.89 | 110 |
| 243 | 7.65 | 116 |
| 244 | 5.06 | 80 |
| 245 | n.t. | |
| 246 | 8.38 | 116 |
| 247 | 7.52 | 109 |
| 248 | n.t. | |
| 249 | 8.08 | 109 |
| 250 | 8.4 | 120 |
| 251 | 8.2 | 116 |
| 252 | n.t. | |
| 253 | 8.21 | 111 |
| 254 | 8.77 | 109 |
| 255 | 8.82 | 107 |
| 256 | 8.44 | 108 |
| 257 | 8.44 | 108 |
| 258 | 8.22 | 108 |
| 259 | 7.75 | 105 |
| 260 | 8.45 | 105 |
| 261 | 7.96 | 107 |
| 262 | 8.21 | 109 |
| 263 | 8.33 | 109 |
| 264 | 8.57 | 108 |
| 265 | 8.26 | 111 |
| 266 | 7.28 | 106 |
| 267 | 7.65 | 107 | n.t. means not tested

2) Reversal of the Effect of the mGluR2 PAM JNJ-42153605 on Scopolamine-Induced Hyperlocomotion Apparatus Motor activity was measured in microprocessor-based motor activity arenas (closed gray PVC cylinders with a height of 39 cm and a diameter of 31 cm). Each arena was placed on an infrared LED (8×8 LEDs) lit box (white PVC squared box; 40×40 cm$^2$; height 12.5 cm. An infrared-sensitive tube camera and a white light source were mounted to the ceiling above the observation chamber to track the animal. The total distance traveled (cm) was recorded and analyzed using the Noldus Ethovision XT Video Tracking System (Version 7.0.418; Noldus, Wageningen, The Netherlands). The intensity of the light within the activity cages (measured in the centre at the level of the floor) ranged between 4 and 8 LUX.

General Procedure

The rats were pretreated with test compound or vehicle at 60 min before the start of the activity recordings and placed into individual cages. The rats were challenged with JNJ-42153605 (3-(cyclopropylmethyl)-7-(4-phenylpiperidin-1-yl)-8-(trifluoromethyl)[1,2,4]triazolo[4,3-a]pyridine; WO2010/130424; Cid et al. *J. Med. Chem.* 2012, 55, 8770-8789) (20 mg/kg, i.v.) 30 min before the start of the activity recording combined with scopolamine (0.16 mg/kg, i.v.) just before the start of the activity measurements. Immediately after the injection of scopolamine, the rats were placed into the activity monitors and total distance travelled over the first 30 min was measured.

Solvent-Pretreated Control Rats.

Figure 1:
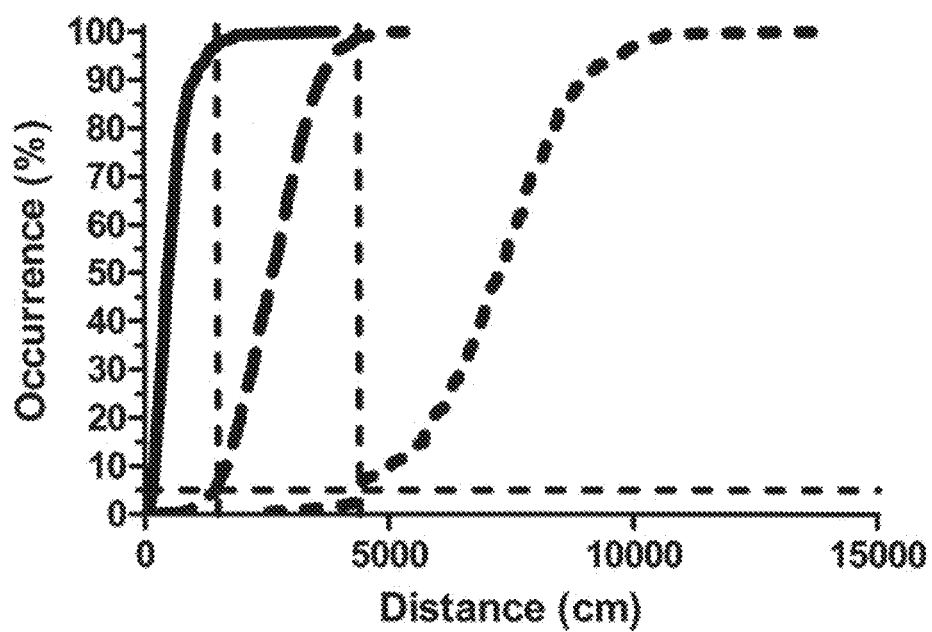
FIG. 1 shows the frequency distributions for distance traveled obtained in historical series of solvent-pretreated control rats.

Frequency distributions obtained in historical series of solvent-pretreated control rats are given in FIG. 1 and Table 8 below. Animals receiving the combination of JNJ-42153605 and scopolamine (n=433) almost always travelled a distance of less than 1500 cm (<1500 cm) (only 2.5% of the control rats travelled a distance of more than 1500 cm (>1500 cm)). On the other hand, animals challenged with scopolamine alone (n=215) always travelled a total distance of more than 1500 cm (>1500 cm) and almost always (in 95.8% of the rats) a distance of more than 4400 cm (>4400 cm). Rats that did not receive any challenge travelled almost always a distance of more than 1500 cm (>1500 cm) (in 93.3% of the rats) and less than 4400 cm (<4400 cm) (in 98.9% of the rats). For reversal of the inhibitory effect of JNJ-42153605 on the scopolamine-induced hyperlocomotion, two all-or-none criteria were adopted: (1) reversal: total distance >1500 cm; (2) normalization: total distance >4400 cm. The results on the reversal of the effect of JNJ-42153605 are shown in table 9 below.

TABLE 8

Frequency distributions obtained in historical series of solvent-pretreated control rats.

|  | Median (cm) | >1500 cm (%) | >4400 cm (%) | $N_{tested}$ |
|---|---|---|---|---|
| Combination | 480 | 2.5 | 0.0 | 433 |
| No challenge | 2618 | 93.3 | 1.1 | 638 |
| Scopolamine | 7246 | 100 | 95.8 | 215 |

$N_{tested}$ means number of animals tested.

TABLE 9

Reversal of the effect of JNJ 42153605 on scopolamine-induced hyperlocomotion.

| Co. No. | Route | $ED_{50}$ | Co. No. | Route | $ED_{50}$ |
|---|---|---|---|---|---|
| 26 | SC | >10 |  | SC | ≥10 |
| 1 | PO | 0.45 | 16 | SC | ≥10 |
|  | SC | 3.54 | 15 | PO | 1.26 |
| 8 | PO | 5 | 12 | PO | 1.25 |
| 2 | PO | 1.26 | 201 | PO | >2.5 |
| 186 | PO | 3.15 | 147 | PO | 0.50 |
| 6 | PO | 0.80 | 142 | PO | 1.99 |
| 200 | PO | 3.15 | 236 | PO | >2.5 |
| 4 | PO | 1.26 | 127 | PO | 1.99 |
| 5 | PO | ≥2.5 | 104 | PO | ≥2.5 |
| 14 | PO | 5 | 103 | PO | 0.96 |
| 19 | PO | ≥10 | 102 | PO | ≥2.5 |
| 3 | PO | 1.99 | 100 | PO | >10 |

TABLE 9-continued

Reversal of the effect of JNJ 42153605 on scopolamine-induced hyperlocomotion.

| Co. No. | Route | $ED_{50}$ | Co. No. | Route | $ED_{50}$ |
|---|---|---|---|---|---|
| 10 | PO | 0.79 | 99 | PO | ≥2.5 |
| 9 | PO | ≥2.5 | 95 | PO | >2.5 |
| 13 | PO | 7.94 | 180 | PO | ≥2.5 |
| 18 | PO | ≥10 | 182 | PO | 1.99 |
| 45 | PO | 1.26 | 237 | PO | 1.99 |
| 46 | PO | ≥2.5 | 242 | PO | >2.5 |
| 43 | PO | 1.26 | 251 | PO | >0.63 |
| 47 | PO | 1.99 | 255 | PO | 0.79 |
| 44 | PO | ≥2.5 | 256 | PO | ≥2.5 |
| 152 | PO | 1.99 | 257 | PO | ≥2.5 |
| 166 | PO | 0.50 |  |  |  |

$ED_{50}$ means effective dose;
PO means oral route;
SC means subcutaneous route.

3) V-Maze Test

The V-maze-test is a two-trial short term visual-spatial working memory task based on spontaneous exploration of a new and a familiar arm in a 2-arm maze (Embrechts et al. (2013) "Longitudinal characterization of the TauPS2APP mouse model of Alzheimer's disease in a two trial discrimination task of visuo-spatial recognition memory", 45$^{th}$ European Brain and Behaviour Society Meeting 6-9 Sep. 2013, Munich, Abstract P202). Performance in this task can be disrupted by a low dose of PCP, such that the animals do not discriminate anymore between the new and a familiar arm.

Method

Male Long Evans rats (Janvier, France, body weight 280 to 295 g) were group housed in enriched individually ventilated cages and habituated to environmental conditions for 5 days. After acclimatization, animals were single housed for 4 days until testing. During this period animals were handled for 2 min per day and received sham dosing once a day for 3 days prior to the test. The V-maze consisted of two arms (L×W×H: 70×10×30 cm) at a 900 angle to each other to form a V-shaped maze connected by guillotine doors to a center zone. The walls of each arm were of a different context displaying horizontally black and white striped in one arm vs. uniform black walls in the other. Background infra-red illumination was provided via the bottom of the maze and a top view video camera above the platform was used for video recording of the experiments. The animal's exploration of each arm was automatically quantified using Ethovision XT 7.0 (Noldus, The Netherlands). Animals were treated with Co. No. 1 or its vehicle (20% HP-13-CD+1 eq. HCl) administered p.o. 4 h before the start of the test. PCP (0.75 mg/kg s.c.) or its vehicle (0.9% NaCl solution) was administered 30 min prior to the test. The test consisted of 2 sessions of 5 min each: in the first session (exploration) the animal was placed in the center zone and given access to one of both arms (=familiar). After 5 min, the animal was taken out of the maze, the door of the other arm (new) was also opened, and the animal was put back in the center zone for a second session (choice). The time spent in the familiar and new arm respectively during the choice session was recorded for 5 min.

Results

Figure 2:
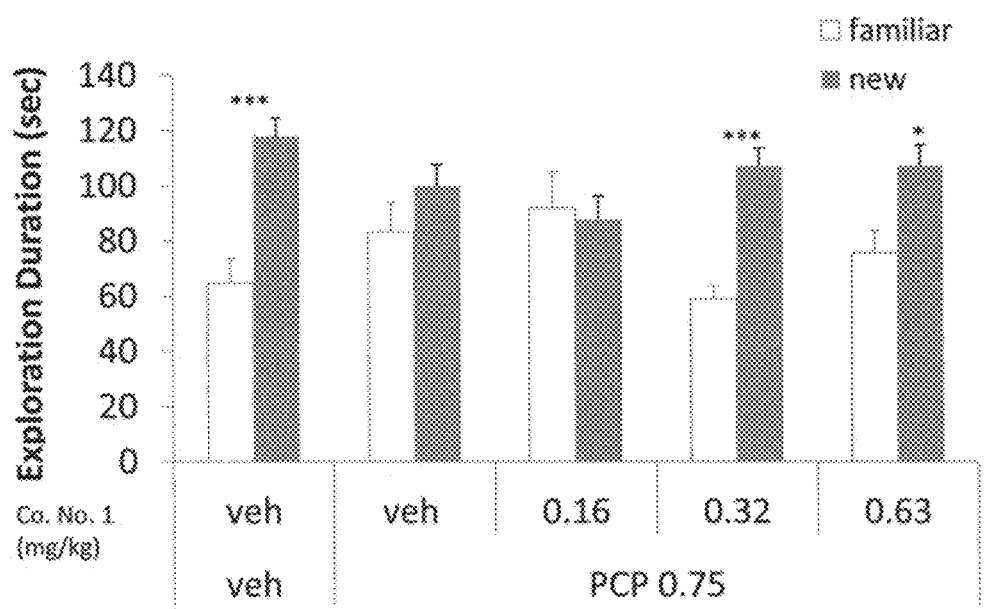
FIG. 2 shows the effect of Co. No. 1 (mg/kg p.o., 4 h prior to test) on exploration times of the new vs. the familiar arm by rats in the absence or presence of PCP (0 (=veh) or 0.75 mg/kg s.c., 0.5 h prior to test) in the V-maze. Data are reported as Mean±SEM, n=12/group; ANOVA with LSD-post hoc, p vs. familiar arm: *** $p<0.001$, *<0.05.

Co. No. 1 was evaluated in rats in a series of dose-response studies evaluating doses from 0.16 to 10 mg/kg. While control animals (treated with vehicle of the test compound and the vehicle of PCP) displayed a strong preference for exploration of the new vs. the familiar arm in the second session, the PCP-treated rats did not discriminate anymore between both arms in each of these studies. PCP-challenged rats that were pretreated with Co. No. 1 at doses from 0.32 mg/kg onwards showed again a clear preference for the new arm (FIG. 2). This reversal effect against PCP was observed up to the highest dose tested (10 mg/kg).

4) Reserpine Interaction Test in Rats

Some exemplified compounds were observed to induce mydriasis in rats. It was investigated to what extent the mydriatic action of test compounds was sufficient to counteract the miosis induced by the monoamines-depleting agent reserpine (10 mg/kg; SC) in Wiga rats. Test compounds induced mydriasis before the reserpine challenge (time=−1 h unless otherwise stated; Table 10).

For instance, Co. No. 1 induced mydriasis before the reserpine challenge ($ED_{50}$: 1.78 mg/kg s.c.; 1.55 mg/kg p.o., −1 h; 0.89 mg/kg, p.o., −4 h) and reversed the reserpine-induced ptosis ($ED_{50}$: 1.03 mg/kg s.c.; 0.78 mg/kg p.o., −1 h; 0.78 mg/kg, p.o., −4 h), miosis ($ED_{50}$: 4.1 mg/kg s.c.; 9.4 mg/kg p.o., −1 h; 9.4 mg/kg, p.o., −4 h) and sedation ($ED_{50}$: 9.4 mg/kg s.c.; 7.1 mg/kg p.o., −1 h; 14 mg/kg, p.o., −4 h). The effects are illustrated in FIG. 3. Co. No. 1 did not affect the tail-pinch response before reserpine nor the reserpine-induced blockade of the tail-pinch response and did not induce scratching or hyperemia after reserpine. The reference mGlu2 NAMs RO-4995819 (40 mg/kg, p.o.), RO-4491533 (40 mg/kg, p.o.; 10 mg/kg, s.c.) and [CAS 579473-69-1] (40 mg/kg, s.c.) were devoid of these interactions with reserpine.

Without wishing to be bound by theory, the observed effect may be mediated by a mechanism different from, and additional to, mGluR2 NAM activity.

TABLE 10

Reversal of reserpine-induced ptosis
(reserpine; 10 mg/kg; SC; −1 h) in Wigarats.

| Co. No. | Route | Time | $ED_{50}$ |
|---|---|---|---|
| 40 | PO | 60 | 0.32 |
| 33 | PO | 60 | 0.5 |
| 26 | PO | 60 | 0.50 |
| 31 | PO | 60 | 0.79 |
| 1 | PO | 60 | 0.67 |
|  |  | 240 | 0.89 |
|  | SC | 60 | 1.01 |
| 2 | PO | 60 | 0.32 |
| 186 | PO | 60 | 3.15 |
| 200 | PO | 60 | 0.13 |
| 35 | PO | 60 | >10 |
| 41 | PO | 60 | 3.15 |
| 38 | PO | 60 | 5 |
| 36 | PO | 60 | 5 |
| 24 | PO | 60 | ≥10 |
| 34 | PO | 60 | 0.8 |
| 22 | PO | 60 | 0.13 |
| 79 | PO | 60 | 5 |
| 78 | PO | 60 | ≥10 |
| 82 | PO | 60 | 5 |
| 81 | PO | 60 | 5 |
| 80 | PO | 60 | >2.5 |
| 148 | PO | 60 | 1.99 |
| 83 | PO | 60 | 5 |
| 86 | PO | 60 | ≥10 |
| 187 | PO | 60 | 3.15 |
| 149 | PO | 60 | 1.99 |
| 84 | PO | 60 | 1.26 |
| 45 | PO | 60 | 1.26 |
| 150 | PO | 60 | >10 |
| 85 | PO | 60 | 1.99 |
| 190 | PO | 60 | 5 |
| 191 | PO | 60 | 3.15 |
| 44 | PO | 60 | 3.15 |
| 194 | PO | 60 | 5 |

TABLE 10-continued

Reversal of reserpine-induced ptosis
(reserpine; 10 mg/kg; SC; −1 h) in Wigarats.

| Co. No. | Route | Time | $ED_{50}$ |
|---|---|---|---|
| 195 | PO | 60 | 1.25 |
| 161 | PO | 60 | 3.15 |
| 167 | PO | 60 | 0.1 |
| 147 | PO | 60 | 7.94 |
| 171 | PO | 60 | 5 |
| 172 | PO | 60 | 1.26 |
| 129 | PO | 60 | ≥10 |
| 125 | PO | 60 | 5 |
| 119 | PO | 60 | >2.5 |
| 116 | PO | 60 | ≥10 |
| 244 | PO | 60 | 7.94 |

5) Ro-4-1284 Interaction Test in Rats

The relative ability of Co. No. 1 to increase palpebral opening was also studied in rats challenged with another monoamines depleting agent, viz. Ro-4-1284 (1.25 mg/kg, s.c.). Effects on body temperature immediately before the injection of Ro-4-1284 were also measured. The cumulative palpebral opening score (every 5 min over a 1-h period) was used for evaluation. The median cumulative palpebral opening in solvent-pretreated control animals (n=70) was 18; a scores >25 occurred in only 1.4% of these control animals and was adopted as all-or-none criterion for drug-induced reversal of the Ro-4-1284-induced palpebral ptose. Co. No. 1 increased palpebral opening to scores >25 ($ED_{50}$: 0.51 mg/kg, p.o.) without affecting body temperature (>10 mg/kg, p.o.).

6) Reversal of LY-404039-Induced Decrease of Palpebral Opening in Apomorphine-Challenged Rats.

Male Wiga Wistar rats (Crl:WI; Charles River Germany; 220±40 g) were housed under standard laboratory conditions (21±2° C.; 50-65% relative humidity; light-dark cycle set at 12 h; lights on at 6.00 h) and fasted overnight prior to the start of the experiments (tap water remained available ad libitum). During the test period, they were housed in individual cages. The local Ethical Committee approved all studies in compliance with the Declaration of Helsinki. Palpebral opening was scored every 5 min over the first hour after injection of apomorphine (1.0 mg/kg, i.v.) in animals either pretreated or not pretreated with LY-404039 (2.5 mg/kg, s.c.) at 1 h prior to the apomorphine injection. The animals were also pretreated with test compound or solvent at a predefined interval before apomorphine challenge. The score system was: (5) exophthalmos, (4) wide open, (3) open for three-quarters, (2) half open, (1) open for one-quarter, (0) closed. The scores for palpebral opening were cumulated over the 60-min observation period. A cumulative palpebral opening score >26 was selected for drug-induced reversal of the LY-404039-induced decrease of palpebral opening (occurrence in 3.2% of control animals pretreated with LY-404039 (n=154) versus in 99.5% of control rats not pretreated with LY-404039 (n=6335)).

Table 11a shows the palpebral opening score in control animals receiving apomorphine alone and in animals receiving apomorphine and LY-404039. In animals receiving apomorphine alone the median palpebral opening is 43 whereas in animals receiving apomorphine and LY-404039, the median palpebral opening is 17. In animals treated with apomorphine alone, the palpebral opening score is almost always (in 95.5% of the rats) greater than 34, whereas in animals treated with the combination (apomorphine+LY-404039) only 3.2% of the animals show palpebral opening greater than 26.

TABLE 11a

Palpebral opening score in control animals.

| Measurement | Apomorphine alone (n = 6335) | Apomorphine + LY-404039 (n = 154) |
|---|---|---|
| Palpebral opening score | | |
| Median score: | 43 | 17 |
| Occurrence score >26 (%): | 99.5 | 3.2 |
| Occurrence score >34 (%): | 95.9 | 0.0 |

TABLE 11b

Reversal of LY-404039-induced decrease of palpebral opening in apomorphine challenged rats.

| Co. No. | Route | ED$_{50}$ |
|---|---|---|
| 33 | PO | >2.5 |
| 31 | PO | ≥10 |
| 1 | PO | 0.45 |
|  | SC | 0.3 |
| 8 | PO | 5 |
| 15 | PO | 11.22 |
| 2 | PO | 0.50 |
| 5 | PO | >10 |
| 45 | PO | 0.79 |
| 46 | PO | 0.32 |
| 44 | PO | 0.50 |
| 167 | PO | >40 |
| 147 | PO | 1.26 |
| 172 | SC | >40 |
| 140 | PO | 1.99 |

7) Reversal of mGluR2-Agonism in Hippocampal Brain Slices

INTRODUCTION

Electrophysiology recordings of field excitatory postsynaptic potentials (fEPSPs) in acute hippocampal brain slices represent a model for testing synaptic transmission and plasticity. The effect of Co. No. 1 on synaptic transmission and plasticity in dentate gyrus synapses was investigated using this model. This region was chosen because of the high expression of mGluR 2 (Shigemoto et al., The Journal of Neuroscience, Oct. 1, 1997, 17(19), 7503-7522).

Methods

Figure 4A:
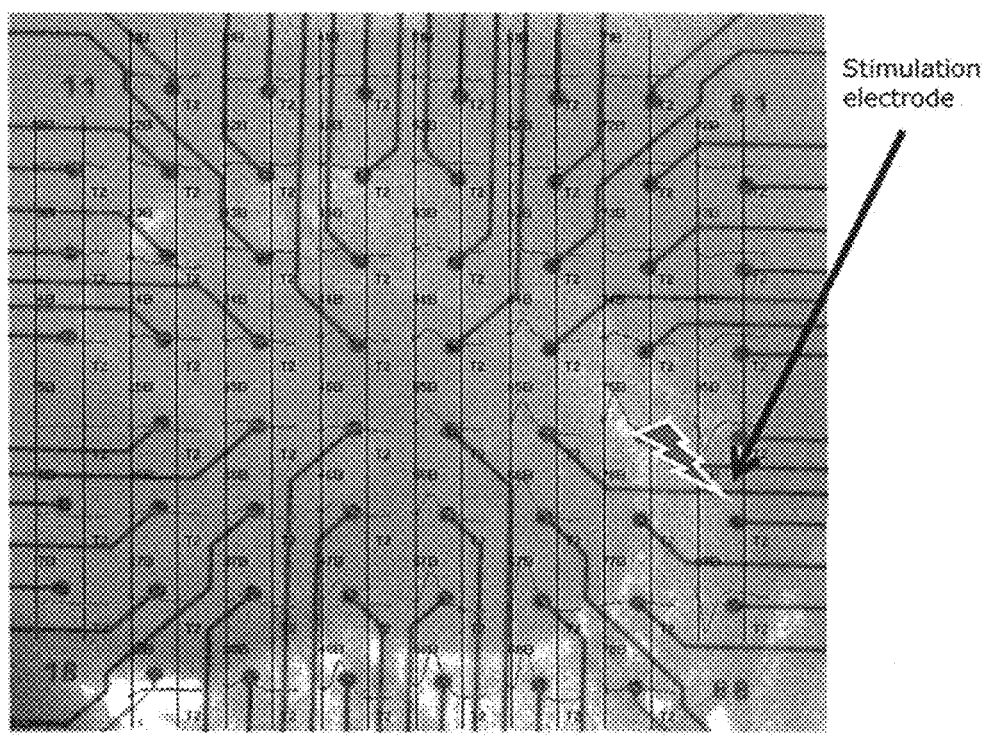
FIGS. 4a-4b illustrate the placement of the hippocampus brain slice in a well of a MEA biochip, with 60×3D-tip electrodes (black dots). Traces show the recorded potential at each electrode (FIG. 4a), and the captured fEPSP traces of paired pulses separated by 30 ms (FIG. 4b). The preparation was perfused with artificial cerebrospinal fluid (ACSF). (3D=three-dimensional; fEPSP=field excitatory postsynaptic potentials; MEA=micro-electrode array; ms=milliseconds).
Figure 4B:
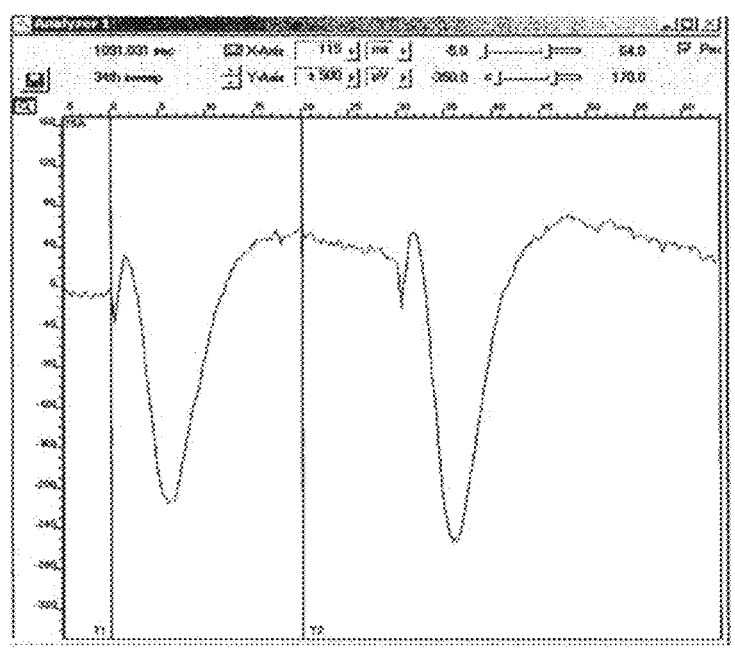

Recordings of fEPSPs were made from hippocampal brain slices using a multi-electrode array (MEA) biochip, and 3-dimensional- (3D) tip electrodes, according to a standard protocol. These recordings were used to monitor glutamate-mediated synaptic transmission (FIG. 4).

Results

Figure 5A:
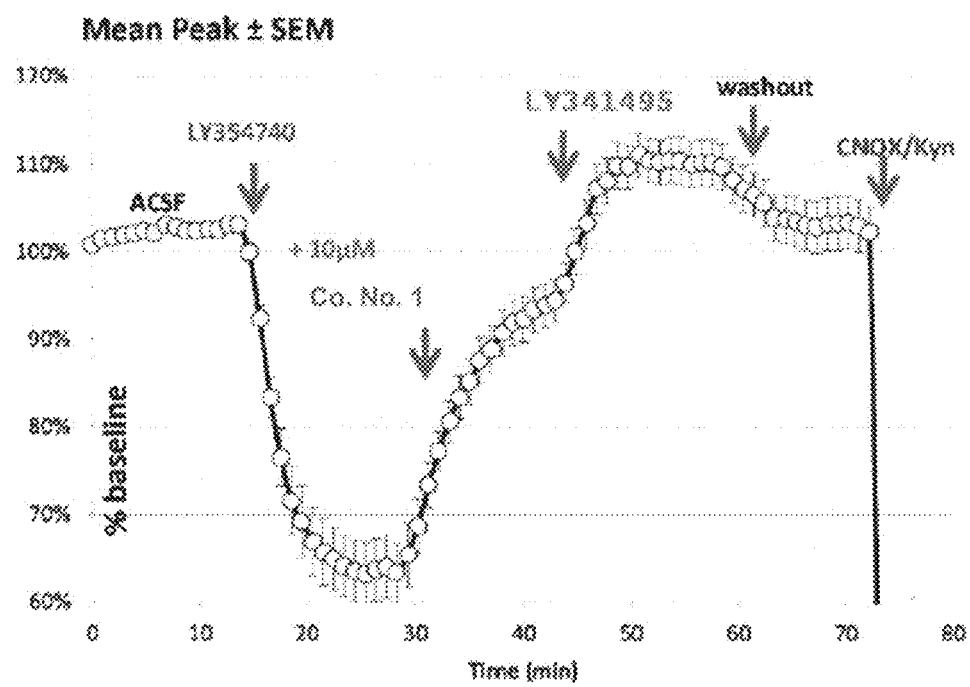
FIGS. 5a-5b show how Co. No. 1 restores fEPSP depressed by 1 μM LY-354740 in the dentate gyrus of rat hippocampal brain slices.
Figure 5B:
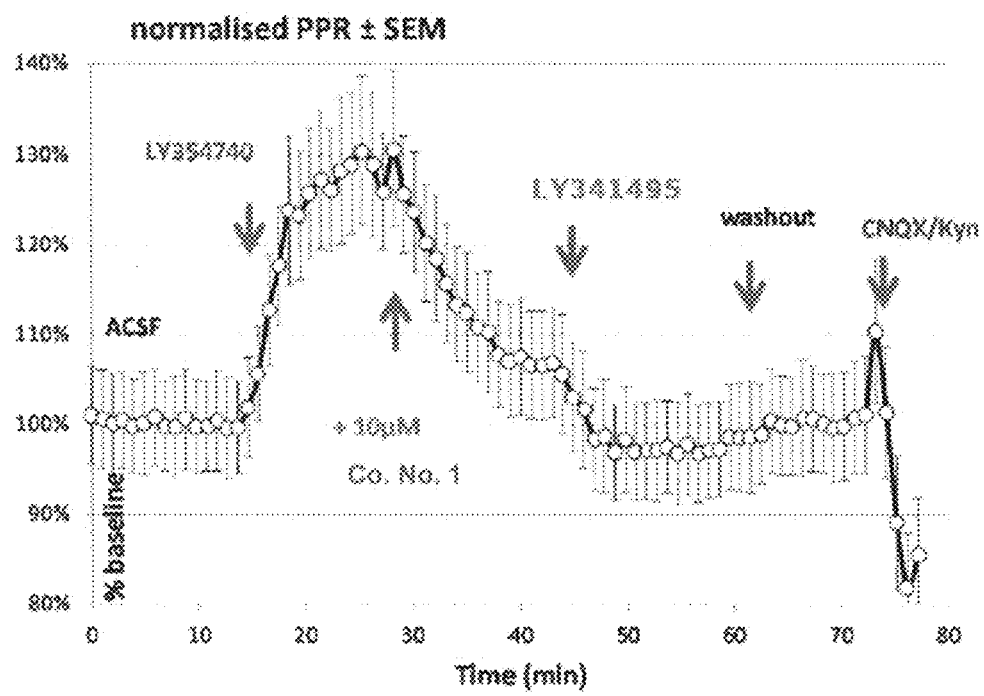

Superfusion of rat hippocampal brain slices with the mGlu2/3-specific agonist LY-354740 (1 µM) depressed fEPSP by 50% within 15 min of application (FIG. 5) and was associated with an increase of the paired-pulse ratio (PPR), indicating a presynaptic mechanism. Fifteen min after the application of 10 µM Co. No. 1 the depression of fEPSP had recovered by 80%. This was associated with a decrease of the PPR, indicating an increase in neurotransmitter release (FIG. 5, n=17 slices from 4 rats).

Subsequently, the effects of Co. No. 1 on synaptic function using long-term potentiation (LTP) protocols in the dentate gyrus (Goeldner et. al., Neuropharmacology 2013, 64, 337-346) were evaluated.

Small magnitude LTP (110%) was induced using isolated glutamatergic-mediated fEPSP: trains of theta-burst stimulation that are known to induce LTP at these particular synapses were applied (Dinklo et al., J. Pharmacol. Exp. Ther. 2011, 336(2), 560-574). In the presence of 10 µM Co. No. 1, the magnitude of LTP was enhanced by 150% compared to baseline (p=0.005). Also noteworthy is the finding that the post-theta potentiation (PTP) in the presence of 10 µM Co. No. 1 was significantly different from vehicle treatment: 160% vs. 120% respectively (p=0.01) (FIG. 6, 22 slices from 4 SD rats). At the end of the experiments, addition of 1 mM kynurenic acid to block glutamatergic neurotransmission, confirmed that the post-synaptic response is mediated by glutamate neurotransmission.

DISCUSSION

LY-354740 stimulates presynaptic mGlu2/3 receptors to limit the release of glutamate. Furthermore, the effects of Group II mGluR agonists and antagonists in rodent models of cognition are totally absent in mGluR2 knock-out mice (Higgins et al. Neuropharmacology, 2004, 46, 907-917). Co. No. 1 reversed synaptic depression evoked by the mGlu2/3-agonist LY-354740. These data illustrate that Co. No. 1 is able to restore depressed synaptic transmission in rat hippocampal slices in vitro. The increase in network excitability, as a result of enhanced excitatory neurotransmission, affected the threshold of LTP induction. Thus, LTP was efficiently induced by weak theta stimulation, but only when Co. No. 1 was pre-applied. Thus, the compound might act as a cognitive enhancer via an ability to elevate the synaptic strength in glutamatergic synapses and by priming the system for enhanced LTP.

Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment
Active ingredient 5 to 1000 mg

| Active ingredient | 5 to 1000 mg |
| --- | --- |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A method for treating a patient suffering from depression, comprising administering to the patient in need thereof a therapeutically effective amount of a compound of Formula (I):

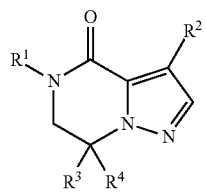

or a pharmaceutically acceptable salt, stereoisomeric form or N-oxide thereof,
wherein:
  $R^1$ is phenyl or 2-pyridinyl, each optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, $C_{1-4}$alkyl-O—$C_{1-4}$alkyl, monohalo$C_{1-4}$alkyloxy, polyhalo$C_{1-4}$alkyloxy, $C_{1-4}$alkyl-OH, $C_{1-4}$alkylthio, monohalo$C_{1-4}$alkylthio, polyhalo$C_{1-4}$alkylthio, cyano, $C_{3-7}$cycloalkyl, and $SF_5$, wherein the $C_{3-7}$cycloalkyl is optionally substituted with trifluoromethyl; or
  $R^1$ is

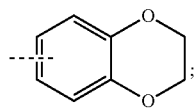

$R^2$ is

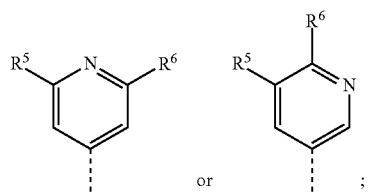

$R^5$ and $R^6$ are each independently selected from the group consisting of hydrogen, halo, cyano, $C_{1-4}$alkyl, $C_{1-4}$alkyl-OH, $C_{3-7}$cycloalkyl, monohalo$C_{1-4}$alkyl, polyhalo$C_{1-4}$alkyl, $C_{1-4}$alkyl-O—$C_{1-4}$alkyl, O—$C_{1-4}$alkyl, monohalo$C_{1-4}$alkyloxy, polyhalo $C_{1-4}$alkyloxy, and NR'R''; and
  R' and R'' are each independently selected from the group consisting of hydrogen and $C_{1-4}$alkyl; or
  R' and R'', together with the nitrogen atom to which they are attached, form a heterocyclic group selected from the group consisting of 1-azetidinyl, 1-pyrrolidinyl, and 1-piperidinyl, wherein the 1-azetidinyl, 1-pyrrolidinyl, and 1-piperidinyl are each optionally substituted with a halo substituent.

$R^3$ is selected from the group consisting of hydrogen and $C_{1-4}$alkyl;
$R^4$ is selected from the group consisting of hydrogen, $C_{1-4}$alkyl, monohalo$C_{1-4}$alkyl, polyhalo$C_{1-4}$alkyl, $C_{1-4}$alkyl-O—$C_{1-4}$alkyl, and $C_{1-4}$alkyl-OH;
$R^5$ and $R^6$ are each independently selected from the group consisting of hydrogen, halo, cyano, $C_{1-4}$alkyl, $C_{1-4}$alkyl-OH, $C_{3-7}$cycloalkyl, monohalo$C_{1-4}$alkyl, polyhalo$C_{1-4}$alkyl, $C_{1-4}$alkyl-O—$C_{1-4}$alkyl, O—$C_{1-4}$alkyl, monohalo$C_{1-4}$alkyloxy, polyhalo$C_{1-4}$alkyloxy, 1-acetylazetidin-3-yl, and NR'R''; and
R' and R'' are each independently selected from the group consisting of hydrogen and $C_{1-4}$alkyl; or
R' and R'', together with the nitrogen atom to which they are attached, form a heterocyclic group selected from the group consisting of 1-azetidinyl, 1-pyrrolidinyl, 1-piperidinyl, 1-piperazinyl, and 4-morpholinyl, wherein the 1-azetidinyl, 1-pyrrolidinyl, 1-piperidinyl, 1-piperazinyl and 4-morpholinyl are each optionally substituted with a substituent selected from the group consisting of halo, hydroxy, $C_{1-4}$alkyl, monohalo$C_{1-4}$alkyl, polyhalo$C_{1-4}$alkyl, and C(O)—$C_{1-4}$alkyl.

2. The method of claim 1, wherein:
$R^1$ is phenyl or 2-pyridinyl, each optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, $C_{1-4}$alkyl-O—$C_{1-4}$alkyl, monohalo$C_{1-4}$alkyloxy, polyhalo$C_{1-4}$alkyloxy, $C_{1-4}$alkyl-OH, monohalo$C_{1-4}$alkylthio, polyhalo$C_{1-4}$alkylthio, cyano, and $SF_5$; or
$R^1$ is

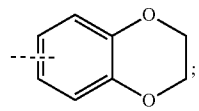

$R^2$ is

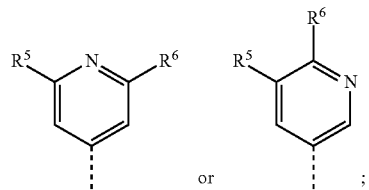

3. The method of claim 1, wherein:

$R^1$ is phenyl, optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, monohalo$C_{1-4}$alkyloxy, polyhalo$C_{1-4}$alkyloxy, cyano, and $SF_5$; or $R^1$ is:

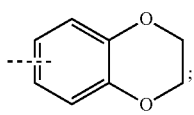

$R^2$ is

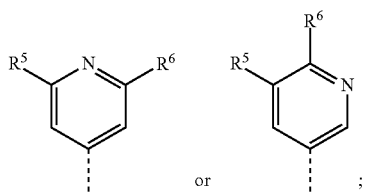

$R^5$ and $R^6$ are each independently selected from the group consisting of hydrogen, $C_{1-4}$alkyl, monohalo$C_{1-4}$alkyl, polyhalo$C_{1-4}$alkyl, $C_{1-4}$alkyl-O—$C_{1-4}$alkyl, O—$C_{1-4}$alkyl, and NR'R''; and R' and R'' are each independently selected from the group consisting of hydrogen and $C_{1-4}$alkyl.

4. The method of claim 1, wherein:

$R^1$ is phenyl, optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, monohalo$C_{1-4}$alkyloxy, polyhalo$C_{1-4}$alkyloxy, cyano, and $SF_5$; or $R^1$ is

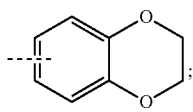

$R^2$ is

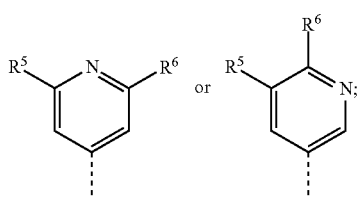

$R^4$ is selected from the group consisting of hydrogen and $C_{1-4}$alkyl;

$R^5$ and $R^6$ are each independently selected from the group consisting of hydrogen, $C_{1-4}$alkyl, $C_{1-4}$alkyl-O—$C_{1-4}$alkyl, O—$C_{1-4}$alkyl, and NR'R''; and R' and R'' are each independently hydrogen.

5. The method of claim 1, wherein:

$R^1$ is phenyl, optionally substituted with one or more substituents independently selected from the group consisting of halo, $C_{1-4}$alkyl, polyhalo$C_{1-4}$alkyl, and $SF_5$;

$R^2$ is

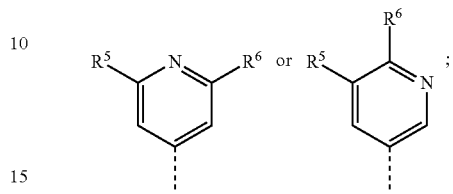

$R^4$ is hydrogen; and $R^5$ and $R^6$ are each independently selected from the group consisting of hydrogen, $C_{1-4}$alkyl, and O—$C_{1-4}$alkyl.

6. The method of claim 1, wherein $R^1$ is selected from the group consisting of:

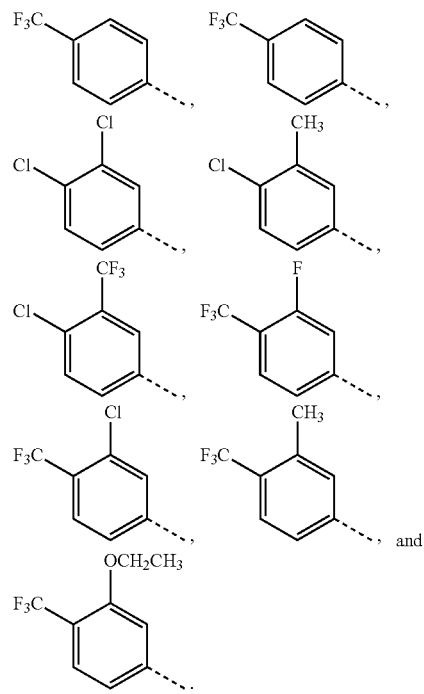

7. The method of claim 1, wherein the compound is:

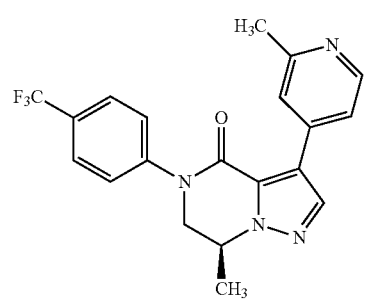

or a pharmaceutically acceptable salt or N-oxide thereof.

8. The method of claim 7, wherein the compound is the free base or a pharmaceutically acceptable salt selected from the group consisting of the hydrochloride salt, the maleate salt, the sulfate salt, and the methanesulfonate salt.

9. The method of claim 1, wherein the compound is:

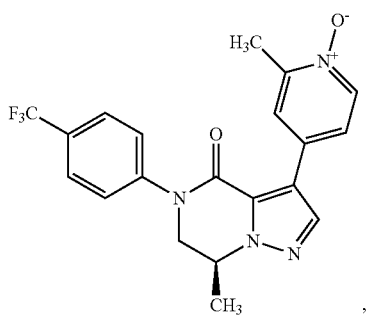

or a pharmaceutically acceptable salt or N-oxide thereof.

10. The method of claim 1, wherein the compound is:

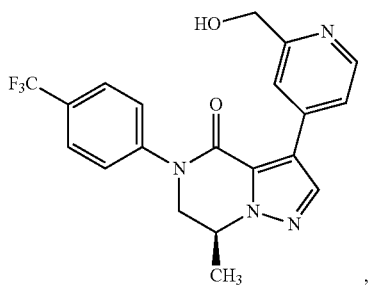

or a pharmaceutically acceptable salt or N-oxide thereof.

11. The method of claim 1, wherein the depression is treatment resistant depression.

12. The method of claim 1, wherein the depression is major depressive disorder.

13. The method of claim 1, wherein the method further comprises administering to the patient in need thereof a therapeutically effective amount of an additional pharmaceutically active agent.

14. A method for treating a patient suffering from dementia, comprising administering to the patient in need thereof a therapeutically effective amount of a compound of Formula (I):

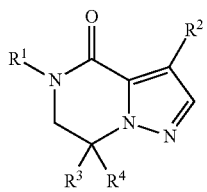

or a pharmaceutically acceptable salt, stereoisomeric form or N-oxide thereof,
wherein:
$R^1$ is phenyl or 2-pyridinyl, each optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, $C_{1-4}$alkyl-O—$C_{1-4}$alkyl, monohalo$C_{1-4}$alkyloxy, polyhalo$C_{1-4}$alkyloxy, $C_{1-4}$alkyl-OH, $C_{1-4}$alkylthio, monohalo$C_{1-4}$alkylthio, polyhalo$C_{1-4}$alkylthio, cyano, $C_{3-7}$cycloalkyl, and $SF_5$, wherein the $C_{3-7}$cycloalkyl is optionally substituted with trifluoromethyl; or
$R^1$ is

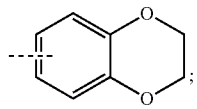

$R^2$ is

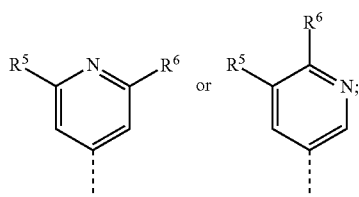

$R^3$ is selected from the group consisting of hydrogen and $C_{1-4}$alkyl;
$R^4$ is selected from the group consisting of hydrogen, $C_{1-4}$alkyl, monohalo$C_{1-4}$alkyl, polyhalo$C_{1-4}$alkyl, $C_{1-4}$alkyl-O—$C_{1-4}$alkyl, and $C_{1-4}$alkyl-OH;
$R^5$ and $R^6$ are each independently selected from the group consisting of hydrogen, halo, cyano, $C_{1-4}$alkyl, $C_{1-4}$alkyl-OH, $C_{3-7}$cycloalkyl, monohalo$C_{1-4}$alkyl, polyhalo$C_{1-4}$alkyl, $C_{1-4}$alkyl-O—$C_{1-4}$alkyl, O—$C_{1-4}$alkyl, monohalo$C_{1-4}$alkyloxy, polyhalo$C_{1-4}$alkyloxy, 1-acetylazetidin-3-yl, and NR'R"; and
R' and R" are each independently selected from the group consisting of hydrogen and $C_{1-4}$alkyl; or
R' and R", together with the nitrogen atom to which they are attached, form a heterocyclic group selected from the group consisting of 1-azetidinyl, 1-pyrrolidinyl, 1-piperidinyl, 1-piperazinyl, and 4-morpholinyl, wherein the 1-azetidinyl, 1-pyrrolidinyl, 1-piperidinyl, 1-piperazinyl and 4-morpholinyl are each optionally substituted with a substituent selected from the group consisting of halo, hydroxy, $C_{1-4}$alkyl, monohalo$C_{1-4}$alkyl, polyhalo$C_{1-4}$alkyl, and C(O)—$C_{1-4}$alkyl.

15. The method of claim 14, wherein:
$R^1$ is phenyl or 2-pyridinyl, each optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, $C_{1-4}$alkyl-O—$C_{1-4}$alkyl, monohalo$C_{1-4}$alkyloxy, polyhalo$C_{1-4}$alkyloxy, $C_{1-4}$alkyl-OH, monohalo$C_{1-4}$alkylthio, polyhalo$C_{1-4}$alkylthio, cyano, and $SF_5$; or
$R^1$ is

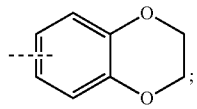

$R^1$ is

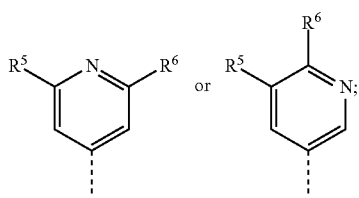

$R^5$ and $R^6$ are each independently selected from the group consisting of hydrogen, halo, cyano, $C_{1-4}$alkyl, $C_{1-4}$alkyl-OH, $C_{3-7}$cycloalkyl, monohalo$C_{1-4}$alkyl, polyhalo$C_{1-4}$alkyl, $C_{1-4}$alkyl-O—$C_{1-4}$alkyl, O—$C_{1-4}$alkyl, monohalo$C_{1-4}$alkyloxy, polyhalo$C_{1-4}$alkyloxy, and NR'R"; and R' and R" are each independently selected from the group consisting of hydrogen and $C_{1-4}$alkyl; or R' and R", together with the nitrogen atom to which they are attached, form a heterocyclic group selected from the group consisting of 1-azetidinyl, 1-pyrrolidinyl, and 1-piperidinyl, wherein the 1-azetidinyl, 1-pyrrolidinyl, and 1-piperidinyl are each optionally substituted with a halo substituent.

16. The method of claim 14, wherein:

$R^1$ is phenyl, optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, monohalo$C_{1-4}$alkyloxy, polyhalo$C_{1-4}$alkyloxy, cyano, and SF$_5$; or $R^1$ is

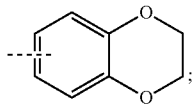

$R^2$ is

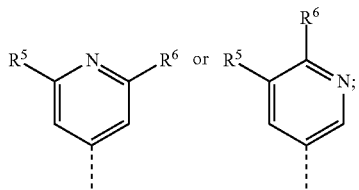

$R^5$ and $R^6$ are each independently selected from the group consisting of hydrogen, $C_{1-4}$alkyl, monohalo$C_{1-4}$alkyl, polyhalo$C_{1-4}$alkyl, $C_{1-4}$alkyl-O—$C_{1-4}$alkyl, O—$C_{1-4}$alkyl, and NR'R"; and R' and R" are each independently selected from the group consisting of hydrogen and $C_{1-4}$alkyl.

17. The method of claim 14, wherein:

$R^1$ is phenyl, optionally substituted with one or more substituents independently selected from the group consisting of halo, $C_{1-4}$alkyl, monohalo$C_{1-4}$alkyl, polyhalo$C_{1-4}$alkyl, O—$C_{1-4}$alkyl, monohalo$C_{1-4}$alkyloxy, polyhalo$C_{1-4}$alkyloxy, cyano, and SF$_5$; or $R^1$ is

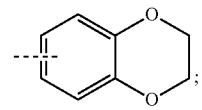

$R^2$ is

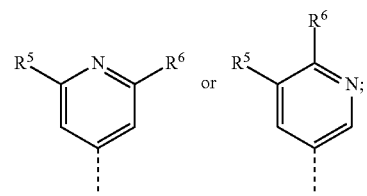

$R^4$ is selected from the group consisting of hydrogen and $C_{1-4}$alkyl;

$R^5$ and $R^6$ are each independently selected from the group consisting of hydrogen, $C_{1-4}$alkyl, $C_{1-4}$alkyl-O—$C_{1-4}$alkyl, O—$C_{1-4}$alkyl, and NR'R"; and R' and R" are each independently hydrogen.

18. The method of claim 14, wherein:

$R^1$ is phenyl, optionally substituted with one or more substituents independently selected from the group consisting of halo, $C_{1-4}$alkyl, polyhalo$C_{1-4}$alkyl, and SF$_5$;

$R^2$ is

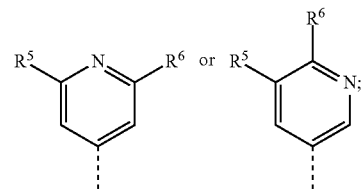

$R^4$ is hydrogen; and $R^5$ and $R^6$ are each independently selected from the group consisting of hydrogen, $C_{1-4}$alkyl, and O—$C_{1-4}$alkyl.

19. The method of claim 14, wherein $R^1$ is selected from the group consisting of:

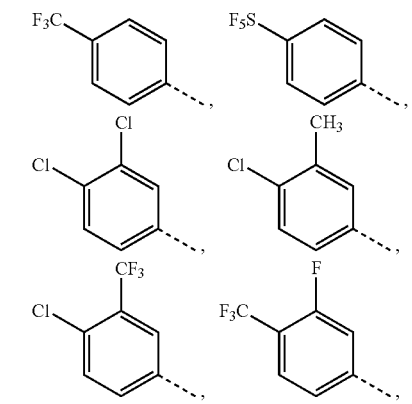

-continued

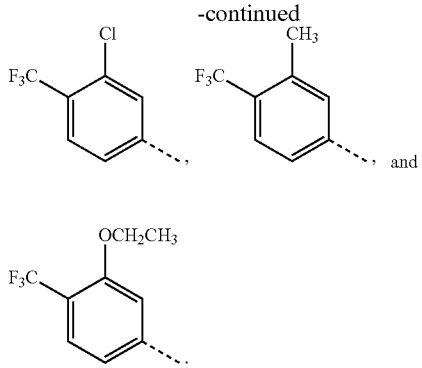

, and

20. The method of claim 14, wherein the compound is:

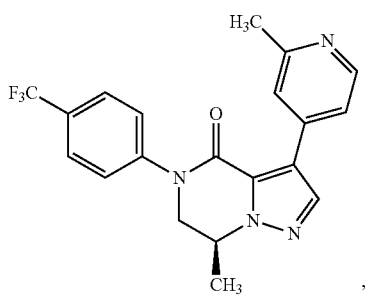 [SMILES: Cc1cc(-c2cnn3c2C(=O)N(c2ccc(C(F)(F)F)cc2)C[C@@H]3C)ccn1]

or a pharmaceutically acceptable salt or N-oxide thereof.

21. The method of claim 20, wherein the compound is the free base or a pharmaceutically acceptable salt selected from the group consisting of the hydrochloride salt, the maleate salt, the sulfate salt, and the methanesulfonate salt.

22. The method of claim 14, wherein the compound is:

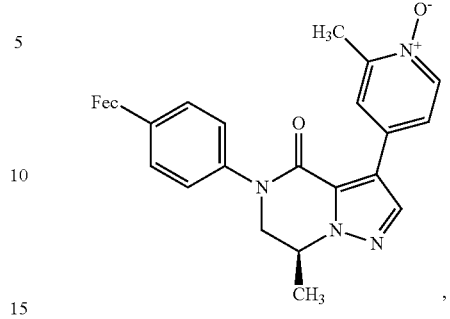

or a pharmaceutically acceptable salt or N-oxide thereof.

23. The method of claim 14, wherein the compound is:

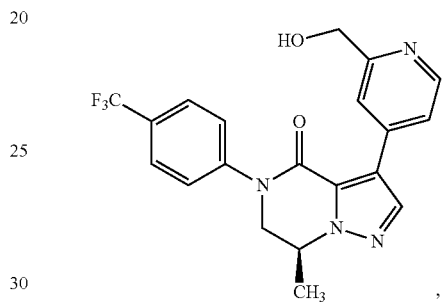

or a pharmaceutically acceptable salt or N-oxide thereof.

24. The method of claim 14, wherein the dementia is due to Alzheimer's disease.

25. The method of claim 14, wherein the method further comprises administering to the patient in need thereof a therapeutically effective amount of an additional pharmaceutically active agent.

* * * * *